(12) United States Patent
Badur et al.

(10) Patent No.: US 7,348,167 B2
(45) Date of Patent: Mar. 25, 2008

(54) INCREASE IN THE VITAMIN E CONTENT IN ORGANISMS DUE TO AN INCREASE IN THE TYROSINE AMINOTRANSFERASE ACTIVITY

(75) Inventors: Ralf Badur, Limburgerhof (DE); Michael Geiger, Heilbronn (DE); Rainer Lemke, Quedlinburg (DE); Klaus-Dieter Salchert, Gernrode (DE); Susanne Tropf, Quedlinburg (DE)

(73) Assignee: SunGene GmbH & Co. KGaA (DE)

( * ) Notice: Subject to any disclaimer, the term of this patent is extended or adjusted under 35 U.S.C. 154(b) by 332 days.

(21) Appl. No.: 10/471,243

(22) PCT Filed: Mar. 7, 2002

(86) PCT No.: PCT/EP02/02492

§ 371 (c)(1),
(2), (4) Date: Sep. 9, 2003

(87) PCT Pub. No.: WO02/072848

PCT Pub. Date: Sep. 19, 2002

(65) Prior Publication Data

US 2004/0086989 A1    May 6, 2004

(30) Foreign Application Priority Data

Mar. 9, 2001  (DE) ................ 101 11 676

(51) Int. Cl.
*C12P 7/26* (2006.01)
*C12N 9/10* (2006.01)
*C12N 1/21* (2006.01)
*C12N 15/74* (2006.01)

(52) U.S. Cl. ................ 435/148; 435/193; 435/471; 435/252.3

(58) Field of Classification Search ......... 435/148, 435/193, 471, 252.3
See application file for complete search history.

(56) References Cited

U.S. PATENT DOCUMENTS 6,624,342 B1  9/2003  Grimm et al.

FOREIGN PATENT DOCUMENTS

| WO | WO-97/27285 A1 | 7/1997 |
| WO | WO-99/04622 A1 | 2/1999 |
| WO | WO-00/08169 A1 | 2/2000 |
| WO | WO-00/61771 A2 | 10/2000 |
| WO | WO-00/63391 A2 | 10/2000 |
| WO | WO-00/68393 A1 | 11/2000 |

OTHER PUBLICATIONS

Sandorf et al. Planta (2002), 216(1), 173-179. Jasmonate is involved in the induction of tyrosine aminotransferase and tocopherol biosynthesis in *Arabidopsis thaliana*.*
Ravishankar et al (Biochemistry International Mar. 1991: 23(4): 679-687.*
Cloning and characterization of a Coronatine-Regulated Tyrosine Aminotransferase from *Arabidopsis*. Plant Physiology, Aug. 2001, vol. 126, pp. 1678-1687.*
Lopoukhina, A., "Characterization of Coronatine-Regulated Genes from *Arabidopsis thaliana*", Dissertation Ruhr-Universitat Bochum, Department of Plant Physiology (1999), pp. 1-92.
Fiedler, E., et al., "The formation of homogentisate in the biosynthesis of tocopherol and plastoquinone in spinach chloroplasts", Planta (1982), vol. 155, pp. 511-515.
Rettenmeier, R., etal., "Isolation and characterization of the human tyrosine aminotransferase gene", Nucleic Acids Research (1990), vol. 18, No. 13, pp. 3853-3861.
Shintani, D., et al., "Elevating the Vitamin E Content of Plants Through Metabolic Engineering", Science (1998), vol. 282, pp. 2098-2100.
Dietrich, J.B., et al., "Expression of mammalian tyrosine aminotransferase in *Saccharomyces cerevisiae* and *Escherichia coli*", Journal of Biochemistry (1991), vol. 201, pp. 399-407.
Montemartini, M., et al., "A recombinant tyrosine aminotransferase from *Trypanosoma cruzi* has both tyrosine aminotransferase and alanine aminotransferase activities", FEMS Microbiology Letters (1995), vol. 133, pp. 17-20.
Schultz, G., "Biosynthesis of α-Tocopherol in Chloroplasts of Higher Plants", Fat Sci. Technol. (1990), vol. 92, No. 2, pp. 86-90.
Hollånder-Czytko, H., et al., "Klonierung und Charakterisierung einer Tyrosinaminotransferase aus *Arabidopsis thaliana*", Symposium 4—Signalerkennung und-verarbeitung, Botanikertagung, Jena, Sep. 17-22, 2000, Jahrestagung der Deutschen Botanischen Gesellschaft und der Vereinigung für Angewandte Botanik.

* cited by examiner

*Primary Examiner*—Rebecca E. Prouty
*Assistant Examiner*—Kagnew Gebreyesus
(74) *Attorney, Agent, or Firm*—Connolly Bove Lodge & Hutz LLP

(57) ABSTRACT

The present invention relates to a process for producing vitamin E by growing organisms, in particular plants, which have an increased tyrosine aminotransferase activity in comparison with the wild type, and to the genetically modified organisms, in particular plants, themselves.

15 Claims, 63 Drawing Sheets

INCREASE IN THE VITAMIN E CONTENT IN ORGANISMS DUE TO AN INCREASE IN THE TYROSINE AMINOTRANSFERASE ACTIVITY

FIELD OF THE INVENTION

The present invention relates to a process for the production of vitamin E by growing organisms, in particular plants, which have an increased tyrosine aminotransferase activity over the wild type, and to the genetically modified organisms, in particular plants, themselves.

BACKGROUND OF THE INVENTION

The naturally occurring eight compounds with vitamin E activity are derivatives of 6-chromanol (Ullmann's Encyclopedia of Industrial Chemistry, Vol. A 27 (1996), VCH Verlagsgesellschaft, Chapter 4., 478-488, Vitamin E). The tocopherol group (1a-d) has a saturated side chain, while the tocotrienol group (2a-d) has an unsaturated side chain:

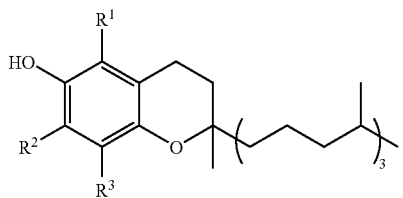

(1)

1a, α-tocopherol: $R^1=R^2=R^3=CH_3$
1b, β-tocopherol: $R^1=R^3=CH_3$, $R^2=H$
1c, γ-tocopherol: $R^1=H$, $R^2=R^3=CH_3$
1d, δ-tocopherol: $R^1=R^2=H$, $R^3=CH_3$

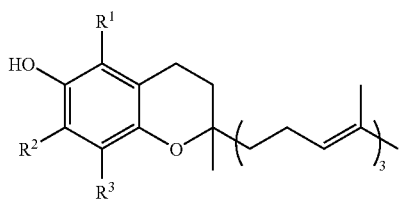

(2)

2a, α-tocotrienol: $R^1=R^2=R^3=CH_3$
2b, β-tocotrienol: $R^1=R^3=CH_3$, $R^2=H$
3c, γ-tocotrienol: $R^1=H$, $R^2=R^3=CH_3$
4d, δ-tocotrienol: $R^1=R^2=H$, $R^3=CH_3$ Within the present invention, vitamin E is understood to include all of the abovementioned tocopherols and tocotrienols with vitamin E activity.

These compounds with vitamin E activity are important natural lipid-soluble and solid antioxidants. Vitamin E deficiency leads to pathophysiological situations in humans and animals. Vitamin E compounds are thus of great economic value as additives in the food-and-feed sector, in pharmaceutical formulations and in cosmetic applications.

An economical process for the production of vitamin E compounds and of foods and feeds with an increased vitamin E content are therefore of great importance.

Particularly economical processes are biotechnological processes which exploit natural vitamin E-producing organisms or vitamin E-producing organisms which have been optimized by genetic modification.

FIG. 62 shows a biosynthesis scheme of α-tocopherol in higher plants.

In higher plants, tyrosine is formed starting from chorismate via prephenate and arogenate. The aromatic amino acid tyrosine is converted into hydroxyphenylpyruvate by the enzyme tyrosine aminotransferase, and hydroxyphenylpyruvate is converted into homogentisic acid by dioxygenation.

Homogentisic acid is subsequently bound to phytyl pyrophosphate (PPP) or geranylgeranyl pyrophosphate in order to form the precursors of α-tocopherol and α-tocotrienol, namely 2-methyl-6-phytylhydroquinone and 2-methyl-6-geranylgeranylhydroquinone. Methylation steps with S-adenosylmethionine as methyl group donor first lead to 2,3-dimethyl-6-phytylquinone, subsequent cyclization leads to γ-tocopherol and further methylation leads to α-tocopherol.

Experiments to increase the metabolite flux in order to increase the tocopherol or tocotrienol content in transgenic organisms by overexpressing individual biosynthesis genes are known.

WO 97/27285 describes a modification of the tocopherol content by increased expression or by downregulation of the enzyme p-hydroxyphenylpyruvate dioxygenase (HPPD).

WO 99/04622 and D. DellaPenna et al., Science 1998, 282, 2098-2100 describe gene sequences encoding a γ-tocopherol methyltransferase from *Synechocystis* PCC6803 and *Arabidopsis thaliana* and their incorporation into transgenic plants which have a modified vitamin E content.

WO 99/23231 shows that the expression of a geranylgeranyl reductase in transgenic plants results in an increased tocopherol biosynthesis.

WO 00/08169 describes gene sequences encoding a 1-deoxy-D-xylose-5-phosphate synthase and a geranylgeranyl-pyrophosphate oxidoreductase and their incorporation into transgenic plants which have a modified vitamin E content.

WO 00/68393 and WO 00/63391 describe gene sequences encoding a phytyl/prenyl transferase and their incorporation into transgenic plants which have a modified vitamin E content.

WO 00/61771 postulates that the combination of a sterol metabolism gene in combination with a tocopherol metabolism gene can lead to an increased tocopherol content in transgenic plants.

*Arabidopsis thaliana* genes which are inducible by the phytotoxin coronatine are disclosed in a PhD thesis by A. Lopoukhina (*Characterization of coronatine regulated genes from Arabidopsis thaliana*, PhD thesis at the Ruhr-Universität Bochum, Department of Plant Physiology, 1999) and in a poster contribution by H. Holländer-Czytko et al. at the "Botanikertagung 2000", Jena, 17-22.9.2000. In one of these genes, the derived amino acid sequence shows approximately 35% homology with known tyrosine aminotransferases. A low degree of enzyme activity of a tyrosine aminotransferase was detected by heterologous expression of the putative tyrosine aminotransferase gene in *E. coli*. It is disclosed that the treatment of plants with coronatine and the wounding of plants lead to an accumulation of the putative tyrosine aminotransferase-specific mRNA, the putative tyrosine aminotransferase and the measurable enzyme activity. Page 72 et seq. of the PhD thesis furthermore disclose that the wounding of plants is known to lead to the formation of reactive oxygen species which are scavenged by antioxidative compounds such as tocopherol, carotenoids or rosmaric acid.

While all of these methods, with the exception of the last-mentioned prior art, give rise to genetically modified organisms, in particular plants, which, as a rule, have a modified vitamin E content, they have the disadvantage that the level of the vitamin E content in the prior-art genetically modified organisms is as yet unsatisfactory.

It was therefore an object of the present invention to provide a further process for the production of vitamin E by growing organisms, or to provide further transgenic organisms which produce vitamin E, which have optimized characteristics such as, for example, a higher vitamin E content, and which do not exhibit the above-described disadvantage of the prior art.

We have found that this object is achieved by a process for the production of vitamin E wherein organisms are grown which have an increased tyrosine aminotransferase activity over the wild type.

DETAILED DESCRIPTION OF THE INVENTION

Figure 1:
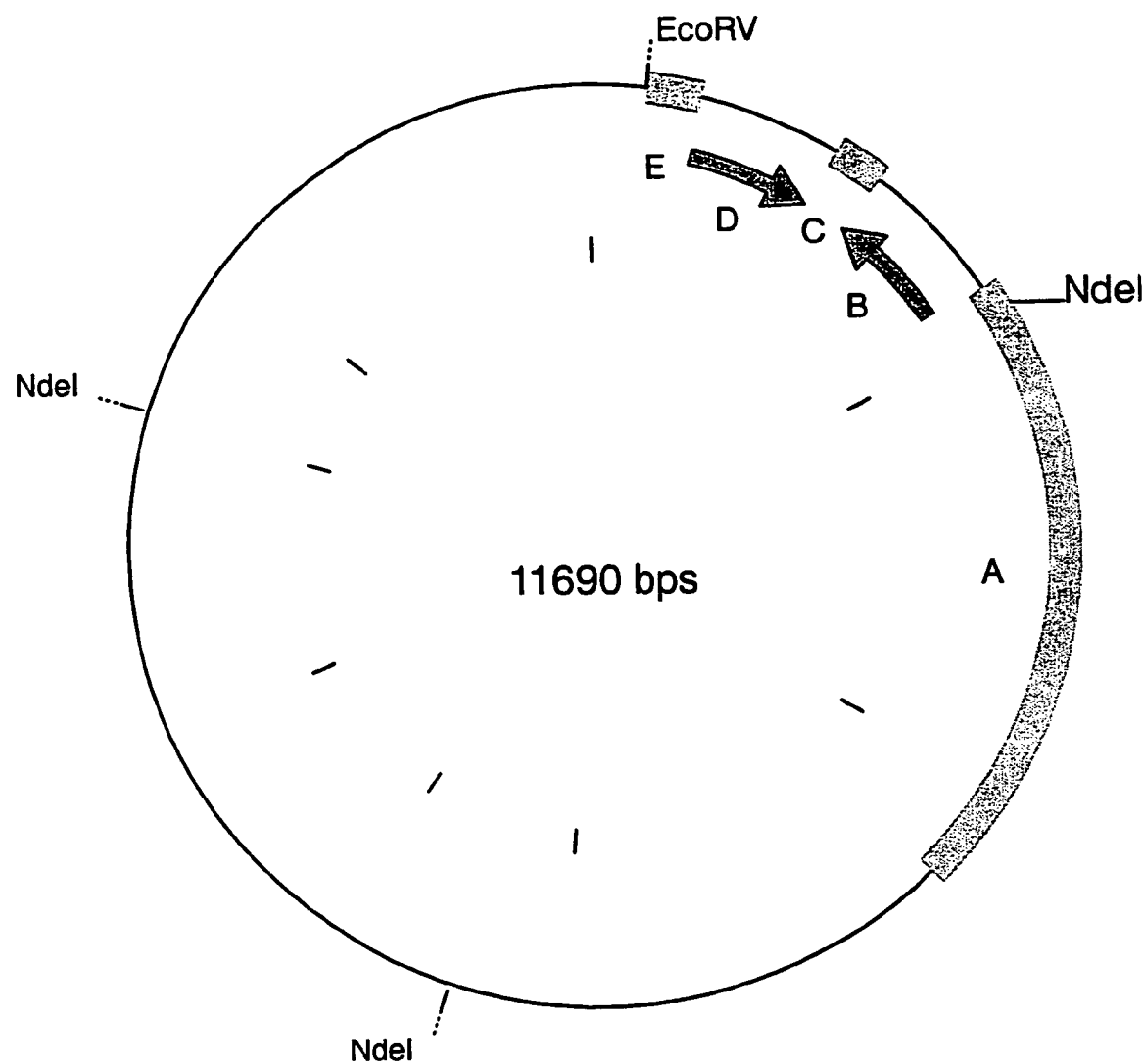
FIG. 1 shows the plasmid pSUN2-Pvic-*BnHGD-STLS1-α*BnHGD-ocsT.

Tyrosine aminotransferase activity is understood as meaning the enzyme activity of a tyrosine aminotransferase.

A tyrosine aminotransferase is understood as meaning a protein which has the enzymatic activity of converting tyrosine into 4-hydroxyphenylpyruvate.

Accordingly, tyrosine aminotransferase activity is understood as meaning the amount of tyrosine converted, or the amount of 4-hydroxyphenylpyruvate formed, by the protein tyrosine aminotransferase within a specific time.

Thus, in the case of an increased tyrosine aminotransferase activity over the wild type, the amount of tyrosine converted, or the amount of 4-hydroxyphenylpyruvate formed, by the protein tyrosine aminotransferase within a specific time is thus increased over the wild type.

This increase in the tyrosine aminotransferase activity preferably amounts to at least 5%, more preferably to at least 20%, more preferably to at least 50%, more preferably to at least 100%, particularly preferably to at least 300%, more particularly preferably to at least 500%, especially to at least 600%, of the tyrosine aminotransferase activity of the wild type.

A wild type is understood as meaning the corresponding non-genetically-modified starting organism. Preferably, and in particular in cases in which the organism or the wild type cannot be assigned unambiguously, the term wild type for increasing the tyrosine aminotransferase activity, increasing the hydroxyphenylpyruvate dioxygenase activity described hereinbelow, increasing the homogentisate phytyltransferase activity described hereinbelow, increasing the geranylgeranyl-pyrophosphate oxidoreductase activity described hereinbelow, increasing the 2-methyl-6-phytylhydroquinone methyltransferase activity described hereinbelow, increasing the tocopherol cyclase activity described hereinbelow, increasing the γ-tocopherol methyltransferase activity described hereinbelow, reducing the homogentisate dioxygenase activity described hereinbelow, reducing the maleylacetoacetate isomerase activity described hereinbelow and reducing the fumarylacetoacetate hydrolase activity described hereinbelow, and for increasing the vitamin E content, is understood as meaning a reference organism. This reference organism is preferably *Brassica napus* cv Westar.

The tyrosine aminotransferase activity can be increased in various ways, for example by eliminating inhibiting regulatory mechanisms at the translation and protein level or by increasing the gene expression of a nucleic acid encoding a tyrosine aminotransferase over the wild type, for example by inducing the tyrosine aminotransferase gene by phytotoxins such as, for example, coronatine, or by introducing nucleic acids encoding a tyrosine aminotransferase.

An increase in the gene expression of a nucleic acid encoding a tyrosine aminotransferase is also understood as meaning, in accordance with the invention, the manipulation of the expression of the endogenous tyrosine aminotransferases of the organisms, in particular plants. This can be achieved, for example, by modifying the promoter DNA sequence for genes encoding tyrosine aminotransferases. Such a modification which entails a modified or, preferably, increased expression rate of at least one endogenous tyrosine aminotransferase gene can be effected by deletion or insertion of DNA sequences.

As described above, it is possible to modify the expression of at least one endogenous tyrosine aminotransferase by applying exogenous stimuli. This can be effected by specific physiological conditions, i.e. by applying foreign substances.

Moreover, a modified, or increased, expression of at least one endogenous tyrosine aminotransferase gene can be achieved by a regulatory protein which does not occur in the untransformed organism interacting with the promoter of these genes.

Such a regulator can constitute a chimeric protein which is composed of a DNA binding domain and a transcription activator domain, as described, for example, in WO 96/06166.

In a preferred embodiment, the tyrosine aminotransferase activity is increased over the wild type by increasing the gene expression of a nucleic acid encoding a tyrosine aminotransferase.

In a further preferred embodiment, the gene expression of a nucleic acid encoding a tyrosine aminotransferase is increased by introducing, into the organism, nucleic acids encoding a tyrosine aminotransferase.

In principle, any tyrosine aminotransferase gene, i.e. any nucleic acid encoding a tyrosine aminotransferase, can be used for this purpose. In the case of genomic tyrosine aminotransferase nucleic acid sequences from eukaryotic sources, which comprise introns, it is preferred to use nucleic acid sequences which have already been processed, such as the corresponding cDNAs, in the event that the host organism is not capable, or cannot be made capable, of expressing the tyrosine aminotransferase in question.

All of the nucleic acids mentioned in the description can be, for example, a RNA, DNA or cDNA sequence.

Examples of nucleic acids encoding a tyrosine aminotransferase, or examples of tyrosine aminotransferases, are the six putative tyrosine aminotransferases TAT I to TAT VI from *Arabidopsis thaliana* TATI: CAA23026 (nucleic acid: SEQ. ID. NO. 5, protein: SEQ. ID. NO. 6), TAT II: CAA23025, TAT III: AAD23027 (nucleic acid: SEQ. ID. NO. 7, protein: SEQ. ID. NO. 8), TAT IV: CAA16881, TAT V: AAD21706 (nucleic acid: SEQ. ID. NO. 9, protein: SEQ. ID. NO. 10), TAT VI: (nucleic acid: SEQ. ID. NO. 11, protein: SEQ. ID. NO. 12)

the *Rattus norvegicus* tyrosine aminotransferase (nucleic acid: SEQ. ID. NO. 1, protein: SEQ. ID. NO. 2), a variant of the *Rattus norvegicus* tyrosine aminotransferase (nucleic acid: SEQ. ID. NO. 3, protein: SEQ. ID. NO. 4), the human tyrosine aminotransferase (Accession No. XP_008081), the *Trypanosoma rangeli* tyrosine aminotransferase (Accession No. AF165323_1), the *Trypanosoma cruzi* tyrosine aminotransferase (Accession No. AI 622965) or the *Rhizobium meliloti* tyrosine aminotransferase (Accession No. L05065).

It is preferred to use nucleic acids which encode proteins comprising the amino sequence SEQ. ID. NO. 2 or a sequence derived from this sequence by amino acid substitution, insertion or deletion which has at least 20% identity, preferably at least 33% identity, more preferably at least 35% identity, more preferably at least 50% identity, more particularly preferably at least 70% identity, most preferably at least 90% identity, at the amino acid level with the sequence SEQ. ID. NO. 2 and which have the enzymatic characteristic of a tyrosine aminotransferase.

Sequence SEQ. ID. NO. 2 constitutes the amino acid sequence of the *Rattus norvegicus* tyrosine aminotransferase.

In the description, the term "substitution" is to be understood as meaning the exchange of one or more amino acids for one or ore amino acids. Exchanges which are preferably carried out are those known as conservative exchanges, in which the replaced amino acid has a similar characteristic to the original amino acid, for example the exchange of Glu for Asp, Gln for Asn, Val for Ile, Leu for Ile, Ser for Thr.

Deletion is the replacement of an amino acid by a direct bond. Preferred positions for deletions are the termini of the polypeptide and the linkages between the individual protein domains.

Insertions are introductions of amino acids into the polypeptide chain, a direct bond formally being replaced by one or more amino acids.

Identity between two proteins is understood as meaning the identity of the amino acids over the entire protein length in each case, in particular the identity which is calculated by alignment with the aid of the Lasergene Software by DNASTAR, Inc. Madison, Wis. (USA) using the Clustal Method (Higgins D G, Sharp P M. Fast and sensitive multiple sequence alignments on a microcomputer. Comput Appl. Biosci. 1989 Apr; 5(2):151-1) with the parameters set as follows:

| Multiple alignment parameter: | |
|---|---|
| Gap penalty | 10 |
| Gap length penalty | 10 |
| Pairwise alignment parameter: | |
| K-tuple | 1 |
| Gap penalty | 3 |
| Window | 5 |
| Diagonals saved | 5 |

A protein with at least 20% identity at the amino acid level with the sequence SEQ. ID. NO. 2, accordingly, is to be understood as meaning a protein which upon alignment of its sequence with the sequence SEQ. ID. NO. 2, in particular using the above program algorithm with the above parameter set, has at least 20% identity.

In accordance with the above program algorithm with the above parameter set, the known tyrosine aminotransferases have the following amino acid sequence identity [%] with SEQ. ID. NO. 2 (*Rattus norvegicus* tyrosine aminotransferases):

| | |
|---|---|
| CAA23026 (TAT I) | 26.8% |
| CAA23025 (TAT II) | 22.3% |
| AAD23027 (TAT III) | 28.3% |
| CAA16881 (TAT IV) | 29.8% |
| AAD21706 (TAT V) | 30.0% |
| TAT VI K19.P17.14 | 33.3% |
| AF165323_1 (*Trypanosoma rangeli*) | 33.3% |
| XP_008081 (human) | 91.6% |

In a further preferred embodiment, nucleic acids which encode proteins comprising the amino acid sequence of the *Rattus norvegicus* tyrosine aminotransferase SEQ. ID. NO. 2 or the amino acid sequence of human tyrosine aminotransferase (Accession No. XP_008081) are introduced into organisms.

Suitable nucleic acid sequences can be obtained, for example, by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in a plant, it is frequently advantageous to use the codon usage of the plant in the backtranslation.

In an especially preferred embodiment, a nucleic acid comprising the sequence SEQ. ID. NO. 1 is introduced into the organism.

Sequence SEQ. ID. NO. 1 constitutes the cDNA of the *Rattus norvegicus* tyrosine aminotransferase (Accession No. NM_012668).

In a preferred embodiment, the organisms which are grown additionally have an increased activity of at least one of the activities selected from the group consisting of hydroxyphenylpyruvate dioxygenase activity, homogentisate phytyltransferase activity, geranylgeranyl-pyrophosphate oxidoreductase activity, 2-methyl-6-phytylhydroquinone methyltransferase activity, tocopherol cyclase activity and γ-tocopherol methyltransferase activity over the wild type.

Hydroxyphenylpyruvate dioxygenase activity is understood as meaning the enzyme activity of a hydroxyphenylpyruvate dioxygenase.

A hydroxyphenylpyruvate dioxygenase is understood as meaning a protein which has the enzymatic activity to convert hydroxyphenylpyruvate into homogentisate.

Accordingly, hydroxyphenylpyruvate dioxygenase activity is understood as meaning the amount of hydroxyphenylpyruvate converted, or the amount of homogentisate produced, by the protein hydroxyphenylpyruvate dioxygenase within a certain time.

Thus, in a hydroxyphenylpyruvate dioxygenase activity which is increased over the wild type, the amount of hydroxyphenylpyruvate converted, or the amount of homogentisate produced, by the protein hydroxyphenylpyruvate dioxygenase within a certain time is increased in comparison with the wild type.

This increase in the hydroxyphenylpyruvate dioxygenase activity preferably amounts to at least 5%, more preferably to at least 20%, more preferably to at least 50%, more preferably to at least 100%, more preferably to at least 300%, even more preferably to at least 500%, in particular to at least 600% of the hydroxyphenylpyruvate dioxygenase activity of the wild type.

Homogentisate phytyltransferase activity is understood as meaning the enzyme activity of a homogentisate phytyltransferase.

A homogentisate phytyltransferase is understood as meaning a protein which has the enzymatic activity to convert homogentisate and phytyl pyrophosphate into 2-methyl-6-phytylhydroquinone.

Accordingly, homogentisate phytyltransferase activity is understood as meaning the amount of homogentisate or phytyl phyrophosphate converted, or the amount of 2-methyl-6-phytylhydroquinone produced, by the protein homogentisate phytyltransferase within a certain time.

Thus, in a homogentisate phytyltransferase activity which is increased over the wild type, the amount of homogentisate or phytyl pyrophosphate converted, or the amount of 2-methyl-6-phytylhydroquinone produced, by the protein homogentisate phytyltransferase within a certain time is increased in comparison with the wild type.

This increase in the homogentisate phytyltransferase activity preferably amounts to at least 5%, more preferably to at least 20%, more preferably to at least 50%, more preferably to at least 100%, more preferably to at least 300%, even more preferably to at least 500%, in particular to at least 600% of the homogentisate phytyltransferase activity of the wild type.

Geranylgeranyl-pyrophosphate oxidoreductase activity is understood as meaning the enzyme activity of a geranylgeranyl-pyrophosphate oxidoreductase.

A geranylgeranyl-pyrophosphate oxidoreductase is understood as meaning a protein which has the enzymatic activity to convert geranylgeranyl pyrophosphate into phytyl pyrophosphate.

Accordingly, geranylgeranyl-pyrophosphate oxidoreductase activity is understood as meaning the amount of geranylgeranyl pyrophosphate converted, or the amount of phytyl pyrophosphate produced, by the protein geranylgeranyl-pyrophosphate oxidoreductase within a certain time.

Thus, in a geranylgeranyl-pyrophosphate oxidoreductase activity which is increased over the wild type, the amount of geranylgeranyl pyrophosphate converted, or the amount of phytyl pyrophosphate produced, by the protein geranylgeranyl-pyrophosphate oxidoreductase within a certain time is increased in comparison with the wild type.

This increase in the geranylgeranyl-pyrophosphate oxidoreductase activity preferably amounts to at least 5%, more preferably to at least 20%, more preferably to at least 50%, more preferably to at least 100%, more preferably to at least 300%, even more preferably to at least 500%, in particular to at least 600% of the geranylgeranyl-pyrophosphate oxidoreductase activity of the wild type.

2-Methyl-6-phytylhydroquinone methyltransferase activity is understood as meaning the enzyme activity of a 2-methyl-6-phytylhydroquinone methyltransferase.

A 2-methyl-6-phytylhydroquinone methyltransferase is understood as meaning a protein which has the enzymatic activity to convert 2-methyl-6-phytylhydroquinone into 2,3-dimethyl-6-phytyl-hydroquinol.

Accordingly, 2-methyl-6-phytylhydroquinone methyltransferase activity is understood as meaning the amount of 2-methyl-6-phytylhydroquinol converted, or the amount of 2,3-dimethyl-6-phytylhydroquinol produced, by the protein 2-methyl-6-phytyl-hydroquinone methyltransferase within a certain time.

Thus, in a 2-methyl-6-phytylhydroquinone methyltransferase activity which is increased over the wild type, the amount of 2-methyl-6-phytylhydroquinone converted, or the amount of 2,3-dimethyl-6-phytylhydroquinone produced, by the protein 2-methyl-6-phytylhydroquinone methyltransferase within a certain time is increased in comparison with the wild type.

This increase in the 2-methyl-6-phytylhydroquinone methyltransferase activity preferably amounts to at least 5%, more preferably to at least 20%, more preferably to at least 50%, more preferably to at least 100%, more preferably to at least 300%, even more preferably to at least 500%, in particular to at least 600% of the 2-methyl-6-phytylhydroquinone methyltransferase activity of the wild type.

Tocopherol cyclase activity is understood as meaning the enzyme activity of a tocopherol cyclase.

A tocopherol cyclase is understood as meaning a protein which has the enzymatic activity to convert 2,3-dimethyl-6-phytylhydroquinone into γ-tocopherol.

Accordingly, tocopherol cyclase activity is understood as meaning the amount of 2,3-dimethyl-6-phytylhydroquinone converted, or the amount of γ-tocopherol produced, by the protein tocopherol cyclase within a certain time.

Thus, in a tocopherol cyclase activity which is increased over the wild type, the amount of 2,3-dimethyl-6-phytylhydroquinone converted, or the amount of γ-tocopherol produced, by the protein tocopherol cyclase within a certain time is increased in comparison with the wild type.

This increase in the tocopherol cyclase activity preferably amounts to at least 5%, more preferably to at least 20%, more preferably to at least 50%, more preferably to at least 100%, more preferably to at least 300%, even more preferably to at least 500%, in particular to at least 600% of the tocopherol cyclase activity of the wild type.

γ-Tocopherol methyltransferase activity is understood as meaning the enzyme activity of a γ-tocopherol methyltransferase.

A γ-tocopherol methyltransferase is understood as meaning a protein which has the enzymatic activity to convert γ-tocopherol into α-tocopherol.

Accordingly, γ-tocopherol methyltransferase activity is understood as meaning the amount of γ-tocopherol converted, or the amount of α-tocopherol produced, by the protein γ-tocopherol methyltransferase within a certain time.

Thus, in a γ-tocopherol methyltransferase activity which is increased over the wild type, the amount of γ-tocopherol converted, or the amount of α-tocopherol produced, by the protein γ-tocopherol methyltransferase within a certain time is increased in comparison with the wild type.

This increase in the γ-tocopherol methyltransferase activity preferably amounts to at least 5%, more preferably to at least 20%, more preferably to at least 50%, more preferably to at least 100%, more preferably to at least 300%, even more preferably to at least 500%, in particular to at least 600% of the γ-tocopherol methyltransferase activity of the wild type.

The increase in at least one of the activities selected from the group consisting of hydroxyphenylpyruvate dioxygenase activity, homogentisate phytyltransferase activity, geranylgeranyl-pyrophosphate oxidoreductase activity, 2-methyl-6-phytylhydroquinone methyltransferase activity, tocopherol cyclase activity and γ-tocopherol methyltransferase activity can be effected independently of one another by various routes, for example by eliminating inhibiting regulatory mechanisms at the expression level and the protein level, or by increasing the gene expression of the nucleic acids in question, that is to say increasing the gene expression of at least one nucleic acid selected from the group of the nucleic acids encoding a hydroxyphenylpyruvate dioxygenase, nucleic acids encoding a homogentisate phytyltransferase, nucleic acids encoding a geranylgeranyl-pyrophosphate oxidoreductase, nucleic acids encoding a 2-methyl-6-phytylhydroquinone methyltransferase, nucleic acids encoding a tocopherol cyclase and nucleic acids encoding a γ-tocopherol methyltransferase over the wild type.

Increasing the gene expression of the nucleic acid in question over the wild type can also be effected by various routes, for example by inducing the relevant genes by activators, that is to say by inducing the hydroxyphenylpyruvate dioxygenase gene, the homogentisate phytyltransferase gene, the geranylgeranyl-pyrophosphate oxidoreductase gene, the 2-methyl-6-phytylhydroquinone methyltransferase gene, the tocopherol cyclase gene or the γ-tocopherol methyltransferase gene by activators or by introducing one or more gene copies of the relevant nucleic acids into the organism, that is to say by introducing at least one of the nucleic acids selected from the group consisting of nucleic acids encoding a hydroxyphenylpyruvate dioxygenase, nucleic acids encoding a homogentisate phytyltransferase, nucleic acids encoding a geranylgeranyl-pyrophosphate oxidoreductase, nucleic acids encoding a 2-methyl-6-phytylhydroquinone methyltransferase, nucleic acids encoding a tocopherol cyclase and nucleic acids encoding a γ-tocopherol methyltransferase.

Increasing the gene expression of a nucleic acid encoding a hydroxyphenylpyruvate dioxygenase, homogentisate phytyltransferase, geranylgeranyl-pyrophosphate oxidoreductase, 2-methyl-6-phytylhydroquinone methyltransferase, tocopherol cyclase or γ-tocopherol methyltransferase is also understood as meaning, in accordance with the invention, the manipulation of the expression of the endogenous hydroxyphenylpyruvate dioxygenases, homogentisate phytyltransferases, geranylgeranyl-pyrophosphate oxidoreductases, 2-methyl-6-phytylhydroquinone methyltransferases, tocopherol cyclases or γ-tocopherol methyltransferases of the organism itself, in particular the plants themselves.

This can be brought about for example by modifying the promoter DNA sequence for genes encoding hydroxyphenylpyruvate dioxygenase, homogentisate phytyltransferase, geranylgeranyl-pyrophosphate oxidoreductase, 2-methyl-6-phytylhydroquinone methyltransferase, tocopherol cyclase or γ-tocopherol methyltransferase. Such a modification, which results in an increased expression rate of the relevant gene, can be effected for example by deletion or insertion of DNA sequences.

As described hereinabove, it is possible to modify the expression of the endogenous hydroxyphenylpyruvate dioxygenase, homogentisate phytyltransferase, geranylgeranyl-pyrophosphate oxidoreductase, 2-methyl-6-phytylhydroquinone methyltransferase, tocopherol cyclase or γ-tocopherol methyltransferase by the application of exogenous stimuli. This can be effected by specific physiological conditions, i.e. by applying exogenous substances.

Moreover, a modified, or increased, expression of endogenous hydroxyphenylpyruvate dioxygenase, homogentisate phytyltransferase, geranylgeranyl-pyrophosphate oxidoreductase, 2-methyl-6-phytylhydroquinone methyltransferase, tocopherol cyclase or γ-tocopherol methyltransferase genes can be achieved by a regulatory protein which does not occur in the untransformed organism interacting with the promoter of these genes.

Such a regulator can constitute a chimeric protein which is composed of a DNA binding domain and a transcription activator domain, as described, for example, in WO 96/06166.

In a preferred embodiment, the increase in gene expression of a nucleic acid encoding a hydroxyphenylpyruvate dioxygenase, hereinbelow also termed HPPD, is effected by introducing, into the organism, at least one nucleic acid encoding an HPPD.

In principle, any HPPD gene, that is to say any nucleic acid which encodes an HPPD, can be used for this purpose.

In the case of genomic HPPD nucleic acid sequences from eukaryotic sources, which comprise introns, it is preferred to use nucleic acid sequences which have already been processed, such as the corresponding cDNAs, in the event that the host organism is not capable, or cannot be made capable, of expressing the HPPD in question.

Examples of HPPD genes are nucleic acids encoding an *Arabidopsis thaliana* HPPD (nucleic acid: Seq. ID. No. 13, protein: Seq. ID. No. 14) or a barley HPPD (WO 99/04021).

In this preferred embodiment, at least one further HPPD gene is thus present in the transgenic organisms according to the invention compared with the wild type. In this preferred embodiment, the organism, accordingly, has at least one exogenous nucleic acid encoding an HPPD or at least two endogenous nucleic acids encoding an HPPD.

Nucleic acids which are preferably used in the above-described preferred embodiment are nucleic acids which encode proteins comprising the amino acid sequence SEQ. ID. NO. 14 or a sequence derived from this sequence by substitution, insertion or deletion of amino acids which have at least 30% identity, preferably at least 50% identity, more preferably at least 70% identity, more preferably at least 90% identity, most preferably at least 95% identity with the sequence SEQ. ID. NO. 14 at the amino acid level and which have the enzymatic property of an HPPD.

The sequence SEQ. ID. NO. 14 constitutes the amino acid sequence of the *Arabidopsis thaliana* HPPD.

Accordingly, a protein which has at least 30% identity with the sequence SEQ. ID. NO. 14 at the amino acid level is understood as meaning a protein which, upon alignment of its sequence with the sequence SEQ. ID. NO. 14, in particular using the above program algorithm with the above parameter set, has at least 30% identity.

Further examples of HPPD and HPPD genes can be found easily from a variety of organisms whose genomic sequence is known by homology comparisons of the amino acid sequences or of the corresponding backtranslated nucleic acid sequences from databases with SEQ ID. NO. 14.

For example, the barley HPPD has 57.5% identity with the *Arabidopsis thaliana* HPPD (SEQ. ID. No. 14).

Further examples of HPPD and HPPD genes can furthermore be found easily, for example starting from the sequence SEQ. ID. No. 13 in various organisms whose genomic sequence is not known, using hybridization and PCR techniques in a manner known per se.

In a further especially preferred embodiment, the hydroxyphenylpyruvate dioxygenase activity is increased by introducing, into organisms, nucleic acids which encode proteins comprising the amino acid sequence of the *Arabidopsis thaliana* HPPD (SEQ. ID. NO. 14).

Suitable nucleic acid sequences can be obtained, for example, by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in plants, it is frequently advantageous to use the codon usage of the plant in the backtranslation.

In an especially preferred embodiment, a nucleic acid comprising the sequence SEQ. ID. NO. 13 is introduced into the organism.

The sequence SEQ. ID. NO. 13 constitutes the genomic DNA of *A. thaliana* which encodes the HPPD of the sequence SEQ. ID. NO. 14.

Furthermore, all of the abovementioned HPPD genes can be synthesized chemically, in a manner known per se, from the nucleotide units such as, for example, by fragment condensation of individual overlapping complementary nucleic acid units of the double helix. The chemical synthesis of oligonucleotides can be carried out for example in the known manner by the phosphoamidite method (Voet, Voet, 2nd Edition, Wiley Press New York, pages 896-897). The addition of synthetic oligonucleotides and the filling-in of gaps with the aid of the Klenow fragment of the DNA polymerase and ligation reactions and general cloning methods are described in Sambrook et al. (1989), Molecular cloning: A laboratory manual, Cold Spring Harbor Laboratory Press.

In a preferred embodiment, the increase in gene expression of a nucleic acid encoding a homogentisate phytyltransferase, hereinbelow also termed HPT, is effected by introducing, into the organism, at least one nucleic acid encoding an HPT.

In principle, any HPT gene, that is to say any nucleic acid which encodes an HPT, can be used for this purpose.

In the case of genomic HPT nucleic acid sequences from eukaryotic sources, which comprise introns, it is preferred to use nucleic acid sequences which have already been processed, such as the corresponding cDNAs, in the event that the host organism is not capable, or cannot be made capable, of expressing the HPT in question.

Examples of HPT genes are nucleic acids encoding an *Arabidopsis thaliana* HPT (nucleic acid: Seq. ID. No. 15, protein: Seq. ID. No. 16) or nucleic acids encoding a *Glycine max, Helianthus annuus, Nicotiana tabacum, Physcomitrella patens, Brassica napus, Oryza sativa, Hordeum vulgaris* or *Synechocystis* sp. PCC6803 HPT.

In this preferred embodiment, at least one further HPT gene is thus present in the transgenic organisms according to the invention compared with the wild type. In this preferred embodiment, the organism, accordingly, has at least one exogenous nucleic acid encoding an HPT or at least two endogenous nucleic acids encoding an HPT.

Nucleic acids which are preferably used in the above-described preferred embodiment are nucleic acids which encode proteins comprising the amino acid sequence SEQ. ID. NO. 16 or a sequence derived from this sequence by substitution, insertion or deletion of amino acids which have at least 30% identity, preferably at least 50% identity, more preferably at least 70% identity, more preferably at least 90% identity, most preferably at least 95% identity with the sequence SEQ. ID. NO. 16 at the amino acid level and which have the enzymatic property of an HPT.

The sequence SEQ. ID. NO. 16 constitutes the amino acid sequence of the *Arabidopsis thaliana* HPT.

Accordingly, a protein which has at least 30% identity with the sequence SEQ. ID. NO. 16 at the amino acid level is understood as meaning a protein which, upon alignment of its sequence with the sequence SEQ. ID. NO. 16, in particular using the above program algorithm with the above parameter set, has at least 30% identity.

Further examples of HPT and HPT genes can be found easily from a variety of organisms whose genomic sequence is known by homology comparisons of the amino acid sequences or of the corresponding backtranslated nucleic acid sequences from databases with SEQ ID. NO. 16.

For example, the *Synechocystis* sp. PCC6803 HPT has 40.9% identity with the *Arabidopsis thaliana* HPT (Seq. ID. No. 16).

Further examples of HPT and HPT genes can furthermore be found easily, for example starting from the sequence SEQ. ID. No. 15 in various organisms whose genomic sequence is not known, using hybridization and PCR techniques in a manner known per se.

In a further especially preferred embodiment, the homogentisate phytyltransferase activity is increased by introducing, into organisms, nucleic acids which encode proteins comprising the amino acid sequence of the *Arabidopsis thaliana* HPT (SEQ. ID. NO. 16).

Suitable nucleic acid sequences can be obtained, for example, by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in plants, it is frequently advantageous to use the codon usage of the plant in the backtranslation.

In an especially preferred embodiment, a nucleic acid comprising the sequence SEQ. ID. NO. 15 is introduced into the organism.

The sequence SEQ. ID. NO. 15 constitutes the genomic DNA of *A. thaliana* which encodes the HPT of the sequence SEQ. ID. NO. 16.

Furthermore, all of the abovementioned HPT genes can be synthesized chemically, in a manner known per se, from the nucleotide units such as, for example, by fragment condensation of individual overlapping complementary nucleic acid units of the double helix. The chemical synthesis of oligonucleotides can be carried out for example in the known manner by the phosphoamidite method (Voet, Voet, 2nd Edition, Wiley Press New York, pages 896-897). The addition of synthetic oligonucleotides and the filling-in of gaps with the aid of the Klenow fragment of the DNA polymerase and ligation reactions and general cloning methods are described in Sambrook et al. (1989), Molecular cloning: A laboratory manual, Cold Spring Harbor Laboratory Press.

In a preferred embodiment, the increase in gene expression of a nucleic acid encoding a geranylgeranyl-pyrophosphate oxidoreductase, hereinbelow also termed GGPPOR, is effected by introducing, into the organism, at least one nucleic acid encoding a GGPPOR.

In principle, any GGPPOR gene, that is to say any nucleic acid which encodes a GGPPOR, can be used for this purpose.

In the case of genomic GGPPOR nucleic acid sequences from eukaryotic sources, which comprise introns, it is preferred to use nucleic acid sequences which have already been processed, such as the corresponding cDNAs, in the event that the host organism is not capable, or cannot be made capable, of expressing the GGPPOR in question.

Examples of GGPPOR genes are nucleic acids encoding a *Nicotiana tabacum* GGPPOR (nucleic acid: Seq. ID. No. 17, protein: Seq. ID. No. 18) or nucleic acids encoding an *Arabidopsis thaliana, Glycine max, Helianthus annuus, Physcomitrella patens, Brassica napus, Oryza sativa, Hordeum vulgaris* or *Synechocystis* sp. PCC6803 GGPPOR.

In this preferred embodiment, at least one further GGPPOR gene is thus present in the transgenic organisms according to the invention compared with the wild type. In this preferred embodiment, the organism, accordingly, has at least one exogenous nucleic acid encoding a GGPPOR or at least two endogenous nucleic acids encoding a GGPPOR.

Nucleic acids which are preferably used in the above-described preferred embodiment are nucleic acids which encode proteins comprising the amino acid sequence SEQ. ID. NO. 18 or a sequence derived from this sequence by substitution, insertion or deletion of amino acids which have at least 30% identity, preferably at least 50% identity, more preferably at least 70% identity, more preferably at least 90% identity, most preferably at least 95% identity with the sequence SEQ. ID. NO. 18 at the amino acid level and which have the enzymatic property of a GGPPOR.

The sequence SEQ. ID. NO. 18 constitutes the amino acid sequence of the *Nicotiana tabacum* GGPPOR.

Accordingly, a protein which has at least 30% identity with the sequence SEQ. ID. NO. 18 at the amino acid level is understood as meaning a protein which, upon alignment of its sequence with the sequence SEQ. ID. NO. 18, in particular using the above program algorithm with the above parameter set, has at least 30% identity.

Further examples of GGPPOR and GGPPOR genes can be found easily from a variety of organisms whose genomic sequence is known by homology comparisons of the amino acid sequences or of the corresponding backtranslated nucleic acid sequences from databases with SEQ ID. NO. 18.

For example, the *Arabidopsis thaliana* GGPPOR has 80% identity with the *Nicotiana tabacum* GGPPOR (SEQ. ID. No. 18).

Further examples of GGPPOR and GGPPOR genes can furthermore be found easily, for example starting from the sequence SEQ. ID. No. 17 in various organisms whose genomic sequence is not known, using hybridization and PCR techniques in a manner known per se.

In a further especially preferred embodiment, the geranylgeranyl-pyrophosphate oxidoreductase activity is increased by introducing, into organisms, nucleic acids which encode proteins comprising the amino acid sequence of the *Nicotiana tabacum* GGPPOR (SEQ. ID. NO. 18).

Suitable nucleic acid sequences can be obtained, for example, by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in plants, it is frequently advantageous to use the codon usage of the plant in the backtranslation.

In an especially preferred embodiment, a nucleic acid comprising the sequence SEQ. ID. NO. 17 is introduced into the organism.

The sequence SEQ. ID. NO. 17 constitutes the genomic DNA of *Nicotiana tabacum* which encodes the GGPPOR of the sequence SEQ. ID. NO. 18.

Furthermore, all of the abovementioned GGPPOR genes can be synthesized chemically, in a manner known per se, from the nucleotide units such as, for example, by fragment condensation of individual overlapping complementary nucleic acid units of the double helix. The chemical synthesis of oligonucleotides can be carried out for example in the known manner by the phosphoamidite method (Voet, Voet, 2nd Edition, Wiley Press New York, pages 896-897). The addition of synthetic oligonucleotides and the filling-in of gaps with the aid of the Klenow fragment of the DNA polymerase and ligation reactions and general cloning methods are described in Sambrook et al. (1989), Molecular cloning: A laboratory manual, Cold Spring Harbor Laboratory Press.

In a preferred embodiment, the increase in gene expression of a nucleic acid encoding a 2-methyl-6-phytylhydroquinone methyltransferase, hereinbelow also termed MT1, is effected by introducing, into the organism, at least one nucleic acid encoding an MT1.

In principle, any MT1 gene, that is to say any nucleic acid which encodes an MT1, can be used for this purpose.

In the case of genomic MT1 nucleic acid sequences from eukaryotic sources, which comprise introns, it is preferred to use nucleic acid sequences which have already been processed, such as the corresponding cDNAs, in the event that the host organism is not capable, or cannot be made capable, of expressing the MT1 in question.

Examples of MT1 genes are nucleic acids encoding a *Synechocystis* sp. PCC6803 MT1 (nucleic acid: Seq. ID. No. 19, protein: Seq. ID. No. 20).

In this preferred embodiment, at least one further MT1 gene is thus present in the transgenic organisms according to the invention compared with the wild type. In this preferred embodiment, the organism, accordingly, has at least one exogenous nucleic acid encoding an MT1 or at least two endogenous nucleic acids encoding an MT1.

Nucleic acids which are preferably used in the above-described preferred embodiment are nucleic acids which encode proteins comprising the amino acid sequence SEQ. ID. NO. 20 or a sequence derived from this sequence by substitution, insertion or deletion of amino acids which have at least 30% identity, preferably at least 50% identity, more preferably at least 70% identity, more preferably at least 90% identity, most preferably at least 95% identity with the sequence SEQ. ID. NO. 20 at the amino acid level and which have the enzymatic property of an MT1.

The sequence SEQ. ID. NO. 20 constitutes the amino acid sequence of the *Synechocystis* sp. PCC6803 MT1.

Accordingly, a protein which has at least 30% identity with the sequence SEQ. ID. NO. 20 at the amino acid level is understood as meaning a protein which, upon alignment of its sequence with the sequence SEQ. ID. NO. 20, in particular using the above program algorithm with the above parameter set, has at least 30% identity.

Further examples of MT1 and MT1 genes can be found easily from a variety of organisms whose genomic sequence is known by homology comparisons of the amino acid sequences or of the corresponding backtranslated nucleic acid sequences from databases with SEQ ID. NO. 20.

Further examples of MT1 and MT1 genes can furthermore be found easily, for example starting from the sequence SEQ. ID. No. 19 in various organisms whose genomic sequence is not known, using hybridization and PCR techniques in a manner known per se.

In a further especially preferred embodiment, the 2-methyl-6-phytylhydroquinone methyltransferase activity is increased by introducing, into organisms, nucleic acids which encode proteins comprising the amino acid sequence of the *Synechocystis* sp. PCC6803 MT1 (SEQ. ID. NO. 20).

Suitable nucleic acid sequences can be obtained, for example, by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in plants, it is frequently advantageous to use the codon usage of the plant in the backtranslation.

In an especially preferred embodiment, a nucleic acid comprising the sequence SEQ. ID. NO. 19 is introduced into the organism.

The sequence SEQ. ID. NO. 19 constitutes the genomic DNA from *Synechocystis* sp. PCC6803, which encodes the MT1 of the sequence SEQ. ID. NO. 20.

Furthermore, all of the abovementioned MT1 genes can be synthesized chemically, in a manner known per se, from the nucleotide units such as, for example, by fragment condensation of individual overlapping complementary nucleic acid units of the double helix. The chemical synthesis of oligonucleotides can be carried out for example in the known manner by the phosphoamidite method (Voet, Voet, 2nd Edition, Wiley Press New York, pages 896-897). The addition of synthetic oligonucleotides and the filling-in of gaps with the aid of the Klenow fragment of the DNA polymerase and ligation reactions and general cloning methods are described in Sambrook et al. (1989), Molecular cloning: A laboratory manual, Cold Spring Harbor Laboratory Press.

In a preferred embodiment, the increase in gene expression of a nucleic acid encoding a tocopherol cyclase, hereinbelow also termed CYC, is effected by introducing, into the organism, at least one nucleic acid encoding a CYC.

In principle, any CYC gene, that is to say any nucleic acid which encodes a CYC, can be used for this purpose.

In the case of genomic CYC nucleic acid sequences from eukaryotic sources, which comprise introns, it is preferred to use nucleic acid sequences which have already been processed, such as the corresponding cDNAs, in the event that the host organism is not capable, or cannot be made capable, of expressing the CYC in question.

Examples of CYC genes are nucleic acids encoding a *Synechocystis* sp. PCC6803 CYC (nucleic acid: Seq. ID. No. 21, protein: Seq. ID. No. 22) or nucleic acids encoding a *Glycine max, Helianthus annuus, Nicotiana tabacum, Physcomitrella patens, Brassica napus, Oryza sativa, Arabidopsis thaliana* or *Hordeum vulgaris* CYC.

In this preferred embodiment, at least one further CYC gene is thus present in the transgenic organisms according to the invention compared with the wild type. In this preferred embodiment, the organism, accordingly, has at least one exogenous nucleic acid encoding a CYC or at least two endogenous nucleic acids encoding a CYC.

Nucleic acids which are preferably used in the above-described preferred embodiment are nucleic acids which encode proteins comprising the amino acid sequence SEQ. ID. NO. 22 or a sequence derived from this sequence by substitution, insertion or deletion of amino acids which have at least 30% identity, preferably at least 50% identity, more preferably at least 70% identity, more preferably at least 90% identity, most preferably at least 95% identity with the sequence SEQ. ID. NO. 22 at the amino acid level and which have the enzymatic property of a CYC.

The sequence SEQ. ID. NO. 22 constitutes the amino acid sequence of the *Synechocystis* sp. PCC6803 CYC.

Accordingly, a protein which has at least 30% identity with the sequence SEQ. ID. No. 22 at the amino acid level is understood as meaning a protein which, upon alignment of its sequence with the sequence SEQ. ID. NO. 22, in particular using the above program algorithm with the above parameter set, has at least 30% identity.

Further examples of CYC and CYC genes can be found easily from a variety of organisms whose genomic sequence is known by homology comparisons of the amino acid sequences or of the corresponding backtranslated nucleic acid sequences from databases with SEQ ID. NO. 22.

For example, the *Arabidopsis thaliana* CYC has 29.1% identity with the *Synechocystis* sp. PCC6803 CYC (SEQ. ID. No. 22).

Further examples of CYC and CYC genes can furthermore be found easily, for example starting from the sequence SEQ. ID. No. 21 in various organisms whose genomic sequence is not known, using hybridization and PCR techniques in a manner known per se.

In a further especially preferred embodiment, the tocopherol cyclase activity is increased by introducing, into organisms, nucleic acids which encode proteins comprising the amino acid sequence of the *Synechocystis* sp. PCC6803 CYC (SEQ. ID. NO. 22).

Suitable nucleic acid sequences can be obtained, for example, by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in plants, it is frequently advantageous to use the codon usage of the plant in the backtranslation.

In an especially preferred embodiment, a nucleic acid comprising the sequence SEQ. ID. NO. 21 is introduced into the organism.

The sequence SEQ. ID. NO. 21 constitutes the genomic DNA of *Synechocystis* sp. PCC6803 which encodes the CYC of the sequence SEQ. ID. NO. 22.

Furthermore, all of the abovementioned CYC genes can be synthesized chemically, in a manner known per se, from the nucleotide units such as, for example, by fragment condensation of individual overlapping complementary nucleic acid units of the double helix. The chemical synthesis of oligonucleotides can be carried out for example in the known manner by the phosphoamidite method (Voet, Voet, 2nd Edition, Wiley Press New York, pages 896-897). The addition of synthetic oligonucleotides and the filling-in of gaps with the aid of the Klenow fragment of the DNA polymerase and ligation reactions and general cloning methods are described in Sambrook et al. (1989), Molecular cloning: A laboratory manual, Cold Spring Harbor Laboratory Press.

In a preferred embodiment, the increase in gene expression of a nucleic acid encoding a γ-tocopherol methyltransferase, hereinbelow also termed γ-TMT, is effected by introducing, into the organism, at least one nucleic acid encoding a γ-TMT.

In principle, any γ-TMT gene, that is to say any nucleic acid which encodes a γ-TMT, can be used for this purpose.

In the case of genomic γ-TMT nucleic acid sequences from eukaryotic sources, which comprise introns, it is preferred to use nucleic acid sequences which have already been processed, such as the corresponding cDNAs, in the event that the host organism is not capable, or cannot be made capable, of expressing the γ-TMT in question.

Examples of γ-TMT genes are nucleic acids encoding an *Arabidopsis thaliana* γ-TMT (nucleic acid: Seq. ID. No. 23, protein: Seq. ID. No. 24) or nucleic acids encoding a *Glycine* max, *Helianthus annuus, Nicotiana tabacum, Physcomitrella patens, Brassica napus, Oryza sativa, Hordeum vulgaris* or *Synechocystis* sp. PCC6803 γ-TMT.

In this preferred embodiment, at least one further γ-TMT gene is thus present in the transgenic organisms according to the invention compared with the wild type. In this preferred embodiment, the organism, accordingly, has at least one exogenous nucleic acid encoding a γ-TMT or at least two endogenous nucleic acids encoding a γ-TMT.

Nucleic acids which are preferably used in the above-described preferred embodiment are nucleic acids which encode proteins comprising the amino acid sequence SEQ. ID. NO. 24 or a sequence derived from this sequence by substitution, insertion or deletion of amino acids which have at least 30% identity, preferably at least 50% identity, more preferably at least 70% identity, more preferably at least 90% identity, most preferably at least 95% identity with the sequence SEQ. ID. NO. 24 at the amino acid level and which have the enzymatic property of a γ-TMT.

The sequence SEQ. ID. NO. 24 constitutes the amino acid sequence of the *Arabidopsis thaliana* γ-TMT.

Accordingly, a protein which has at least 30% identity with the sequence SEQ. ID. NO. 24 at the amino acid level is understood as meaning a protein which, upon alignment of its sequence with the sequence SEQ. ID. No. 24, in particular using the above program algorithm with the above parameter set, has at least 30% identity.

Further examples of γ-TMT and γ-TMT genes can be found easily from a variety of organisms whose genomic sequence is known by homology comparisons of the amino acid sequences or of the corresponding backtranslated nucleic acid sequences from databases with SEQ ID. NO. 24.

For example, the *Synechocystis* sp. PCC6803 γ-TMT has 26.7% identity with the *Arabidopsis thaliana* γ-TMT (SEQ. ID. No. 24).

Further examples of γ-TMT and γ-TMT genes can furthermore be found easily, for example starting from the sequence SEQ. ID. No. 23 in various organisms whose genomic sequence is not known, using hybridization and PCR techniques in a manner known per se.

In a further especially preferred embodiment, the γ-tocopherol methyltransferase activity is increased by introducing, into organisms, nucleic acids which encode proteins comprising the amino acid sequence of the *Arabidopsis thaliana* γ-TMT (SEQ. ID. NO. 24).

Suitable nucleic acid sequences can be obtained, for example, by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in plants, it is frequently advantageous to use the codon usage of the plant in the backtranslation.

In an especially preferred embodiment, a nucleic acid comprising the sequence SEQ. ID. NO. 23 is introduced into the organism.

The sequence SEQ. ID. NO. 23 constitutes the genomic DNA of *A. thaliana* which encodes the γ-TMT of the sequence SEQ. ID. NO. 24.

Furthermore, all of the abovementioned γ-TMT genes can be synthesized chemically, in a manner known per se, from the nucleotide units such as, for example, by fragment condensation of individual overlapping complementary nucleic acid units of the double helix. The chemical synthesis of oligonucleotides can be carried out for example in the known manner by the phosphoamidite method (Voet, Voet, 2nd Edition, Wiley Press New York, pages 896-897). The addition of synthetic oligonucleotides and the filling-in of gaps with the aid of the Klenow fragment of the DNA polymerase and ligation reactions and general cloning methods are described in Sambrook et al. (1989), Molecular cloning: A laboratory manual, Cold Spring Harbor Laboratory Press.

In a further preferred embodiment of the process, the organisms additionally have a reduced activity of at least one of the activities selected from the group consisting of homogentisate dioxygenase activity, maleylacetoacetate isomerase activity and fumarylacetoacetate hydrolase activity which is reduced in comparison with the wild type.

A reduced activity is understood as meaning both the reduced and the complete elimination of the activity. Accordingly, a reduced activity also encompasses a quantitative reduction of the protein in question in the organism down to a complete absence of the protein in question, which can be tested, for example, by a lacking detectability of the enzyme activity in question or by a lacking immunological detectability of the proteins in question.

Homogentisate dioxygenase activity is understood as meaning the enzyme activity of a homogentisate dioxygenase.

A homogentisate dioxygenase is understood as meaning a protein which has the enzymatic activity of converting homogentisate into maleylacetoacetate.

Accordingly, homogentisate dioxygenase activity is understood as meaning the amount of homogentisate converted, or the amount of maleylacetoacetate produced, by the protein homogentisate dioxygenase in a specific time.

Thus, a reduced homogentisate dioxygenase activity in comparison with the wild type is understood as meaning the amount of homogentisate converted, or the amount of maleylacetoacetate produced, by the protein homogentisate dioxygenase within a certain time compared with the wild type.

Preferably, this reduction in the homogentisate dioxygenase activity amounts to at least 5%, more preferably to at least 20%, more preferably to at least 50%, more preferably to 100%. Especially preferred is the complete elimination of the homogentisate dioxygenase activity.

Maleylacetoacetate isomerase activity is understood as meaning the enzyme activity of a maleylacetoacetate isomerase.

A maleylacetoacetate isomerase is understood as meaning a protein which has the enzymatic activity of converting maleyl acetoacetate into fumarylacetoacetate.

Accordingly, maleylacetoacetate isomerase activity is understood as meaning the amount of maleylacetoacetate converted, or the amount of fumarylacetoacetate produced, by the protein maleylacetoacetate isomerase in a specific time.

Thus, a reduced maleylacetoacetate isomerase activity in comparison with the wild type is understood as meaning the amount of maleylacetoacetate converted, or the amount of fumarylacetoacetate produced, by the protein maleylacetoacetate isomerase within a certain time compared with the wild type.

Preferably, this reduction in the maleylacetoacetate isomerase activity amounts to at least 5%, more preferably to at least 20%, more preferably to at least 50%, more preferably to 100%. Especially preferred is the complete elimination of the maleylacetoacetate isomerase activity.

Fumarylacetoacetate hydrolase activity is understood as meaning the enzyme activity of a fumarylacetoacetate hydrolase.

A fumarylacetoacetate hydrolase is understood as meaning a protein which has the enzymatic activity of converting fumarylacetoacetate into fumarate.

Accordingly, fumarylacetoacetate hydrolase activity is understood as meaning the amount of fumarylacetoacetate converted, or the amount of fumerate produced, by the protein fumarylacetoacetate hydrolase in a specific time.

Thus, a reduced fumarylacetoacetate hydrolase activity in comparison with the wild type is understood as meaning the amount of fumarylacetoacetate converted, or the amount of fumarate produced, by the protein fumarylacetoacetate hydrolase within a certain time compared with the wild type.

Preferably, this reduction in the fumarylacetoacetate hydrolase activity amounts to at least 5%, more preferably to at least 20%, more preferably to at least 50%, more preferably to 100%. Especially preferred is the complete elimination of the fumarylacetoacetate hydrolase activity.

Homogentisate dioxygenase is hereinbelow also termed HGD, maleylacetoacetate isomerase is hereinbelow also termed MAAI, and fumarylacetoacetate hydrolase is hereinbelow also termed FAAH.

There exist many different ways of reducing the HGD, MAAI and/or FAAH activities in the desired manner.

One possible method encompasses the use of at least one nucleic acid sequence, hereinbelow also termed anti-HGD, anti-MAAI or anti-FAAH, which can be transcribed into an antisense nucleic acid sequence which is capable of inhibiting the HGD, MAAI and/or FAAH activity, for example by inhibiting the expression of endogenous HGD, MAAI and/or FAAH.

In accordance with a preferred embodiment, these anti-HGD, anti-MAAI or anti-FAAH nucleic acid sequences can comprise the encoding nucleic acid sequences of HGD, MAAI and/or FAAH or functionally equivalent fragments of the respective sequences in antisense orientation.

The antisense strategy can advantageously be combined with a ribozyme method. Ribozymes are catalytically active RNA sequences which, coupled to the antisense sequences, catalytically cleave the target sequences (Tanner N K. FEMS Microbiol Rev. 1999; 23(3):257-75). This can increase the efficacy of an antisense strategy.

Further methods of reducing the HGD, MAAI and/or FAAH expression, in particular in plants as organisms, comprise the overexpression of homologous HGD, MAAI and/or FAAH nucleic acid sequences which lead to cosuppression (Jorgensen et al., Plant Mol. Biol. 1996, 31(5):957-973) or the induction of the specific RNA degradation by the plant with the aid of a viral expression system (amplicon) (Angell, SM et al., Plant J. 1999, 20(3):357-362). These methods are also termed post-transcriptional gene silencing (PTGS).

Further methods are the introduction of nonsense mutations into the endogen by introducing RNA/DNA oligonucleotides into the plant (Zhu et al., Nat. Biotechnol. 2000, 18(5):555-558) or the generation of knock-out mutants with the aid of, for example, T-DNA mutagenesis (Koncz et al., Plant Mol. Biol. 1992, 20(5):963-976) or homologous recombination (Hohn, B. and Puchta, H, Proc. Natl. Acad. Sci. USA. 1999, 96:8321-8323.). Furthermore, gene overexpression or gene repression with specific DNA-binding factors, for example with the abovementioned factors of the zinc-finger transcription factor type is also possible. Furthermore, it is possible to introduce, into a cell, factors which inhibit the target protein itself. The protein-binding factors can be, for example, aptamers (Famulok M, and Mayer G. Curr Top Microbiol Immunol. 1999; 243:123-36).

A further method of reducing at least one of the above-described activities is the use of RNA which contains a region with duplex structure and, within this region, contains a nucleic acid sequence which is identical to part of the target sequence to be reduced. A detailed description of this method, also referred to as RNAi technology, is disclosed in WO 99/32619.

In a preferred embodiment, the additional reduction of at least one of the activities selected from the group consisting of HGD, MAAI and FAAH activity is effected by reducing the gene expression of at least one nucleic acid selected from the group consisting of the nucleic acids encoding a homogentisate dioxygenase, nucleic acids encoding a maleylacetoacetate isomerase and nucleic acids encoding a fumarylacetoacetate hydrolase in comparison with the wild type.

A reduction of the gene expression of at least one nucleic acid selected from the group consisting of the nucleic acids encoding a homogentisate dioxygenase, nucleic acids encoding a maleylacetoacetate isomerase and nucleic acids encoding a fumarylacetoacetate hydrolase in comparison with the wild type can be achieved as described above, preferably by using the following methods:

a) introducing antisense nucleic acid sequences;
b) introducing antisense nucleic acid sequences in combination with a ribozyme method
c) introducing nucleic acid sequences which encode homologous HGDs, MAAIs and/or FAAHs and which lead to cosuppression
d) introduction of expression constructs and viral nucleic acid sequences which bring about the degradation of HGDs, MAAIs and/or FAAHs;
e) introduction of nonsense mutants of endogenous nucleic acid sequences encoding HGDs, MAAIs and/or FAAHs;
f) introduction of knock-out mutants;
g) introduction of nucleic acid sequences suitable for homologous recombination;
h) introduction of RNA which contains a region with duplex structure and within this region contains a nucleic acid sequence which is identical to part of the endogenous target nucleic acid sequence.

A combined application of the above-described methods is also feasible.

In an especially preferred embodiment of the process, the organisms have a reduced homogentisate dioxygenase activity.

This is especially preferably achieved by introducing, into the organism, an RNA which contains a region with duplex structure and, within this region, contains a nucleic acid sequence which is identical to part of the endogenous nucleic acid encoding a homogentisate dioxygenase. A detailed description of this method, also referred to as RNAi technology, is disclosed in WO 99/32619.

Depending on the organism used, a different part-fragment of the endogenous nucleic acid encoding a homogentisate dioxygenase is to be used, accordingly.

For example, SEQ. ID. No. 25 constitutes a part-fragment of the HGD-encoding nucleic acid from *Brassica napus* which, integrated into a suitable RNAi construct, reduces the HGD activity in *Brassica napus*.

In further preferred embodiments of the process according to the invention, vitamin E is produced by growing organisms, in particular plants, which, in comparison with the wild type, show an increased tyrosine aminotransferase activity, an increased tyrosine aminotransferase activity and an increased hydroxyphenylpyruvate dioxygenase activity, an increased tyrosine aminotransferase activity and an increased homogentisate phytyltransferase activity, an increased tyrosine aminotransferase activity and an increased geranylgeranyl-pyrophosphate oxidoreductase activity, an increased tyrosine aminotransferase activity and an increased 2-methyl-6-phytylhydroquinone methyltransferase activity, an increased tyrosine aminotransferase activity and an increased tocopherol cyclase activity, an increased tyrosine aminotransferase activity and an increased γ-tocopherol methyltransferase activity, an increased tyrosine aminotransferase activity and a reduced homogentisate dioxygenase activity, an increased tyrosine aminotransferase activity and a reduced maleylacetoacetate isomerase activity, an increased tyrosine aminotransferase activity and a reduced fumarylacetoacetate hydrolase activity, an increased tyrosine aminotransferase activity, an increased hydroxyphenylpyruvate dioxygenase activity and a reduced homogentisate dioxygenase activity, an increased tyrosine aminotransferase activity and an increased homogentisate phytyltransferase activity and a reduced homogentisate dioxygenase activity, an increased tyrosine aminotransferase activity and an increased geranylgeranyl-pyrophosphate oxidoreductase activity and a reduced homogentisate dioxygenase activity, an increased tyrosine aminotransferase activity and an increased 2-methyl-6-phytylhydroquinone methyltransferase activity and a reduced homogentisate dioxygenase activity, an increased tyrosine aminotransferase activity and an increased tocopherol cyclase activity and a reduced homogentisate dioxygenase activity, an increased tyrosine aminotransferase activity and an increased γ-tocopherol methyltransferase activity and a reduced homogentisate dioxygenase activity, an increased tyrosine aminotransferase activity and an increased hydroxyphenylpyruvate dioxygenase activity and a homogentisate phytyltransferase activity and a reduced homogentisate dioxygenase activity, an increased tyrosine aminotransferase activity and an increased hydroxyphenylpyruvate dioxygenase activity and an increased geranylgeranyl-pyrophosphate oxidoreductase activity and a reduced homogentisate dioxygenase activity, an increased tyrosine aminotransferase activity and an increased hydroxyphenylpyruvate dioxygenase activity and a 2-methyl-6-phytylhydroquinone methyltransferase activity and a reduced homogentisate dioxygenase activity, an increased tyrosine aminotransferase activity and an increased hydroxyphenylpyruvate dioxygenase activity and an increased tocopherol cyclase activity and a reduced homogentisate dioxygenase activity, an increased tyrosine aminotransferase activity and an increased hydroxyphenylpyruvate dioxygenase activity and an increased γ-tocopherol methyltransferase activity and a reduced homogentisate dioxygenase activity, an increased tyrosine aminotransferase activity and an increased hydroxyphenylpyruvate dioxygenase activity and an increased homogentisate phytyltransferase activity and an increased geranylgeranyl-pyrophosphate oxidoreductase activity and a reduced homogentisate dioxygenase activity, an increased tyrosine aminotransferase activity and an increased hydroxyphenylpyruvate dioxygenase activity and an increased homogentisate phytyltransferase activity and an increased 2-methyl-6-phytylhydroquinone methyltransferase activity and a reduced homogentisate dioxygenase activity, an increased tyrosine aminotransferase activity and an increased hydroxyphenylpyruvate dioxygenase activity and an increased homogentisate phytyltransferase activity and an increased tocopherol cyclase activity and a reduced homogentisate dioxygenase activity, an increased tyrosine aminotransferase activity and an increased hydroxyphenylpyruvate dioxygenase activity and an increased homogentisate phytyltransferase activity and an increased γ-tocopherol methyltransferase and a reduced homogentisate dioxygenase activity, an increased tyrosine aminotransferase activity and an increased hydroxyphenylpyruvate dioxygenase activity and an increased homogentisate phytyltransferase activity and an increased geranylgeranyl-pyrophosphate oxidoreductase activity and an increased 2-methyl-6-phytylhydroquinone methyltransferase activity and a reduced homogentisate dioxygenase activity, an increased tyrosine aminotransferase activity and an increased hydroxyphenylpyruvate dioxygenase activity and an increased homogentisate phytyltransferase activity and an increased geranylgeranyl-pyrophosphate oxidoreductase activity, an increased tocopherol cyclase activity and a reduced homogentisate dioxygenase activity, an increased tyrosine aminotransferase activity and an increased hydroxyphenylpyruvate dioxygenase activity, an increased homogentisate phytyltransferase activity and an increased geranylgeranyl-pyrophosphate oxidoreductase activity and an increased γ-tocopherol methyltransferase activity and a reduced homogentisate dioxygenase activity, an increased tyrosine aminotransferase activity and an increased hydroxyphenylpyruvate dioxygenase activity and an increased homogentisate phytyltransferase activity and an increased geranylgeranyl-pyrophosphate oxidoreductase activity and an increased 2-methyl-6-phytylhydroquinone methyltransferase activity and an increased tocopherol cyclase activity and a reduced homogentisate dioxygenase activity, an increased tyrosine aminotransferase activity and an increased hydroxyphenylpyruvate dioxygenase activity and an increased homogentisate phytyltransferase activity and an increased geranylgeranyl-pyrophosphate oxidoreductase activity, and an increased 2-methyl-6-phytylhydroquinone methyltransferase activity and an increased γ-tocopherol methyltransferase activity and a reduced homogentisate dioxygenase activity, an increased tyrosine aminotransferase activity and an increased hydroxyphenylpyruvate dioxygenase activity and an increased homogentisate phytyltransferase activity and an increased geranylgeranyl-pyrophosphate oxidoreductase activity and an increased 2-methyl-6-phytylhydroquinone methyltransferase activity and an increased tocopherol cyclase activity, and an increased γ-tocopherol methyltransferase and a reduced homogentisate dioxygenase activity.

Organisms are understood as meaning, in accordance with the invention, prokaryotic organisms or eukaryotic organisms such as, for example, bacteria, yeast, algae, mosses, fungi or plants, which, as the wild type or owing to genetic modification, are capable of producing vitamin E. Preferred organisms are photosynthetically active organisms such as, for example, cyanobacteria, mosses, algae or plants, who as wild type are already capable of producing vitamin E.

Especially Preferred Organisms are Plants.

Preferred plants are *Tagetes*, sunflower, *Arabidopsis*, tobacco, red pepper, soybean, tomato, eggplant, capsicum, carrot, potato, maize, lettuces and cabbage species, cereals, alfalfa, oats, barley, rye, wheat, triticale, sorghum and millet, rice, lucerne, flax, cotton, hemp, *Brassicaceae* such as, for example, oilseed rape or canola, sugar beet, sugar cane, nut and grapevine species, or woody species such as, for example, aspen or yew.

Especially preferred are *Arabidopsis thaliana, Tagetes erecta, Brassica napus, Nicotiana tabacum*, sunflower, canola, potato or soybean.

In the process according to the invention for the production of vitamin E, the step in which the genetically modified organisms, hereinbelow also termed transgenic organisms, are grown is preferably followed by harvesting the organisms and isolating vitamin E from the organisms.

The organisms are harvested in a manner known per se to suit the organism in question. Microorganisms such as bacteria, mosses, yeasts and fungi or plant cells, which can be grown by fermentation in liquid media, can be separated, for example, by centrifugation, decanting or filtration. Plants are grown on media in a manner known per se and harvested in a suitable fashion.

Vitamin E is isolated from the harvested biomass in a manner known per se, for example by extraction and, if appropriate, further chemical or physical purification processes such as, for example, precipitation methods, crystallography, thermal separation methods, such as rectification methods, or physical separation methods such as, for example, chromatography.

Vitamin E is isolated from oil-containing plants, for example, preferably by chemical conversion and distillation from vegetable oils or from the steam distillates obtained in the deodorization of vegetable oils (deodorizer condensates).

Further methods of isolating vitamin E from deodorizer condensates are described, for example, in DE 31 26 110 A1, EP 171 009 A2, GB 2 145 079, EP 333 472 A2 and WO 94/05650.

The transgenic organisms, in particular plants, are preferably generated by transformation of the starting organisms, in particular plants, with a nucleic acid construct comprising the above-described nucleic acids encoding a tyrosine aminotransferase which are linked operably to one or more regulatory signals which ensure the transcription and translation in organisms.

Preferably, the nucleic acid constructs according to the invention additionally comprise one, two or three nucleic acids selected from the group consisting of nucleic acids encoding a hydroxyphenylpyruvate dioxygenase, nucleic acids encoding a homogentisate phytyltransferase, nucleic acids encoding a geranylgeranyl-pyrophosphate oxidoreductase, nucleic acids encoding a 2-methyl-6-phytylhydroquinone methyltransferase, nucleic acids encoding a tocopherol cyclase and nucleic acids encoding a γ-tocopherol methyltransferase which are linked operably to one or more regulatory signals which ensure the transcription and translation in organisms.

In a further preferred embodiment, the above-described nucleic acid constructs additionally comprise, in operable linkage, an RNA which has a region with duplex structure and within this region has a nucleic acid sequence which is identical to part of a nucleic acid encoding a homogentisate dioxygenase.

In plants, in particular, it is technically difficult to increase or to reduce more than four activities with one nucleic acid construct. This is why it is preferred to use combinations of nucleic acid constructs in order to increase or reduce the activities, in particular to increase or reduce more than four activities, in the organism.

However, it is also possible to hybridize genetically modified organisms which already comprise modified activities. For example, hybridizing genetically modified organisms which comprise in each case two modified activities makes it possible to generate organisms with four modified activities. The same can also be achieved by introducing, into the organism, a combination of two nucleic acid constructs, each of which modifies 2 activities.

In a preferred embodiment, the preferred genetically modified organisms are generated by introducing combinations of nucleic acid constructs.

Accordingly, the invention relates in particular to a combination of nucleic acid constructs, where the combination encompasses a nucleic acid construct comprising the above-described nucleic acids encoding a tyrosine aminotransferase in operable linkage with one or more regulatory signals which ensure the transcription and translation in organisms, and a) at least one further nucleic acid construct selected from the group consisting of A to F A nucleic acid construct comprising nucleic acids encoding a hydroxyphenylpyruvate dioxygenase which are linked operably to one or more regulatory signals which ensure the transcription and translation in organisms, B nucleic acid construct comprising nucleic acids encoding a homogentisate phytyltransferase which are linked operably to one or more regulatory signals which ensure the transcription and translation in organisms, C nucleic acid construct comprising nucleic acids encoding a geranylgeranyl-pyrophosphate oxidoreductase which are linked operably to one or more regulatory signals which ensure the transcription and translation in organisms, D nucleic acid construct comprising nucleic acids encoding a 2-methyl-6-phytylhydroquinone methyltransferase which are linked operably to one or more regulatory signals which ensure the transcription and translation in organisms, E nucleic acid construct comprising nucleic acids encoding a tocopherol cyclase which are linked operably to one or more regulatory signals which ensure the transcription and translation in organisms, and F nucleic acid construct comprising nucleic acids encoding a γ-tocopherol methyltransferase which are linked operably to one or more regulatory signals which ensure the transcription and translation in organisms, or b) at least one further nucleic acid construct comprising two, three or four nucleic acid constructs selected from the group consisting of the nucleic acid constructs A to F.

These nucleic acid constructs in which the encoding nucleic acid sequences are linked operably to one or more regulatory signals which ensure the transcription and translation in organisms, in particular in plants, are also termed expression cassettes hereinbelow.

Accordingly, the invention furthermore relates to nucleic acid constructs, in particular nucleic acid constructs which act as expression cassettes, comprising a nucleic acid encoding a tyrosine aminotransferase which is linked operably to one or more regulatory signals which ensure the transcription and translation in organisms, in particular in plants.

The regulatory signals preferably comprise one or more promoters which ensure the transcription and translation in organisms, in particular in plants.

The expression cassettes comprise regulatory signals, i.e. regulatory nucleic acid sequences, which govern the expression of the coding sequence in the host cell. In accordance with a preferred embodiment, an expression cassette comprises upstream, i.e. at the 5'-end of the coding sequence, a promoter and downstream, i.e. at the 3'-end, a polyadenylation signal and, if appropriate, further regulatory elements which are linked operably to the interposed coding sequence for at least one of the above-described genes. Operable linkage is understood as meaning the sequential arrangement of promoter, coding sequence, terminator and, if appropriate, further regulatory elements in such a way that each of the regulatory elements can, upon expression of the coding sequence, fulfill its function as intended.

When using plants as the organism, the nucleic acid constructs and expression cassettes according to the invention preferably comprise a nucleic acid encoding a plastid transit peptide which ensures localization in plastids.

The following text will describe examples of the preferred nucleic acid constructs, expression cassettes and vectors for plants and methods for generating transgenic plants as well as the transgenic plants themselves.

The sequences preferred for operable linkage, but not limited thereto, are targeting sequences for ensuring subcellular localization in the apoplasts, in the vacuole, in plastids, in the mitochondrion, in the endoplasmic reticulum (ER), in the nucleus, in elaioplasts, or other compartments and translation enhancers such as the tobacco mosaic virus 5'-leader sequence (Gallie et al., Nucl. Acids Res. 15 (1987), 8693-8711).

Suitable promoters in the expression cassette are, in principle, all promoters which are capable of controlling the expression of foreign genes in plants. It is preferable to use in particular a plant promoter or a promoter derived from a plant virus. Especially preferred is the cauliflower mosaic virus CaMV 35S promoter (Franck et al., Cell 21 (1980), 285-294). As is known, this promoter comprises different recognition sequences for transcriptional effectors which, in their totality, lead to permanent and constitutive expression of the gene which has been introduced (Benfey et al., EMBO J. 8 (1989), 2195-2202).

The expression cassette may also comprise a chemically inducible promoter, by means of which the expression of the target gene in the plant can be controlled at a particular point in time. Examples of such promoters which can be used are the PRP1 promoter (Ward et al., Plant. Mol. Biol. 22 (1993), 361-366), a salicylic-acid-inducible promoter (WO 95/19443), a benzenesulfonamide-inducible promoter (EP-A 388186), a tetracycline-inducible promoter (Gatz et al., (1992) Plant J. 2, 397-404), an abscisic-acid-inducible promoter (EP-A 335528) or an ethanol- or cyclohexanone-inducible promoter (WO 93/21334).

Further preferred promoters are in particular those which ensure the expression in tissues or plant parts in which, for example, the biosynthesis of vitamin E or its precursors takes place. Promoters which must be mentioned in particular are those which ensure leaf-specific expression. Those to be mentioned are the potato cytosolic FBPase promoter or the potato ST-LSI promoter (Stockhaus et al., EMBO J. 8 (1989), 2445-245).

A foreign protein was expressed stably in an amount of up to 0.67% of the total soluble seed protein in the seeds of transgenic tobacco plants with the aid of a seed-specific promoter (Fiedler and Conrad, Bio/Technology 10 (1995), 1090-1094). The expression cassette can therefore comprise, for example, a seed-specific promoter (preferably the phaseolin promoter (U.S. Pat. No. 5,504,200), the USP promoter (Baumlein, H. et al., Mol. Gen. Genet. (1991) 225 (3), 459-467), the LEB4 promoter (Fiedler and Conrad, 1995), the sucrose binding protein promoter (reference), the LEB4 signal peptide, the gene to be expressed and an ER retention signal.

The biosynthesis site of vitamin E in plants is, inter alia, the leaf tissue, so that leaf-specific expression of the nucleic acids according to the invention encoding a tyrosine aminotransferase makes sense. However, this is not limiting since the expression can also take place in a tissue-specific manner in all the remaining parts of the plant, in particular in fatty seeds.

A further preferred embodiment therefore relates to a seed-specific expression of the above-described nucleic acids.

In addition, a constitutive expression of exogenous target genes is advantageous. On the other hand, however, inducible expression may also be desirable.

The expression efficacy of the recombinantly expressed target genes can be determined, for example, in vitro by shoot-meristem propagation. Moreover, an expression of the target gene, which has been modified with regard to type and level, and its effect on the vitamin E biosynthesis rate may be tested in greenhouse experiments using test plants.

An expression cassette is preferably generated by fusing a suitable promoter to an above-described target nucleic acid and, preferably, to a nucleic acid inserted between promoter and target nucleic acid sequence, which nucleic acid encodes a chloroplast-specific transit peptide, and also to a polyadenylation signal, using customary recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley-Interscience (1987).

Especially preferred are inserted nucleic acid sequences which ensure targeting in the plastids.

However, it is also possible to use expression cassettes whose nucleic acid sequence encodes a target protein fusion protein, one moiety of the fusion protein being a transit peptide which governs the translocation of the polypeptide. Preferred are chloroplast-specific transit peptides, which, after translocation of the target protein into the chloroplasts, are cleaved enzymatically from the target protein moiety.

Especially preferred is the transit peptide which is derived from the *Nicotiana tabacum* plastid transketolase or from another transit peptide (for example the transit peptide of the Rubisco small subunit or of ferredoxin NADP oxidoreductase or else the isopentenyl-pyrophosphate isomerase-2) or its functional equivalent.

Especially preferred are nucleic acid sequences of three cassettes of the plastid transit peptide of the tobacco plastid transketolase in three reading frames as KpnI/BamHI fragments with an ATG codon in the NcoI cleavage site:

```
pTP09
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGGGATCC_BamHI pTP10
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGCTGGATCC_BamHI pTP11
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGGGATCC_BamHI
```

A further example of a plastid transit peptide is the transit peptide of the *Arabidopsis thaliana* plastid isopentenyl-pyrophosphate isomerase-2 (IPP-2).

The nucleic acids according to the invention can have been prepared synthetically or obtained naturally or comprise a mixture of synthetic and natural nucleic acid constituents or else be composed of various heterologous gene segments of various organisms.

Preferred are, as described above, synthetic nucleotide sequences with codons which are preferred by plants. These codons which are preferred by plants can be determined from codons with the highest protein frequency which are expressed in most of the plant species of interest.

When preparing an expression cassette, it is possible to manipulate various DNA fragments in order to obtain a nucleotide sequence which expediently reads in the correct direction and which is equipped with a correct reading frame. To connect the DNA fragments to each other, adapters or linkers may be attached to the fragments.

The promoter and the terminator regions can expediently be provided, in the direction of transcription, with a linker or polylinker comprising one or more restriction sites for inserting this sequence. As a rule, the linker has 1 to 10, in most cases 1 to 8, preferably 2 to 6, restriction sites. In general, the linker within the regulatory regions has a size of less than 100 bp, frequently less than 60 bp, but at least 5 bp. The promoter can be either native, or homologous, or else foreign, or heterologous, relative to the host plant. The expression cassette preferably comprises, in the 5'-3' direction of transcription, the promoter, a coding nucleic acid sequence or a nucleic acid construct and a region for transcriptional termination. Various termination regions can be exchanged for each other as desired.

Furthermore, manipulations can be employed which provide suitable restriction cleavage sites or which remove excess DNA or restriction cleavage sites. Where insertions, deletions or substitutions such as, for example, transitions and transversions, are suitable, in-vitro mutagenesis, primer repair, restriction or ligation can be used.

In the case of suitable manipulations, such as, for example, restrictions, chewing-back or filling in overhangs for blunt ends, complementary ends of the fragments can be provided for ligation.

Preferred polyadenylation signals are plant polyadenylation signals, preferably those which essentially correspond to T-DNA polyadenylation signals from *Agrobacterium tumefaciens*, in particular of gene 3 of the T-DNA (octopine synthase) of the Ti plasmid pTiACH5 (Gielen et al., EMBO J. 3 (1984), 835 et seq.) or functional equivalents.

The invention furthermore relates to the use of the above-described nucleic acids encoding a tyrosine aminotransferase or of the above-described nucleic acid constructs or of tyrosine aminotransferase for generating transgenic organisms, in particular plants.

Preferably, these transgenic plants have a vitamin E content which is increased in comparison with the wild type.

The invention therefore furthermore relates to the use of the nucleic acids according to the invention or of the nucleic acid constructs according to the invention for increasing the vitamin E content in organisms whose wild type is capable of producing vitamin E.

It is known that plants with a high vitamin E content have an increased resistance to abiotic stress. Abiotic stress is understood as meaning, for example, low temperatures, frost, drought, high temperatures and salinity.

The invention therefore furthermore relates to the use of the nucleic acids according to the invention for generating transgenic plants which have an increased resistance to abiotic stress in comparison with the wild type.

The above-described proteins and nucleic acids can be used for producing fine chemicals in transgenic organisms, preferably for producing vitamin E in transgenic plants.

The transfer of foreign genes into the genome of an organism, in particular of a plant, is termed transformation.

In addition, in plants, in particular, methods known per se for the transformation and regeneration of plants from plant tissues or plant cells can be used for transient or stable transformation.

Suitable methods for the transformation of plants are the protoplast transformation by polyethylene-glycol-induced DNA uptake, the biolistic method with the gene gun—what is known as the particle bombardment method, electroporation, the incubation of dry embryos in DNA-containing solution, microinjection and the above-described *Agrobacterium*-mediated gene transfer. The abovementioned methods are described, for example, in B. Jenes et al., Techniques for Gene Transfer, in: Transgenic Plants, Vol. 1, Engineering and Utilization, edited by S. D. Kung and R. Wu, Academic Press (1993), 128-143 and in Potrykus, Annu. Rev. Plant Physiol. Plant Molec. Biol. 42 (1991), 205-225.

The construct to be expressed is preferably cloned into a vector which is suitable for the transformation of *Agrobacterium tumefaciens*, for example pBin19 (Bevan et al., Nucl. Acids Res. 12 (1984), 8711).

Accordingly, the invention furthermore relates to vectors comprising the above-described nucleic acids, nucleic acid constructs or expression cassettes.

Agrobacteria which have been transformed with an expression cassette can be used in the known manner for transforming plants, for example by bathing scarified leaves or leaf sections in an agrobacterial solution and subsequently growing them in suitable media.

The expression cassette can be employed not only in the plants, but also for the transformation of bacteria, in particular cyanobacteria, mosses, yeasts, filamentous fungi and algae.

For the preferred generation of genetically modified plants, also termed transgenic plants hereinbelow, the fused expression cassette which expresses a tyrosine aminotransferase is cloned into a vector, for example pBin19, which is suitable for the transformation of *Agrobacterium tumefaciens*.

Agrobacteria which have been transformed with such a vector can then be used in the known fashion for the transformation of plants, in particular crop plants, for example by bathing scarified leaves or leaf sections in an agrobacterial solution and subsequently growing them in suitable media.

The transformation of plants by agrobacteria is known, inter alia, from F. F. White, Vectors for Gene Transfer in Higher Plants; in Transgenic Plants, Vol. 1, Engineering and Utilization, edited by S. D. Kung and R. Wu, Academic Press, 1993, pp. 15-38. Transgenic plants which comprise a gene for the expression of a nucleic acid encoding a tyrosine aminotransferase integrated in the expression cassette can be regenerated in a known fashion from the transformed cells of the scarified leaves or leaf sections.

To transform a host plant with a nucleic acid encoding a tyrosine aminotransferase, an expression cassette is incorporated into a recombinant vector in the form of an insertion, the DNA of the vector thereof additionally comprising functional regulatory signals, for example sequences for replication or integration. Suitable vectors are described, inter alia, in "Methods in Plant Molecular Biology and Biotechnology" (CRC Press), Chapter 6/7, pp. 71-119 (1993).

For example, the plant expression cassette can be incorporated into a derivative of the transformation vector pBin-19 with 35S promoter (Bevan, M., Nucleic Acids Research 12: 8711-8721 (1984)).

Using the above-cited recombination and cloning techniques, the expression cassettes can be cloned into suitable vectors which make possible their amplification, for example in *E. coli*. Examples of suitable cloning vectors are, inter alia, pBR322, pUC series, M13mp series and pACYC184. Especially suitable are binary vectors which are capable of replication both in *E. coli* and in agrobacteria.

The invention therefore furthermore relates to the use of the above-described nucleic acids, of the above-described nucleic acid constructs, in particular the expression cassettes, for the generation of genetically modified plants or for the transformation of plants, plant cells, plant tissues or plant parts.

The use is preferably aimed at increasing the vitamin E content of the plant or plant parts.

Depending on the choice of the promoter, the expression may take place specifically in the leaves, in the seeds, petals or other parts of the plant.

Accordingly, the invention furthermore relates to a method of generating genetically modified organisms by introducing an above-described nucleic acid or an above-described nucleic acid construct or an above-described combination of nucleic acid constructs into the genome of the starting organism.

The invention furthermore relates to the above-described genetically modified organisms themselves.

As mentioned above, the genetically modified organisms, in particular plants, have an increased vitamin E content.

The increase in the tyrosine aminotransferase activity in the organism to a further effect. Not only is the total vitamin E content increased, but the tocotrienols are additionally selectively increased in comparison with the tocopherols.

Materials used as organisms and for the generation of organisms with an increased fine chemicals content in comparison with the wild type are, in a preferred embodiment, as mentioned above, photosynthetically active organisms such as, for example, cyanobacteria, mosses, algae or plants, especially preferably plants, as starting organisms and, accordingly, also as genetically modified organisms.

Such transgenic plants, their propagation material and their plant cells, plant tissues or plant parts are a further subject of the present invention.

Preferred plants are, as mentioned above, *Tagetes*, sunflower, *Arabidopsis*, tobacco, red pepper, soybean, tomato, eggplant, capsicum, carrot, potato, maize, lettuces and cabbage species, cereals, alfalfa, oats, barley, rye, wheat, triticale, sorghum and millet, rice, lucerne, flax, cotton, hemp, *Brassicaceae* such as, for example, oilseed rape or canola, sugar beet, sugar cane, nut and grapevine species, or woody species such as, for example, aspen or yew.

Especially preferred are *Arabidopsis thaliana, Tagetes erecta, Brassica napus, Nicotiana tabacum*, sunflower, canola, potato or soybean.

As described above, the genetically modified organisms, in particular plants, can be used for the production of vitamin E.

Genetically modified plants according to the invention with an increased vitamin E content which can be consumed by humans and animals can also be used, for example directly or, following processing known per se, as food or feed, or as feed or food supplements.

The plants which have been genetically modified in accordance with the invention can furthermore be used for the production of vitamin E-containing extracts.

Increasing the vitamin E content preferably means, for the purposes of the present invention, the artificially acquired capability of an increased biosynthesis rate of these compounds in the plant in comparison with the non-genetically modified plant, preferably for the duration of at least one plant generation.

As a rule, an increased vitamin E content is understood as meaning an increased total tocopherol content. However, an increased vitamin E content is also understood as meaning, in particular, a modified content of the above-described 8 compounds with tocopherol activity.

For example, introduction of a tyrosine aminotransferase gene into plants surprisingly leads to a particularly pronounced increase in the tocotrienol content.

The invention will now be illustrated by examples which follow, but is not limited thereto:

EXAMPLES

General Experimental Conditions:

Sequence analysis of recombinant DNA

Recombinant DNA molecules were sequenced with a Licor laser fluorescence DNA sequencer (available from MWG Biotech, Ebersbach) using the method of Sanger (Sanger et al., Proc. Natl. Acad. Sci. USA 74 (1977), 5463-5467).

Example 1

Cloning the tyrosine aminotransferase gene encoding the *Rattus norvegicus* tyrosine aminotransferase.

RNA was prepared from rat liver in a manner known per se as described by S. Kar and B. J. Carr in Biochem. Biophys. Res. Commun. 1995, 212(1), 21-6 (*Differential display and cloning of messenger RNAs from the late phase of rat liver regeneration*).

The cDNA synthesis was carried out using the SuperScript II cDNA synthesis kit (Gibco BRL) following the manufacturer's instructions.

The nucleic acid encoding a tyrosine aminotransferase was amplified from *Rattus norvegicus* by means of polymerase chain reaction (PCR) using a sense-specific primer (tyrosine aminotransferase 5' SEQ. ID No. 3) and an antisense-specific primer (tyrosine aminotransferase 3' SEQ. ID No. 4).

The PCR conditions were as follows:
The PCR was carried out with a 50 µl reaction mix consisting of:
  2 µl of a *Rattus norvegicus* cDNA (prepared as described above)
  0.2 mM dATP, dTTP, dGTP, dCTP
  1.5 mM Mg(OAc)$_2$
  5 µg of bovine serum albumin
  40 pmol of tyrosine aminotransferase 5' primer
  40 pmol of tyrosine aminotransferase 3' primer
  15 µl of 3.3×rTth DNA polymerase XL buffer (PE Applied Biosystems)
  5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 55° C. (annealing)
Step 4: 2 minutes at 72° C. (elongation) 30 cycles of steps 2-4
Step 5: 10 minutes at 72° C. (post-elongation)
Step 6: 4° C. (waiting loop)

The amplicon was cloned into the PCR cloning vector pGEM-Te (Promega) using standard methods. The identity of the amplicon generated in the vector pGEM-Te/RnTATase1 was confirmed by sequencing using the M13F (−40) primer and the M13R primer (SEQ. ID. No. 1 and SEQ. ID. NO. 3).

Example 2

Cloning the tyrosine aminotransferase gene 1 encoding the *Arabidopsis thaliana* tyrosine aminotransferase 1.

The DNA encoding the tyrosine aminotransferase gene 1 was amplified from *Arabidopsis thaliana* by means of polymerase chain reaction (PCR) using a sense-specific primer (At1 tyrosine aminotransferase 5' SEQ. ID. No. 28) and an antisense-specific primer (At1 tyrosine aminotransferase 3' SEQ. ID. No. 29).

The PCR conditions were as follows:
The PCR was carried out with a 50 µl reaction mix consisting of:
  2 µl of an *Arabidopsis thaliana* cDNA
  0.2 mM dATP, dTTP, dGTP, dCTP
  1.5 mM Mg(OAc)$_2$
  5 µg of bovine serum albumin
  40 pmol of At1 tyrosine aminotransferase 5' primer
  40 pmol of At1 tyrosine aminotransferase 3' primer
  15 µl of 3.3×rTth DNA polymerase XL buffer (PE Applied Biosystems)
  5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute 55° C. (annealing)
Step 4: 2 minutes at 72° C. (elongation) 30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/AtTATase1 was confirmed by complete sequencing using the M13F (−40) primer and the M13R primer (Seq. ID. No. 5).

Example 3

Cloning the tyrosine aminotransferase gene 3 encoding the *Arabidopsis thaliana* tyrosine aminotransferase 3.

The DNA encoding the tyrosine aminotransferase gene 3 was amplified from *Arabidopsis thaliana* by means of polymerase chain reaction (PCR) using a sense-specific primer (At3 tyrosine aminotransferase 5': SEQ. ID. No. 30) and an antisense-specific primer (At3 tyrosine aminotransferase 3': SEQ. ID. No. 31).

The PCR conditions were as follows:
The PCR was carried out with a 50 µl reaction mix consisting of:
  2 µl of an *Arabidopsis thaliana* cDNA
  0.2 mM dATP, dTTP, dGTP, dCTP
  1.5 mM Mg(OAc)$_2$
  5 µg of bovine serum albumin
  40 pmol of At3 tyrosine aminotransferase 5' primer
  40 pmol of Ar3 tyrosine aminotransferase 3' primer
  15 µl of 3.3×rTth DNA polymerase XL buffer (PE Applied Biosystems)
  5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 56° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/AtTATase3 was confirmed by complete sequencing using the M13F (−40) primer and the M13R primer (Seq. ID. No. 7).

Example 4

Cloning the tyrosine aminotransferase gene 5 encoding the *Arabidopsis thaliana* tyrosine aminotransferase 5.

The DNA encoding the tyrosine aminotransferase gene 5 was amplified from *Arabidopsis thaliana* by means of polymerase chain reaction (PCR) using a sense-specific primer (At5 tyrosine aminotransferase 5': SEQ. ID. No. 32) and an antisense-specific primer (At5 tyrosine aminotransferase 3': SEQ. ID. No. 33).

The PCR conditions were as follows:
The PCR was carried out with a 50 µl reaction mix consisting of:
  2 µl of an *Arabidopsis thaliana* cDNA
  0.2 mM dATP, dTTP, dGTP, dCTP
  1.5 mM Mg(OAc)$_2$
  5 µg of bovine serum albumin
  40 pmol of At5 tyrosine aminotransferase 5' primer
  40 pmol of At5 tyrosine aminotransferase 3' primer
  15 µl of 3.3×rTth DNA polymerase XL buffer (PE Applied Biosystems)
  5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 56° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/AtTATase5 was confirmed by complete sequencing using the M13F (−40) primer and the M13R primer (Seq. ID. No. 9).

Example 5

Cloning the tyrosine aminotransferase gene 6 encoding the *Arabidopsis thaliana* tyrosine aminotransferase 6.

The DNA encoding the tyrosine aminotransferase gene 6 was amplified from *Arabidopsis thaliana* by means of polymerase chain reaction (PCR) using a sense-specific primer (At6 tyrosine aminotransferase 5': SEQ. ID. No. 34) and an antisense-specific primer (At6 tyrosine aminotransferase 3': SEQ. ID. No. 35).

The PCR conditions were as follows:
The PCR was carried out with a 50 µl reaction mix consisting of:
  2 µl of an *Arabidopsis thaliana* cDNA
  0.2 mM dATP, dTTP, dGTP, dCTP
  1.5 mM Mg(OAc)$_2$
  5 µg of bovine serum albumin
  40 pmol of At6 tyrosine aminotransferase 5' primer
  40 pmol of Ar6 tyrosine aminotransferase 3' primer
  15 µl of 3.3×rTth DNA polymerase XL buffer (PE Applied Biosystems)
  5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 56° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/AtTATase6 was confirmed by complete sequencing using the M13F (−40) primer and the M13R primer (Seq. ID. No. 11).

Example 6

Cloning the geranylgeranyl-pyrophosphate oxidoreductase gene encoding the *Nicotiana tabacum* geranylgeranyl-pyrophosphate oxidoreductase The DNA encoding the geranylgeranyl-pyrophosphate oxidoreductase gene was amplified from Nicotiana tabacum by means of polymerase chain reaction (PCR) using a sense-specific primer (geranylgeranyl-pyrophosphate oxidoreductase 5': SEQ. ID. NO. 36) and an antisense-specific primer (geranylgeranyl-pyrophosphate oxidoreductase 3': SEQ. ID. No. 37).

The PCR conditions were as follows:
The PCR was carried out with a 50 µl reaction mix consisting of:
  2 µl of a *Nicotiana tabacum* cDNA
  0.2 mM dATP, dTTP, dGTP, dCTP
  1.5 mM Mg(OAc)$_2$
  5 µg of bovine serum albumin
  40 pmol of geranylgeranyl-pyrophosphate oxidoreductase 5' primer
  40 pmol of geranylgeranyl-pyrophosphate oxidoreductase 3' primer
  15 µl of 3.3×rTth DNA polymerase buffer (PE Applied Biosystems)
  5 U of rTth DNA polymerase (PE Applied Biosystems)

The PCR was carried out under the following cycle conditions:
Step 1: 5 minutes at 94° C. (denaturing)
Step 2: 3 seconds at 94° C.
Step 3: 1 minute at 56° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEMTe (Promega) using standard methods. The identity of the amplicon generated in the vector pGEMTe/NtGGPPOR was confirmed by complete sequencing using the M13F (−40) primer and the M13R primer (Seq. ID. No. 17).

Example 7

Cloning the hydroxyphenylpyruvate dioxygenase gene encoding the *Arabidopsis thaliana* hydroxyphenylpyruvate dioxygenase.

The DNA encoding the hydroxyphenylpyruvate dioxygenase gene was amplified from *Arabidopsis thaliana* by means of polymerase chain reaction (PCR) using a sense-specific primer (At hydroxyphenylpyruvate dioxygenase 5': SEQ. ID. No. 38) and an antisense-specific primer (At hydroxyphenylpyruvate dioxygenase 3': SEQ. ID. No. 39).

The PCR conditions were as follows:
The PCR was carried out with a 50 µl reaction mix consisting of:
  2 µl of an *Arabidopsis thaliana* cDNA
  0.2 mM dATP, dTTP, dGTP, dCTP
  1.5 mM Mg(OAc)$_2$
  5 µg of bovine serum albumin
  40 pmol of At hydroxyphenylpyruvate dioxygenase 5' primer
  40 pmol of At hydroxyphenylpyruvate dioxygenase 3' primer
  15 µl of 3.3×rTth DNA polymerase XL buffer (PE Applied Biosystems)
  5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 58° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/AtHPPD was confirmed by complete sequencing using the M13F (−40) primer and the M13R primer (Seq. ID. No. 13).

Example 8

Cloning the homogentisate prenyltransferase gene encoding the *Arabidopsis thaliana* homogentisate prenyltransferase.

The DNA encoding the homogentisate prenyltransferase gene was amplified from *Arabidopsis thaliana* by means of polymerase chain reaction (PCR) using a sense-specific primer (At homogentisate prenyltransferase 5': SEQ. ID. No. 40) and an antisense-specific primer (At homogentisate prenyltransferase 3': SEQ. ID. No. 41).

The PCR conditions were as follows:
The PCR was carried out with a 50 µl reaction mix consisting of:
2 µl of an *Arabidopsis thaliana* cDNA
0.2 mM dATP, dTTP, dGTP, dCTP
1.5 mM Mg(OAc)$_2$
5 µg of bovine serum albumin
40 pmol of At homogentisate prenyltransferase 5' primer
40 pmol of At homogentisate prenyltransferase 3' primer
15 µl of 3.3×rTth DNA polymerase XL buffer (PE Applied Biosystems)
5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 58° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/AtHPT was confirmed by complete sequencing using the M13F (−40) primer and the M13R primer (Seq. ID. No. 15).

Example 9

Cloning the 2-methyl-6-phytylhydroquinone methyltransferase gene encoding the *Synechocystis* sp. PCC6803 2-methyl-6-phytyl-hydroquinone methyltransferase.

The DNA encoding the 2-methyl-6-phytylhydroquinone methyl-transferase gene was amplified from *Synechocystis* sp. PCC6803 by means of polymerase chain reaction (PCR) using a sense-specific primer (2-methyl-6-phytylhydroquinone methyltransferase 5': SEQ. ID. No. 42) and an antisense-specific primer (2-methyl-6-phytyl-hydroquinone methyltransferase 3': SEQ. ID. No. 43).

The PCR conditions were as follows:
The PCR was carried out with a 50 µl reaction mix consisting of:
2 µl of a *Synechocystis* sp. PCC6803 DNA
0.2 mM dATP, dTTP, dGTP, dCTP
1.5 mM Mg(OAc)$_2$
5 µg of bovine serum albumin
40 pmol of 2-methyl-6-phytylhydroquinone methyltransferase 5' primer
40 pmol of 2-methyl-6-phytylhydroquinone methyltransferase 3' primer
15 µl of 3.3×rTth DNA polymerase XL buffer (PE Applied Biosystems)
5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 58° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/SynMT1 was confirmed by complete sequencing using the M13F (−40) primer and the M13R primer (Seq ID. No. 19).

Example 10

Cloning the tocopherol cyclase gene (also referred to as 2,3-dimethyl-5-phytylplastoquinol cyclase gene) encoding the *Synechocystis* sp. PCC6803 tocopherol cyclase (also referred to as 2,3-dimethyl-5-phytylplastoquinol cyclase).

The DNA encoding the 2,3-dimethyl-5-phytylplastoquinol cyclase gene was amplified from *Synechocystis* sp. PCC6803 by means of polymerase chain reaction (PCR) using a sense-specific primer (2,3-dimethyl-5-phytylplastoquinol cyclase 5': SEQ. ID. No. 44) and an antisense-specific primer (2,3-dimethyl-5-phytylplastoquinol cyclase 3': SEQ. ID No. 45).

The PCR conditions were as follows:
The PCR was carried out with a 50 µl reaction mix consisting of:
2 µl of a *Synechocystis* sp. PCC6803 DNA
0.2 mM dATP, dTTP, dGTP, dCTP
1.5 mM Mg(OAc)$_2$
5 µg of bovine serum albumin
40 pmol of 2,3-dimethyl-5-phytylplastoquinol cyclase 5' primer
40 pmol of 2,3-dimethyl-5-phytylplastoquinol cyclase 3' primer
15 µl of 10×Pful-Turbo DNA polymerase buffer (Stratagene)
5 U of Pful-Turbo DNA polymerase (Stratagene)

The PCR was carried out under the following cycle conditions:
Step 1: 5 minutes at 94° C. (denaturing)
Step 2: 3 seconds at 94° C.
Step 3: 1 minute at 60° C. (annealing)
Step 4: 1.5 minutes at 72° C. (elongation)
30 cycles of steps 2-4
Step 5: 10 minutes at 72° C. (post-elongation)

The amplicon was cloned into the PCR cloning vector pCRTopo4blunt (Invitrogen) using standard methods. The identity of the amplicon generated in the vector pCR4topoblunt/SynCyc was confirmed by complete sequencing using the M13F (−20) primer and the M13R primer (Seq. ID. No. 21).

Example 11

Cloning the γ-tocopherol methyltransferase gene encoding the *Arabidopsis thaliana* γ-tocopherol methyltransferase.

The DNA encoding the γ-tocopherol methyltransferase gene was amplified from *Arabidopsis thaliana* by means of polymerase chain reaction (PCR) using a sense-specific primer (Atγ-tocopherol methyltransferase 5': SEQ. ID. No. 46) and an antisense-specific primer (Atγ-tocopherol methyltransferase 3': SEQ. ID. No. 47).

The PCR conditions were as follows:
The PCR was carried out with a 50 μl reaction mix consisting of:
2 μl of an *Arabidopsis thaliana* cDNA
0.2 mM dATP, dTTP, dGTP, dCTP
1.5 mM Mg(OAc)$_2$
5 μg of bovine serum albumin
40 pmol of Atγ-tocopherol methyltransferase 5' primer
40 pmol of Atγ-tocopherol methyltransferase 3' primer
15 μl of 3.3×rTth DNA polymerase XL buffer (PE Applied Biosystems)
5 U of rTth DNA polymerase XL (PE Applied Biosystems)

The PCR was carried out under the following cycle conditions:
Step 1: 5 minutes at 94° C. (denaturing)
Step 2: 3 seconds at 94° C.
Step 3: 1 minute at 58° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/AtγTMT was confirmed by complete sequencing using the M13F (−40) primer and the M13R primer (Seq. ID. No. 23).

Example 12

Cloning a part-fragment of the homogentisate dioxygenase gene encoding the *Brassica napus* homogentisate dioxygenase.

The DNA encoding a part-fragment of the homogentisate dioxygenase gene was amplified from *Brassica napus* by means of polymerase chain reaction (PCR) using a sense-specific primer (homogentisate dioxygenase 5': SEQ. ID. No. 48) and an antisense-specific primer (homogentisate dioxygenase 3': SEQ. ID. No. 49).

The PCR conditions were as follows:
The PCR was carried out with a 50 μl reaction mix consisting of:
2 μl of a *Brassica napus* cDNA
0.2 mM dATP, dTTP, dGTP, dCTP
1.5 mM Mg(OAc)$_2$
5 μg of bovine serum albumin
40 pmol of homogentisate dioxygenase 5' primer
40 pmol of homogentisate dioxygenase 3' primer
15 μl of 3.3×rTth DNA polymerase XL buffer (PE Applied Biosystems)
5 U of rTth DNA polymerase (PE Applied Biosystems)

The PCR was carried out under the following cycle conditions:
Step 1: 5 minutes at 94° C. (denaturing)
Step 2: 3 seconds at 94° C.
Step 3: 1 minute at 56° C. (annealing)
Step 4: 2 minutes at 72° C. (elongation)
30 cycles of steps 2-4
Step 5: 10 minutes at 72° C. (post-elongation)

The amplicon was cloned into the PCR cloning vector pGEM-Te (Promega) using standard methods. The identity of the amplicon generated in the vector pGEMTe/*BnHGD was confirmed by complete sequencing using the M13F (−40) primer and the M13R primer (Seq. ID. No. 25).

Example 13

Generation of the DNA construct for the seed-specific suppression of the expression of the *Brassica napus* homogentisate dioxygenase gene.

To prepare chimeric DNA constructs for generating transgenic *Brassica napus* plants which express a reduced expression of the *Brassica napus* homogentisate dioxygenase gene under the control of a seed-specific promoter, the vector pSUN2 (WO 02/00900) was used. This vector was modified in such a way that it comprises the seed-specific promoter of the *Vicia faba* vicilin gene (Weschke W., Bassüner R., van Hai N., Czihal A., Bäumlein H., Wobus U. The structure of a *Vicia faba* Vicilin Gene. Biochem. Physiol. plants 183,233-242 (1988)) and the Intron 2 (IV2) of the *Solanum tuberosum* ST-LS1 gene (Vancanneyt G., Schmidt R., O'Connor-Sanchez A., Willmitzer L., Rocha-Sosa M. Construction of an intron-containing marker gene: Splicing of the intron in transgenic plants and its use in monitoring early events in *Agrobacterium*-mediated plant transformation. MGG (1990)) and the termination signal 2 of the *Agrobacterium tumefaciens* octopine synthase gene (Gielen et al. 1984).

The DNA fragment encoding the part-fragment of the *Brassica napus* homogentisate dioxygenase gene was cloned as SacI/ScaI fragment from plasmid pGEMTe/*BnHGD into the SmaI-opened pSUN2-Pvic-STLS1-ocsT after the overhanging ends of the fragment had been made blunt-ended with T4 polymerase. The resulting plasmid pSUN2-Pvic-*BnHGD-STLS1-ocsT was digested with ScaI. The fragment of the *Brassica napus* homogentisic acid dioxygenase gene was cloned from plasmid pGEMTe/*BnHGD as blunt-ended SacI/ScaI fragment into this linearized vector. In doing so, care was taken that the two BnHGD fragments are present in opposite orientation on the two sides of the STLS1 intron. This plasmid (pSUN2-Pvic-*BnHGD-STLS1-α*BnHGD-ocsT (FIG. 1) is used for generating transgenic *Brassica napus* and *A. thaliana* plants.

Fragment A (2559 bp) in FIG. 1 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has, in the vector, the opposite orientation of B. Fragment E (208 bp) encodes the termination signal 2 of the octopine gene.

Example 14

Generation of DNA constructs for expressing the *Rattus norvegicus* tyrosine aminotransferase under the control of a seed-specific promoter.

To prepare chimeric DNA constructs for generating transgenic *A. thaliana, Nicotiana tabacum* and *Brassica napus* plants which express the *Rattus norvegicus* tyrosine aminotransferase under the control of a seed-specific promoter, the vector pSUN2 (patent WO 02/00900) was used. This vector was modified in such a way that it comprises the seed-specific promoter of the *Vicia faba* unknown seed protein gene (USPP) (Bäumlein H., Boerjan W., Nagy I., Bassüner R., van Montagu M., Inzé D., Wobus U. A novel seed protein gene from *Vicia faba* is developmentally regulated in transgenic tobacco and *Arabidopsis* plants. MGG 225:459-467 (1991)), the sequence encoding the chloroplast transit peptide of the *Vicia faba* ribulose-bisphosphate carboxylase (rbcS) gene (Guerineau F., Woolston S., Brooks L., Mullineaux P. An expression cassette for targeting foreign proteins into chloroplasts. Nucleic Acids Res 16(23): 11380. (1988)) and the termination signal of the *A. tumefaciens* nopaline synthase gene (Depicker A, Stachel S, Dhaese P, Zambryski P, Goodman H M. Nopaline synthase: transcript mapping and DNA sequence. J Mol Appl Genet. 1982;1(6): 561-73).

The DNA fragment encoding the *Rattus norvegicus* tyrosine aminotransferase gene was cloned from plasmid pGEMTe/RnTATase as EcoR5 fragment into pSUN2-USPP-rbcS-nosT after the latter had been digested with the restriction enzyme SmaI. This gave a translational fusion with the transit peptide of ribulose-bisphosphate carboxylase (rbcS), thus ensuring the import of the *Rattus norvegicus* tyrosine aminotransferase into the plastids.

This plasmid (pSUN2USPP-rbcS-RnTATase-nosT, FIG. 2) is used for generating transgenic *Brassica napus* and *A. thaliana* plants.

Figure 2:
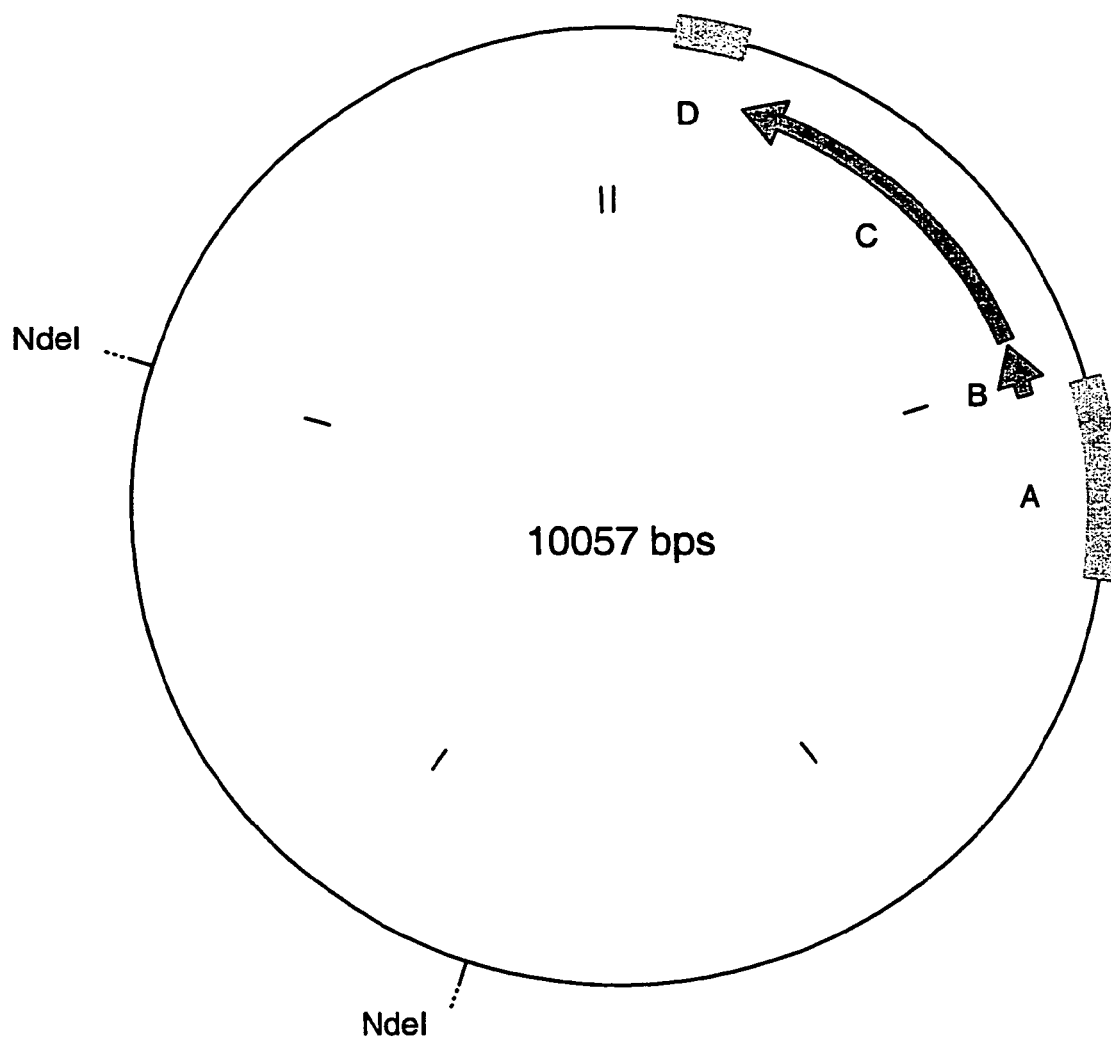
FIG. 2 shows the plasmid pSUN2-USPP-rbcS-RnTATase-nosT.

Fragment A (678 bp) in FIG. 2 comprises the promoter of the *Vicia faba* unknown seed protein gene (USPP), fragment B (235 bp) encodes the *Vicia faba* ribulose-bisphosphate carboxylase (rbcS) transit peptide. Fragment C (1365 bp) encodes the *Rattus norvegicus* tyrosine aminotransferase gene. Fragment D (272 bp) encodes the termination signal of the *A. tumefaciens* nopaline synthase gene.

Example 15

Generation of DNA constructs for expressing the *Arabidopsis thaliana* tyrosine aminotransferase 1 under the control of a seed-specific promoter.

To prepare chimeric DNA constructs for generating transgenic *Brassica napus* plants which express the *Arabidopsis thaliana* tyrosine aminotransferase under the control of a seed-specific promoter, the vector pSUN2 (WO 02/00900) was used.

This vector was modified in such a way that it comprises the seed-specific promoter of the *Vicia faba* unknown seed protein (USPP) (Bäumlein et al., 1991) and the termination signal of the *Agrobacterium tumefaciens* nopaline synthase gene (GIELEN, J., de BEUCKELEER, M., SEURINCK, J., DEBROECK, H., de GREVE, H., LEMMERS, M., van MONTAGU, M., SCHELL, J. The complete nucleotide sequence of the TL-DNA of the *Agrobacterium tumefaciens* plasmid pTiAch5. EMBO J. 3: 835-846. (1984)).

The DNA fragment encoding the *Arabidopsis thaliana* tyrosine aminotransferase gene 1 was isolated as SalI fragment from plasmid pGEMTe/AtTATase1 and, after the SalI ends had been filled in with Klenow enzyme, cloned into pSUN2-USPP-nosT after the latter had been digested partially with the restriction enzyme SmaI (size of the linearized vector 8250 bp).

This plasmid (pSUN2-USPP-AtTATase1-nosT, FIG. 3) is used for generating transgenic *Brassica napus* plants.

Figure 3:
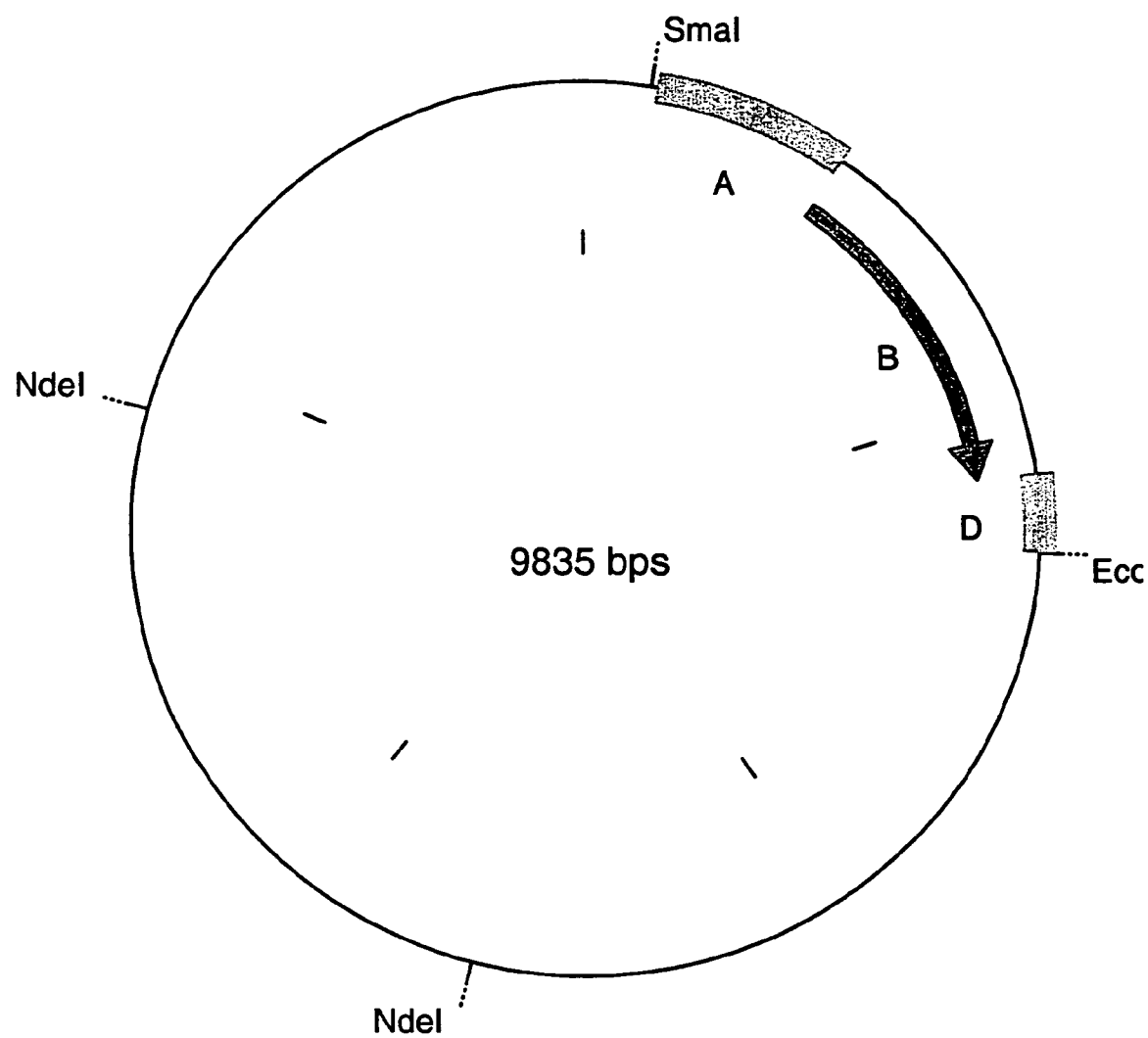
FIG. 3 shows the plasmid pSUN2-USPP-AtTATase1-nosT.

Fragment A (678 bp) in FIG. 3 comprises the promoter of the *Vicia faba* unknown seed protein gene (USPP), fragment B (1269 bp) encodes the *Arabidopsis thaliana* tyrosine aminotransferase gene 1, and fragment C (272 bp) encodes the termination signal of the nopaline synthase gene.

Example 16

Generation of DNA constructs for expressing the *Arabidopsis thaliana* tyrosine aminotransferase 3 under the control of a seed-specific promoter.

To prepare chimeric DNA constructs for generating transgenic *Brassica napus* plants which express the *Arabidopsis thaliana* tyrosine aminotransferase 3 under the control of a seed-specific promoter, the vector pSUN2 (WO 02/00900) was used.

This vector was modified in such a way that it comprises the seed-specific promoter of the *Vicia faba* unknown seed protein (USPP) (Bäumlein et al., 1991) and the termination signal of the *Agrobacterium nopaline* synthase gene (Gielen et al. 1984).

The DNA fragment encoding the *Arabidopsis thaliana* tyrosine aminotransferase gene 3 was isolated as SalI fragment from plasmid pGEMTe/AtTATase3 and, after the SalI end had been filled in with Klenow enzyme, cloned into pSUN2-USPP-nosT after the latter had been digested partially with the restriction enzyme SmaI (size of the linearized vector 8250 bp).

This plasmid (pSUN2USPP-AtTATase3-nosT, FIG. 4) is used for generating transgenic *Brassica napus* plants.

Figure 4:
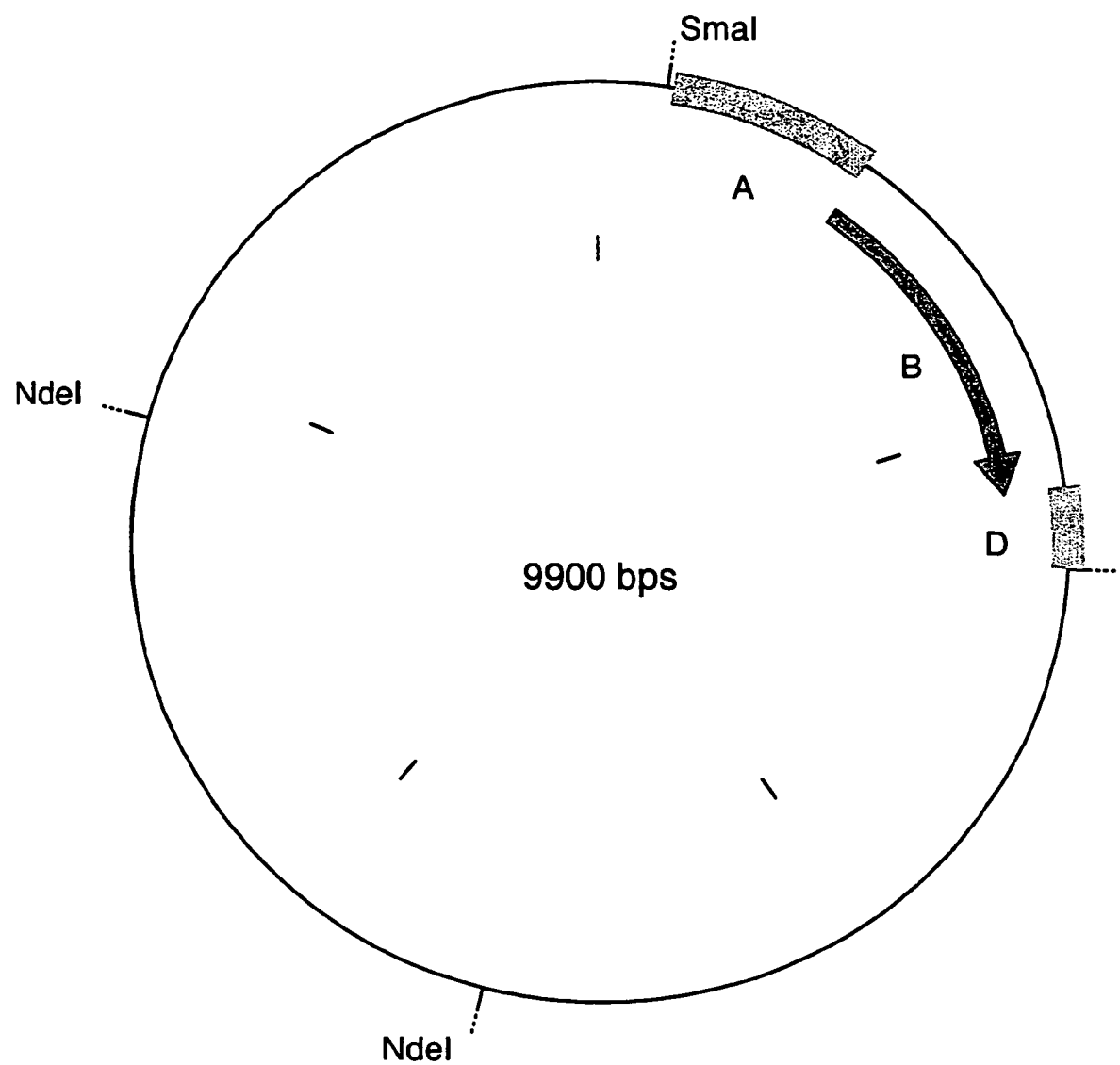
FIG. 4 shows the plasmid pSUN2-USPP-AtTATase3-nosT.

Fragment A (678 bp) in FIG. 4 comprises the promoter of the *Vicia faba* unknown seed protein gene (USPP), fragment B (1334 bp) encodes the *Arabidopsis thaliana* tyrosine aminotransferase gene 3, and fragment C (272 bp) encodes the termination signal of the nopaline synthase gene.

Example 17

Generation of DNA constructs for expressing the *Arabidopsis thaliana* tyrosine aminotransferase 5 under the control of a seed-specific promoter.

To prepare chimeric DNA constructs for generating transgenic *Brassica napus* plants which express the *Arabidopsis thaliana* tyrosine aminotransferase 5 under the control of a seed-specific promoter, the vector pSUN2 (WO 02/00900) was used.

This vector was modified in such a way that it comprises the seed-specific promoter of the *Vicia faba* unknown seed protein (USPP) (Bäumlein et al., 1991) and the termination signal of the *Agrobacterium nopaline* synthase gene (Gielen et al. 1984).

The DNA fragment encoding the *Arabidopsis thaliana* tyrosine aminotransferase gene 5 was isolated as BamHI fragment from plasmid pGEMTe/AtTATase5 and, after the SalI end had been filled in with Klenow enzyme, cloned into pSUN2-USPP-nosT after the latter had been digested partially with the restriction enzyme SmaI (size of the linearized vector 8250 bp).

This plasmid (pSUN2-USPP-AtTATase5-nosT, FIG. 5) is used for generating transgenic *Brassica napus* plants.

Figure 5:
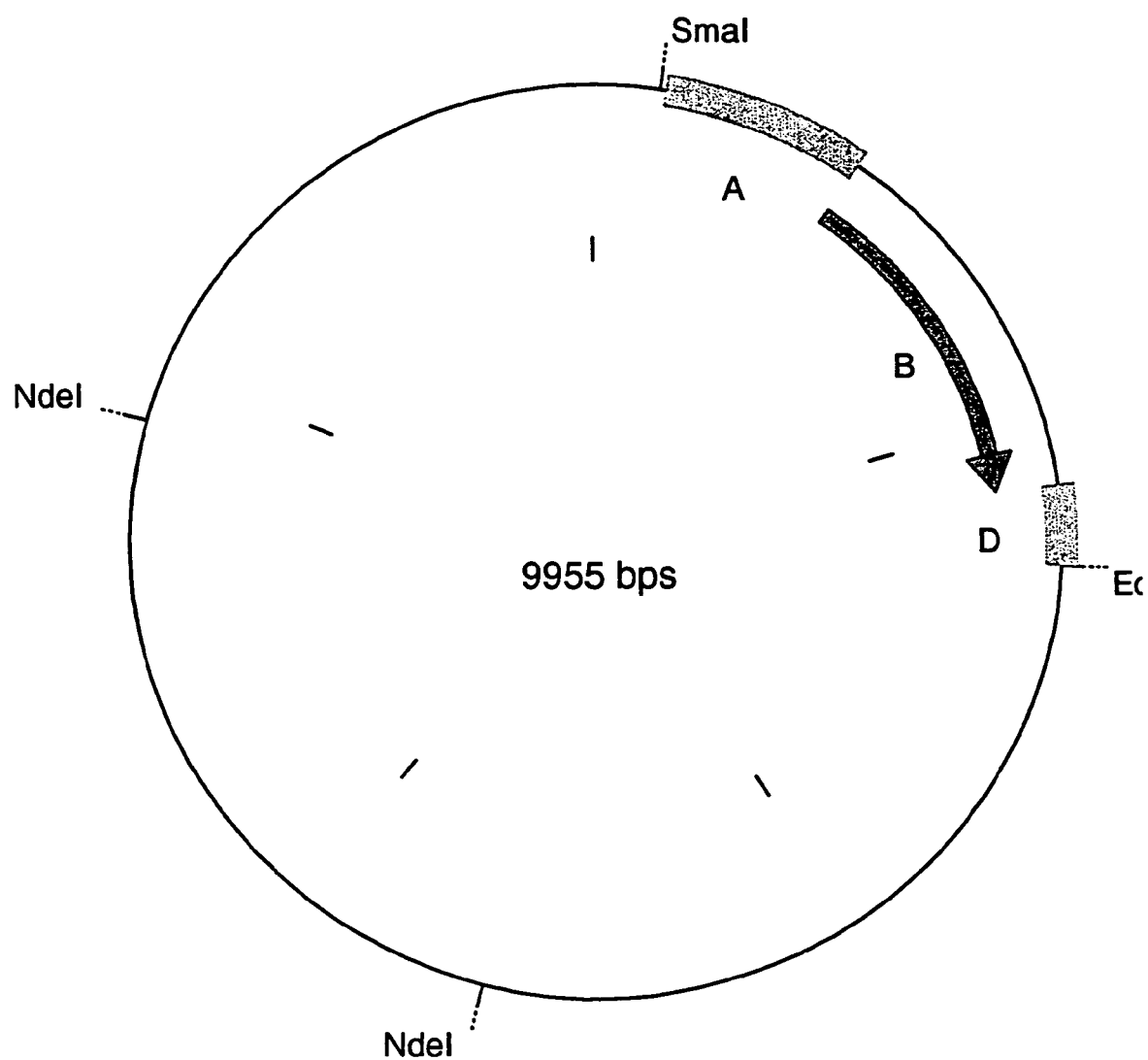
FIG. 5 shows the plasmid pSUN2-USPP-AtTATase5-nosT.

Fragment A (678 bp) in FIG. 5 comprises the promoter of the *Vicia faba* unknown seed protein gene, fragment B (1389 bp) encodes the *Arabidopsis thaliana* tyrosine aminotransferase gene 5, and fragment C (272 bp) encodes the termination signal of the nopaline synthase gene.

Example 18

Generation of DNA constructs for expressing the *Arabidopsis thaliana* tyrosine aminotransferase 6 under the control of a seed-specific promoter.

To prepare chimeric DNA constructs for generating transgenic *Brassica napus* plants which express the *Arabidopsis thaliana* tyrosine aminotransferase 6 under the control of a seed-specific promoter, the vector pSUN2 (WO 02/00900) was used.

This vector was modified in such a way that it comprises the seed-specific promoter of the *Vicia faba* unknown seed protein gene (USPP) (Bäumlein et al., 1991) and the termination signal of the *Agrobacterium* nopaline synthase gene (Gielen et al. 1984).

The DNA fragment encoding the *Arabidopsis thaliana* tyrosine aminotransferase gene 6 was isolated as SalI fragment from plasmid pGEMTe/AtTATase6 and, after the SalI ends had been filled with Klenow enzyme, cloned into pSUN2-USPP-nosT after the latter had been digested partially with the restriction enzyme SmaI (size of the linearized vector 8250 bp).

This plasmid (pSUN2-USPP-AtTATase6-nosT, FIG. 6) is used for generating transgenic *Brassica napus* plants.

Figure 6:
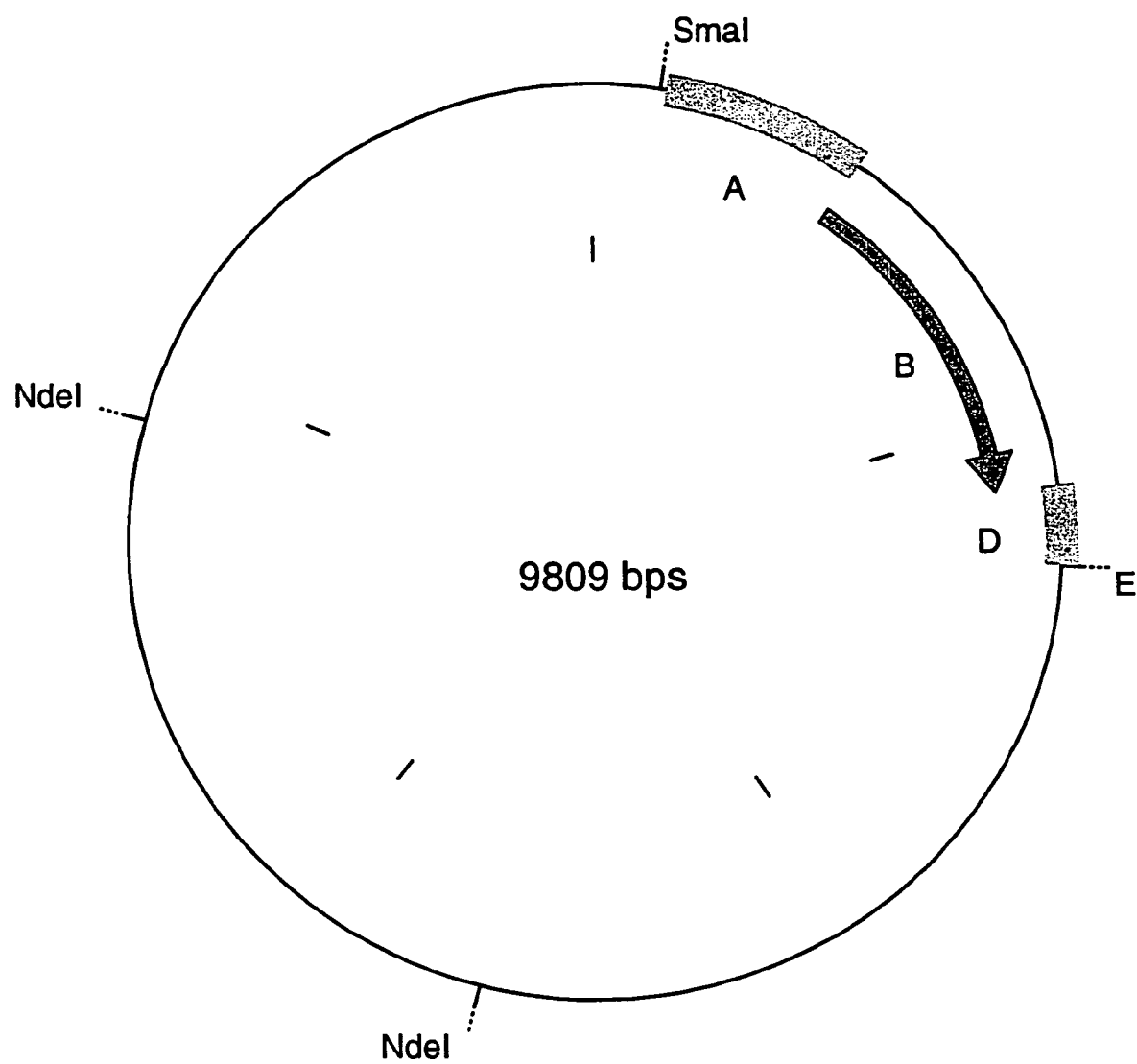
FIG. 6 shows the plasmid pSUN2-USPP-AtTATase6-nosT.

Fragment A (678 bp) in FIG. 6 comprises the promoter of the *Vicia faba* unknown seed protein gene, fragment B (1243 bp) encodes the *Arabidopsis thaliana* tyrosine aminotransferase gene 6, and fragment C (272 bp) encodes the termination signal of the nopaline synthase gene.

Example 19

Generation of DNA constructs for expressing the *Nicotiana tabacum* geranylgeranyl-pyrophosphate oxidoreductase under the control of a seed-specific promoter.

To prepare chimeric DNA constructs for generating transgenic *Brassica napus* plants which express the *Nicotianum tabacum* geranylgeranyl-pyrophosphate oxidoreductase under the control of a seed-specific promoter, the vector pSUN2 (WO 02/00900) was used.

First, vector puc19 (New England Biolabs) was modified in such a way that it comprises the seed-specific promoter of the legumin B4 gene (Kafatos et al., 1986) and the termination signal of the *A. tumefaciens* nopaline synthase (Depicker et al., 1982). The resulting vector is known as puc19-LeB4-nosT.

The DNA fragment encoding the *Nicotiana tabacum* geranylgeranyl-pyrophosphate oxidoreductase gene was cloned as KpnI/SalI fragment into puc19LeB4nosT after the latter had been digested with the restriction enzymes KpnI/SalI.

The DNA consisting of LeB4 promoter, geranylgeranyl-pyrophosphate oxidoreductase gene (nucleotides 1 to 1323 of Seq. ID 7) was isolated from vector puc19-LeB4-NtGGPPOR-nosT as SmaI/Hind3 fragment and cloned into vector pSUN2 after the latter had been digested with the restriction enzyme SmaI/Hind3. The resulting vector is known as pSUN2-LeB4-NtGGPPOR (nuc.1-1323). The DNA composed of geranylgeranyl-pyrophosphate oxidoreductase gene (nucleotide 1319 to 1509 of Seq. ID. No. 17), nos termination sequence was isolated as Hind3 fragment from the vector puc19-LeB4-NtGGPPOR-nosT after the latter had also been cleaved with Hind3.

This plasmid (pSUN2-LeB4-NtGGPPOR-nosT, FIG. 7) is used for generating transgenic *Brassica napus* plants.

Figure 7:
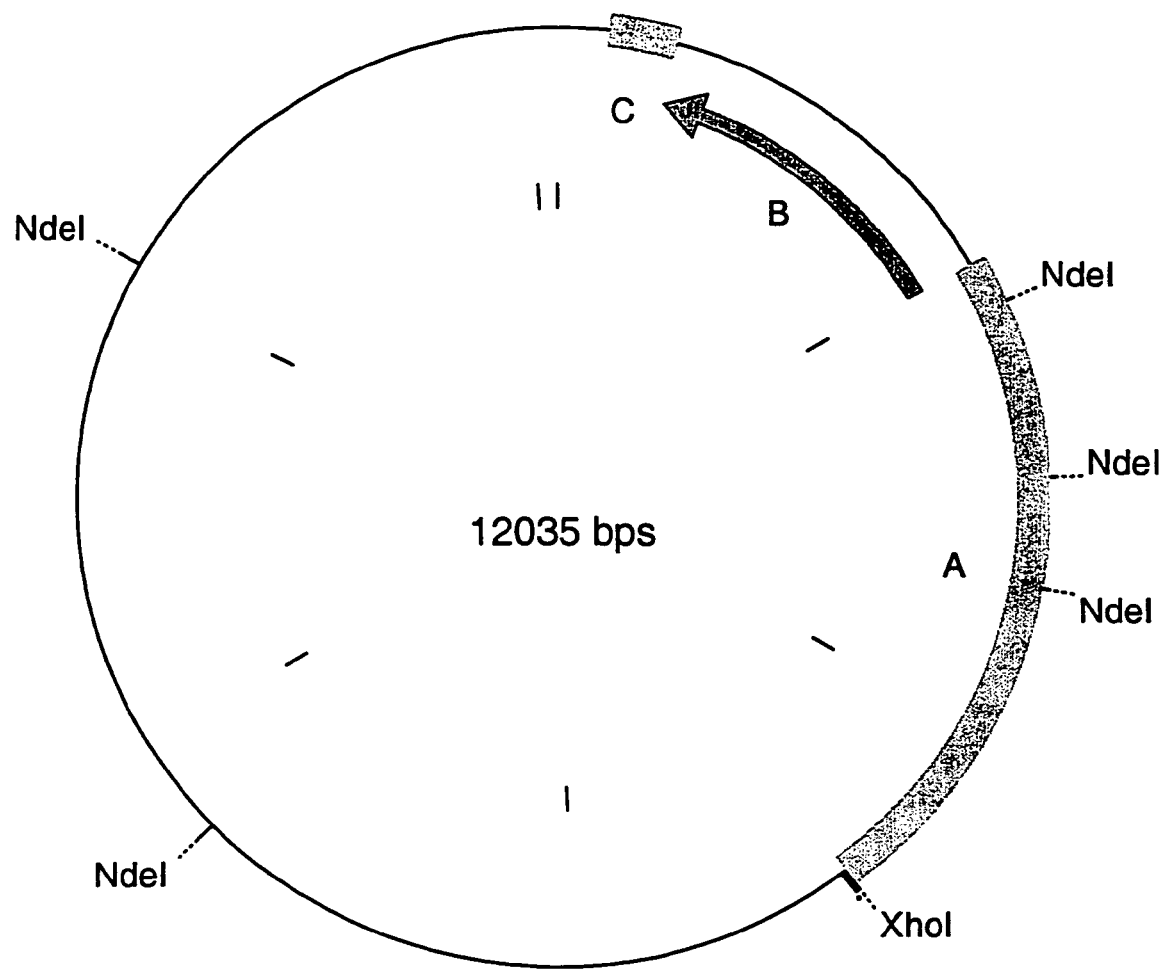
FIG. 7 shows the plasmid pSUN2-LeB4-NtGGPPOR-nosT.

Fragment A (2764 bp) in FIG. 7 comprises the promoter of the *Vicia faba* legumin B4 gene, fragment B (1509 bp) encodes the *Nicotiana tabacum* geranylgeranyl-pyrophosphate oxidoreductase gene, and fragment C (272 bp) encodes the termination signal of the nopaline synthase gene.

Example 20

Generation of DNA constructs for expressing the *Arabidopsis thaliana* hydroxyphenylpyruvate dioxygenase under the control of a seed-specific promoter.

To prepare chimeric DNA constructs for generating transgenic *Brassica napus* plants which express the *Arabidopsis thaliana* hydroxyphenylpyruvate dioxygenase under the control of a seed-specific promoter, the vector pSUN2 (WO 02/00900) was used.

This vector was modified in such a way that it comprises the seed-specific promoter of the *Vicia faba* unknown seed protein gene (USPP) (Bäumlein et al., 1988) and the termination signal 1 of the *A. tumefaciens* octopine synthase gene (Depicker et al., 1982).

The DNA fragment encoding the *Arabidopsis thaliana* hydroxyphenylpyruvate dioxygenase was isolated as BamHI/SalI fragment from plasmid pGEMTe/AtHPPD and, after the BamHI end and SalI end had been filled in with Klenow enzyme, cloned into the vector pSUN2-USPP-ocsT which had been digested partially with the restriction enzyme SmaI (size of the linearized vector 8691 bp).

This plasmid (pSUN2-USPP-AtHPPD-ocsT, FIG. 8) is used for generating transgenic *Brassica napus* plants.

Figure 8:
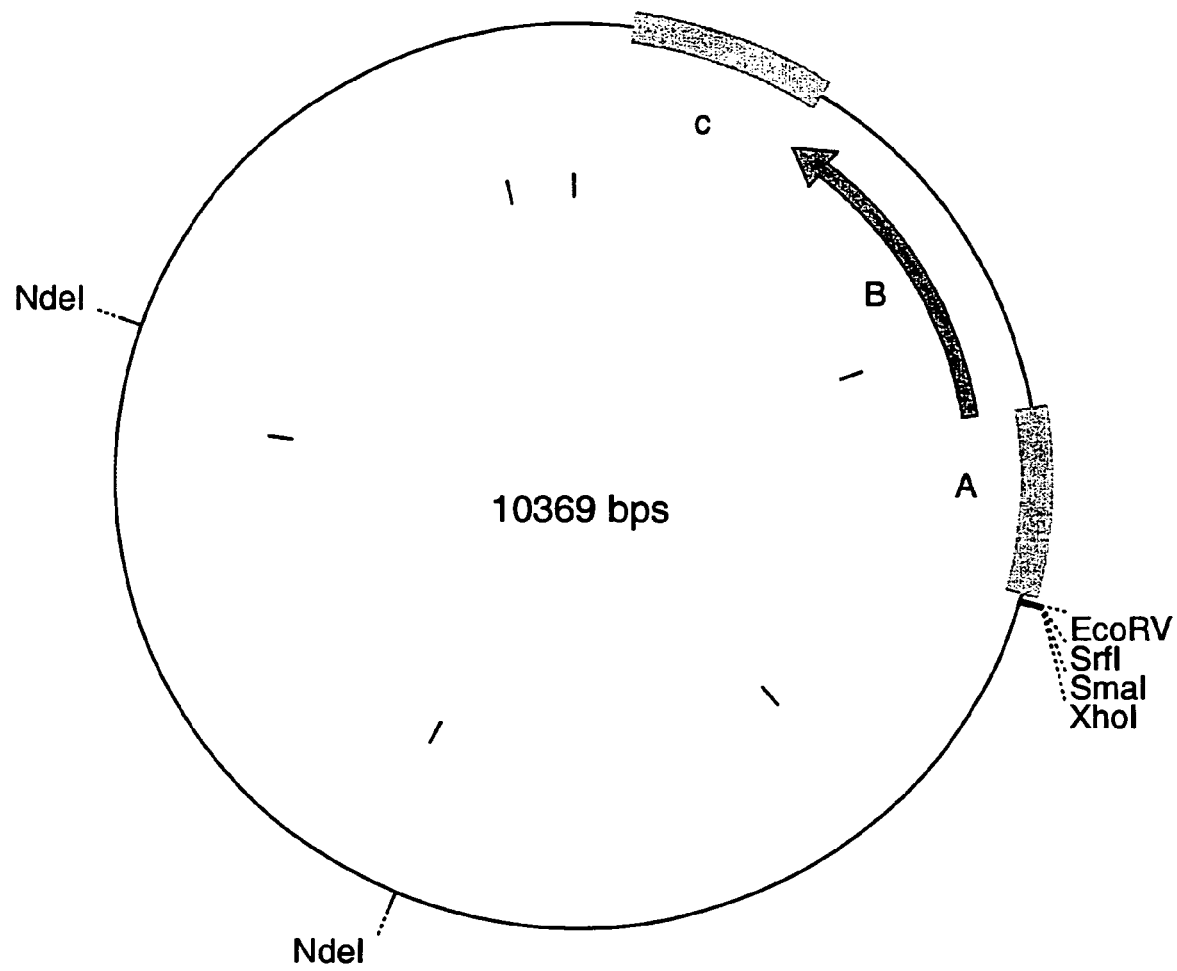
FIG. 8 shows the plasmid pSUN2-USPP-AtHPPD-ocsT.

Fragment A (678 bp) in FIG. 8 comprises the promoter of the *Vicia faba* unknown seed protein gene, fragment B (1338 bp) encodes the *Arabidopsis thaliana* hydroxyphenylpyruvate dioxygenase gene, and fragment C (713 bp) encodes the termination signal 1 of the octopine synthase gene.

Example 21

Generation of DNA constructs for expressing the *Arabidopsis thaliana* homogentisate phytyltransferase under the control of a seed-specific promoter.

To prepare chimeric DNA constructs for generating transgenic *Brassica napus* plants which express the *Arabidopsis thaliana* homogentisate phytyltransferase under the control of a seed-specific promoter, the vector pSUN2 (WO 02/00900) was used.

This vector was modified in such a way that it comprises the seed-specific promoter of the *Vicia faba* unknown seed protein gene (USPP) (Bäumlein et al., 1991) and the termination signal 1 of the *A. tumefaciens* nopaline synthase gene (Depicker et al., 1982).

The DNA fragment encoding the *Arabidopsis thaliana* homogentisate phytyltransferase was isolated as BamHI fragment from plasmid pGEMTe/AtHPT and, after the BamHI ends had been filled in with Klenow enzyme, cloned into pSUN2-USPP-ocsT after the latter had been digested partially with SmaI (size of the linearized vector 88691 bp).

This plasmid (pSUN2-USPP-AtHPT-ocsT, FIG. 9) is used for generating transgenic *Brassica napus* plants.

Figure 9:
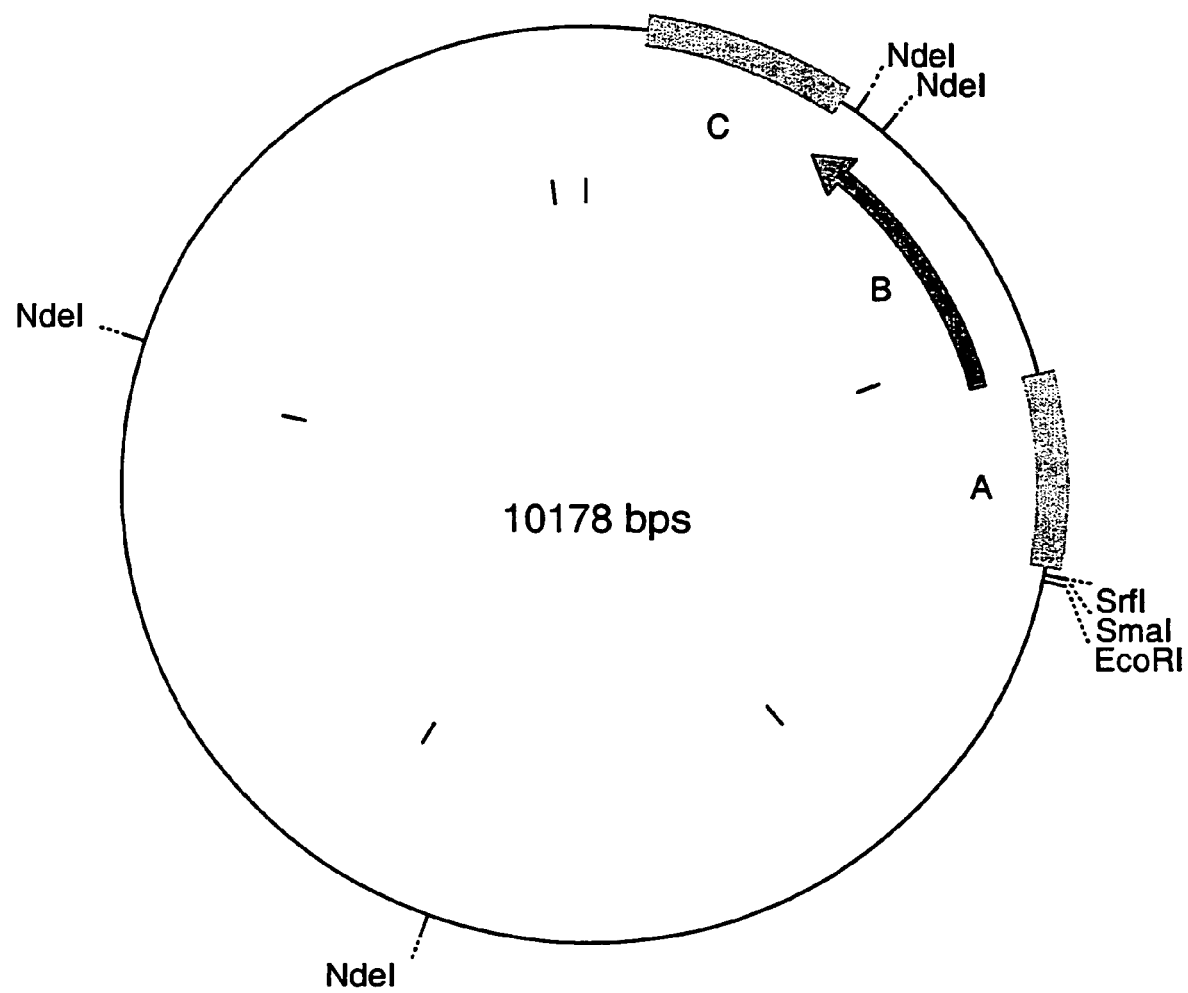
FIG. 9 shows the plasmid pSUN2-USPP-AtHPT-ocsT.

Fragment A (678 bp) in FIG. 9 comprises the promoter of the *Vicia faba* unknown seed protein gene, fragment B (1182 bp) encodes the *Arabidopsis thaliana* homogentisate phytyltransferase gene, and fragment C (713 bp) encodes the termination signal 1 of the octopine synthase gene.

Example 22

Generation of DNA constructs for expressing the *Synechocystis sp.* PCC6803 2-methyl-6-phytylhydroquinone methyltransferase under the control of a seed-specific promoter.

To prepare chimeric DNA constructs for generating transgenic *Brassica napus* plants which express the *Synechocystis* sp. PCC6803 2-methyl-6-phytylhydroquinone methyltransferase under the control of a seed-specific promoter, the vector pSUN2 (WO 02/00900) is used.

This vector is modified in such a way that it comprises the seed-specific promoter of the legumin B4 gene (Kafatos et al., 1986), the sequence encoding the transit peptide of the *A. thaliana* plastid-specific isopentenyl-pyrophosphate isomerase-2 (IPP-2) and the termination signal of the *A. tumefaciens* nopaline synthase gene (Depicker et al., 1982).

The DNA fragment encoding the *Synechocystis* sp. PCC6803 2-methyl-6-phytylhydroquinone methyltransferase is isolated as BamHI fragment from plasmid pGEMTe/SynMT1 and, after the BamHI ends have been filled in with Klenow enzyme, and cloned into the SalI-digested pSUN2-Leb4P-IPP-nosT whose SalI ends are also filled in with Klenow enzyme. This generates a translational fusion with the IPP-2 transit peptide, thus ensuring the import of 2-methyl-6-phytylhydroquinone methyltransferase into the chloroplasts.

This plasmid (pSUN2LeB4-IPP-SynMT1-nosT, FIG. 10) is used for generating transgenic *Brassica napus* plants.

Figure 10:
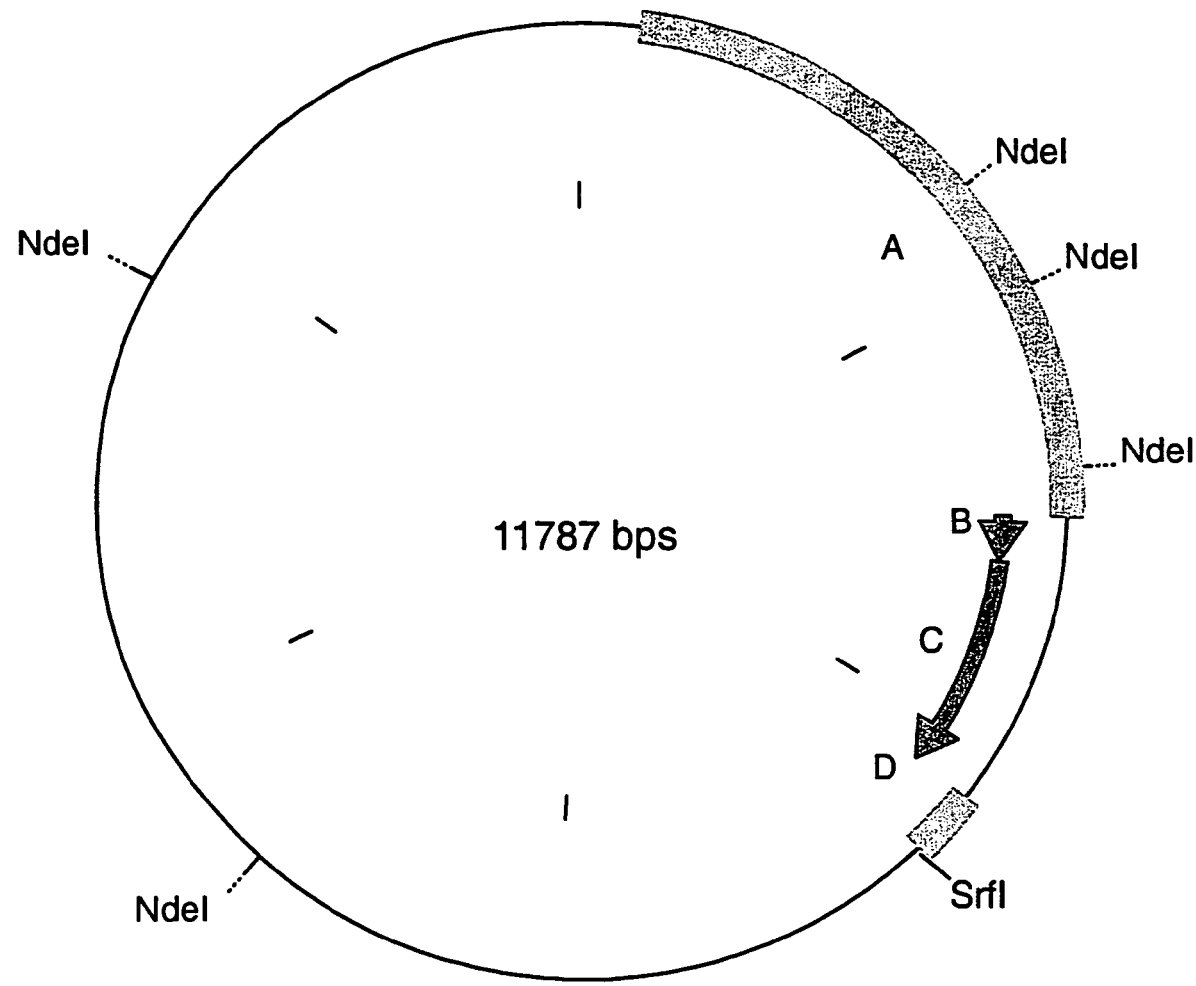
FIG. 10 shows the plasmid pSUN2-LeB4-IPP-SynMT1-nosT.

Fragment A (2764 bp) in FIG. 10 comprises the promoter of the *Vicia faba* legumin B4 gene, fragment B (235 bp) encodes the transit peptide of the *A. thaliana* isopentenyl-pyrophosphate isomerase-2. Fragment C (957 bp) encodes the *Synechocystis* sp. PCC6803 2-methyl-6-phytylhydroquinone methyltransferase gene, and fragment D (272 bp) encodes the termination signal of the nopaline synthase gene.

Example 23

Generation of DNA constructs for expressing the *Synechocystis* sp. PCC6803 2,3-dimethyl-5-phytylplastoquinol cyclase under the control of a seed-specific promoter.

To prepare chimeric DNA constructs for generating transgenic *Brassica napus* plants which express the *Synechocystis* sp. PCC6803 2,3-dimethyl-5-phytylplastoquinol cyclase under the control of a seed-specific promoter, the vector pSUN2 (WO 02/00900) was used.

This vector is modified in such a way that it comprises the seed-specific promoter of the legumin B4 gene (Kafatos et al., 1986), the sequence encoding the transit peptide of the *A. thaliana* plastid-specific isopentenyl-pyrophosphate isomerase-2 (IPP-2) and the termination signal of the *A. tumefaciens* nopaline synthase gene (Depicker et al., 1982).

The DNA fragment encoding the *Synechocystis* sp. PCC6803 2,3-dimethyl-5-phytylplastoquinol cyclase is isolated as BamHI fragment from plasmid pGEMTe/SynCyc and, after the BamHI ends have been filled in with Klenow enzyme, cloned into the SalI-digested pSUN2-Leb4P-IPP-nosT whose SalI ends are also filled in with Klenow enzyme. This generates a translational fusion with the IPP-2 transit peptide, thus ensuring the import of 2,3-dimethyl-5-phytylplastoquinol cyclase into the chloroplasts.

This plasmid (pSUN2-LeB4P-IPP-SynCyc-nosT, FIG. 11) is used for generating transgenic *Brassica napus* plants.

Figure 11:
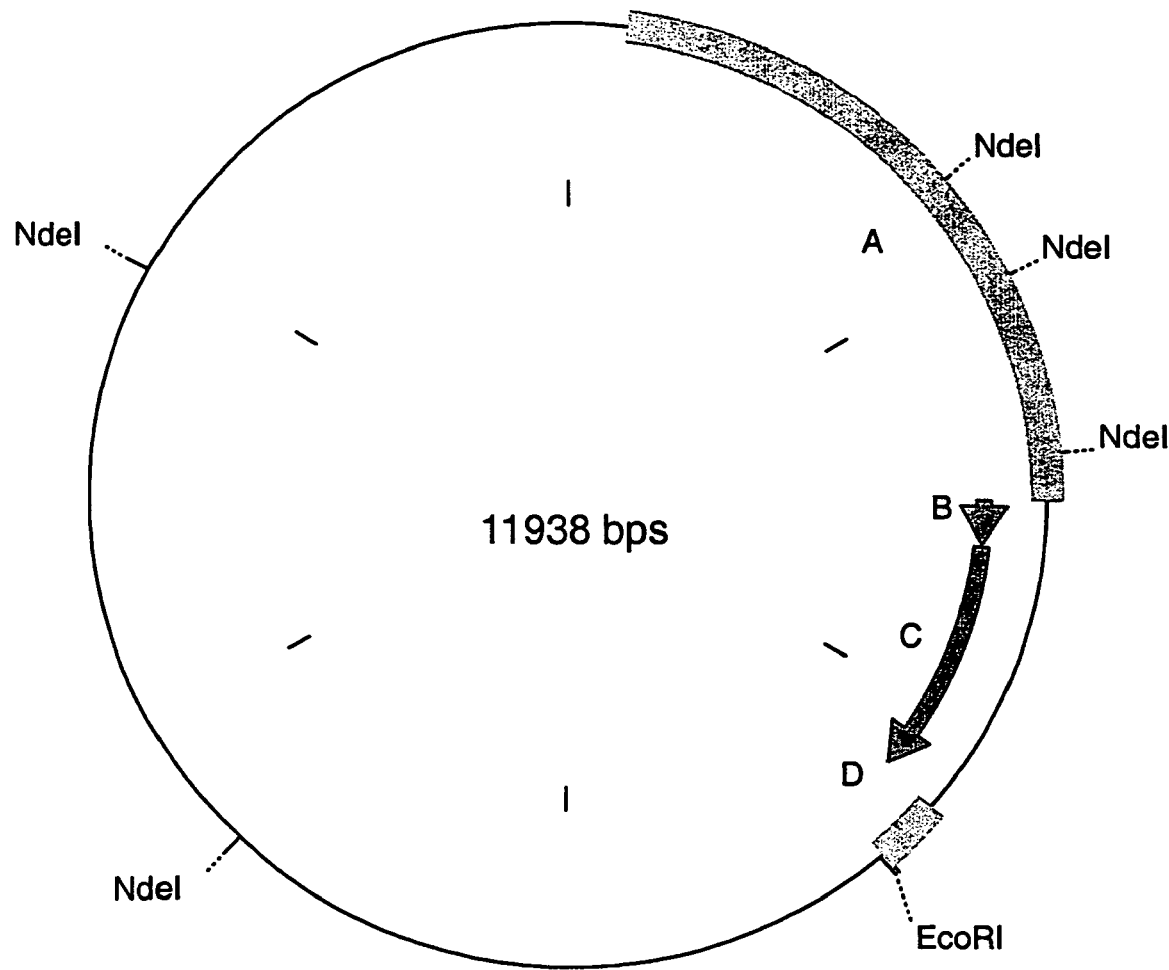
FIG. 11 shows the plasmid pSUN2-LeB4-IPP-SynCyc-nosT.

Fragment A (2764 bp) in FIG. 11 comprises the promoter of the *Vicia faba* legumin B4 gene, fragment B (235 bp) encodes the *A. thaliana* isopentenyl-pyrophosphate isomerase-2 transit peptide. Fragment C (1100 bp) encodes the *Synechocystis* sp. PCC6803 2,3-dimethyl-5-phytylplastoquinol cyclase gene, and fragment D (272 bp) encodes the termination signal of the nopaline synthase gene.

Example 24 generation of DNA constructs for expressing the *Arabidopsis thaliana* γ-tocopherol methyltransferase under the control of a seed-specific promoter.

To prepare chimeric DNA constructs for generating transgenic *Brassica napus* plants which express the *Arabidopsis thaliana* γ-tocopherol methyltransferase under the control of a seed-specific promoter, the vector pSUN2 (WO 02/00900) was used.

First, the vector puc19 (New England Biolabs) was modified in such a way that it comprises the seed-specific promoter of the sucrose binding protein gene (SBP-P) (DE 19852195 C2) and the 35S termination sequence of the cauliflower mosaic virus (FRANCK, A., GUILLEY, H., JONARD, G., RICHARDS, K., HIRTH, L. Nucleotide sequence of cauliflower mosaic virus DNA. Cell 21: 285-294. (1980)). The resulting vector is referred to as puc19-SBPP-35ST.

The DNA fragment encoding the *Arabidopsis thaliana* γ-tocopherol methyltransferase gene was cloned as BamHI/SalI fragment into puc19-SBPP-AtγTMT-35ST after the latter had been digested with the restriction enzyme BamHI/SalI.

The expression cassette consisting of: SBP promoter, *Arabidopsis thaliana* γ-tocopherol methyltransferase gene and 35ST termination sequence was amplified by PCR using a sense-specific primer (SBPP-XbaI 5': SEQ. ID. No. 50) and an antisense-specific primer (35ST-XbaI 3': SEQ. ID. No. 51) and cloned into the vector pCR4topoblunt (Invitrogen).

The PCR conditions were as follows:
The PCR was carried out with a 50 µl reaction mix consisting of:
  1 µl of a puc19-SBPP-AtγTMT-35ST plasmid DNA
  0.2 mM dATP, dTTP, dGTP, dCTP
  1.5 mM $Mg(OAc)_2$
  5 µg of bovine serum albumin
  40 pmol of SBPP-XbaI 5' primer
  40 pmol of 35ST-XbaI 3' primer
  5 µl of 10×Pful DNA polymerase buffer (Stratagene)
  5 U of Pful DNA polymerase (Stratagene)
The PCR was carried out under the following cycle conditions:
Step 1: 5 minutes at 94° C. (denaturing)
Step 2: 3 seconds at 94° C.
Step 3: 1 minute at 55° C. (annealing)
Step 4: 10 minutes at 68° C. (elongation)
30 cycles of steps 2-4
Step 5: 10 minutes at 72° C. (post-elongation)

The DNA fragment consisting of SBP promoter, *Arabidopsis thaliana* γ-tocopherol methyltransferase gene and 35ST termination sequence was isolated as XbaI fragment from the plasmid pCR4TOPOblunt/SBPP-γTMT-35ST and cloned into the vector pSUN2 after the latter had been digested with the restriction enzyme XbaI.

This plasmid (pSUN2-SBPP-γTMT-35ST, FIG. 12) is used for generating transgenic *Brassica napus* plants.

Figure 12:
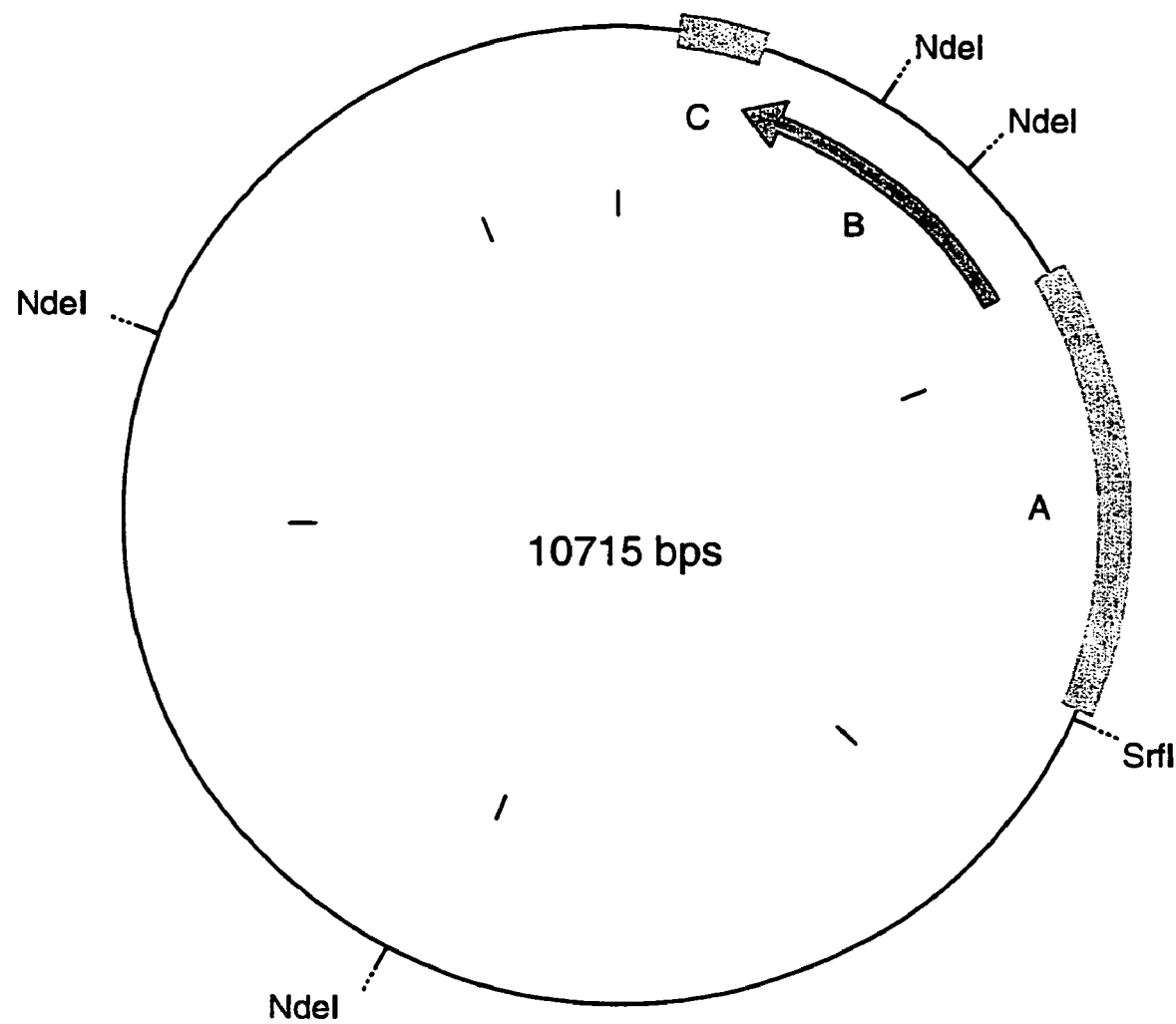
FIG. 12 shows the plasmid pSUN2-SBPP-AtγTMT-35ST.

Fragment A (1788 bp) in FIG. 12 comprises the promoter of the *Vicia faba* SBP gene, fragment B (1047 bp) encodes the *Arabidopsis thaliana* γ-tocopherol methyltransferase gene, and fragment C (291 bp) encodes the cauliflower mosaic virus 35S terminator.

Example 25

Generation of DNA constructs for expressing the *Rattus norvegicus* tyrosine aminotransferase gene under the control of a seed-specific promoter in combination with the seed-specific suppression of the expression of the *Brassica napus* homogentisate dioxygenase gene.

To prepare chimeric DNA constructs for generating transgenic *Brassica napus* plants which express the *Rattus norvegicus* tyrosine aminotransferase under the control of a seed-specific promoter and simultaneously confer the seed-specific suppression of the expression of the *Brassica napus* homogentisate dioxygenase gene, the vector pSUN2-Pvic-BnHGD*-STLS1-αBnHGD*-ocsT and the vector pSUN2USPP-rbcS-RnTATase-nosT were used.

The expression cassette consisting of: USP promoter, rbcS transit peptide, *Rattus norvegicus* tyrosine aminotransferase gene and nos termination sequence was amplified from the vector pSUN2USPP-rbcS-RnTATase-nosT by means of PCR using a sense-specific primer (USPP-SrfI 5': SEQ. ID. No. 52) and an antisense-specific primer (nosT-SrfI 3': SEQ. ID. No. 53) and cloned into the vector pCR4topoblunt (Invitrogen).

The PCR conditions were as follows:
The PCR was carried out with a 50 µl reaction mix consisting of:
1 µl of the pSUN2-USPP-rbcS-RnTATase-nosT plasmid DNA
0.2 mM dATP, dTTP, dGTP, dCTP
1.5 mM Mg (OAc)$_2$
5 µg of bovine serum albumin
40 pmol of USPP-SrfI 5' primer
40 pmol of nosT-SrfI 3' primer
5 µl of 10×Pfu1 Turbo DNA polymerase buffer (Stratagene)
5 U of Pful Turbo DNA polymerase (Stratagene)
The PCR was carried out under the following cycle conditions:
Step 1: 5 minutes at 94° C. (denaturing)
Step 2: 3 seconds at 94° C.
Step 3: 1 minute at 55° C. (annealing)
Step 4: 8 minutes at 68° C. (elongation)
30 cycles of steps 2-4
Step 5: 10 minutes at 72° C. (post-elongation)

The DNA fragment consisting of USP promoter, rbcS transit peptide, *Rattus norvegicus* tyrosine aminotransferase gene and nos termination sequence was isolated as SrfI fragment from the plasmid pCR4TOPOblunt/USPP-rbcS-RnATase-nosT and cloned into the vector pSUN2-Pvic-*BnHGD-STLS1-α*BnHGD-ocsT after the latter had been digested with the restriction enzyme EcoRV.

Figure 13:
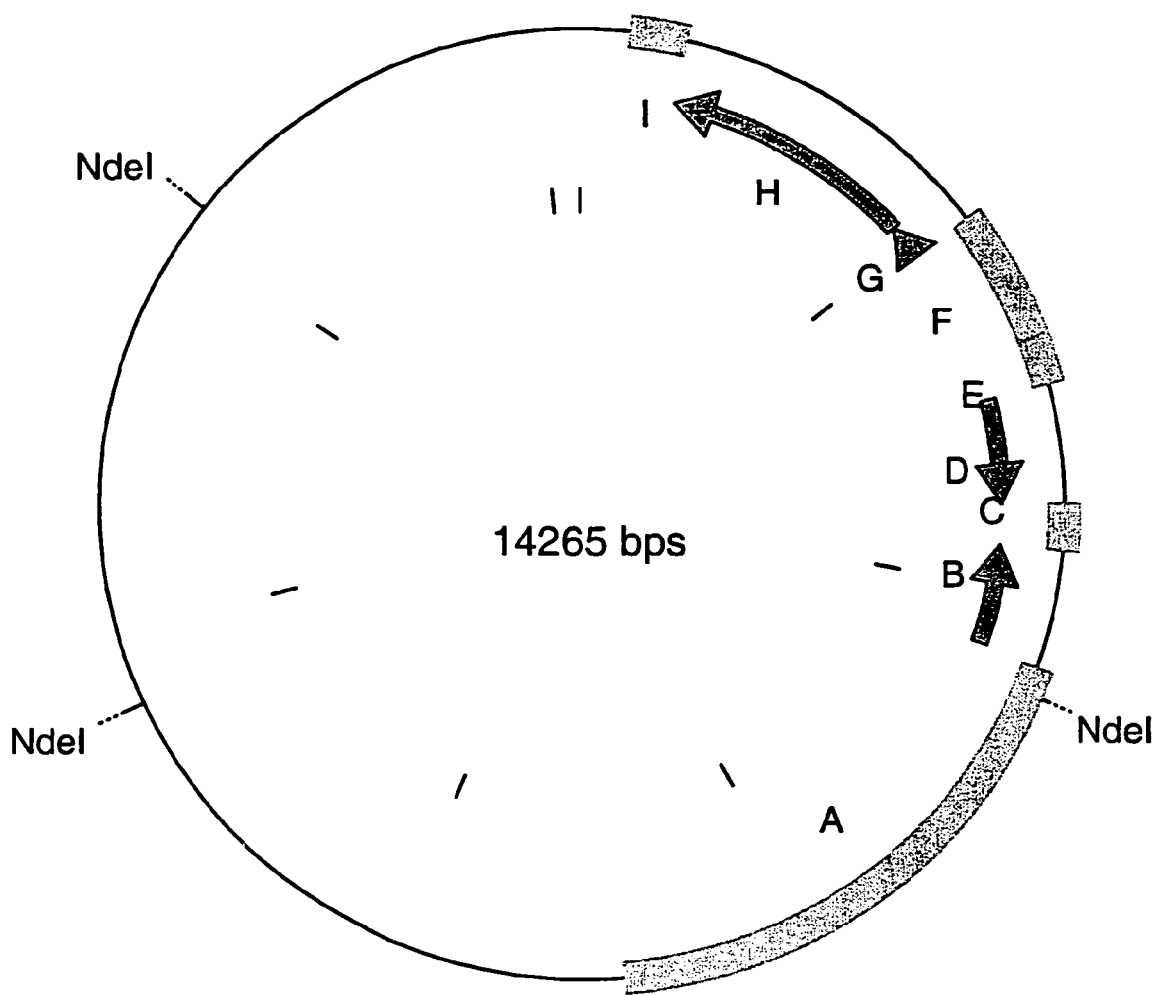
FIG. 13 shows the plasmid pSUN2-Pvic-*BnHGD-STLS1-α*BnHGD-ocsT-USPP-rbcS-RnTATase-nosT.

This plasmid (pSUN2-Pvic-*BnHGD-STLS1-α*BnHGD-ocsT-USPP-rbcS-RnATase-nosT, FIG. 13) is used for generating transgenic *Brassica napus* plants.

Fragment A (2559 bp) in FIG. 13 comprises the promoter of the *Vicia faba* vicilin gene, fragment B (580 bp) encodes a fragment of the *Brassica napus* homogentisate dioxygenase gene, and fragment C (198 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal 2 of the octopine gene. Fragment F (678 bp) comprises the promoter of the *Vicia faba* unknown seed protein gene, fragment G (235 bp) encodes the transit peptide of the *Vicia faba* ribulose-bisphosphate carboxylase (rbcS). Fragment H (1365 bp) encodes the *Rattus norvegicus* tyrosine aminotransferase gene, and fragment I (272 bp) encodes the termination signal of the *Agrobacterium tumefaciens* nopaline synthase gene.

Example 26

Generation of DNA constructs for expressing the *Arabidopsis thaliana* tyrosine aminotransferase 1 under the control of a seed-specific promoter and for the seed-specific suppression of the expression of the *Brassica napus* homogentisate dioxygenase gene To prepare chimeric DNA constructs for generating transgenic *Brassica napus* plants which express the *Arabidopsis thaliana* tyrosine aminotransferase 1 under the control of a seed-specific promoter and which suppress the expression of the endogenous *Brassica napus* homogentisate dioxygenase gene in a seed-specific fashion, the vector pSUN2-USPP-AtTATase1-nosT and the vector pSUN2-Pvic-*BnHGD-STLS1-α*BnHGD-ocsT were combined with each other.

The DNA fragment encoding the expression cassette consisting of: USP promoter, *Arabidopsis thaliana* tyrosine aminotransferase 1 gene and nos terminator was isolated as EcoRI/SmaI fragment from the plasmid pSUN2-USPP-AtTATase1-nosT, the EcoRI end was filled in with Klenow enzyme, and the construct was cloned into the vector pSUN-Pvic-*BnHGD-STLS1-α*BnHGD-ocsT which had been digested with EcoRV.

This plasmid (pSUN2-Pvic-*BnHGD-STLS1-α*Bn-HGD-ocsT/USPP-AtTATase1-nosT, FIG. 14) is used for generating transgenic *Brassica napus* plants.

Figure 14:
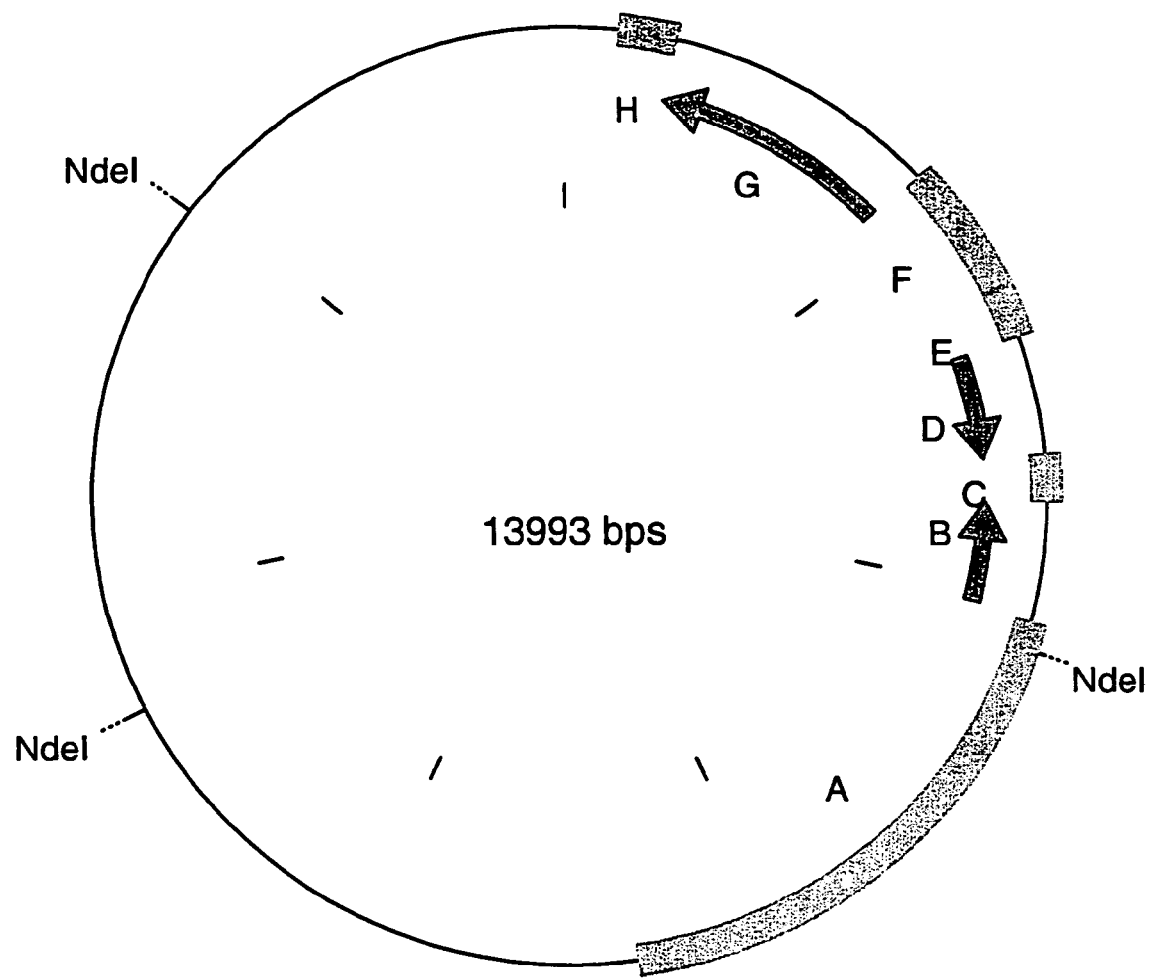
FIG. 14 shows the plasmid pSUN2-Pvic-*BnHGD-STLS1-α*BnHGD-ocsT-USPP-AtTATase1-nosT.

Fragment A (2559 bp) in FIG. 14 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal 2 of the octopine gene. Fragment F (678 bp) comprises the promoter of the *Vicia faba* unknown seed protein gene (USPP), fragment G (1269 bp) encodes the *Arabidopsis thaliana* tyrosine aminotransferase gene 1, and fragment H (272 bp) encodes the termination signal of the nopaline synthase gene.

Example 27

Generation of DNA constructs for expressing the *Arabidopsis thaliana* tyrosine aminotransferase-3 under the control of a seed-specific promoter and for the seed-specific suppression of the expression of the *Brassica napus* homogentisate dioxygenase gene To prepare chimeric DNA constructs for generating transgenic *Brassica napus* plants which express the *Arabidopsis thaliana* tyrosine aminotransferase 3 under the control of a seed-specific promoter and which suppress the expression of the endogenous *Brassica napus* homogentisate dioxygenase gene in a seed-specific fashion, the vector pSUN2-USPP-AtTATase3-nosT and the vector pSUN2-Pvic-*BnHGD-STLS1-*BnHGD-ocsT were combined with each other.

The DNA fragment encoding the expression cassette consisting of: USP promoter, *Arabidopsis thaliana* tyrosine aminotransferase 3 gene and nos terminator was isolated as EcoRI/SmaI fragment from the plasmid pSUN2-USPP-AtTATase1-nosT, the EcoRI end was filled in with Klenow enzyme, and the construct was cloned into the vector pSUN2-Pvic-*BnHGD-STLS1-α*BnHGD-ocsT which had been digested with EcoRV.

This plasmid (pSUN2-Pvic-*BnHGD-STLS1-α*BnHGD-ocsT/USPP-AtTATase3-nosT, FIG. 15) is used for generating transgenic Brassica napus plants.

Figure 15:
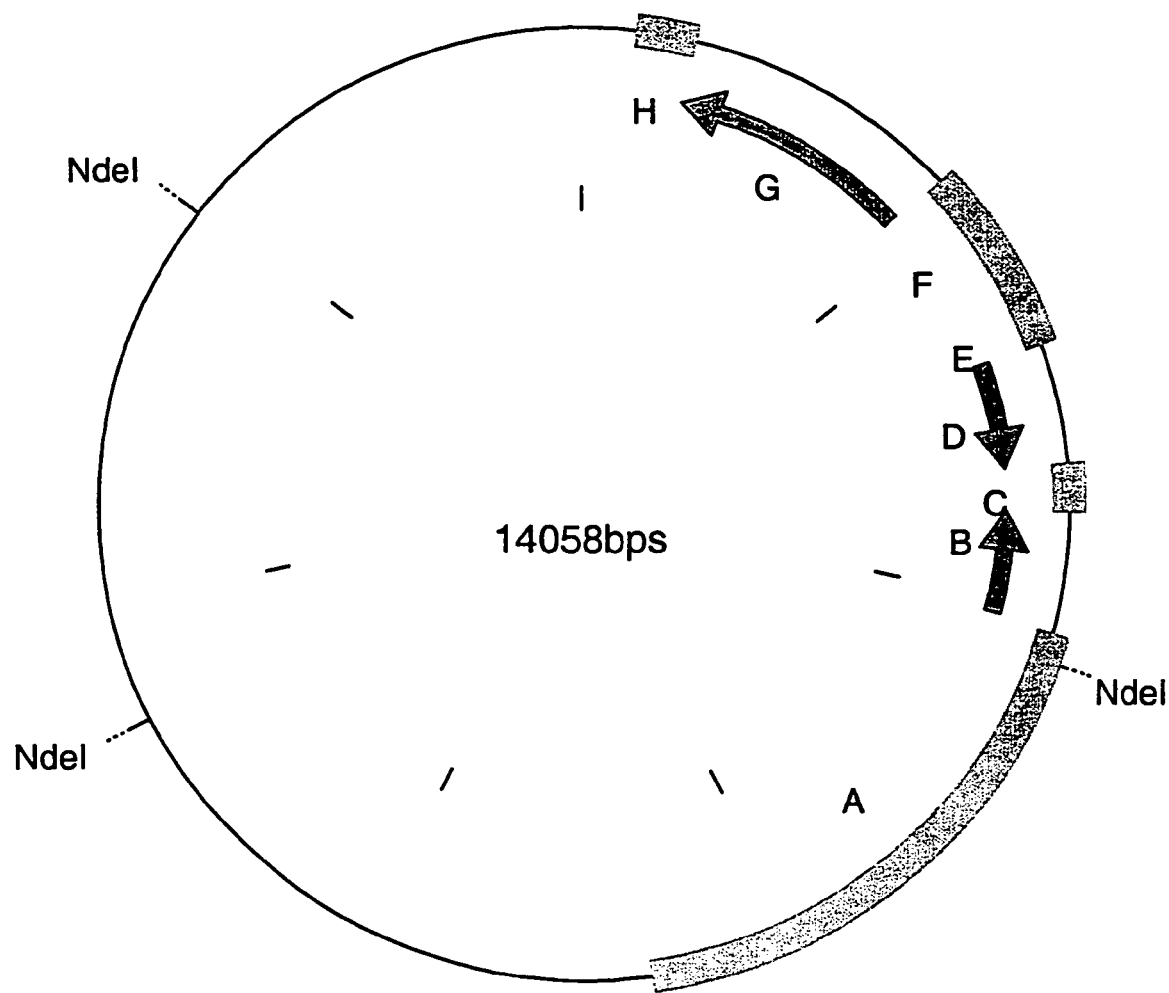
FIG. 15 shows the plasmid pSUN2-Pvic-*BnHGD-STLS1-α*BnHGD-ocsT-USPP-AtTATase3-nosT.

Fragment A (2559 bp) in FIG. 15 comprises the promoter of the Vicia faba vicilin gene, fragment B (580 bp) encodes a fragment of the Brassica napus homogentisate dioxygenase gene. Fragment C (190 bp) encodes the intron 2 (IV2) of the Solanum tuberosum ST-LS1 gene. Fragment D is identical with fragment B, but has the opposite orientation in the vector relative to B. Fragment E (208 bp) encodes the termination signal 2 of the octopine gene. Fragment F (678 bp) comprises the promoter of the Vicia faba "unknown seed protein" gene (USPP), fragment G (1334 bp) encodes the Arabidopsis thaliana tyrosine aminotransferase gene 3, and fragment H (272 bp) encodes the termination signal of the nopaline synthase gene.

Example 28

Generation of DNA constructs for expressing the Arabidopsis thaliana tyrosine aminotransferase 5 under the control of a seed-specific promoter and for the seed-specific suppression of the expression of the Brassica napus homogentisate dioxygenase gene To prepare chimeric DNA constructs for generating transgenic Brassica napus plants which express the Arabidopsis thaliana tyrosine aminotransferase 5 under the control of a seed-specific promoter and which suppress the expression of the endogenous Brassica napus homogentisate dioxygenase gene in a seed-specific fashion, the vector pSUN2-USPP-AtTATase5-nosT and the vector pSUN2-Pvic-*BnHGD-STLS1-α*BnHGD-ocsT were combined with each other.

The DNA fragment encoding the expression cassette consisting of: USP promoter, Arabidopsis thaliana tyrosine aminotransferase 5 gene and nos terminator was isolated as SmaI/EcoRI fragment from the plasmid pSUN2-USPP-AtTATase5-nosT, the EcoRI end was filled in with Klenow enzyme, and the construct was cloned into the vector pSUN2-Pvic-*BnHGD-STLS1-α*BnHGD-ocsT which had been digested with EcoRV.

This plasmid (pSUN2-Pvic-*BnHGD-STLS1-α*BnHGD-ocsT/USPP-AtTATase5-nosT, FIG. 16) is used for generating transgenic Brassica napus plants.

Figure 16:
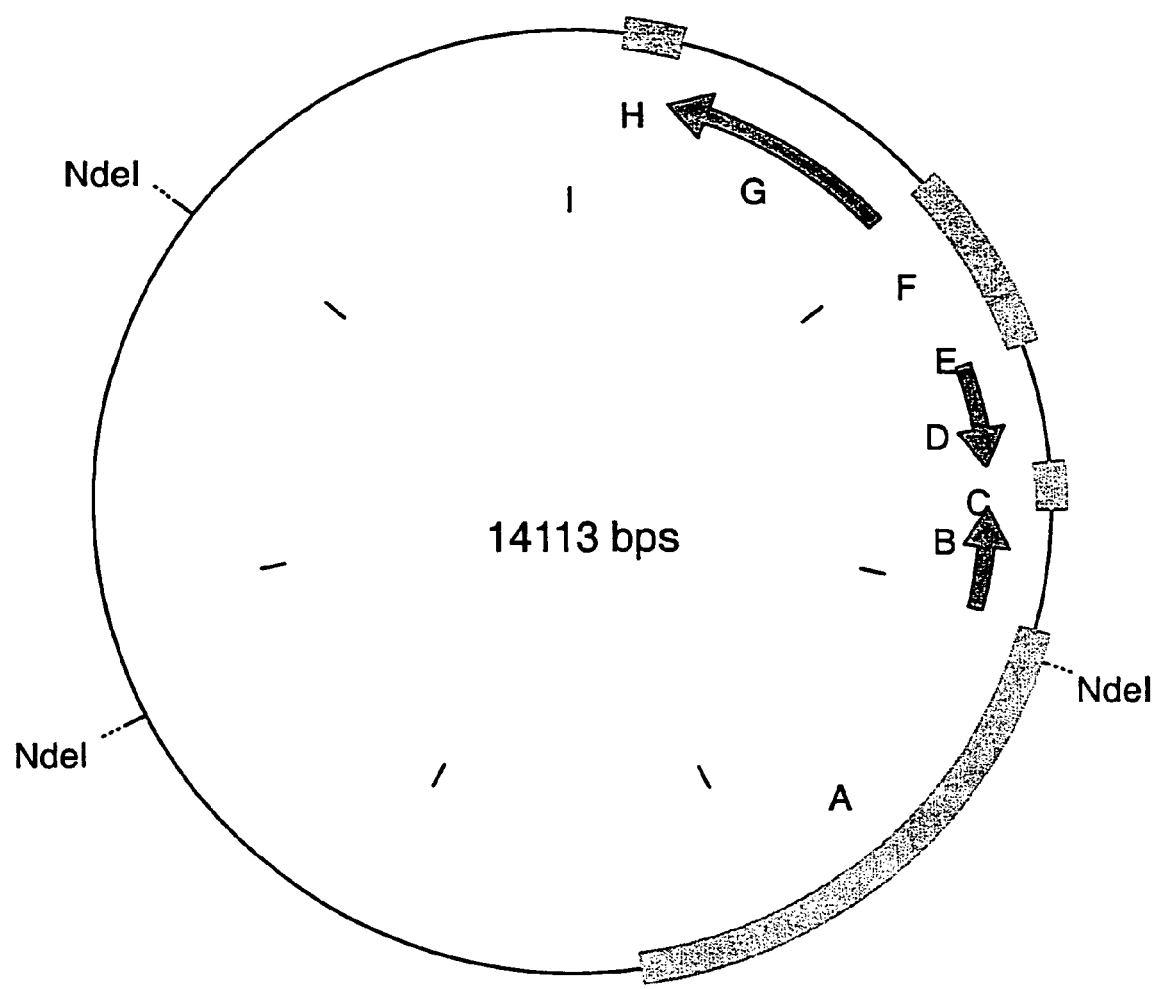
FIG. 16 shows the plasmid pSUN2-Pvic-*BnHGD-STLS1-α*BnHGD-ocsT-USPP-AtTATase5-nosT.

Fragment A (2559 bp) in FIG. 16 comprises the promoter of the Vicia faba vicilin gene, fragment B (580 bp) encodes a fragment of the Brassica napus homogentisate dioxygenase gene. Fragment C (190 bp) encodes the intron 2 (IV2) of the Solanum tuberosum ST-LS1 gene. Fragment D is identical with fragment B, but has the opposite orientation in the vector relative to B. Fragment E (208 bp) encodes the termination signal 2 of the octopine gene. Fragment F (678 bp) comprises the promoter of the Vicia faba "unknown seed protein" gene, fragment G (1389 bp) encodes the Arabidopsis thaliana tyrosine aminotransferase gene 5 and fragment H (272 bp) encodes the termination signal of the nopaline synthase gene.

Example 29

Generation of DNA constructs for expressing the Arabidopsis thaliana tyrosine aminotransferase 6 under the control of a seed-specific promoter and for the seed-specific suppression of the expression of the Brassica napus homogentisate dioxygenase gene To prepare chimeric DNA constructs for generating transgenic Brassica napus plants which express the Arabidopsis thaliana tyrosine aminotransferase 6 under the control of a seed-specific promoter, and which suppress the expression of the endogenous Brassica napus homogentisate dioxygenase gene in a seed-specific fashion, the vector pSUN2-USPP-AtTATase6-nosT and the vector pSUN2-Pvic-*BnHGD-STLS1-α*BnHGD-ocsT were combined with each other.

The DNA fragment encoding the expression cassette consisting of: SP promoter, Arabidopsis thaliana tyrosine aminotransferase 6 gene and nos terminator was isolated as SmaI/EcoRI fragment from the plasmid pSUN2-USPP-AtTATase6-nosT, the EcoRI end was filled in with Klenow enzyme, and the construct was cloned into the vector pSUN2-Pvic-*BnHGD-STLS1-α*BnHGD-ocsT which had been digested with EcoRV.

This plasmid (pSUN2-Pvic-*BnHGD-STLS1-α*BnHGD-ocsT/USPP-AtTATase6-nosT, FIG. 17) is used for generating transgenic Brassica napus plants.

Figure 17:
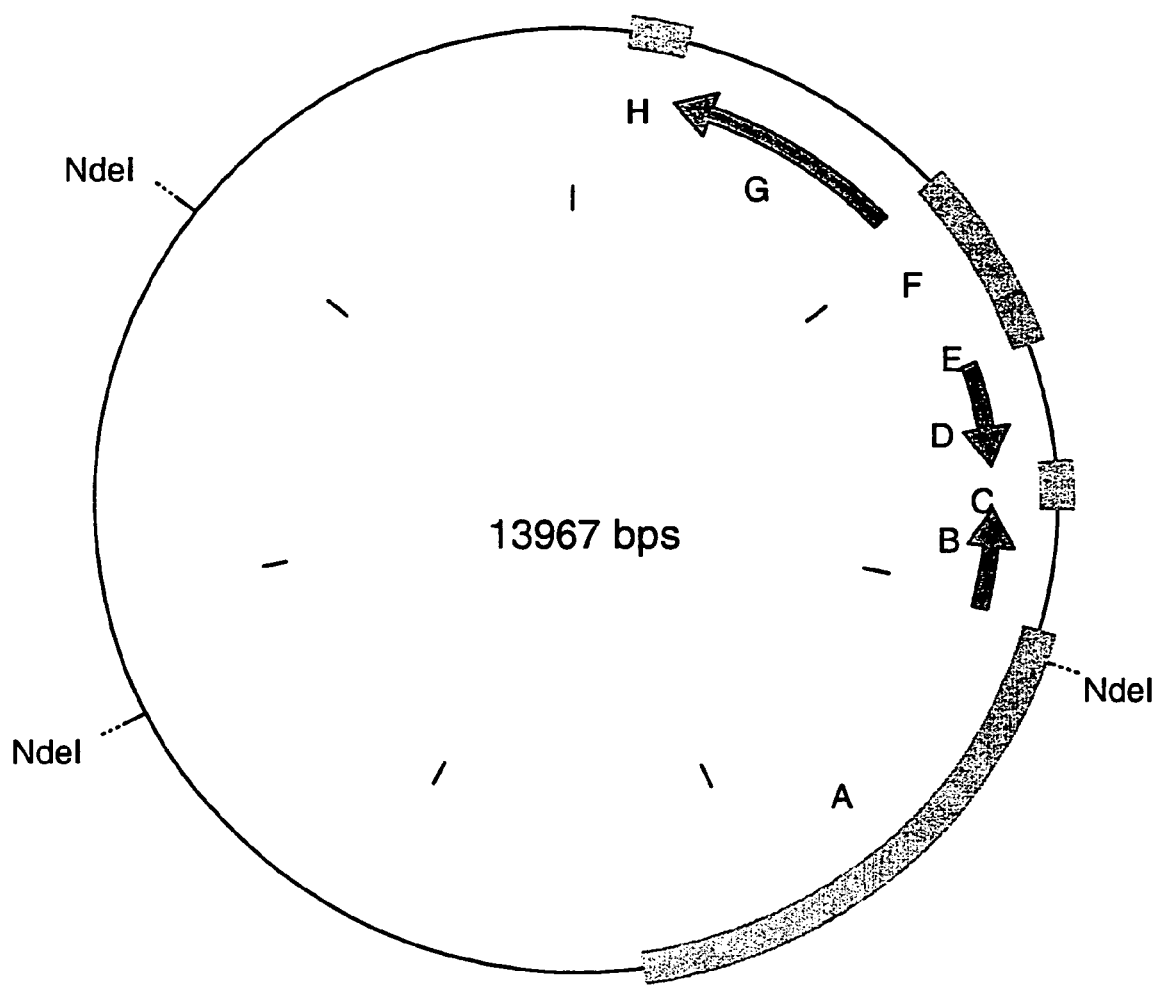
FIG. 17 shows the plasmid pSUN2-Pvic-*BnHGD-STLS1-α*BnHGD-ocsT-USPP-AtTATase6-nosT.

Fragment A (2559 bp) in FIG. 17 comprises the promoter of the Vicia faba vicilin gene, fragment B (580 bp) encodes a fragment of the Brassica napus homogentisate dioxygenase gene. Fragment C (190 bp) encodes the intron 2 (IV2) of the Solanum tuberosum ST-LS1 gene. Fragment D is identical with fragment B, but has the opposite orientation in the vector relative to B. Fragment E (208 bp) encodes the termination signal 2 of the octopine gene. Fragment F (678 bp) comprises the promoter of the Vicia faba "unknown seed protein" gene, fragment G (1243 bp) encodes the Arabidopsis thaliana tyrosine aminotransferase gene 6 and fragment H (272 bp) encodes the termination signal of the nopaline synthase gene.

Example 30

Generation of DNA constructs for expressing the Rattus norvegicus tyrosine aminotransferase under the control of a seed-specific promoter and the Nicotiana tabacum geranylgeranyl-pyrophosphate oxidoreductase under the control of a seed-specific promoter To prepare chimeric DNA constructs for generating transgenic Brassica napus plants which encode the Rattus norvegicus tyrosine aminotransferase under the control of a seed-specific promoter and which express the Nicotiana tabacum geranylgeranyl-pyrophosphate oxidoreductase in a seed-specific fashion, the vectors pSUN2-LEB4-NtGGP-POR-nosT and pCR4topoblunt-USPP-rbcS-RnTATase1-nosT are combined with each other.

The DNA fragment consisting of USP promoter, Rattus norvegicus tyrosine aminotransferase and nos termination sequence is isolated as SrfI fragment from the plasmid pCR4TOPOblunt/USPP-rbcS-RnTATase1-nosT and cloned into the XhoI-digested vector pSUN2-LeB4-NtGGPPOR-nosT whose XhoI ends had previously been made blunt-ended with Klenow enzyme.

This plasmid (pSUN2-LeB4-NtGGPPORnosT/USPP-rbcS-RnTATase1-nosT, FIG. 18) is used for generating transgenic Brassica napus plants.

Figure 18:
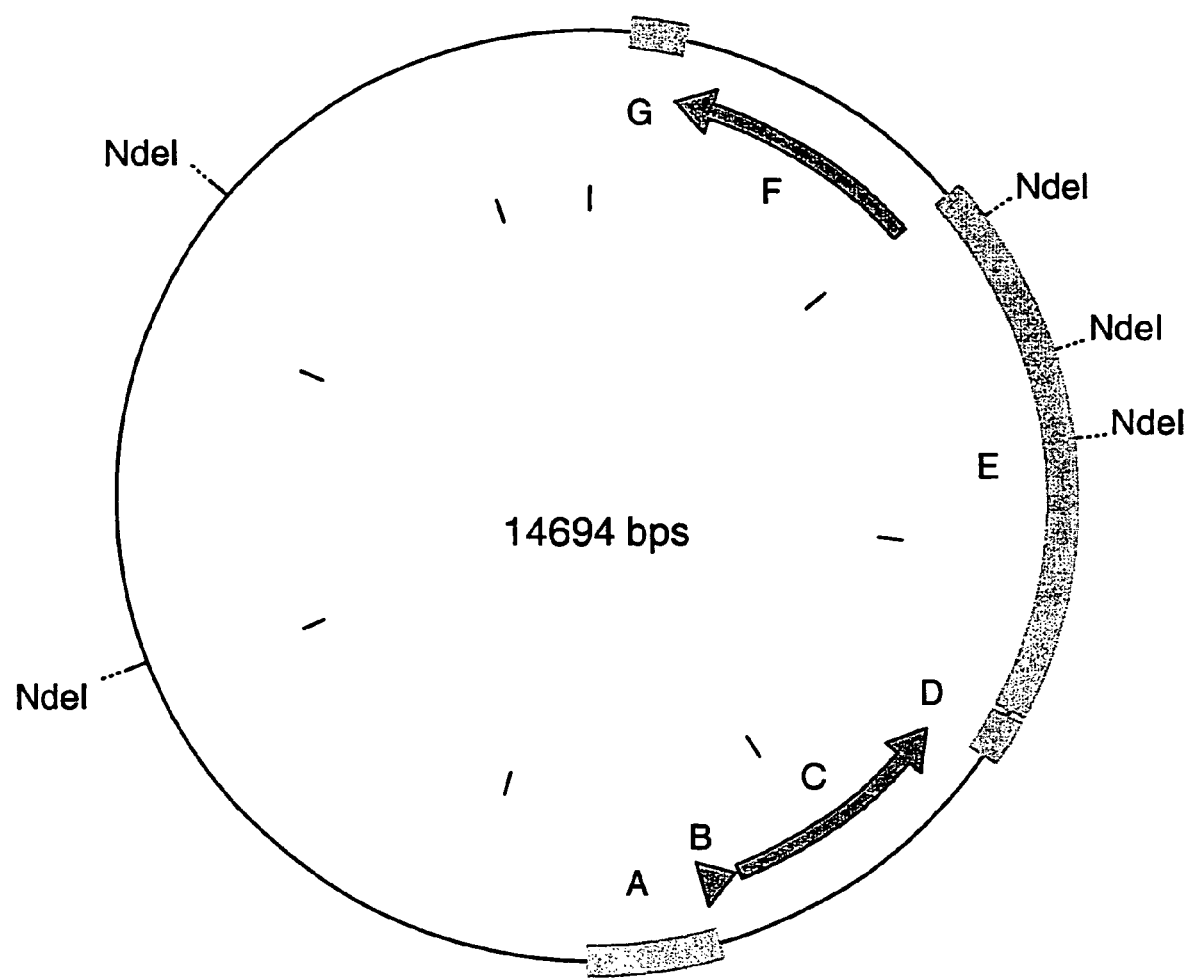
FIG. 18 shows the plasmid pSUN2-LeB4-NtGGPPOR-nosT-USPP-rbcS-RnTATase1-nosT.

Fragment A (678 bp) in FIG. 18 comprises the promoter of the Vicia faba unknown seed protein gene (USPP), fragment B (235 bp) encodes the transit peptide of the Vicia faba ribulose-bisphosphate carboxylase (rbcS). Fragment C (1365 bp) encodes the Rattus norvegicus tyrosine aminotransferase gene. Fragment D (272 bp) encodes the termination signal of the A. tumefaciens nopaline synthase gene. Fragment E (2764 bp) comprises the promoter of the

*Vicia faba* legumin B4 gene, fragment F (1509 bp) encodes the *Nicotiana tabacum* geranylgeranyl-pyrophosphate oxidoreductase gene. Fragment G (272 bp) encodes the termination signal of the nopaline synthase gene.

Example 31

Generation of DNA constructs for expressing the *Arabidopsis thaliana* tyrosine aminotransferase 1 under the control of a seed-specific promoter and the *Nicotiana tabacum* geranylgeranyl-pyrophosphate oxidoreductase under the control of a seed-specific promoter To prepare chimeric DNA constructs for generating transgenic *Brassica napus* plants which express the *Arabidopsis thaliana* tyrosine aminotransferase 1 under the control of a seed-specific promoter and which express the *Nicotiana tabacum* geranylgeranyl-pyrophosphate oxidoreductase in a seed-specific fashion, the vectors pSUN2-LeB4-NtGGP-POR-nosT and pSUN2-USPP-AtTATase1-nosT were combined with each other.

The DNA fragment encoding the expression cassette consisting of: USP promoter, *Arabidopsis thaliana* tyrosine aminotransferase 1 gene and nos terminator is isolated as SmaI/EcoRI fragment from the plasmid pSUN2-USPP-AtTATase1-nosT, the EcoRI end is filled in with Klenow enzyme, and the construct is cloned into the XhoI-digested vector pSUN2-LeB4-NtGGPPOR-nosT whose XhoI ends have previously been made blunt-ended with Klenow enzyme.

Figure 19:
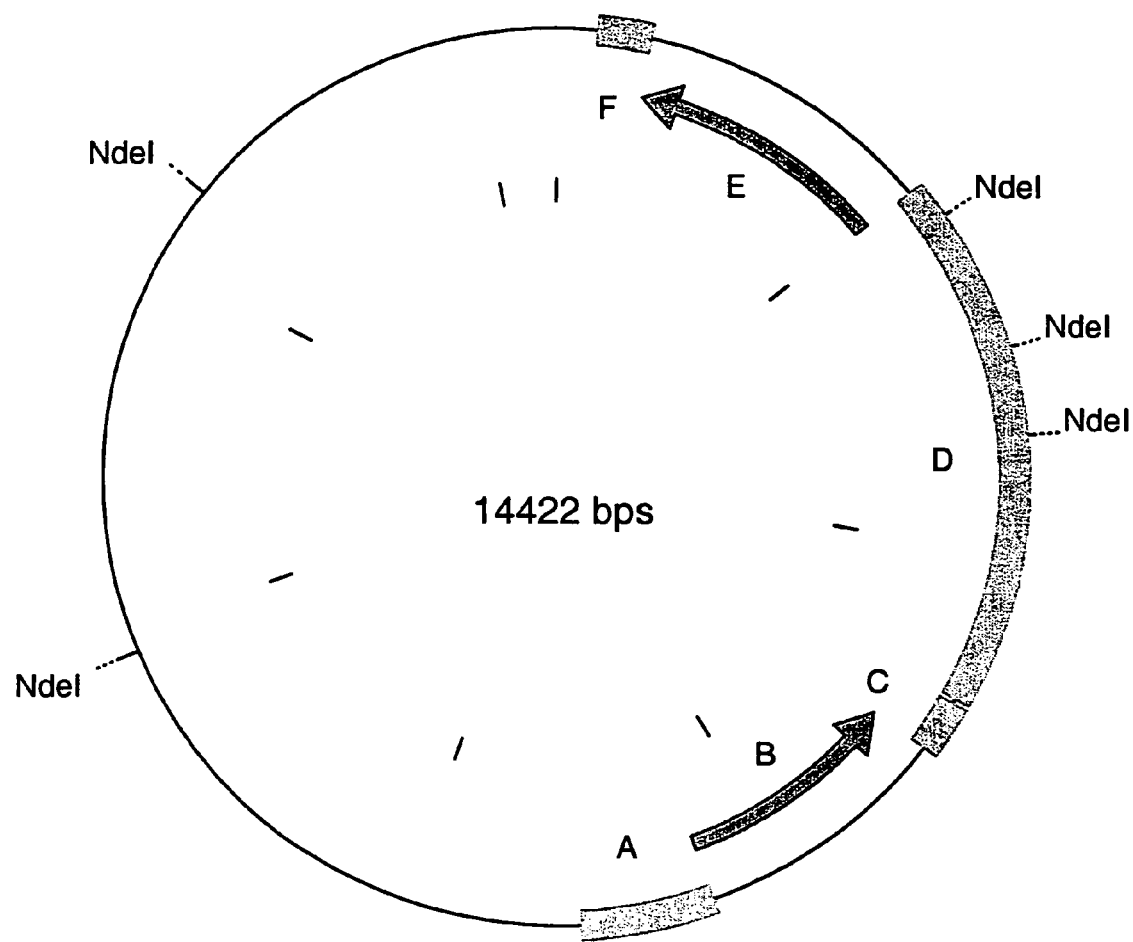
FIG. 19 shows the plasmid pSUN2-LeB4-NtGGPPOR-nosT-USPP-AtTATase1-nosT.

This plasmid (pSUN2-LeB4-NtGGPPOR-nosT/USPP-AtTATase1-nosT, FIG. 19) is used for generating transgenic *Brassica napus* plants.

Fragment A. (678 bp) in FIG. 19 comprises the promoter of the *Vicia faba* unknown seed protein gene (USPP), fragment B (1269 bp) encodes the *Arabidopsis thaliana* tyrosine aminotransferase gene 1 and fragment C (272 bp) encodes the termination signal of the nopaline synthase gene. Fragment D (2764 bp) comprises the promoter of the *Vicia faba* legumin B4 gene, fragment E (1509 bp) encodes the *Nicotiana tabacum* geranylgeranyl-pyrophosphate oxidoreductase gene. Fragment F (272 bp) encodes the termination signal of the nopaline synthase gene.

Example 32

Generation of DNA constructs for expressing the *Arabidopsis thaliana* tyrosine aminotransferase 3 under the control of a seed-specific promoter and the *Nicotiana tabacum* geranylgeranyl-pyrophosphate oxidoreductase under the control of a seed-specific promoter To prepare chimeric DNA constructs for generating transgenic *Brassica napus* plants which express the *Arabidopsis thaliana* tyrosine aminotransferase 3 under the control of a seed-specific promoter and which express the *Nicotiana tabacum* geranylgeranyl-pyrophosphate oxidoreductase in a seed-specific fashion, the vectors pSUN2-LeB4-NtGGP-POR-nosT and pSUN2-USPP-AtTATase3-nosT were combined with each other.

The DNA fragment encoding the expression cassette consisting of: USP promoter, *Arabidopsis thaliana* tyrosine aminotransferase 3 gene and nos terminator is isolated as SmaI/EcoRI fragment from the plasmid pSUN2-USPP-AtTATase3-nosT, the EcoRI end is filled in with Klenow enzyme, and the construct is cloned into the XhoI-digested vector pSUN2-LeB4-NtGGPPOR-nosT whose XhoI-ends have previously been made blunt-ended with Klenow enzyme.

This plasmid (pSUN2-LeB4-NtGGPPORnosT/USPP-AtTATase3-nosT, FIG. 20) is used for generating transgenic *Brassica napus* plants.

Figure 20:
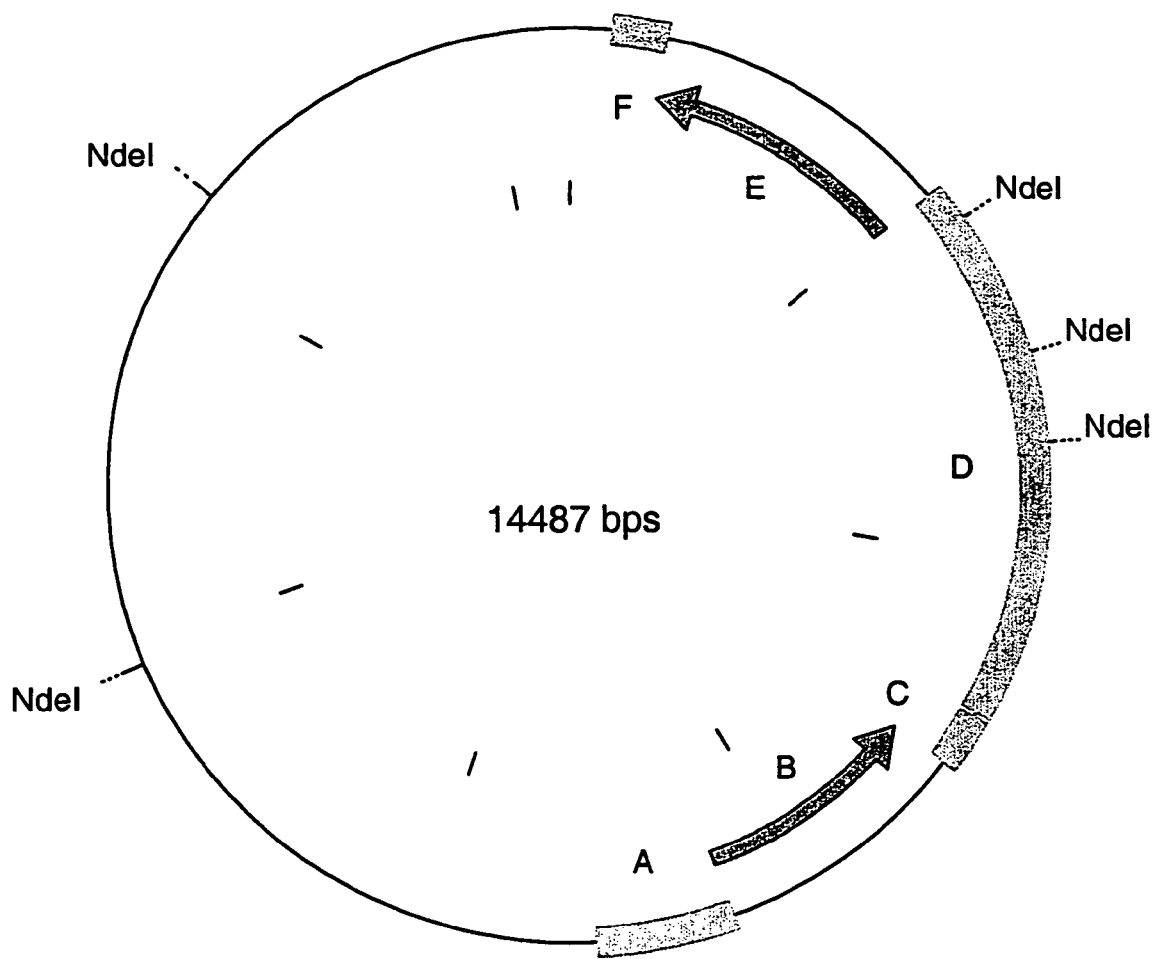
FIG. 20 shows the plasmid pSUN2-LeB4-NtGGPPOR-nosT-USPP-AtTATase3-nosT.

Fragment A (678 bp) in FIG. 20 comprises the promoter of the *Vicia faba* "unknown seed protein gene" (USPP), fragment B (1334 bp) encodes the *Arabidopsis thaliana* tyrosine aminotransferase gene 3 and fragment C (272 bp) encodes the termination signal of the nopaline synthase gene. Fragment D (2764 bp) comprises the promoter of the *Vicia faba* legumin B4 gene, fragment E (1509 bp) encodes the *Nicotiana tabacum* geranylgeranyl-pyrophosphate oxidoreductase gene. Fragment F (272 bp) encodes the termination signal of the nopaline synthase gene.

Example 33

Generation of DNA constructs for expressing the *Arabidopsis thaliana* tyrosine aminotransferase 5 under the control of a seed-specific promoter and the *Nicotiana tabacum* geranylgeranyl-pyrophosphate oxidoreductase under the control of a seed-specific promoter To prepare chimeric DNA constructs for generating transgenic *Brassica napus* plants which express the *Arabidopsis thaliana* tyrosine aminotransferase 5 under the control of a seed-specific promoter and which express the *Nicotiana tabacum* geranylgeranyl-pyrophosphate oxidoreductase in a seed-specific fashion, the vectors pSUN2-LeB4-NtGGP-POR-nosT and pSUN2-USPP-AtTATase5-nosT are combined with each other.

The DNA fragment encoding the expression cassette consisting of: USP promoter, *Arabidopsis thaliana* tyrosine aminotransferase 5 gene and nos terminator is isolated as SmaI/EcoRI fragment from the plasmid pSUN2-USPP-AtTATase5-nosT, the EcoRI end is filled in with Klenow enzyme, and the construct is cloned into the XhoI-digested vector pSUN2-LeB4-NtGGPPOR-nosT whose XhoI ends have previously been made blunt-ended with Klenow enzyme.

This plasmid (pSUN2-LeB4-NtGGPPORnosT/USPP-AtTATase5-nosT, FIG. 21) is used for generating transgenic *Brassica napus* plants.

Figure 21:
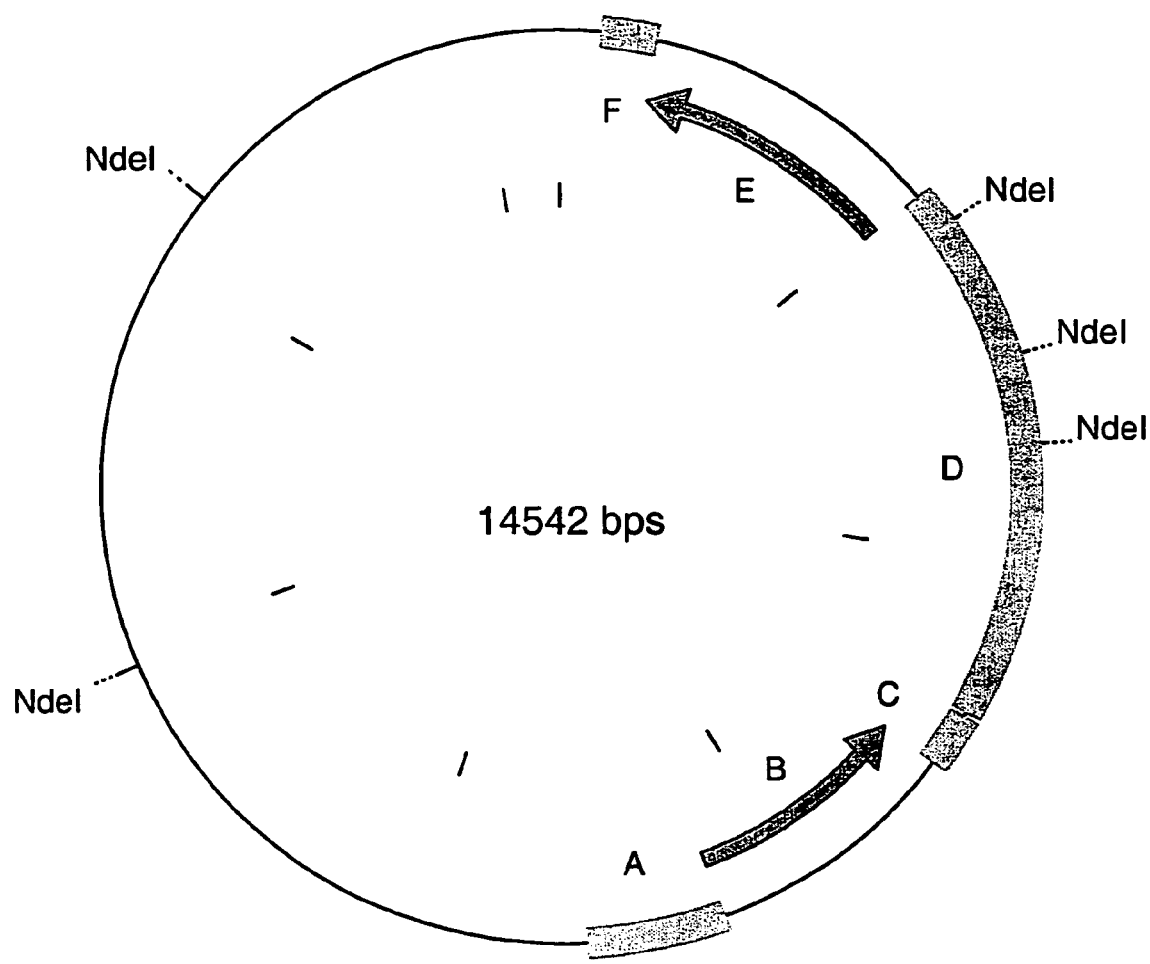
FIG. 21 shows the plasmid pSUN2-LeB4-NtGGPPOR-nosT-USPP-AtTATase5-nosT.

Fragment A (678 bp) in FIG. 21 comprises the promoter of the *Vicia faba* "unknown seed protein gene", fragment B (1389 bp) encodes the *Arabidopsis thaliana* tyrosine aminotransferase gene 5 and fragment C (272 bp) encodes the termination signal of the nopaline synthase gene. Fragment D (2764 bp) comprises the promoter of the *Vicia faba* legumin B4 gene, fragment E (1509 bp) encodes the *Nicotiana tabacum* geranylgeranyl-pyrophosphate oxidoreductase gene. Fragment F (272 bp) encodes the termination signal of the nopaline synthase gene.

Example 34

Generation of DNA constructs for expressing the *Arabidopsis thaliana* tyrosine aminotransferase 6 under the control of a seed-specific promoter and the *Nicotiana tabacum* geranylgeranyl-pyrophosphate oxidoreductase under the control of a seed-specific promoter To prepare chimeric DNA constructs for generating transgenic *Brassica napus* plants which express the *Arabidopsis thaliana* tyrosine aminotransferase 6 under the control of a seed-specific promoter and which express the *Nicotiana tabacum* geranylgeranyl-pyrophosphate oxidoreductase in a seed-specific fashion, the vectors pSUN2-LeB4-NtGGP-POR-nosT and pSUN2-USPP-AtTATase6-nosT are combined with each other.

The DNA fragment encoding the expression cassette consisting of: USP promoter, *Arabidopsis thaliana* tyrosine aminotransferase 6 gene and nos terminator is isolated as SmaI/EcoRI fragment from the plasmid pSUN2-USPP-AtTATase6-nosT, the EcoRI end is filled in with Klenow enzyme, and the construct is cloned into the XhoI-digested vector pSUN2-LeB4-NtGGPPOR-nosT whose XhoI ends have previously been made blunt-ended with Klenow enzyme.

This plasmid (pSUN2-LeB4-NtGGPPORnosT/USPP-AtTATase6-nosT, FIG. 22) is used for generating transgenic *Brassica napus* plants.

Figure 22:
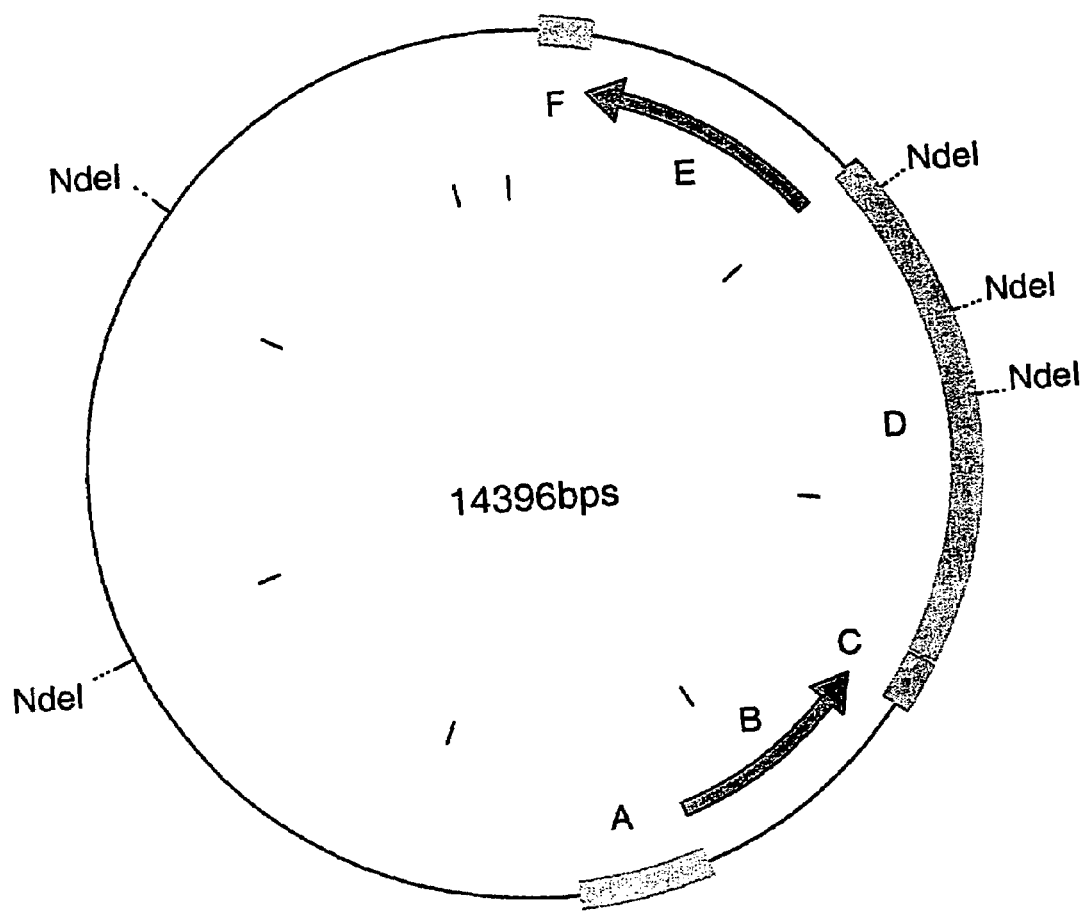
FIG. 22 shows the plasmid pSUN2-LeB4-NtGGPPOR-nosT-USPP-AtTATase6-nosT.

Fragment A (678 bp) in FIG. 22 comprises the promoter of the *Vicia faba* "unknown seed protein gene", fragment B (1243 bp) encodes the *Arabidopsis thaliana* tyrosine aminotransferase gene 6 and fragment C (272 bp) encodes the termination signal of the nopaline synthase gene. Fragment D (2764 bp) comprises the promoter of the *Vicia faba* legumin B4 gene, fragment E (1509 bp) encodes the *Nicotiana tabacum* geranylgeranyl-pyrophosphate oxidoreductase gene. Fragment F (272 bp) encodes the termination signal of the nopaline synthase gene.

Example 35

Generation of DNA constructs for expressing the *Rattus norvegicus* tyrosine aminotransferase under the control of a seed-specific promoter and the *Arabidopsis thaliana* hydroxyphenylpyruvate dioxygenase under the control of a seed-specific promoter To prepare chimeric DNA constructs for the generation of transgenic *Brassica napus* plants which express the *Rattus norvegicus* tyrosine aminotransferase under the control of a seed-specific promoter and which express the *Arabidopsis thaliana* hydroxyphenylpyruvate dioxygenase in a seed-specific fashion, the vectors pSUN2-USPP-AtHPPD-ocsT and pCR4topoblunt-USPP-rbcS-RnTATase1-nosT are combined with each other.

The DNA fragment consisting of USP promoter, *Rattus norvegicus* tyrosine aminotransferase and nos termination sequence is isolated as SrfI fragment from the plasmid pCR4TOPOblunt/USPP-rbcS-RnTATase1-nosT and cloned into the SrfI-digested vector pSUN2-USPP-AtHPPD-ocsT.

This plasmid (pSUN2-USPP-AtHPPD-ocsT/USPP-rbcS-RnTATase1-nosT, FIG. 23) is used for generating transgenic *Brassica napus* plants.

Figure 23:
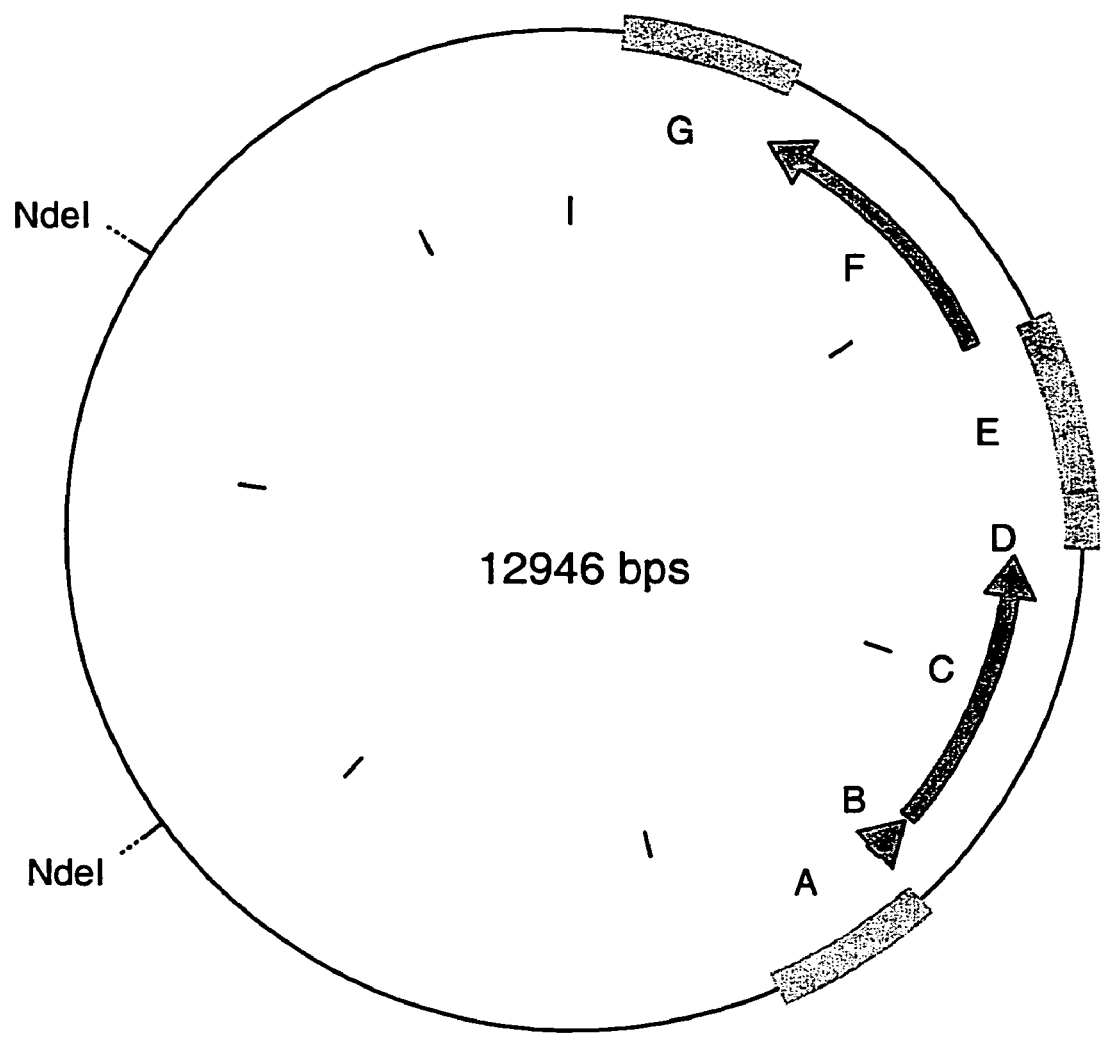
FIG. 23 shows the plasmid pSUN2-USPP-AtHPPD-ocsT-USPP-rbcS-RnTATase1-nosT.

Fragment A (678 bp) in FIG. 23 comprises the promoter of the *Vicia faba* unknown seed protein gene (USPP), fragment B (235 bp) encodes the transit peptide of the *Vicia faba* ribulose-bisphosphate carboxylase (rbcS). Fragment C (1365 bp) encodes the *Rattus norvegicus* tyrosine aminotransferase gene. Fragment D (272 bp) encodes the termination signal of the *A. tumefaciens* nopaline synthase gene. Fragment E (678 bp) comprises the promoter of the *Vicia faba* "unknown seed protein gene", fragment F (1338 bp) encodes the *Arabidopsis thaliana* hydroxyphenylpyruvate dioxygenase gene. Fragment G (713 bp) encodes the termination signal 1 of the octopine synthase gene.

Example 36

Generation of DNA constructs for expressing the *Arabidopsis thaliana* tyrosine aminotransferase 1 under the control of a seed-specific promoter and the *Arabidopsis thaliana* hydroxyphenylpyruvate dioxygenase under the control of a seed-specific promoter To prepare chimeric DNA constructs for generating transgenic *Brassica napus* plants which express the *Arabidopsis thaliana* tyrosine aminotransferase 1 under the control of a seed-specific promoter and which express the *Arabidopsis thaliana* hydroxyphenylpyruvate dioxygenase in a seed-specific manner, the vectors pSUN2-USPP-AtHPPD-ocsT and pSUN2-USPP-AtTATase1-nosT are combined with each other.

The DNA fragment encoding the expression cassette consisting of: USP promoter, *Arabidopsis thaliana* tyrosine aminotransferase 1 gene and nos terminator is isolated as SmaI/EcoRI fragment from the plasmid pSUN2-USPP-AtTATase1-nosT, the EcoRI end is filled up with Klenow enzyme, and the construct is cloned into the SrfI-digested vector pSUN2-USPP-AtHPPD-ocsT.

This plasmid (pSUN2-USPP-AtHPPD-ocsT/USPP-AtTATase1-nosT, FIG. 24) is used for generating transgenic *Brassica napus* plants.

Figure 24:
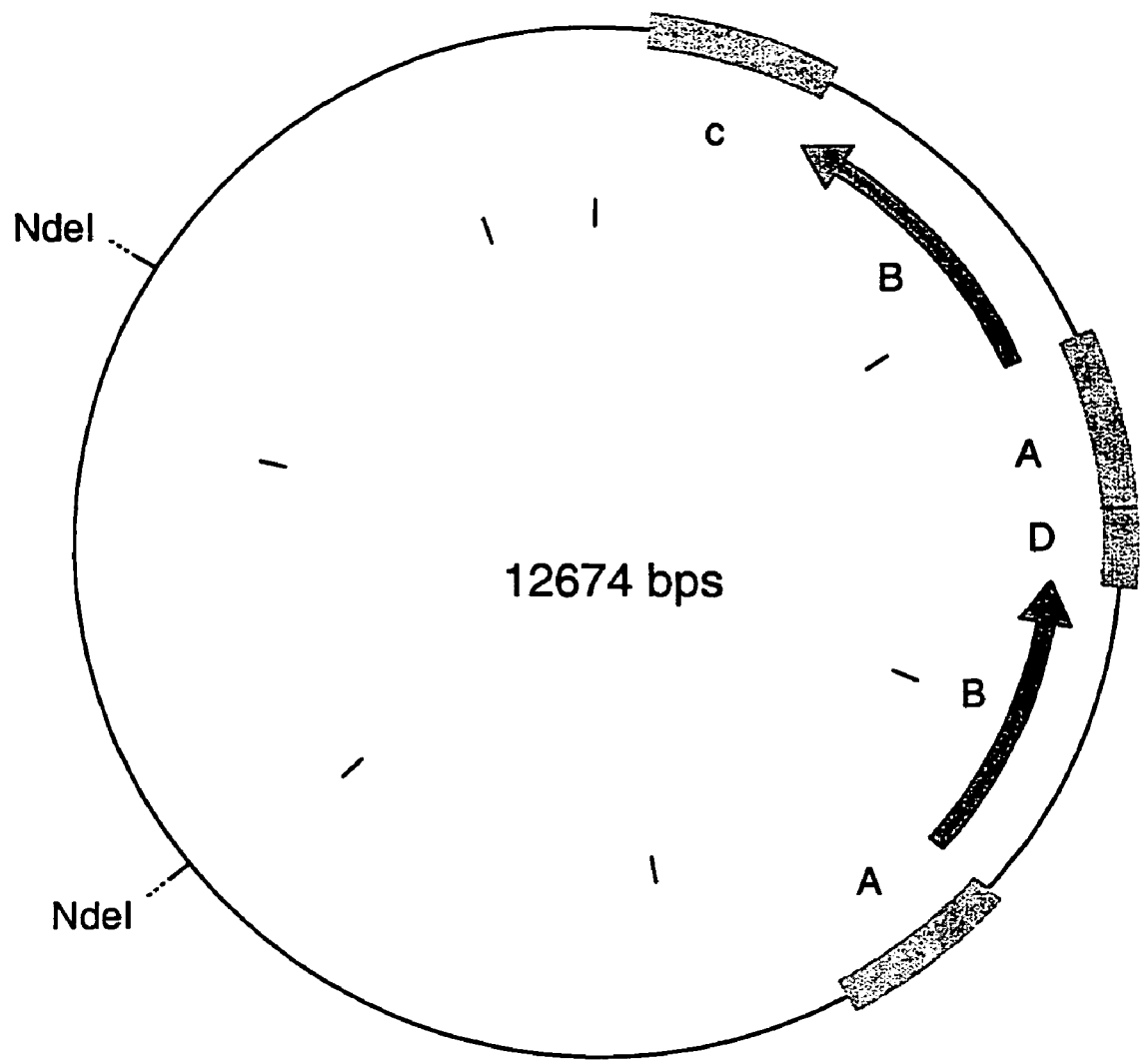
FIG. 24 shows the plasmid pSUN2-USPP-AtHPPD-ocsT-USPP-AtTATase1-nosT.

Fragment A (678 bp) in FIG. 24 comprises the promoter of the *Vicia faba* unknown seed protein gene (USPP), fragment B (1269 bp) encodes the *Arabidopsis thaliana* tyrosine aminotransferase gene 1 and fragment C (272 bp) encodes the termination signal of the nopaline synthase gene. Fragment D (678 bp) comprises the promoter of the *Vicia faba* "unknown seed protein gene", fragment E (1338 bp) encodes the *Arabidopsis thaliana* hydroxyphenylpyruvate dioxygenase gene. Fragment F (713 bp) encodes the termination signal 1 of the octopine synthase gene.

Example 37

Generation of DNA constructs for expressing the *Arabidopsis thaliana* tyrosine aminotransferase 3 under the control of a seed-specific promoter and the *Arabidopsis thaliana* hydroxyphenylpyruvate dioxygenase under the control of a seed-specific promoter To prepare chimeric DNA constructs for generating transgenic *Brassica napus* plants which express the *Arabidopsis thaliana* tyrosine aminotransferase 3 under the control of a seed-specific promoter and which express the *Arabidopsis thaliana* hydroxyphenylpyruvate dioxygenase in a seed-specific manner, the vectors pSUN2-USPP-AtHPPD-ocsT and pSUN2-USPP-AtTATase3-nosT are combined with each other.

The DNA fragment encoding the expression cassette consisting of: USP promoter, *Arabidopsis thaliana* tyrosine aminotransferase 3 gene and nos terminator is isolated as SmaI/EcoRI fragment from the plasmid pSUN2-USPP-AtTATase3-nosT, the EcoRI end is filled in with Klenow enzyme, and the construct is cloned into the SrfI-digested vector pSUN2-USPP-AtHPPD-ocsT.

This plasmid (pSUN2-USPP-AtHPPD-ocsT/USPP-AtTATase3-nosT, FIG. 25) is used for generating transgenic *Brassica napus* plants.

Figure 25:
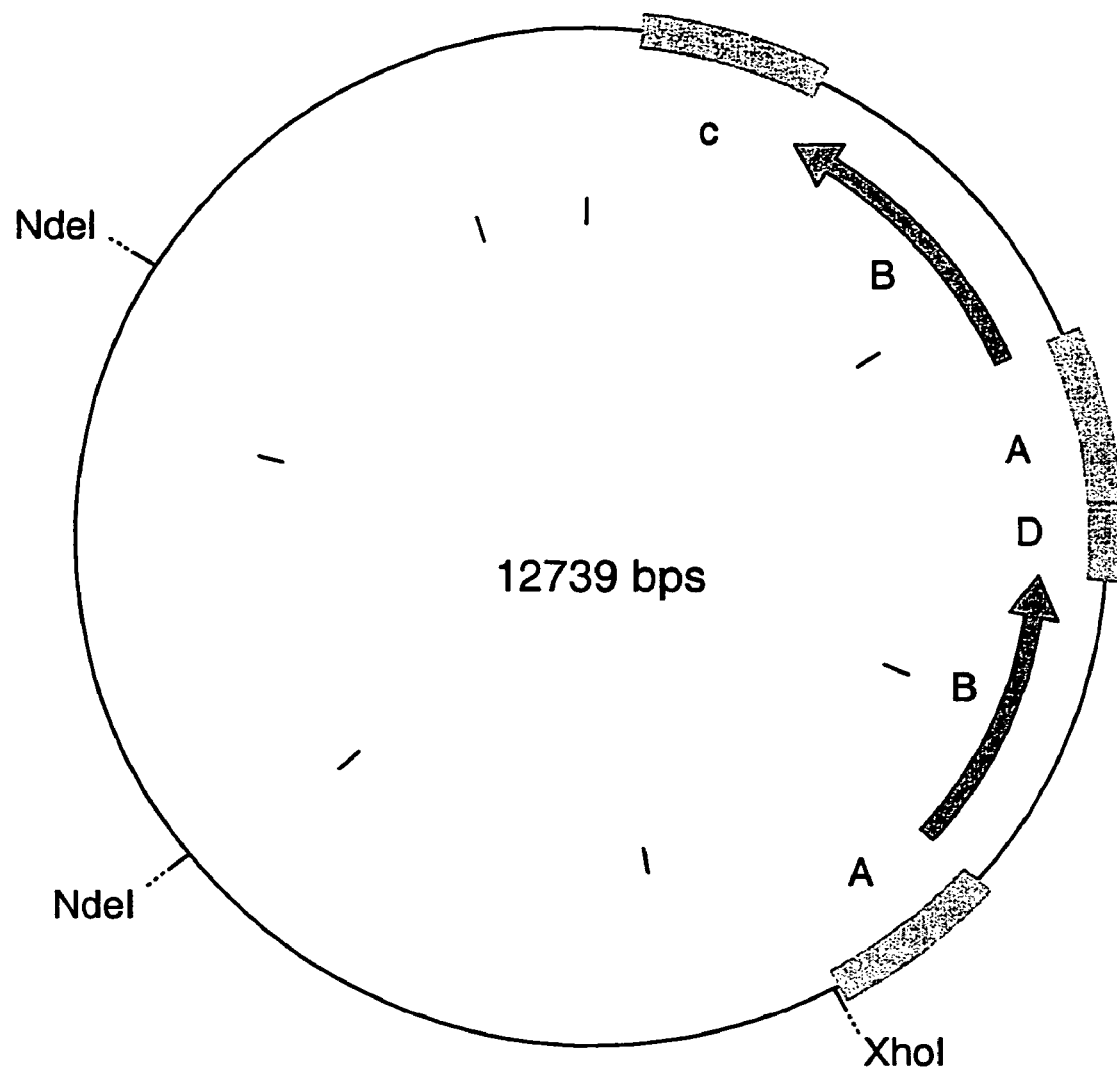
FIG. 25 shows the plasmid pSUN2-USPP-AtHPPD-ocsT-USPP-AtTATase3-nosT.

Fragment A (678 bp) in FIG. 25 comprises the promoter of the *Vicia faba* "unknown seed protein gene" (USPP), fragment B (1334 bp) encodes the *Arabidopsis thaliana* tyrosine aminotransferase gene 3 and fragment C (272 bp) encodes the termination signal of the nopaline synthase gene. Fragment D (678 bp) comprises the promoter of the *Vicia faba* "unknown seed protein gene", fragment E (1338 bp) encodes the *Arabidopsis thaliana* hydroxyphenylpyruvate dioxygenase gene. Fragment F (713 bp) encodes the termination signal 1 of the octopine synthase gene.

Example 38

Generation of DNA constructs for expressing the *Arabidopsis thaliana* tyrosine aminotransferase 5 under the control of a seed-specific promoter and the *Arabidopsis thaliana* hydroxyphenylpyruvate dioxygenase under the control of a seed-specific promoter To prepare chimeric DNA constructs for generating transgenic *Brassica napus* plants which express the *Arabidopsis thaliana* tyrosine aminotransferase 5 under the control of a seed-specific promoter and which express the *Arabidopsis thaliana* hydroxyphenylpyruvate dioxygenase in a seed-specific manner, the vectors pSUN2-USPP-AtHPPD-ocsT and pSUN2-USPP-AtTATase5-nosT are combined with each other.

The DNA fragment encoding the expression cassette consisting of: USP promoter, *Arabidopsis thaliana* tyrosine aminotransferase 5 gene and nos terminator is isolated as SmaI/EcoRI fragment from the plasmid pSUN2-USPP-AtTATase5-nosT, the EcoRI end is filled in with Klenow enzyme, and the construct is cloned into the SrfI-digested vector pSUN2-SBPP-AtγTMT-35sT.

This plasmid (pSUN2-USPP-AtHPPD-ocsT/USPP-AtTATase5-nosT, FIG. 26) is used for generating transgenic *Brassica napus* plants.

Figure 26:
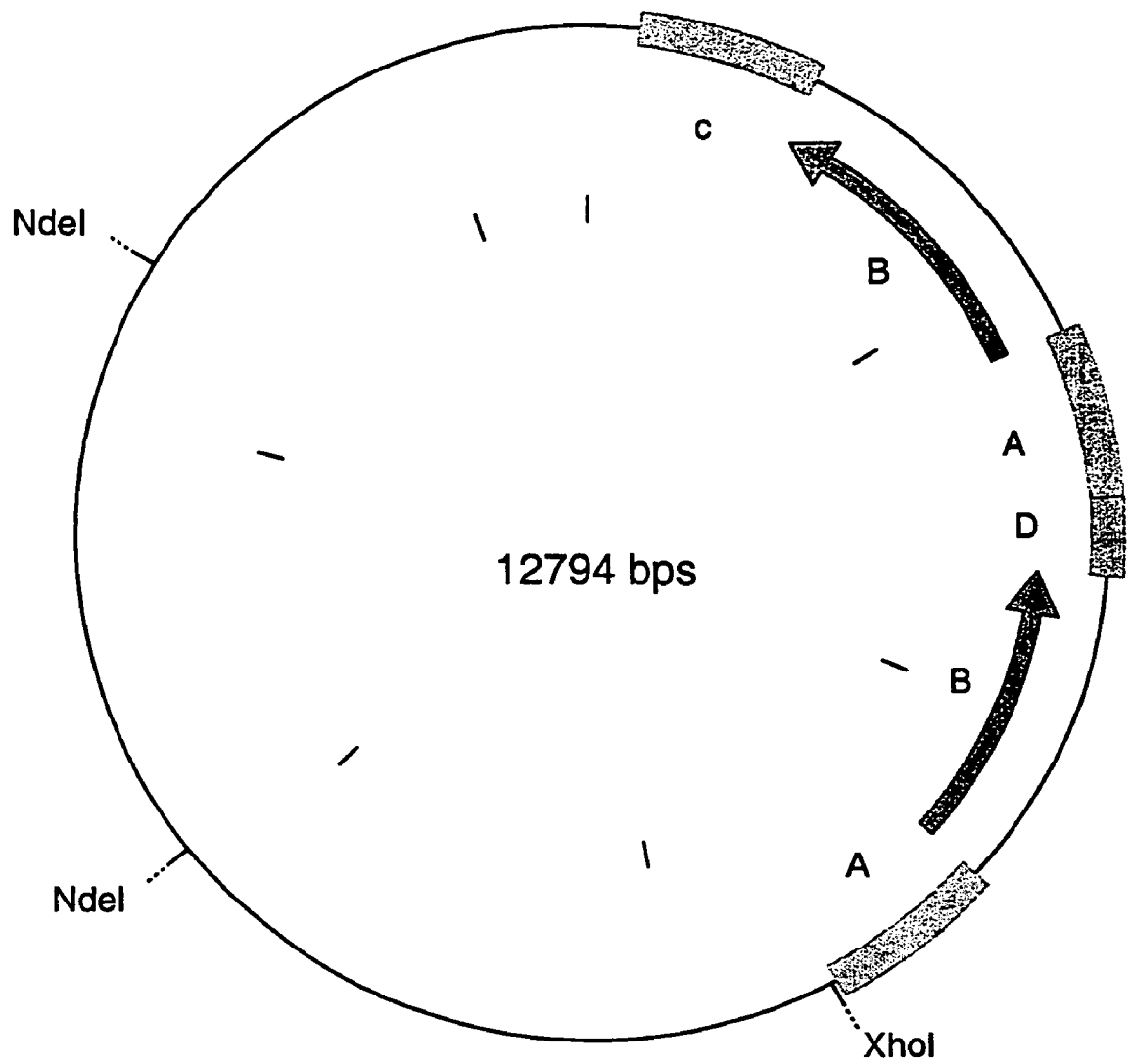
FIG. 26 shows the plasmid pSUN2-USPP-AtHPPD-ocsT-USPP-AtTATase5-nosT.

Fragment A (678 bp) in FIG. 26 comprises the promoter of the *Vicia faba* "unknown seed protein gene", fragment B (1389 bp) encodes the *Arabidopsis thaliana* tyrosine aminotransferase gene 5 and fragment C (272 bp) encodes the termination signal of the nopaline synthase gene. Fragment D (678 bp) comprises the promoter of the *Vicia faba* "unknown seed protein gene", fragment E (1338 bp) encodes the *Arabidopsis thaliana* hydroxyphenylpyruvate dioxygenase gene. Fragment F (713 bp) encodes the termination signal 1 of the octopine synthase gene.

Example 39

Generation of DNA constructs for expressing the *Arabidopsis thaliana* tyrosine aminotransferase 6 under the control of a seed-specific promoter and the *Arabidopsis thaliana* hydroxyphenylpyruvate dioxygenase under the control of a seed-specific promoter To prepare chimeric DNA constructs for generating transgenic *Brassica napus* plants which express the *Arabidopsis thaliana* tyrosine aminotransferase 6 under the control of a seed-specific promoter and which express the *Arabidopsis thaliana* hydroxyphenylpyruvate dioxygenase in a seed-specific fashion, the vectors pSUN2-USPP-AtHPPD-ocsT and pSUN2-USPP-AtTATase6-nosT are combined with each other.

The DNA fragment encoding the expression cassette consisting of: USP promoter, *Arabidopsis thaliana* tyrosine aminotransferase 6 gene and nos terminator is isolated as SmaI/EcoRI fragment from the plasmid pSUN2-USPP-AtTATase6-nosT, the EcoRI end is filled in with Klenow enzyme, and the construct is cloned into the SrfI-digested vector pSUN2-USPP-AtHPPD-ocsT.

This plasmid (pSUN2-USPP-AtHPPD-ocsT/USPP-AtTATase6-nosT, FIG. 27) is used for generating transgenic *Brassica napus* plants.

Figure 27:
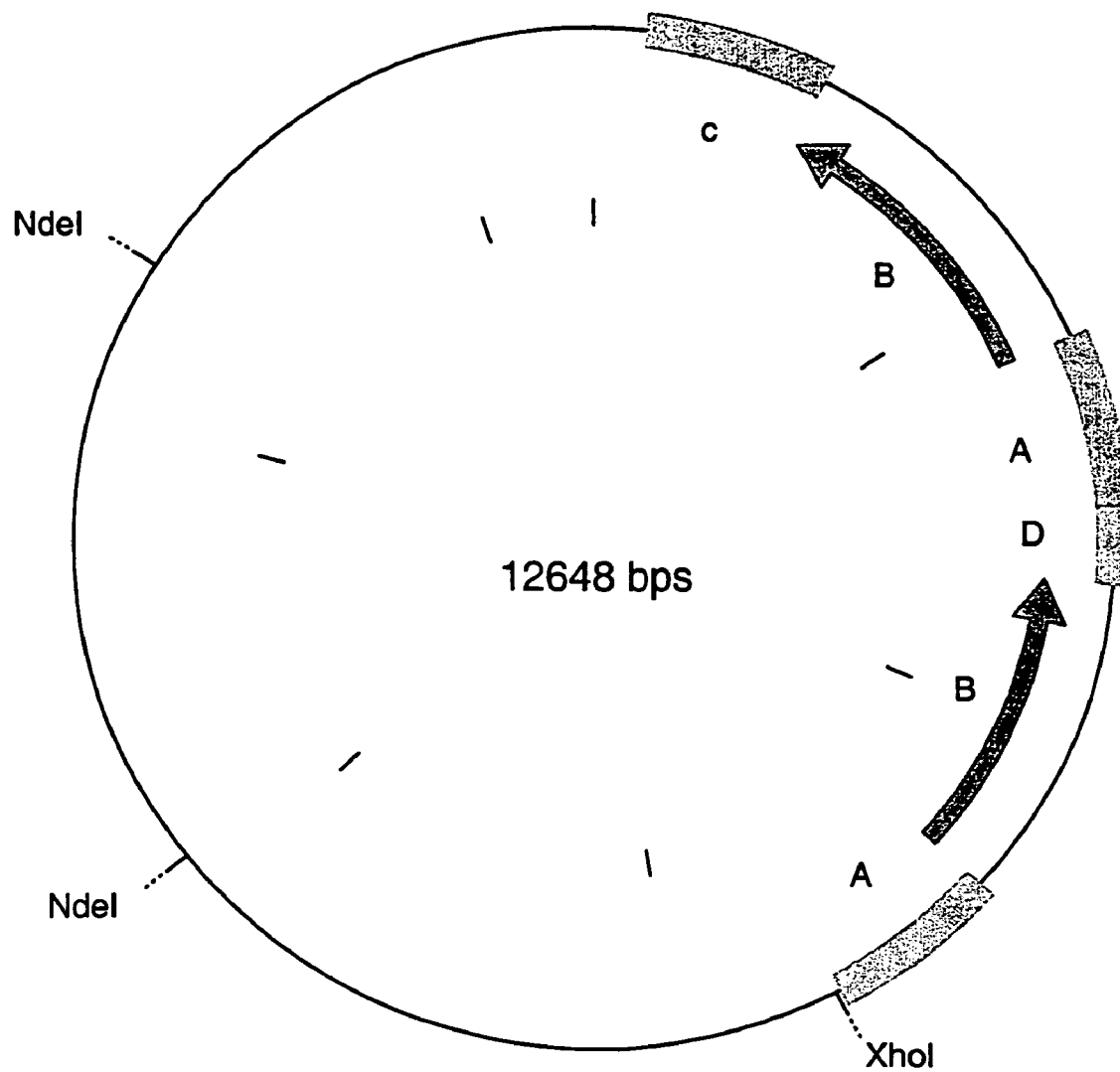
FIG. 27 shows the plasmid pSUN2-USPP-AtHPPD-ocsT-USPP-AtTATase6-nosT.

Fragment A (678 bp) in FIG. 27 comprises the promoter of the *Vicia faba* "unknown seed protein gene", fragment B (1243 bp) encodes the *Arabidopsis thaliana* tyrosine aminotransferase gene 6 and fragment C (272 bp) encodes the termination signal of the nopaline synthase gene. Fragment D (678 bp) comprises the promoter of the *Vicia faba* "unknown seed protein gene", fragment E (1338 bp) encodes the *Arabidopsis thaliana* hydroxyphenylpyruvate dioxygenase gene. Fragment F (713 bp) encodes the termination signal 1 of the octopine synthase gene.

Example 40

Generation of DNA constructs for expressing the *Rattus norvegicus* tyrosine aminotransferase under the control of a seed-specific promoter and the *Arabidopsis thaliana* homogentisate phytyltransferase under the control of a seed-specific promoter To prepare chimeric DNA constructs for generating transgenic *Brassica napus* plants which express the *Rattus norvegicus* tyrosine aminotransferase under the control of a seed-specific promoter and the *Arabidopsis thaliana* homogentisate phytyltransferase in a seed-specific manner, the vectors pSUN2-USPP-AtHPT-ocsT and pCR4topoblunt-USPP-rbcS-RnTATase1-nosT are combined with each other.

The DNA fragment consisting of USP promoter, *Rattus norvegicus* tyrosine aminotransferase and nos termination sequence is isolated as SrfI fragment from the plasmid pCR4TOPOblunt/USPP-rbcS-RnTATase1-nosT and the construct is cloned into the SrfI-digested vector pSUN2-USPP-AtHPT-ocsT.

This plasmid (pSUN2-USPP-AtHPT-ocsT/USPP-rbcS-RnTATase1-nosT, FIG. 28) is used for generating transgenic *Brassica napus* plants.

Figure 28:
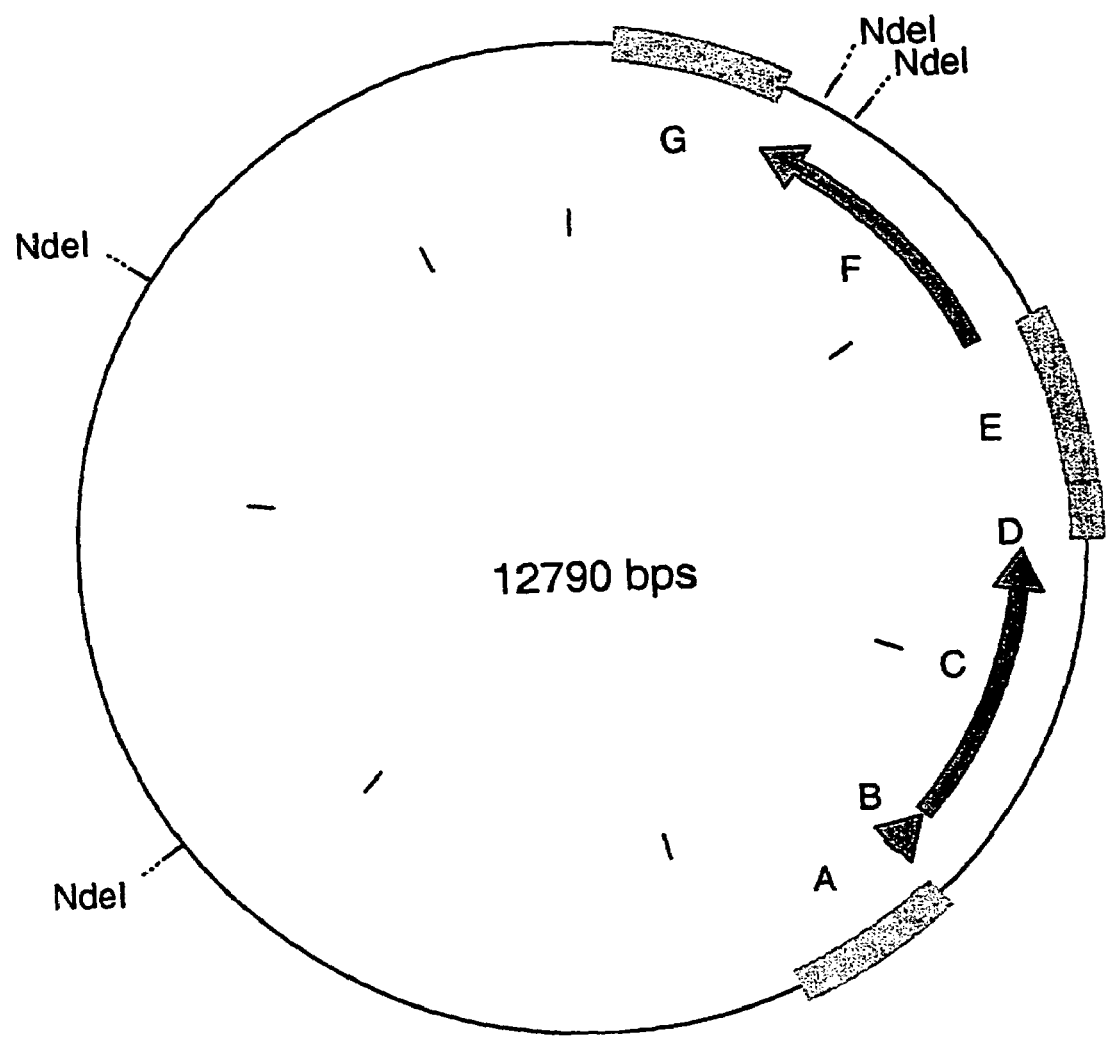
FIG. 28 shows the plasmid pSUN2-USPP-AtHPT-ocsT-USPP-rbcS-RnTATase1-nosT.

Fragment A (678 bp) in FIG. 28 comprises the promoter of the *Vicia faba* unknown seed protein gene (USPP), fragment B (235 bp) encodes the transit peptide of the *Vicia faba* ribulose-bisphosphate carboxylase (rbcS). Fragment C (1365 bp) encodes the *Rattus norvegicus* tyrosine aminotransferase gene. Fragment D (272 bp) encodes the termination signal of the *A. tumefaciens* nopaline synthase gene. Fragment E (678 bp) comprises the promoter of the *Vicia faba* "unknown seed protein gene", fragment F (1182 bp) encodes the *Arabidopsis thaliana* homogentisate phytyltransferase gene. Fragment G (713 bp) encodes the termination signal 1 of the octopine synthase gene.

Example 41

Generation of DNA constructs for expressing the *Arabidopsis thaliana* tyrosine aminotransferase 1 under the control of a seed-specific promoter and the *Arabidopsis thaliana* homogentisate phytyltransferase under the control of a seed-specific promoter To prepare chimeric DNA constructs for generating transgenic *Brassica napus* plants which express the *Arabidopsis thaliana* tyrosine aminotransferase 1 under the control of a seed-specific promoter and which express the *Arabidopsis thaliana* homogentisate phytyltransferase in a seed-specific manner, the vectors pSUN2-USPP-AtHPT-ocsT and pSUN2-USPP-AtTATase1-nosT are combined with each other.

The DNA fragment encoding the expression cassette consisting of: USP promoter, *Arabidopsis thaliana* tyrosine aminotransferase 1 gene and nos terminator is isolated as SmaI/EcoRI fragment from the plasmid pSUN2-USPP-AtTATase1-nosT, the EcoRI end is filled in with Klenow enzyme, and the construct is cloned into the SrfI-digested vector pSUN2-USPP-AtHPT-ocsT.

This plasmid (pSUN2-USPP-AtHPT-ocsT/USPP-AtTATase1-nosT, FIG. 29) is used for generating transgenic *Brassica napus* plants.

Figure 29:
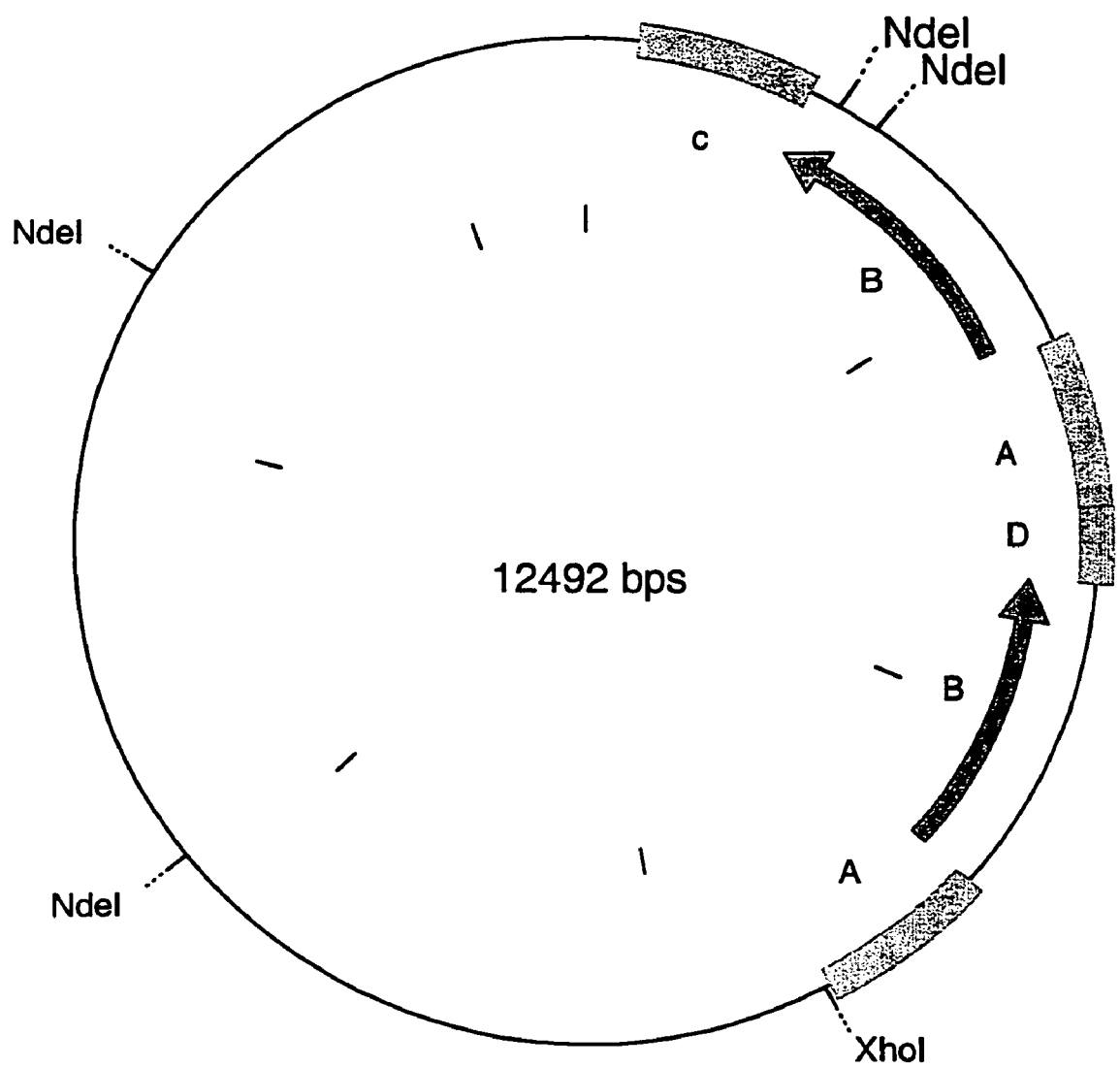
FIG. 29 shows the plasmid pSUN2-USPP-AtHPT-ocsT-USPP-AtTATase1-nosT.

Fragment A (678 bp) in FIG. 29 comprises the promoter of the *Vicia faba* unknown seed protein gene (USPP), fragment B (1269 bp) encodes the *Arabidopsis thaliana* tyrosine aminotransferase gene 1 and fragment C (272 bp) encodes the termination signal of the nopaline synthase gene. Fragment D (678 bp) comprises the promoter of the *Vicia faba* "unknown seed protein gene", fragment E (1182 bp) encodes the *Arabidopsis thaliana* homogentisate phytyltransferase gene. Fragment F (713 bp) encodes the termination signal 1 of the octopine synthase gene.

Example 42

Generation of DNA constructs for expressing the *Arabidopsis thaliana* tyrosine aminotransferase 3 under the control of a seed-specific promoter and the *Arabidopsis thaliana* homogentisate phytyltransferase under the control of a seed-specific promoter To prepare chimeric DNA constructs for generating transgenic *Brassica napus* plants which express the *Arabidopsis thaliana* tyrosine aminotransferase 3 under the control of a seed-specific promoter and which express the *Arabidopsis thaliana* homogentisate phytyltransferase in a seed-specific manner, the vectors pSUN2-USPP-AtHPT-ocsT and pSUN2-USPP-AtTATase3-nosT are combined with each other.

The DNA fragment encoding the expression cassette consisting of: USP promoter, *Arabidopsis thaliana* tyrosine aminotransferase 3 gene and nos terminator is isolated as SmaI/EcoRI fragment from the plasmid pSUN2-USPP-AtTATase3-nosT, the EcoRI end is filled in with Klenow enzyme, and the construct is cloned into the SrfI-digested vector pSUN2-USPP-AtHPT-ocsT.

This plasmid (pSUN2-USPP-AtHPT-ocsT/USPP-AtTATase3-nosT, FIG. 30) is used for generating transgenic *Brassica napus* plants.

Figure 30:
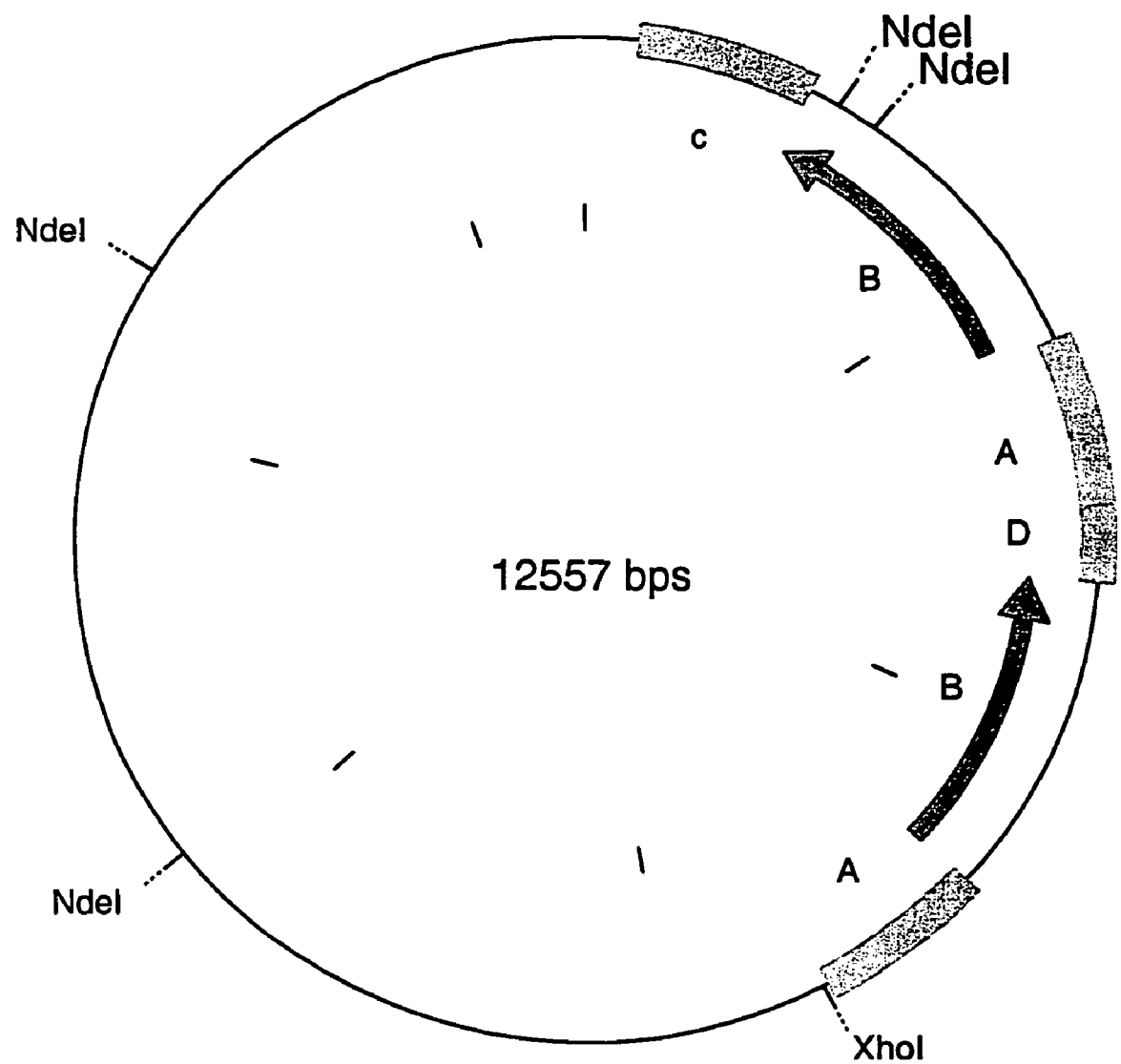
FIG. 30 shows the plasmid pSUN2-USPP-AtHPT-ocsT-USPP-AtTATase3-nosT.

Fragment A (678 bp) in FIG. 30 comprises the promoter of the *Vicia faba* "unknown seed protein gene" (USPP), fragment B (1334 bp) encodes the *Arabidopsis thaliana* tyrosine aminotransferase gene 3 and fragment C (272 bp) encodes the termination signal of the nopaline synthase gene. Fragment D (678 bp) comprises the promoter of the *Vicia faba* "unknown seed protein gene", fragment E (1182 bp) encodes the *Arabidopsis thaliana* homogentisate phytyltransferase gene. Fragment F (713 bp) encodes the termination signal 1 of the octopine synthase gene.

Example 43

Generation of DNA constructs for expressing the *Arabidopsis thaliana* tyrosine aminotransferase 5 under the control of a seed-specific promoter and the *Arabidopsis thaliana* homogentisate phytyltransferase under the control of a seed-specific promoter To prepare chimeric DNA constructs for generating transgenic *Brassica napus* plants which express the *Arabidopsis thaliana* tyrosine aminotransferase-5 under the control of a seed-specific promoter and which express the *Arabidopsis thaliana* homogentisate phytyltransferase in a seed-specific manner, the vectors pSUN2-USPP-AtHPT-ocsT and pSUN2-USPP-AtTATase5-nosT were combined with each other.

The DNA fragment encoding the expression cassette consisting of: USP promoter, *Arabidopsis thaliana* tyrosine aminotransferase 5 gene and nos terminator is isolated as SmaI/EcoRI fragment from the plasmid pSUN2-USPP-AtTATase5-nosT, the EcoRI end is filled in with Klenow enzyme, and the construct is cloned into the SrfI-digested vector pSUN2-USPP-AtHPT-ocsT.

This plasmid (pSUN2-USPP-AtHPT-ocsT/USPP-AtTATase5-nosT, FIG. 31) is used for generating transgenic *Brassica napus* plants.

Figure 31:
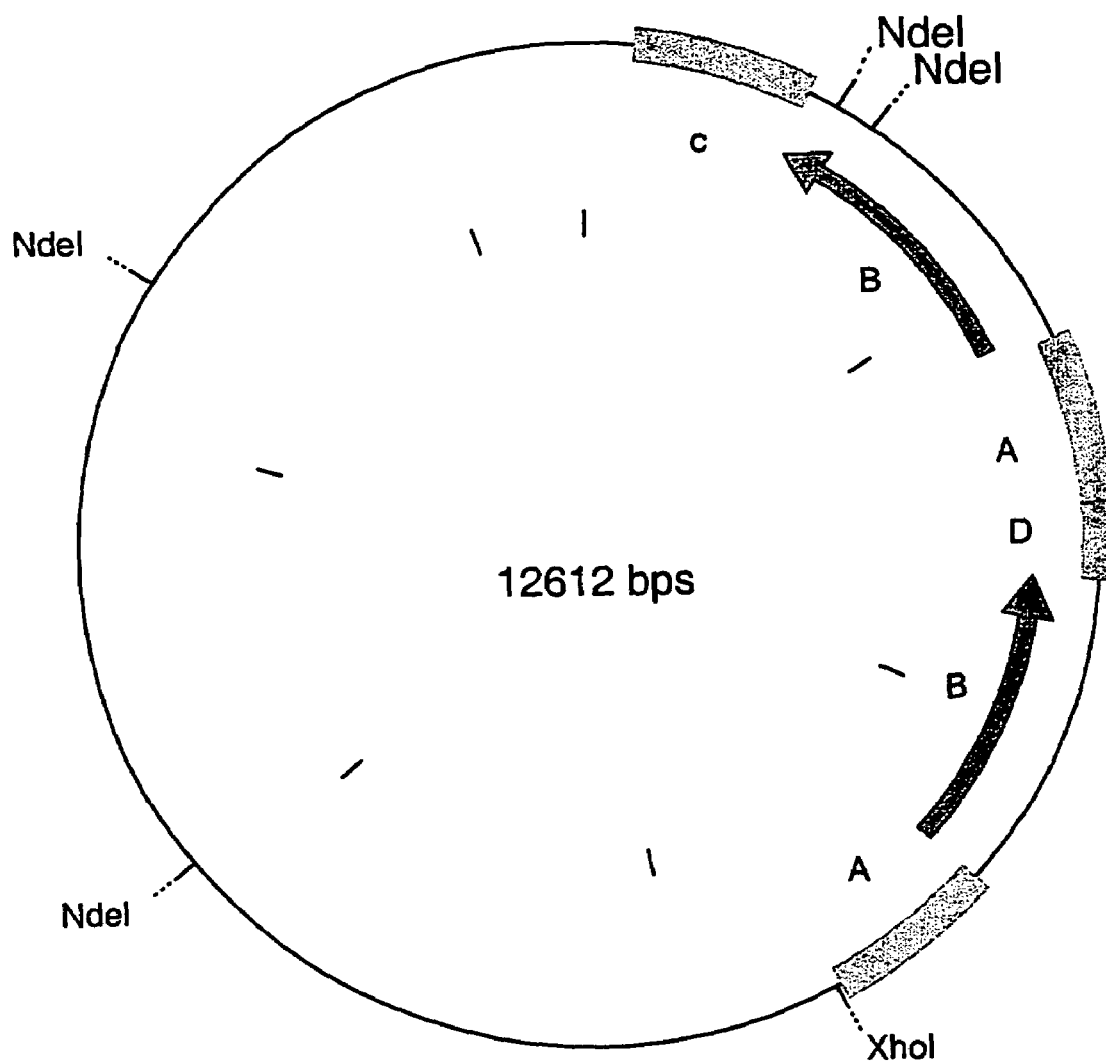
FIG. 31 shows the plasmid pSUN2-USPP-AtHPT-ocsT-USPP-AtTATase5-nosT.

Fragment A (678 bp) in FIG. 31 comprises the promoter of the *Vicia faba* "unknown seed protein gene", fragment B (1389 bp) encodes the *Arabidopsis thaliana* tyrosine aminotransferase gene 5 and fragment C (272 bp) encodes the termination signal of the nopaline synthase gene. Fragment D (678 bp) comprises the promoter of the *Vicia faba* "unknown seed protein gene", fragment E (1182 bp) encodes the *Arabidopsis thaliana* homogentisate phytyltransferase gene. Fragment F (713 bp) encodes the termination signal 1 of the octopine synthase gene.

Example 44

Generation of DNA constructs for expressing the *Arabidopsis thaliana* tyrosine aminotransferase 6 under the control of a seed-specific promoter and the *Arabidopsis thaliana* homogentisate phytyltransferase under the control of a seed-specific promoter To prepare chimeric DNA constructs for generating transgenic *Brassica napus* plants which express the *Arabidopsis thaliana* tyrosine aminotransferase 6 under the control of a seed-specific promoter and which express the *Arabidopsis thaliana* homogentisate phytyltransferase in a seed-specific manner, the vectors pSUN2-USPP-AtHPT-ocsT and pSUN2-USPP-AtTATase6-nosT were combined with each other.

The DNA fragment encoding the expression cassette consisting of: USP promoter, *Arabidopsis thaliana* tyrosine aminotransferase 6 gene and nos terminator is isolated as SmaI/EcoRI fragment from the plasmid pSUN2-USPP-AtTATase6-nosT, the EcoRI end is filled in with Klenow enzyme, and the construct is cloned into the SrfI-digested vector pSUN2-USPP-AtHPT-ocsT.

This plasmid (pSUN2-USPP-AtHPT-ocsT/USPP-AtTATase6-nosT, FIG. 32) is used for generating transgenic *Brassica napus* plants.

Figure 32:
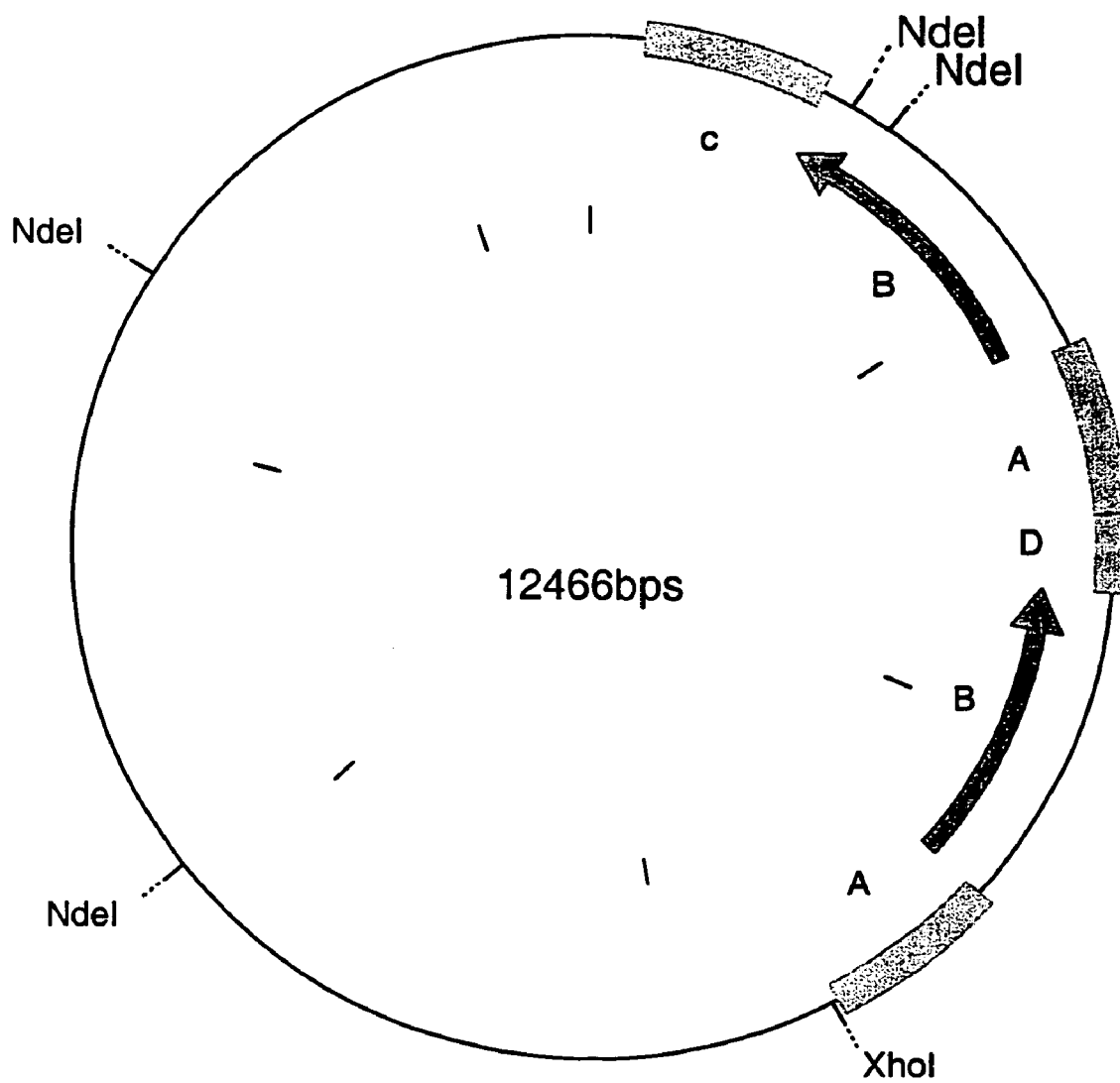
FIG. 32 shows the plasmid pSUN2-USPP-AtHPT-ocsT-USPP-AtTATase6-nosT.

Fragment A (678 bp) in FIG. 32 comprises the promoter of the *Vicia faba* "unknown seed protein gene", fragment B (1243 bp) encodes the *Arabidopsis thaliana* tyrosine aminotransferase gene 6 and fragment C (272 bp) encodes the termination signal of the nopaline synthase gene. Fragment D (678 bp) comprises the promoter of the *Vicia faba* "unknown seed protein gene", fragment E (1182 bp) encodes the *Arabidopsis thaliana* homogentisate phytyltransferase gene. Fragment F (713 bp) encodes the termination signal 1 of the octopine synthase gene.

Example 45

Generation of DNA constructs for expressing the *Rattus norvegicus* tyrosine aminotransferase under the control of a seed-specific promoter and *Synechocystis* sp. PCC6803 2-methyl-6-phytylhydroquinone Methyltransferase under the control of a seed-specific promoter To prepare chimeric DNA constructs for generating transgenic *Brassica napus* plants which express the *Rattus norvegicus* tyrosine aminotransferase under the control of a seed-specific promoter and the *Synechocystis* sp. PCC6803 2-methyl-6-phytylhydroquinone methyltransferase in a seed-specific manner, the vectors pSUN2-LeB4-IPP-SynMT1-nosT and pCR4topoblunt-USPP-rbcS-RnTATase1-nosT are combined with each other.

The DNA fragment consisting of USP promoter, *Rattus norvegicus* tyrosine aminotransferase and nos termination sequence is isolated as SrfI fragment from the plasmid pCR4TOPOblunt/USPP-rbcS-RnTATase1-nosT and cloned into the SrfI-digested vector pSUN2-LeB4-IPP-SynMT1-nosT.

This plasmid (pSUN2-LeB4-IPP-SynMT1-nosT/USPP-rbcS-RnTATase1-nosT, FIG. 33) is used for generating transgenic *Brassica napus* plants.

Figure 33:
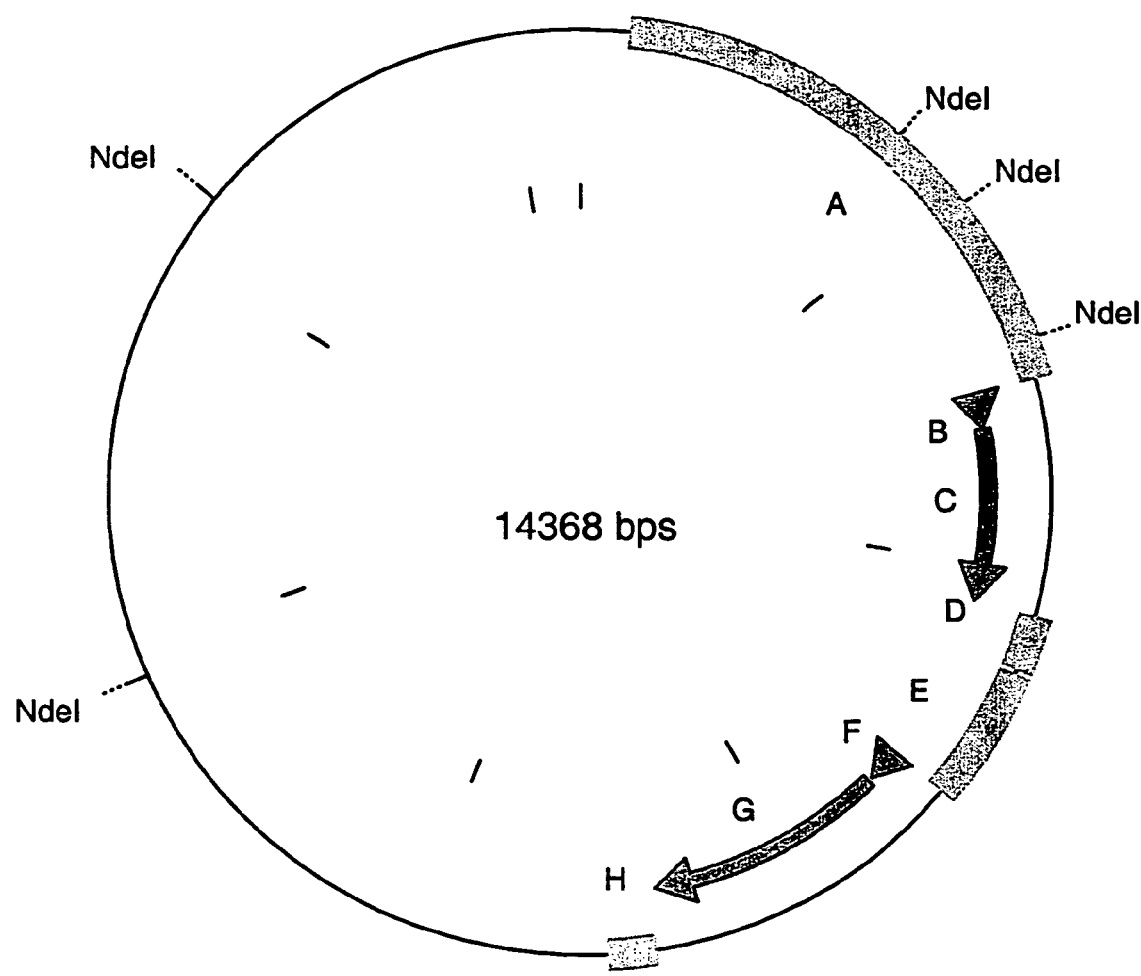
FIG. 33 shows the plasmid pSUN2-LeB4-IPP-SynMT1-nosT-USPP-rbcS-RnTATase1-nosT.

Fragment A (2764 bp) in FIG. 33 comprises the promoter of the *Vicia faba* legumin B4 gene, fragment B (235 bp) encodes the transit peptide of the *A. thaliana* isopentenyl-pyrophosphate isomerase 2. Fragment C (957 bp) encodes the *Synechocystis* sp. PCC6803 2-methyl-6-phytylhydroquinone methyltransferase gene. Fragment D (272 bp) encodes the termination signal of the nopaline synthase gene. Fragment E (678 bp) comprises the promoter of the *Vicia faba* unknown seed protein gene (USPP), fragment F (235 bp) encodes the *Vicia faba* ribulose-bisphosphate carboxylase (rbcS) transit peptide. Fragment G (1365 bp) encodes the *Rattus norvegicus* tyrosine aminotransferase gene. Fragment H (272 bp) encodes the termination signal of the *A. tumefaciens* nopaline synthase gene.

Example 46

Generation of DNA constructs for expressing the *Arabidopsis thaliana* tyrosine aminotransferase 1 under the control of a seed-specific promoter and the *Synechocystis* sp. PCC6803 2-methyl-6-phytylhydroquinone methyltransferase under the control of a seed-specific promoter To prepare chimeric DNA constructs for generating transgenic *Brassica napus* plants which express the *Arabidopsis thaliana* tyrosine aminotransferase 1 under the control of a seed-specific promoter and the *Synechocystis* sp. PCC6803 2-methyl-6-phytylhydroquinone methyltransferase in a seed-specific manner, the vectors pSUN2-LeB4-IPP-SynMT1-nosT and pSUN2-USPP-AtTATase1-nosT are combined with each other.

The DNA fragment encoding the expression cassette consisting of: USP promoter, *Arabidopsis thaliana* tyrosine aminotransferase 1 gene and nos terminator is isolated as SmaI/EcoRI fragment from the plasmid pSUN2-USPP-AtTATase1-nosT, the EcoRI end is filled in with Klenow enzyme, and the construct is cloned into the SrfI-digested vector pSUN2-LeB4-IPP-SynMT1-nosT.

This plasmid (pSUN2-LeB4-IPP-SynMT1-nosT/USPP-AtTATase1-nosT, FIG. 34) is used for generating transgenic *Brassica napus* plants.

Figure 34:
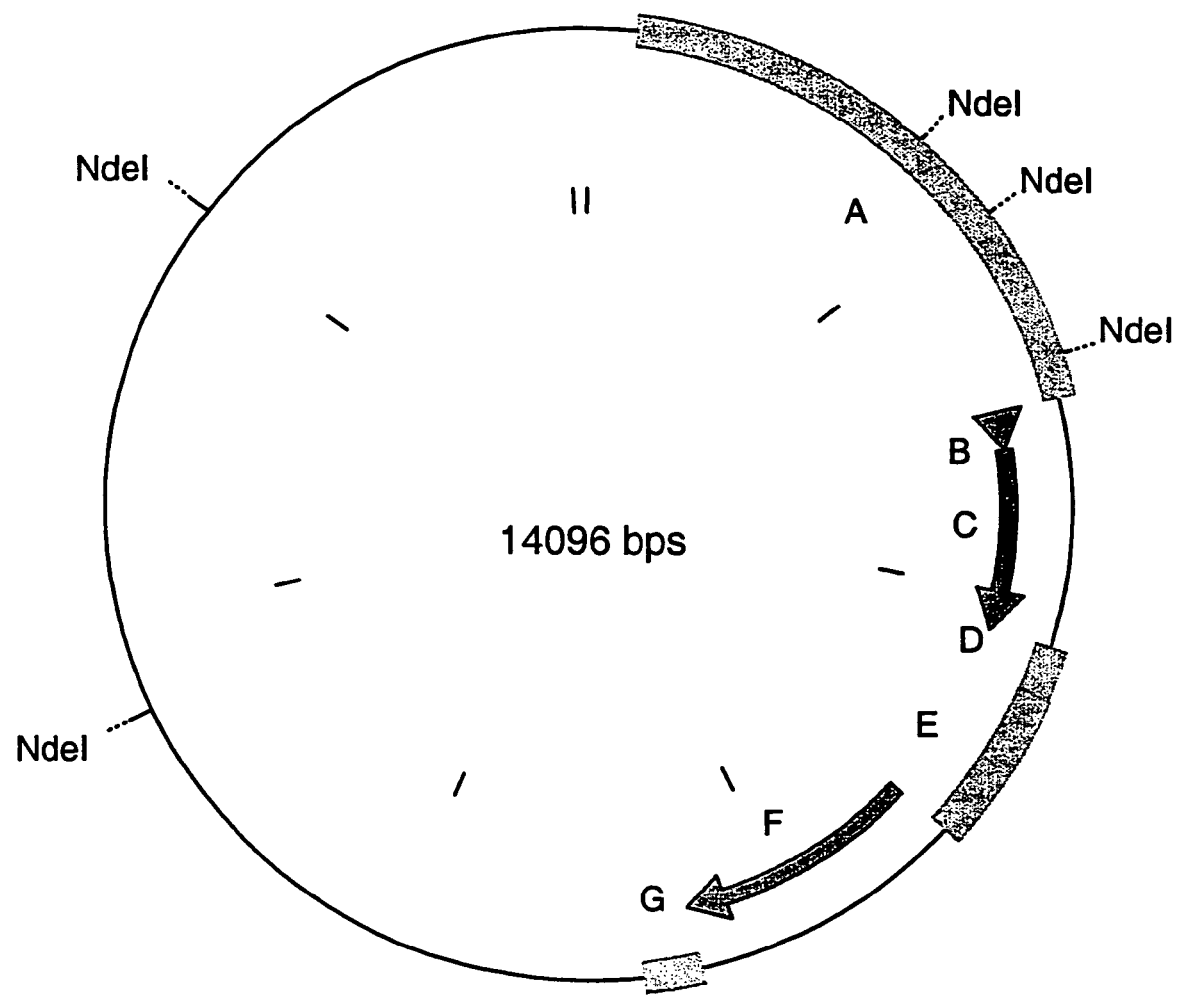
FIG. 34 shows the plasmid pSUN2-LeB4-IPP-SynMT1-nosT-USPP-AtTATase1-nosT.

Fragment A (2764 bp) in FIG. 34 comprises the promoter of the *Vicia faba* legumin B4 gene, fragment B (235 bp) encodes the transit peptide of the *A. thaliana* isopentenyl-pyrophosphate isomerase 2. Fragment C (957 bp) encodes the *Synechocystis* sp. PCC6803 2-methyl-6-phytylhydroquinone methyltransferase gene. Fragment D (272 bp) encodes the termination signal of the nopaline synthase gene. Fragment E (678 bp) comprises the promoter of the *Vicia faba* unknown seed protein gene (USPP), fragment F (1269 bp) encodes the *Arabidopsis thaliana* tyrosine aminotransferase gene 1. Fragment G (272 bp) encodes the termination signal of the nopaline synthase gene.

Example 47

Generation of DNA constructs for expressing the *Arabidopsis thaliana* tyrosine aminotransferase 3 under the control of a seed-specific promoter and the *Synechocystis* sp. PCC6803 2-methyl-6-phytylhydroquinone methyltransferase under the control of a seed-specific promoter To prepare chimeric DNA constructs for generating transgenic *Brassica napus* plants which express the *Arabidopsis thaliana* tyrosine aminotransferase 3 under the control of a seed-specific promoter and the *Synechocystis* sp. PCC6803 2-methyl-6-phytylhydroquinone methyltransferase in a seed-specific manner, the vectors pSUN2-LeB4-IPP-SynMT1-nosT and pSUN2-USPP-AtTATase3-nosT are combined with each other.

The DNA fragment encoding the expression cassette consisting of: USP promoter, *Arabidopsis thaliana* tyrosine aminotransferase 3 gene and nos terminator is isolated as SmaI/EcoRI fragment from the plasmid pSUN2-USPP-AtTATase3-nosT, the EcoRI end is filled in with Klenow enzyme, the construct is cloned into the SrfI-digested vector pSUN2-LeB4-IPP-SynMT1-nosT.

This plasmid (pSUN2-LeB4-IPP-SynMT1-nosT/USPP-AtTATase3-nosT, FIG. 35) is used for generating transgenic *Brassica napus* plants.

Figure 35:
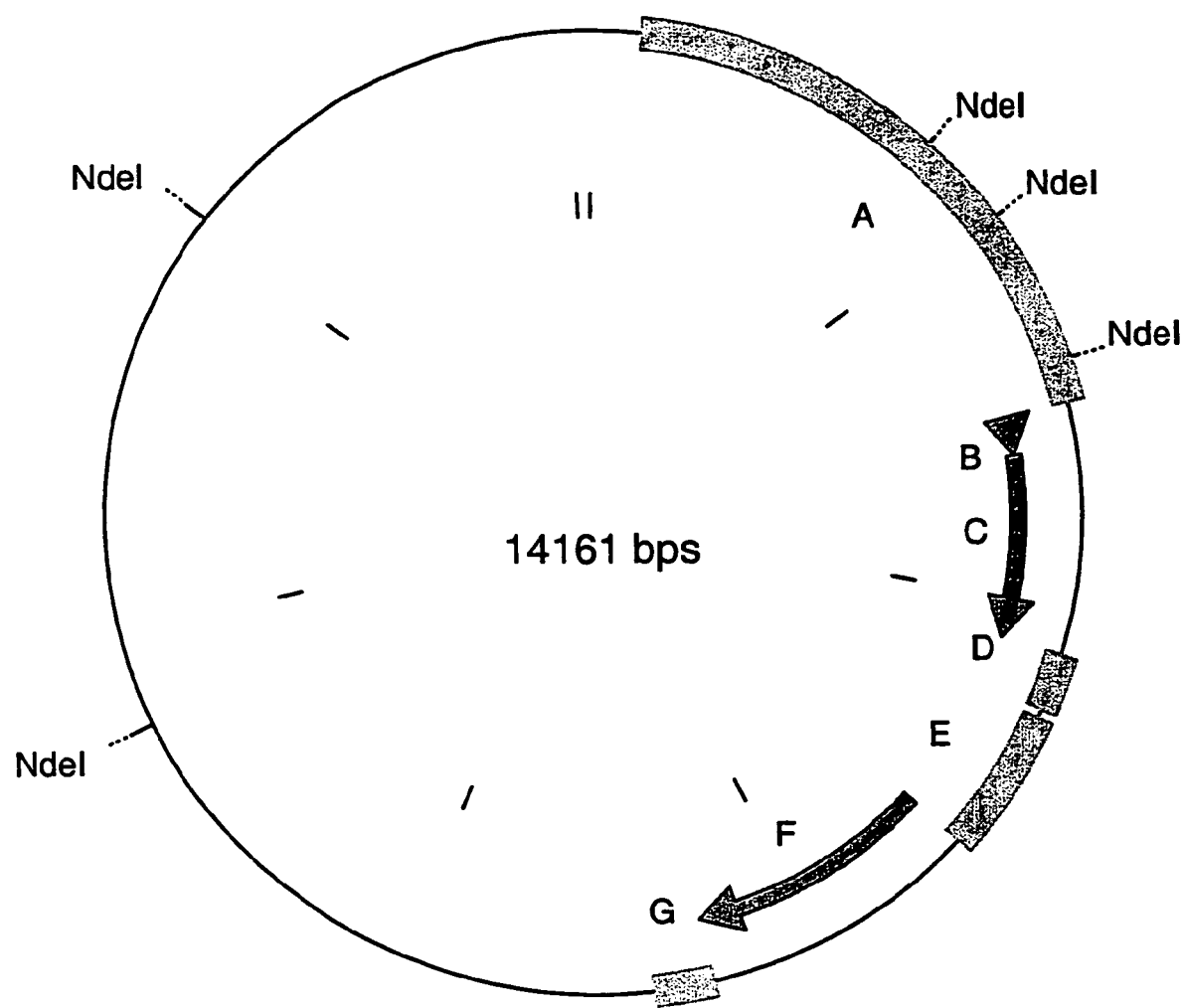
FIG. 35 shows the plasmid pSUN2-LeB4-IPP-SynMT1-nosT-USPP-AtTATase3-nosT.

Fragment A (2764 bp) in FIG. 35 comprises the promoter of the *Vicia faba* legumin B4 gene, fragment B (235 bp) encodes the transit peptide of the *A. thaliana* isopentenyl-pyrophosphate isomerase 2. Fragment C (957 bp) encodes the *Synechocystis* sp. PCC6803 2-methyl-6-phytylhydroquinone methyltransferase gene. Fragment D (272 bp) encodes the termination signal of the nopaline synthase gene. Fragment E (678 bp) comprises the promoter of the *Vicia faba* "unknown seed protein gene" (USPP), fragment F (1334 bp) encodes the *Arabidopsis thaliana* tyrosine aminotransferase gene 3. Fragment G (272 bp) encodes the termination signal of the nopaline synthase gene.

Example 48

Generation of DNA constructs for expressing the *Arabidopsis thaliana* tyrosine aminotransferase 5 under the control of a seed-specific promoter and the *Synechocystis* sp. PCC6803 2-methyl-6-phytylhydroquinone methyltransferase under the control of a seed-specific promoter To prepare chimeric DNA constructs for generating transgenic *Brassica napus* plants which express the *Arabidopsis thaliana* tyrosine aminotransferase 5 under the control of a seed-specific promoter and the *Synechocystis* sp. PCC6803 2-methyl-6-phytylhydroquinone methyltransferase in a seed-specific manner, the vectors pSUN2-LeB4-IPP-SynMT1-nosT and pSUN2-USPP-AtTATase5-nosT are combined with each other.

The DNA fragment encoding the expression cassette consisting of: USP promoter, *Arabidopsis thaliana* tyrosine aminotransferase 5 gene and nos terminator is isolated as SmaI/EcoRI fragment from the plasmid pSUN2-USPP-AtTATase5-nosT, the EcoRI end is filled in with Klenow enzyme, and the construct is cloned into the SrfI-digested vector pSUN2-LeB4-IPP-SynMT1-nosT.

This plasmid (pSUN2-LeB4-IPP-SynMT1-nosT/USPP-AtTATase5-nosT, FIG. 36) is used for generating transgenic *Brassica napus* plants.

Figure 36:
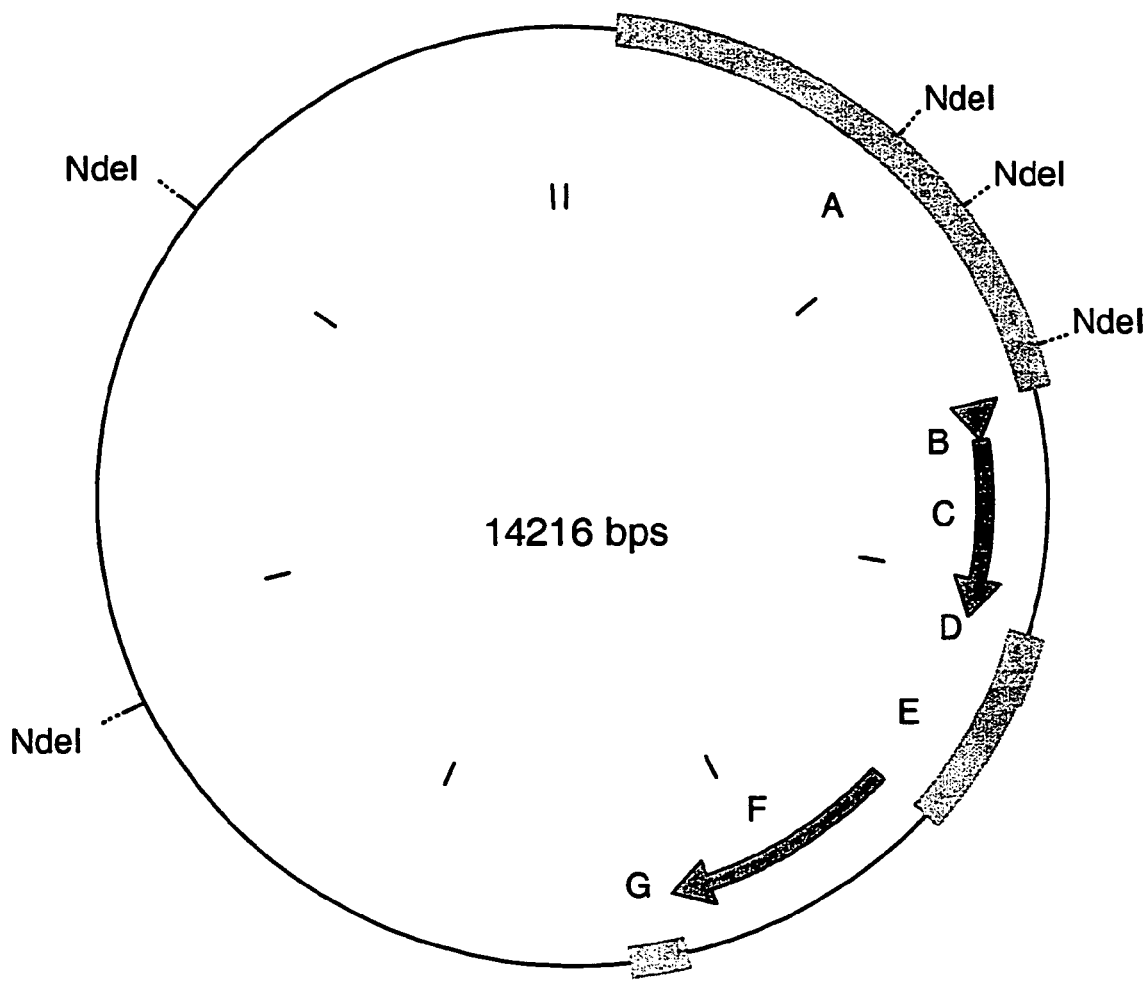
FIG. 36 shows the plasmid pSUN2-LeB4-IPP-SynMT1-nosT-USPP-AtTATase5-nosT.

Fragment A (2764 bp) in FIG. 36 comprises the promoter of the *Vicia faba* legumin B4 gene, fragment B (235 bp) encodes the transit peptide of the *A. thaliana* isopentenyl-pyrophosphate isomerase 2. Fragment C (957 bp) encodes the *Synechocystis* sp. PCC6803 2-methyl-6-phytylhydroquinone methyltransferase gene. Fragment D (272 bp) encodes the termination signal of the nopaline synthase gene. Fragment E (678 bp) comprises the promoter of the *Vicia faba* "unknown seed protein gene", fragment F (1389 bp) encodes the *Arabidopsis thaliana* tyrosine aminotransferase gene 5. Fragment G (272 bp) encodes the termination signal of the nopaline synthase gene.

Example 49

Generation of DNA constructs for expressing the *Arabidopsis thaliana* tyrosine aminotransferase 6 under the control of a seed-specific promoter and the *Synechocystis* sp. PCC6803 2-methyl-6-phytylhydroquinone methyltransferase under the control of a seed-specific promoter To prepare chimeric DNA constructs for generating transgenic *Brassica napus* plants which express the *Arabidopsis thaliana* tyrosine aminotransferase 6 under the control of a seed-specific promoter and the *Synechocystis* sp. PCC6803 2-methyl-6-phytylhydroquinone methyltransferase in a seed-specific manner, the vectors pSUN2-LeB4-IPP-SynMT1-nosT and pSUN2-USPP-AtTATase6-nosT are combined with each other.

The DNA fragment encoding the expression cassette consisting of: USP promoter, *Arabidopsis thaliana* tyrosine aminotransferase 6 gene and nos terminator is isolated as SmaI/EcoRI fragment from the plasmid pSUN2-USPP-AtTATase6-nosT, the EcoRI end is filled in with Klenow enzyme, and the construct is cloned into the SrfI-digested vector pSUN2-LeB4-IPP-SynMT1-nosT.

This plasmid (pSUN2-LeB4-IPP-SynMT1-nosT/USPP-AtTATase6-nosT, FIG. 37) is used for generating transgenic *Brassica napus* plants.

Figure 37:
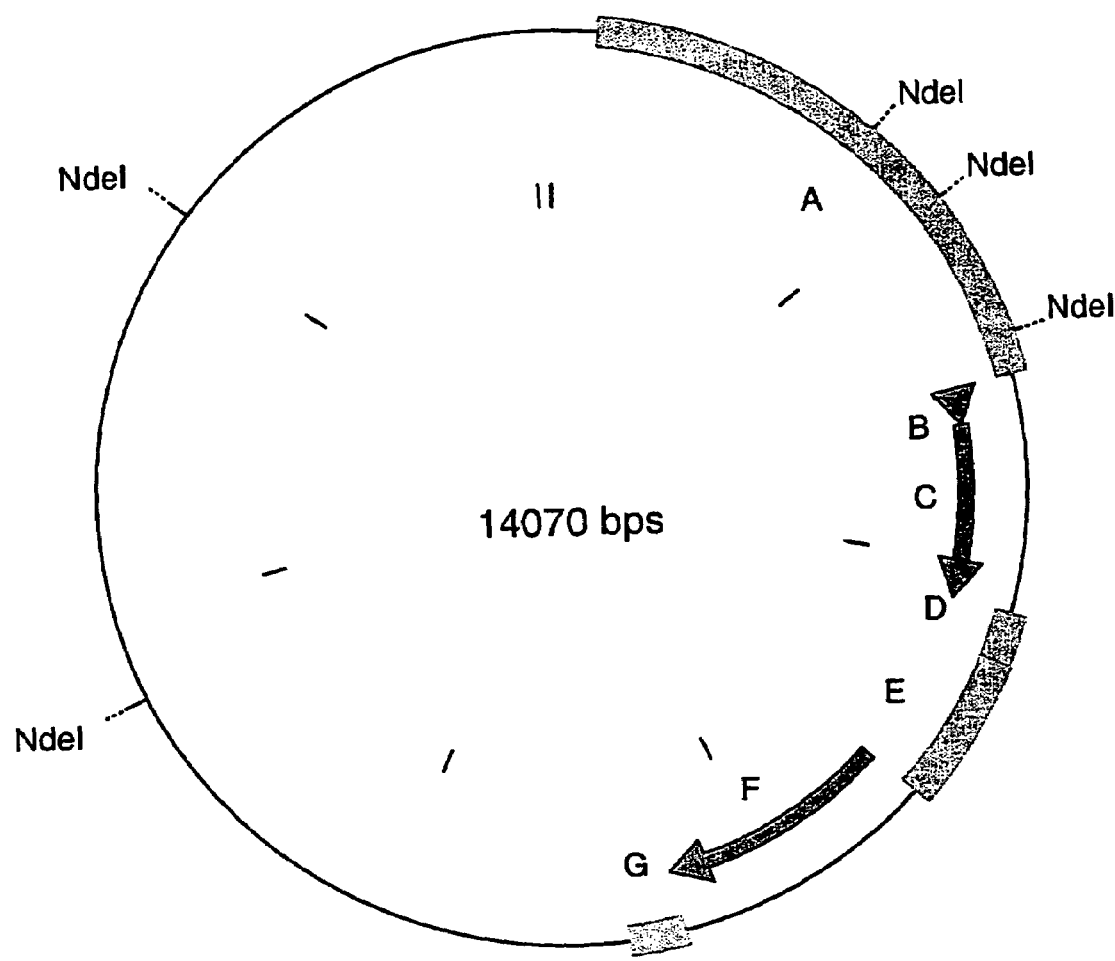
FIG. 37 shows the plasmid pSUN2-LeB4-IPP-SynMT1-nosT-USPP-AtTATase6-nosT

Fragment A (2764 bp) in FIG. 37 comprises the promoter of the *Vicia faba* legumin B4 gene, fragment B (235 bp) encodes the transit peptide of the *A. thaliana* isopentenyl-pyrophosphate isomerase 2. Fragment C (957 bp) encodes the *Synechocystis* sp. PCC6803 2-methyl-6-phytylhydroquinone methyltransferase gene. Fragment D (272 bp) encodes the termination signal of the nopaline synthase gene. Fragment E (678 bp) comprises the promoter of the *Vicia faba* "unknown seed protein gene", fragment F (1243 bp) encodes the *Arabidopsis thaliana* tyrosine aminotransferase gene 6. Fragment G (272 bp) encodes the termination signal of the nopaline synthase gene.

Example 50

Generation of DNA constructs for expressing the *Rattus norvegicus* tyrosine aminotransferase under the control of a seed-specific promoter and *Synechocystis* sp. PCC6803 2,3-dimethyl-5-phytylplastoquinol cyclase under the control of a seed-specific promoter To prepare chimeric DNA constructs for generating transgenic *Brassica napus* plants which express the *Rattus norvegicus* tyrosine aminotransferase under the control of a seed-specific promoter and the *Synechocystis* sp. PCC6803 2,3-dimethyl-5-phytylplastoquinol cyclase under the control of a seed-specific promoter, the vectors pSUN2-LeB4-IPP-SynCyc-nosT and pCR4topoblunt-USPP-rbcS-RnTATase1-nosT are combined with each other.

The DNA fragment consisting of USP promoter, *Rattus norvegicus* tyrosine aminotransferase and nos termination sequence is isolated as SrfI fragment from the plasmid pCR4TOPOblunt/USPP-rbcS-RnTATase1-nosT and cloned into the EcoRI-digested vector pSUN2-LeB4-IPP-SynCyc-nosT, whose EcoRI ends are also filled in.

This plasmid (pSUN2-LeB4-IPP-SynCyc-nosT/USPP-rbcS-RnTATase1-nosT, FIG. 38) is used for generating transgenic *Brassica napus* plants.

Figure 38:
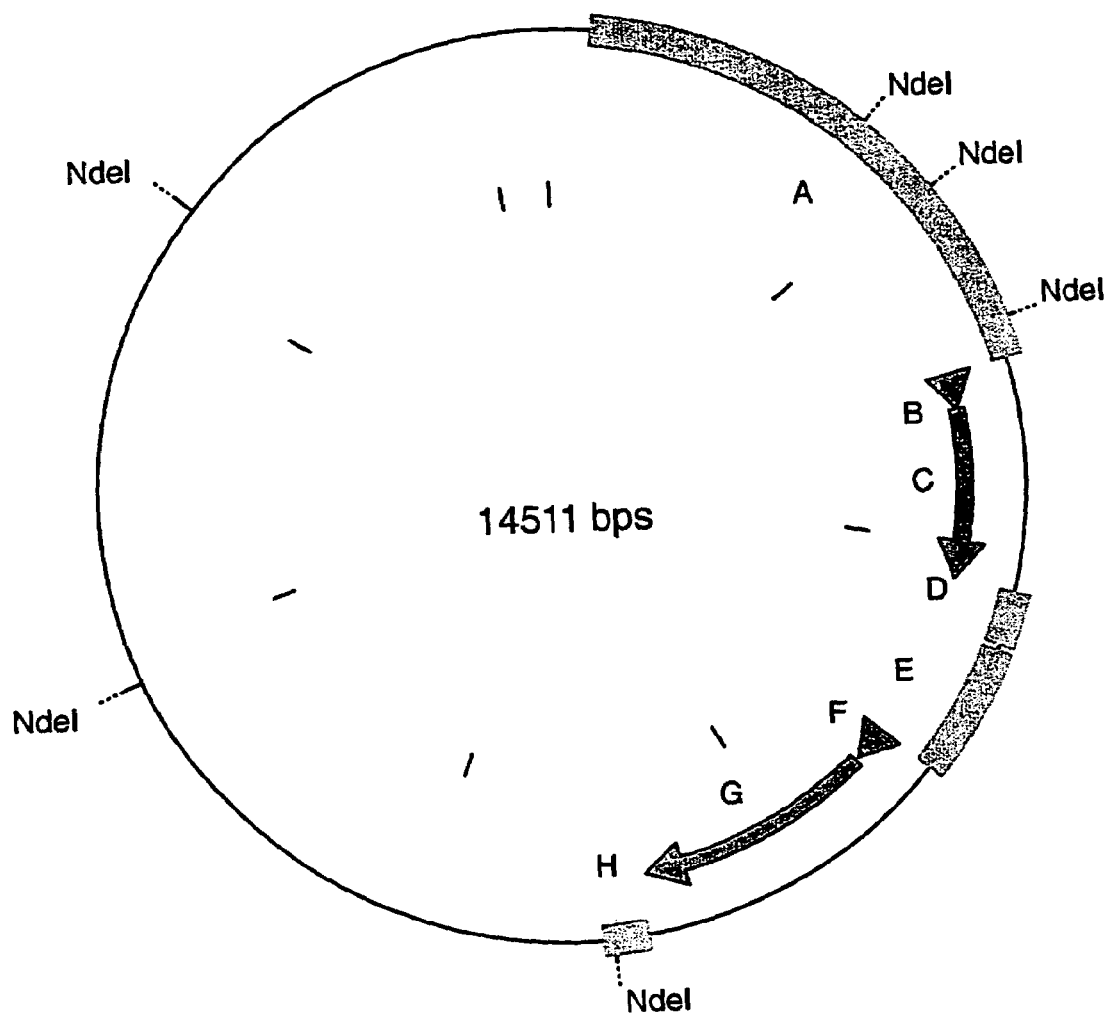
FIG. 38 shows the plasmid pSUN2-LeB4-IPP-SynCyc-nosT-USPP-rbcS-RnTATase1-nosT.

Fragment A (2764 bp) in FIG. 38 comprises the promoter of the *Vicia faba* legumin B4 gene, fragment B (235 bp) encodes the transit peptide of the *A. thaliana* isopentenyl-pyrophosphate isomerase 2. Fragment C (1100 bp) encodes the *Synechocystis* sp. PCC6803 2,3-dimethyl-5-phytylplastoquinol cyclase gene. Fragment D (272 bp) encodes the termination signal of the nopaline synthase gene. Fragment E (678 bp) comprises the promoter of the *Vicia faba* unknown seed protein gene (USPP), fragment F (235 bp) encodes the *Vicia faba* ribulose-bisphosphate carboxylase (rbcS) transit peptide. Fragment G (1365 bp) encodes the *Rattus norvegicus* tyrosine aminotransferase gene. Fragment H (272 bp) encodes the termination signal of the *A. tumefaciens* nopaline synthase gene.

Example 51

Generation of DNA constructs for expressing the *Arabidopsis thaliana* tyrosine aminotransferase 1 under the control of a seed-specific promoter and the *Synechocystis* sp. PCC6803 2,3-dimethyl-5-phytylplastoquinol cyclase under the control of a seed-specific promoter To prepare chimeric DNA constructs for generating transgenic *Brassica napus* plants which express the *Arabidopsis thaliana* tyrosine aminotransferase 1 under the control of a seed-specific promoter and the *Synechocystis* sp. PCC6803 2,3-dimethyl-5-phytylplastoquinol cyclase in a seed-specific manner, the vectors pSUN2-LeB4-IPP-SynCyc-nosT and pSUN2-USPP-AtTATase1-nosT are combined with each other.

The DNA fragment encoding the expression cassette consisting of: USP promoter, *Arabidopsis thaliana* tyrosine aminotransferase 1 gene and nos terminator is isolated as SmaI/EcoRI fragment from the plasmid pSUN2-USPP-AtTATase1-nosT, the EcoRI end is filled in with Klenow enzyme, and the construct is cloned into the EcoRI-digested vector pSUN2-LeB4-IPP-SynCyc-nosT whose EcoRI ends are filled in with Klenow enzyme.

This plasmid (pSUN2-LeB4-IPP-SynCyc-nosT/USPP-AtTATase1-nosT, FIG. 39) is used for generating transgenic *Brassica napus* plants.

Figure 39:
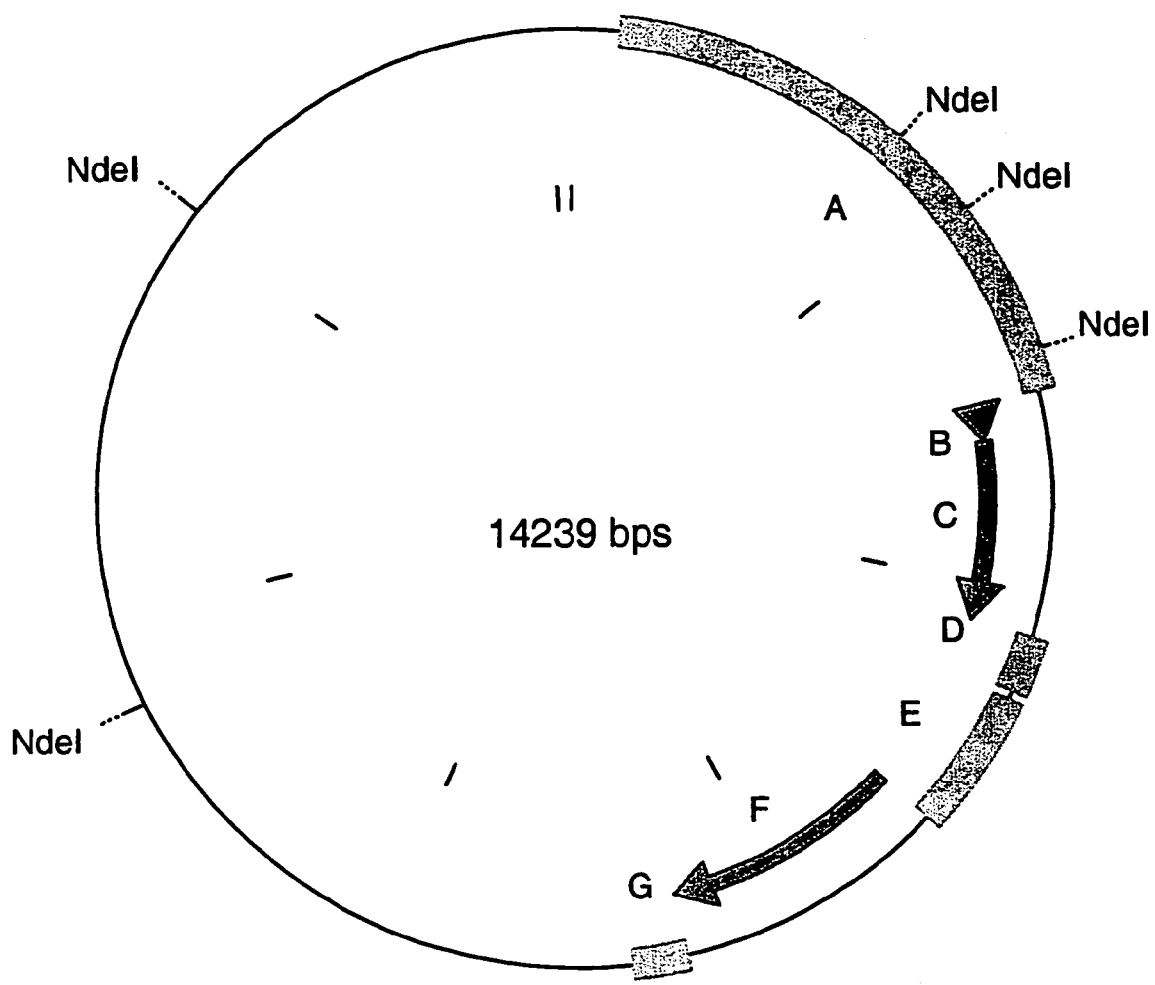
FIG. 39 shows the plasmid pSUN2-LeB4-IPP-SynCyc-nosT-USPP-AtTATase1-nosT.

Fragment A (2764 bp) in FIG. 39 comprises the promoter of the *Vicia faba* legumin B4 gene, fragment B (235 bp) encodes the transit peptide of the *A. thaliana* isopentenyl-pyrophosphate isomerase 2. Fragment C (1100 bp) encodes the *Synechocystis* sp. PCC6803 2,3-dimethyl-5-phytylplastoquinol cyclase gene. Fragment D (272 bp) encodes the termination signal of the nopaline synthase gene. Fragment E (678 bp) comprises the promoter of the *Vicia faba* unknown seed protein gene (USPP), fragment F (1269 bp) encodes the *Arabidopsis thaliana* tyrosine aminotransferase gene 1. Fragment G (272 bp) encodes the termination signal of the nopaline synthase gene.

Example 52

Generation of DNA constructs for expressing the *Arabidopsis thaliana* tyrosine aminotransferase 3 under the control of a seed-specific promoter and the *Synechocystis* sp. PCC6803 2,3-dimethyl-5-phytylplastoquinol cyclase under the control of a seed-specific promoter To prepare chimeric DNA constructs for generating transgenic *Brassica napus* plants which express the *Arabidopsis thaliana* tyrosine aminotransferase 3 under the control of a seed-specific promoter and the *Synechocystis* sp. PCC6803 2,3-dimethyl-5-phytylplastoquinol cyclase in a seed-specific manner, the vectors pSUN2-LeB4-IPP-SynCyc-nosT and pSUN2-USPP-AtTATase3-nosT are combined with each other.

The DNA fragment encoding the expression cassette consisting of: USP promoter, Arabidopsis thaliana tyrosine aminotransferase 3 gene and nos terminator is isolated as SmaI/EcoRI fragment from the plasmid pSUN2-USPP-AtTATase3-nosT, the EcoRI end is filled in with Klenow enzyme, and the construct is cloned into the EcoRI-digested vector pSUN2-LeB4-IPP-SynCyc-nosT whose EcoRI ends are likewise filled in.

This plasmid (pSUN2-LeB4-IPP-SynCyc-nosT/USPP-AtTATase3-nosT, FIG. 40) is used for generating transgenic Brassica napus plants.

Figure 40:
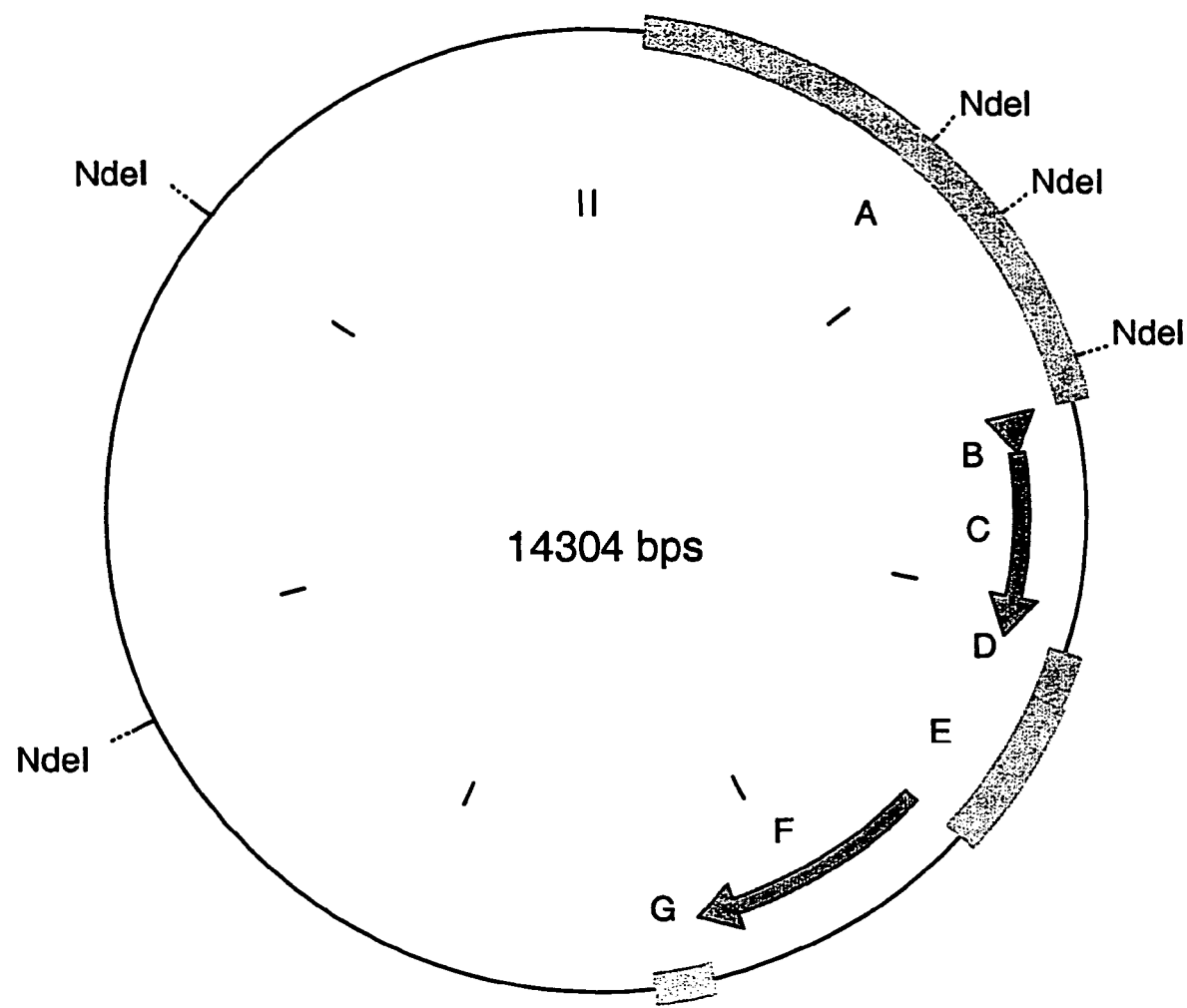
FIG. 40 shows the plasmid pSUN2-LeB4-IPP-SynCyc-nosT-USPP-AtTATase3-nosT.

Fragment A (2764 bp) in FIG. 40 comprises the promoter of the Vicia faba legumin B4 gene, fragment B (235 bp) encodes the transit peptide of the A. thaliana isopentenylpyrophosphate isomerase 2. Fragment C (1100 bp) encodes the Synechocystis sp. PCC6803 2,3-dimethyl-5-phytylplastoquinol cyclase gene. Fragment D (272 bp) encodes the termination signal of the nopaline synthase gene. Fragment E (678 bp) comprises the promoter of the Vicia faba "unknown seed protein gene" (USPP), fragment F (1334 bp) encodes the Arabidopsis thaliana tyrosine aminotransferase gene 3. Fragment G (272 bp) encodes the termination signal of the nopaline synthase gene.

Example 53

Generation of DNA constructs for expressing the Arabidopsis thaliana tyrosine aminotransferase 5 under the control of a seed-specific promoter and the Synechocystis sp. PCC6803 2,3-dimethyl-5-phytylplastoquinol cyclase under the control of a seed-specific promoter To prepare chimeric DNA constructs for generating transgenic Brassica napus plants which express the Arabidopsis thaliana tyrosine aminotransferase 5 under the control of a seed-specific promoter and the Synechocystis sp. PCC6803 2,3-dimethyl-5-phytylplastoquinol cyclase in a seed-specific manner, the vectors pSUN2-LeB4-IPP-SynCyc-nosT and pSUN2-USPP-AtTATase5-nosT are combined with each other.

The DNA fragment encoding the expression cassette consisting of: USP promoter, Arabidopsis thaliana tyrosine aminotransferase 5 gene and nos terminator is isolated as SmaI/EcoRI fragment from the plasmid pSUN2-USPP-AtTATase5-nosT, the EcoRI end is filled in with Klenow enzyme, and the construct is cloned into the EcoRI-digested vector pSUN2-LeB4-IPP-SynCyc-nosT whose EcoRI ends are likewise filled in.

This plasmid (pSUN2-LeB4-IPP-SynCyc-nosT/USPP-AtTATase5-nosT, FIG. 41) is used for generating transgenic Brassica napus plants.

Figure 41:
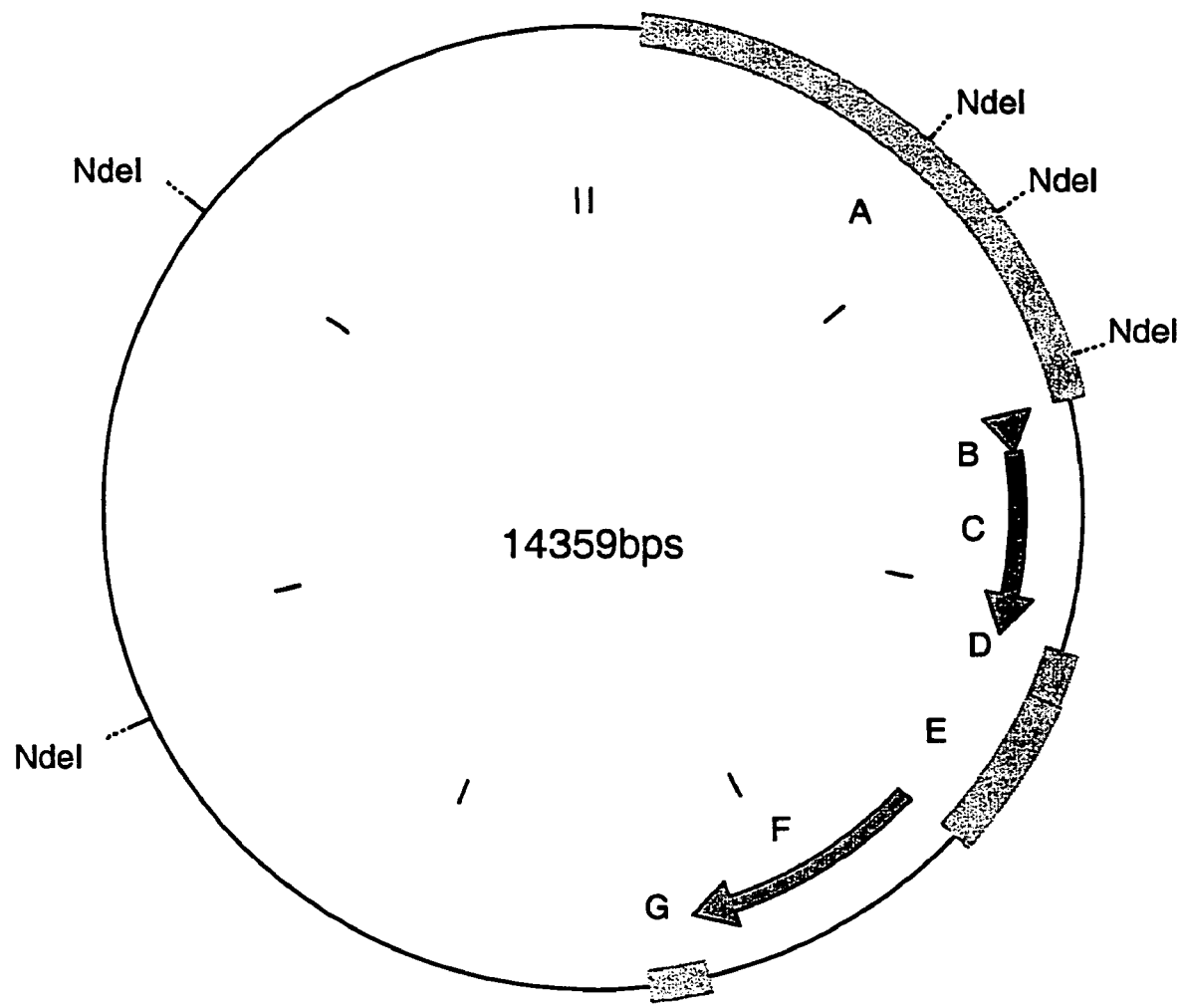
FIG. 41 shows the plasmid pSUN2-LeB4-IPP-SynCyc-nosT-USPP-AtTATase5-nosT.

Fragment A (2764 bp) in FIG. 41 comprises the promoter of the Vicia faba legumin B4 gene, fragment B (235 bp) encodes the transit peptide of the A. thaliana isopentenylpyrophosphate isomerase 2. Fragment C (1100 bp) encodes the Synechocystis sp. PCC6803 2,3-dimethyl-5-phytylplastoquinol cyclase gene. Fragment D (272 bp) encodes the termination signal of the nopaline synthase gene. Fragment E (678 bp) comprises the promoter of the Vicia faba "unknown seed protein gene", fragment F (1389 bp) encodes the Arabidopsis thaliana tyrosine aminotransferase gene 5. Fragment G (272 bp) encodes the termination signal of the nopaline synthase gene.

Example 54

Generation of DNA constructs for expressing the Arabidopsis thaliana tyrosine aminotransferase 6 under the control of a seed-specific promoter and the Synechocystis sp. PCC6803 2,3-dimethyl-5-phytylplastoquinol cyclase under the control of a seed-specific promoter To prepare chimeric DNA constructs for generating transgenic Brassica napus plants which express the Arabidopsis thaliana tyrosine aminotransferase 6 under the control of a seed-specific promoter and the Synechocystis sp. PCC6803 2,3-dimethyl-5-phytylplastoquinol cyclase in a seed-specific manner, the vectors pSUN2-LeB4-IPP-SynCyc-nosT and pSUN2-USPP-AtTATase6-nosT are combined with each other.

The DNA fragment encoding the expression cassette consisting of: USP promoter, Arabidopsis thaliana tyrosine aminotransferase 6 gene and nos terminator is isolated as SmaI/EcoRI fragment from the plasmid pSUN2-USPP-AtTATase6-nosT, the EcoRI end is filled in with Klenow enzyme, and the construct is cloned into the EcoRI-digested vector pSUN2-LeB4-IPP-SynCyc-nosT whose EcoRI ends are likewise filled in.

This plasmid (pSUN2-LeB4-IPP-SynCyc-nosT/USPP-AtTATase6-nosT, FIG. 42) is used for generating transgenic Brassica napus plants.

Figure 42:
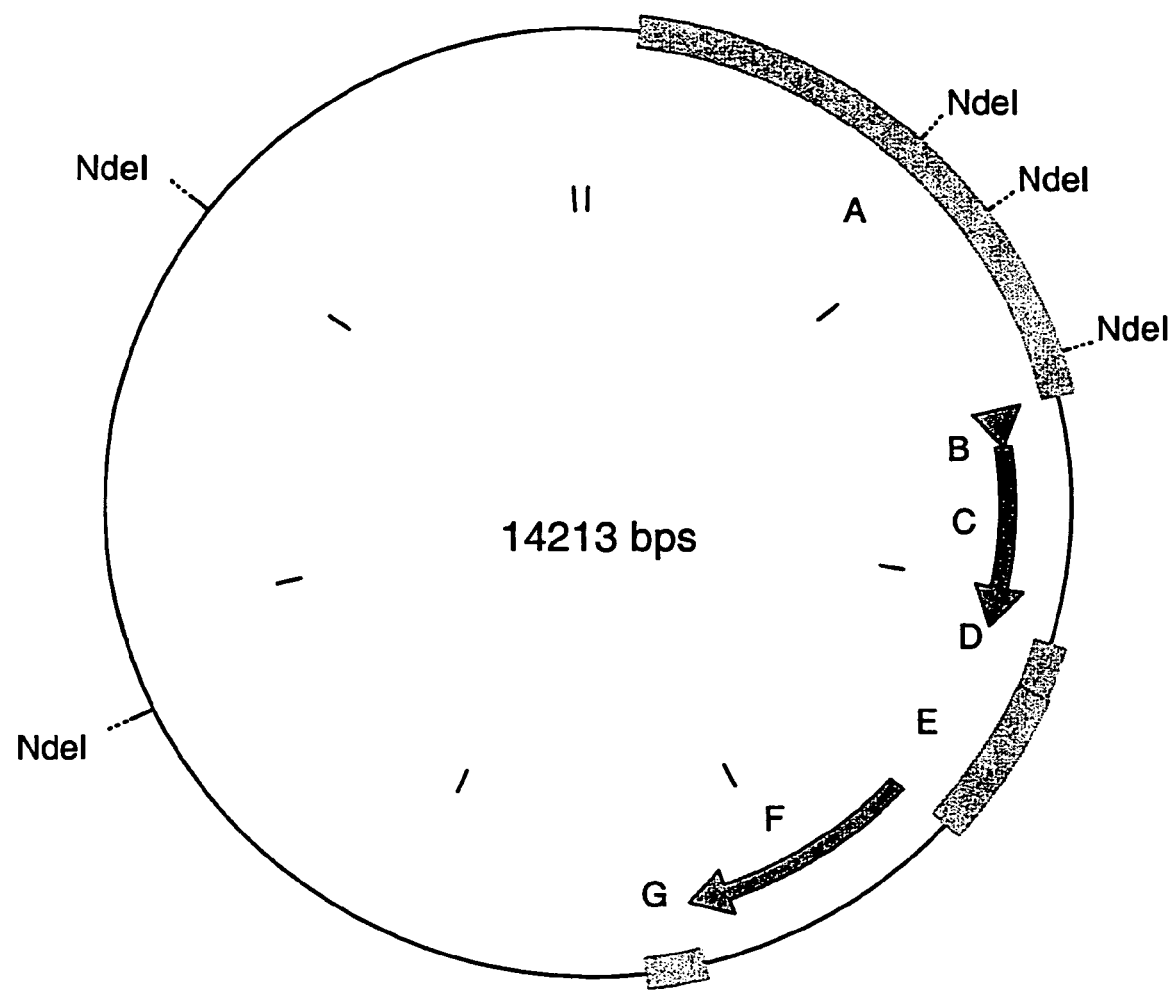
FIG. 42 shows the plasmid pSUN2-LeB4-IPP-SynCyc-nosT-USPP-AtTATase6-nosT.

Fragment A (2764 bp) in FIG. 42 comprises the promoter of the Vicia faba legumin B4 gene, fragment B (235 bp) encodes the transit peptide of the A. thaliana isopentenylpyrophosphate isomerase 2. Fragment C (1100 bp) encodes the Synechocystis sp. PCC6803 2,3-dimethyl-5-phytylplastoquinol cyclase gene. Fragment D (272 bp) encodes the termination signal of the nopaline synthase gene. Fragment E (678 bp) comprises the promoter of the Vicia faba "unknown seed protein gene", fragment F (1243 bp) encodes the Arabidopsis thaliana tyrosine aminotransferase gene 6. Fragment G (272 bp) encodes the termination signal of the nopaline synthase gene.

Example 55

Generation of DNA constructs for expressing the Rattus norvegicus tyrosine aminotransferase under the control of a seed-specific promoter and the Arabidopsis thaliana γ-tocopherol methyltransferase under the control of a seed-specific promoter To prepare chimeric DNA constructs for generating transgenic Brassica napus plants which express the Rattus norvegicus tyrosine aminotransferase under the control of a seed-specific promoter and the Arabidopsis thaliana γ-tocopherol methyltransferase in a seed-specific manner, the vectors pSUN2-SBPP-AtγTMT-35ST and pCR4topoblunt-USPP-rbcS-RnTATase1-nosT are combined with each other.

The DNA fragment consisting of USP promoter, Rattus norvegicus tyrosine aminotransferase and nos termination sequence is isolated as SrfI fragment from the plasmid pCR4TOPOblunt/USPP-rbcS-RnTATase1-nosT and cloned into the SrfI-digested vector pSUN2-SBPP-AtγTMT-35sT.

This plasmid (pSUN2-SBPP-AtγTMT-35sT/USPP-rbcS-RnTATase1-nosT, FIG. 43) is used for generating transgenic Brassica napus plants.

Figure 43:
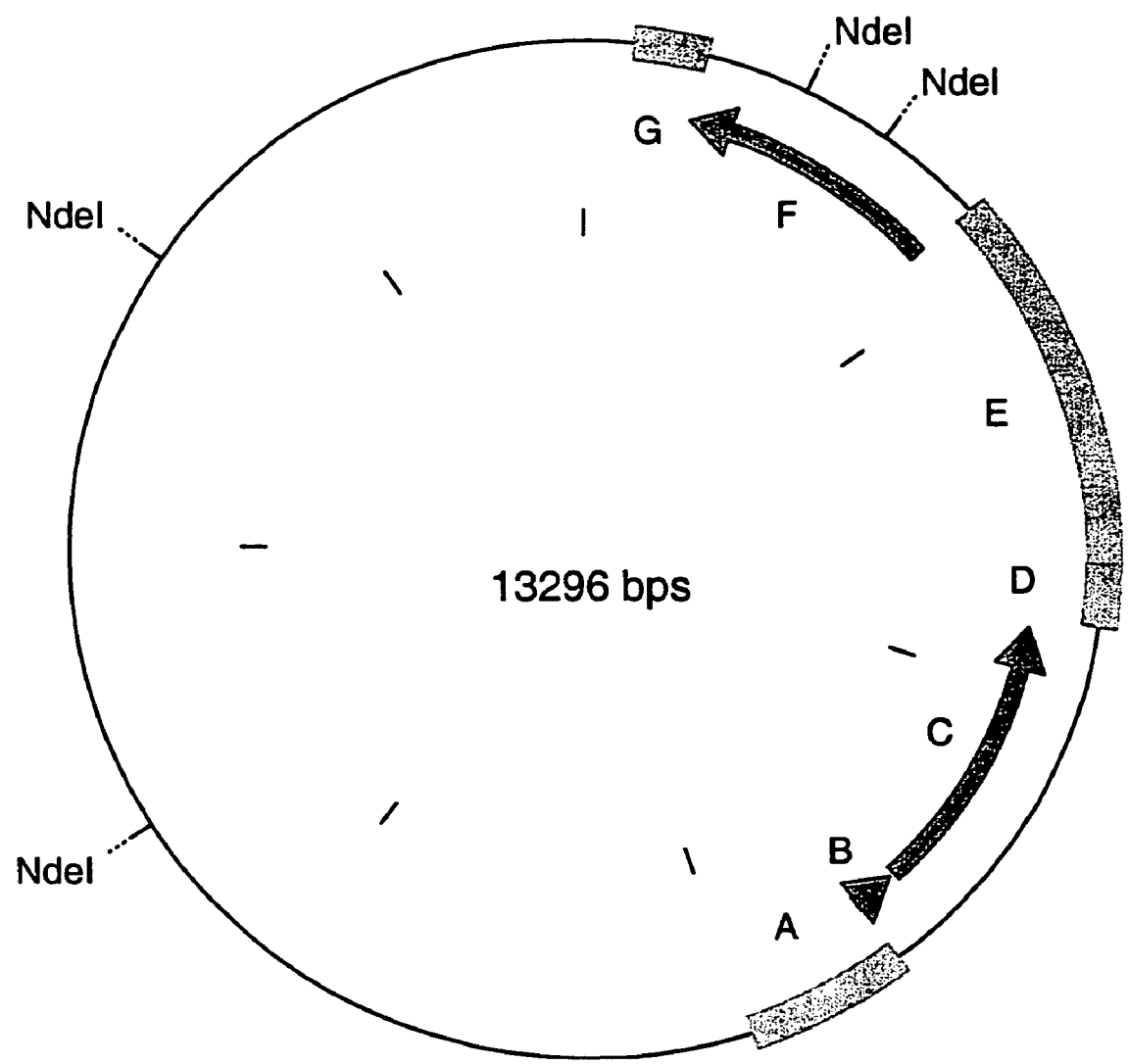
FIG. 43 shows the plasmid pSUN2-SBPP-AtγTMT-35ST-USPP-rbcS-RnTATase1-nosT.

Fragment A (678 bp) in FIG. 43 comprises the promoter of the Vicia faba unknown seed protein gene (USPP), fragment B (235 bp) encodes the transit peptide of the Vicia faba ribulose-bisphosphate carboxylase (rbcS). Fragment C (1365 bp) encodes the Rattus norvegicus tyrosine aminotransferase gene. Fragment D (272 bp) encodes the termination signal of the *A. tumefaciens* nopaline synthase gene. Fragment E (1788 bp) comprises the promoter of the *Vicia faba* SBP gene, fragment F (1047 bp) encodes the *Arabidopsis thaliana* γ-tocopherol methyltransferase gene, fragment G (291 bp) encodes the cauliflower mosaic virus 35S terminator.

Example 56

Generation of DNA constructs for expressing the *Arabidopsis thaliana* tyrosine aminotransferase 1 under the control of a seed-specific promoter and the *Arabidopsis thaliana* γ-tocopherol methyltransferase under the control of a seed-specific promoter To prepare chimeric DNA constructs for generating transgenic *Brassica napus* plants which express the *Arabidopsis thaliana* tyrosine aminotransferase 1 under the control of a seed-specific promoter and the *Arabidopsis thaliana* γ-tocopherol methyltransferase in a seed-specific manner, the vectors SUN2-SBPP-AtγTMT-35sT and pSUN2-USPP-AtTATase1-nosT are combined with each other.

The DNA fragment encoding the expression cassette consisting of: USP promoter, *Arabidopsis thaliana* tyrosine aminotransferase 1 gene and nos terminator is isolated as SmaI/EcoRI fragment from the plasmid pSUN2-USPP-AtTATase1-nosT, the EcoRI end is filled in with Klenow enzyme, and the construct is cloned into the SrfI-digested vector pSUN2-SBPP-AtγTMT-35sT.

This plasmid (pSUN2LeB4-SBPP-AtγTMT-35sT/USPP-AtTATase1-nosT, FIG. 44) is used for generating transgenic *Brassica napus* plants.

Figure 44:
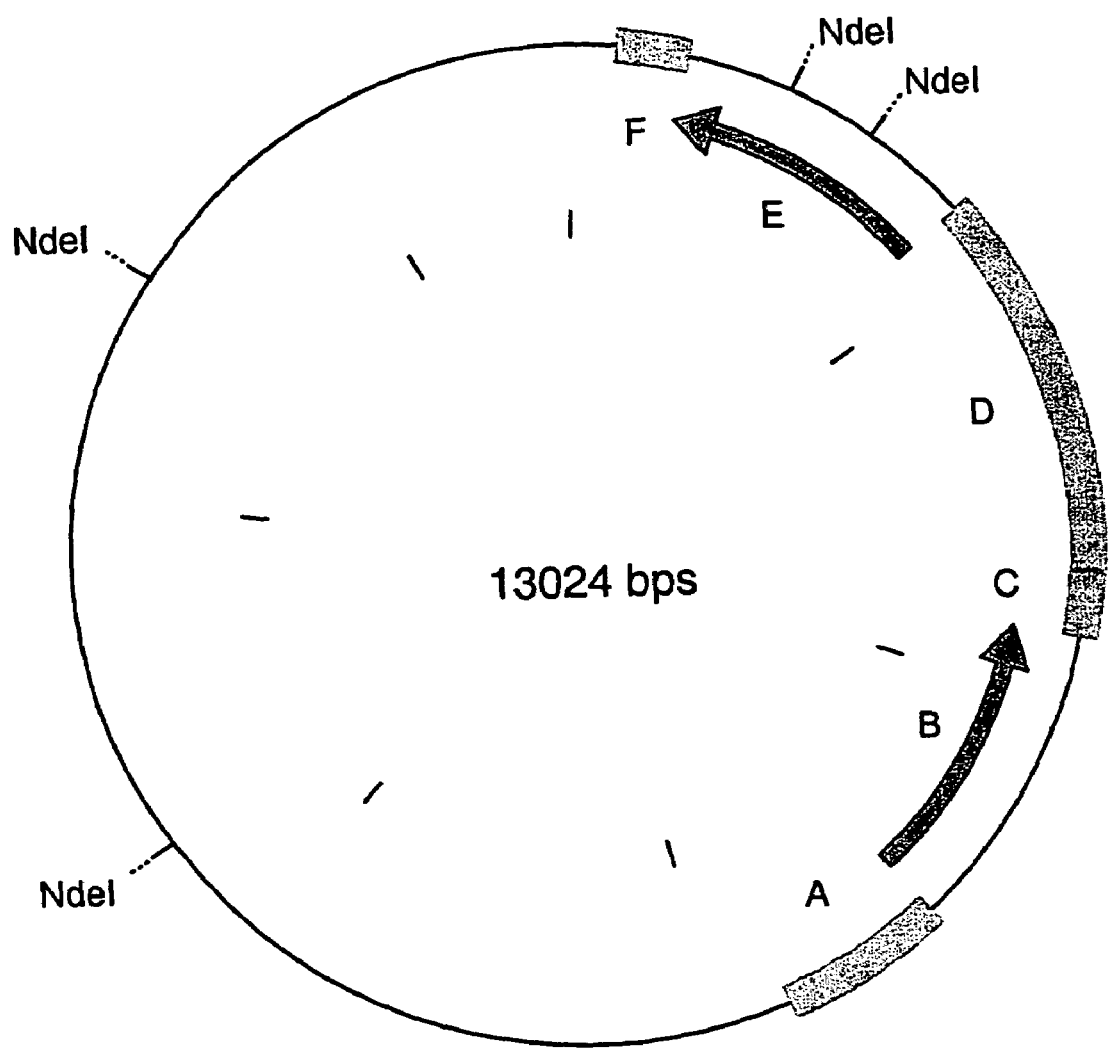
FIG. 44 shows the plasmid pSUN2-SBPP-AtγTMT-35ST-USPP-AtTATase1-nosT.

Fragment A (678 bp) in FIG. 44 comprises the promoter of the *Vicia faba* unknown seed protein gene (USPP), fragment B (1269 bp) encodes the *Arabidopsis thaliana* tyrosine aminotransferase gene 1 and fragment C (272 bp) encodes the termination signal of the nopaline synthase gene. Fragment D (1788 bp) comprises the promoter of the *Vicia faba* SBP gene, fragment E (1047 bp) encodes the *Arabidopsis thaliana* γ-tocopherol methyltransferase gene, fragment F (291 bp) encodes the cauliflower mosaic virus 35S terminator.

Example 57

Generation of DNA constructs for expressing the *Arabidopsis thaliana* tyrosine aminotransferase 3 under the control of a seed-specific promoter and the *Arabidopsis thaliana* γ-tocopherol methyltransferase under the control of a seed-specific promoter To prepare chimeric DNA constructs for generating transgenic *Brassica napus* plants which express the *Arabidopsis thaliana* tyrosine aminotransferase 3 under the control of a seed-specific promoter and the *Arabidopsis thaliana* γ-tocopherol methyltransferase in a seed-specific manner, the vectors pSUN2-SBPP-AtγTMT-35sT and pSUN2-USPP-AtTATase3-nosT are combined with each other.

The DNA fragment encoding the expression cassette consisting of: USP promoter, *Arabidopsis thaliana* tyrosine aminotransferase 3 gene and nos terminator is isolated as SmaI/EcoRI fragment from the plasmid pSUN2-USPP-AtTATase3-nosT, the EcoRI end is filled in with Klenow enzyme, and the construct is cloned into the SrfI-digested vector pSUN2-SBPP-AtγTMT-35sT.

This plasmid (pSUN2-SBPP-AtγTMT-35sT/USPP-AtTATase3-nosT, FIG. 45) is used for generating transgenic *Brassica napus* plants.

Figure 45:
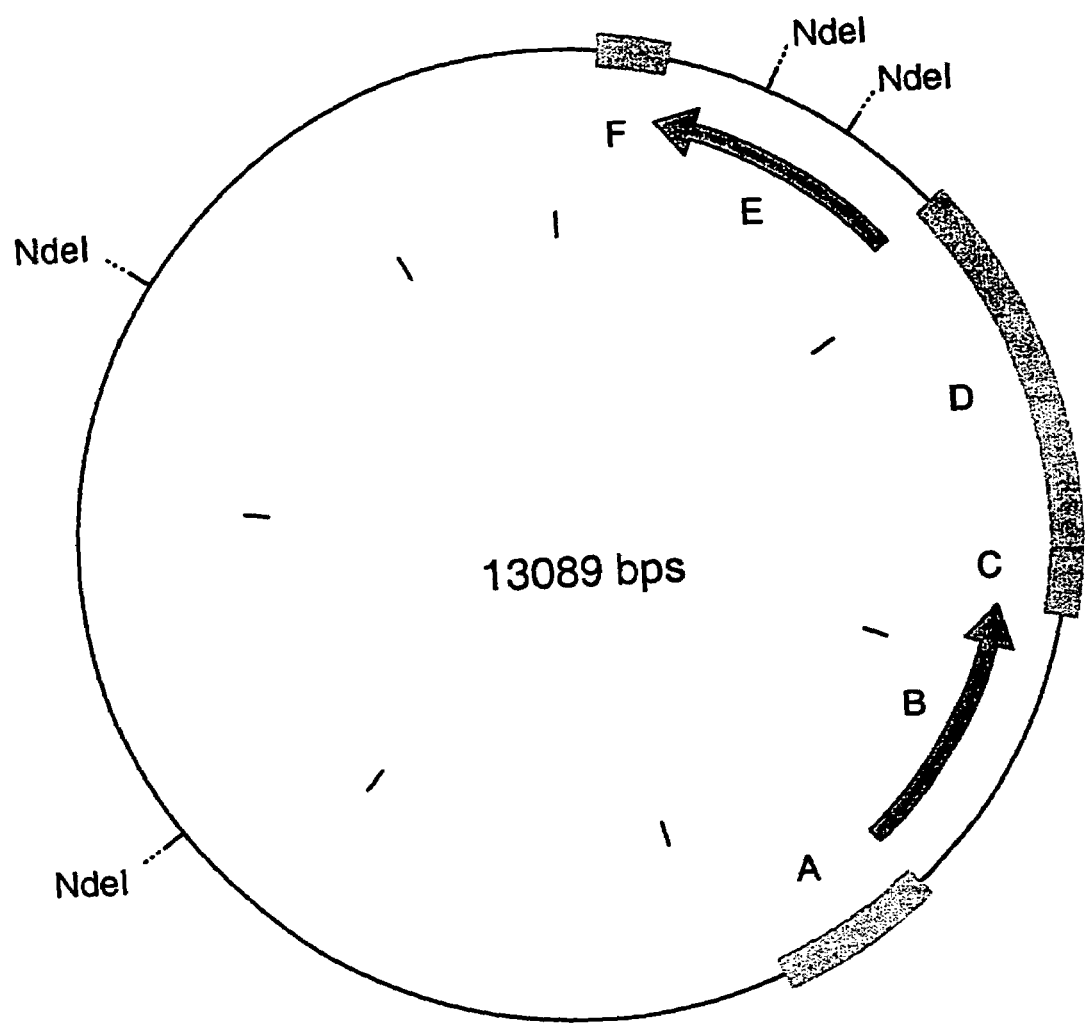
FIG. 45 shows the plasmid pSUN2-SBPP-AtγTMT-35ST-USPP-AtTATase3-nosT.

Fragment A (678 bp) in FIG. 45 comprises the promoter of the *Vicia faba* "unknown seed protein gene" (USPP), fragment B (1334 bp) encodes the *Arabidopsis thaliana* tyrosine aminotransferase gene 3 and fragment C (272 bp) encodes the termination signal of the nopaline synthase gene. Fragment D (1788 bp) comprises the promoter of the *Vicia faba* SBP gene, fragment E (1047 bp) encodes the *Arabidopsis thaliana* γ-tocopherol methyltransferase gene, fragment F (291 bp) encodes the cauliflower mosaic virus 35S terminator.

Example 58

Generation of DNA constructs for expressing the *Arabidopsis thaliana* tyrosine aminotransferase 5 under the control of a seed-specific promoter and the *Arabidopsis thaliana* γ-tocopherol methyltransferase under the control of a seed-specific promoter To prepare chimeric DNA constructs for generating transgenic *Brassica napus* plants which express the *Arabidopsis thaliana* tyrosine aminotransferase 5 under the control of a seed-specific promoter and the *Arabidopsis thaliana* γ-tocopherol methyltransferase in a seed-specific manner, the vectors pSUN2-SBPP-AtγTMT-35sT and pSUN2-USPP-AtTATase5-nosT are combined with each other.

The DNA fragment encoding the expression cassette consisting of: USP promoter, *Arabidopsis thaliana* tyrosine aminotransferase 5 gene and nos terminator is isolated as SmaI/EcoRI fragment from the plasmid pSUN2-USPP-AtTATase5-nosT, the EcoRI end is filled in with Klenow enzyme, and the construct is cloned into the SrfI-digested vector pSUN2-SBPP-AtγTMT-35sT.

This plasmid (pSUN2-SBPP-AtγTMT-35sT/USPP-AtTATase5-nosT, FIG. 46) is used for generating transgenic *Brassica napus* plants.

Figure 46:
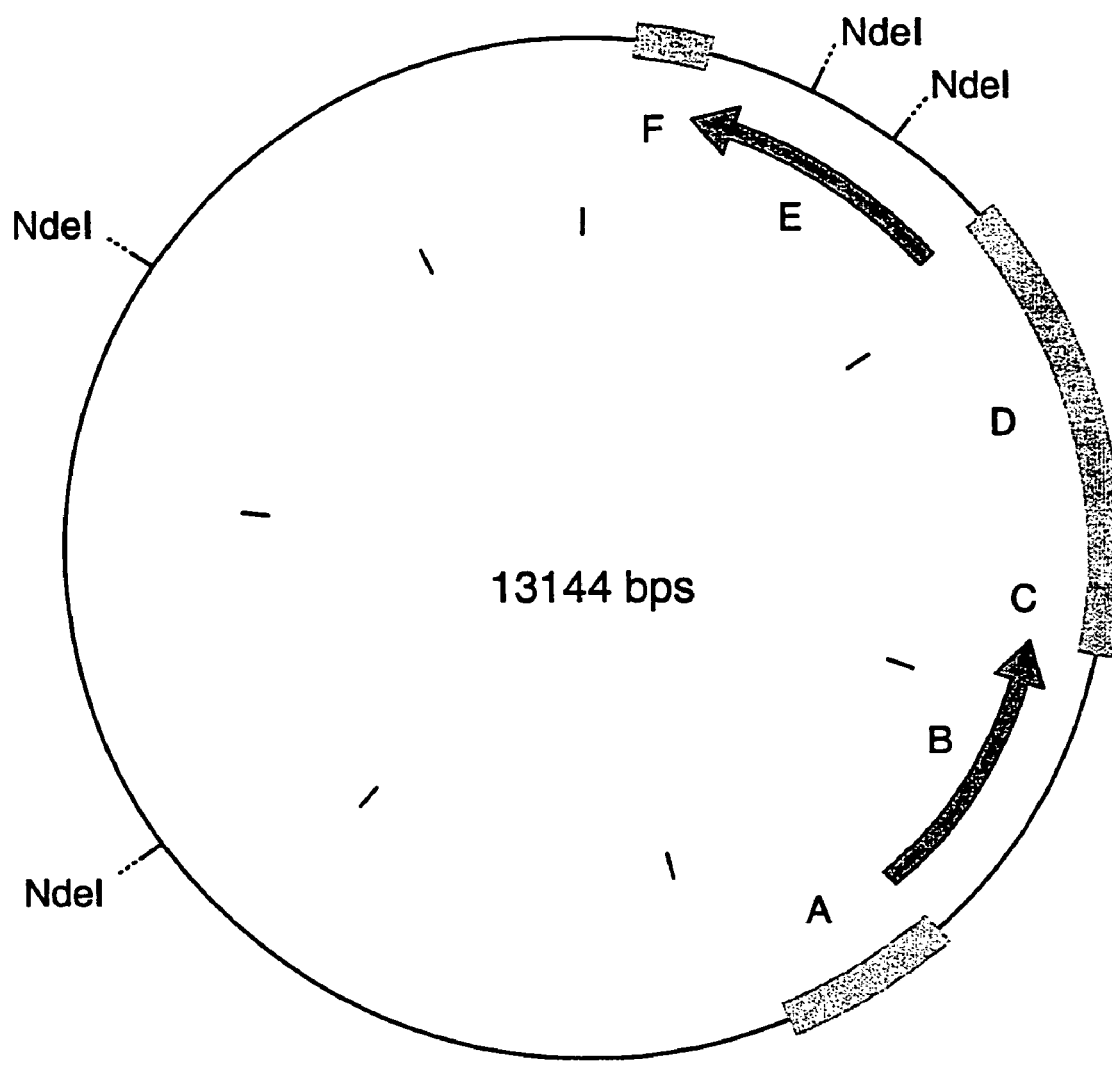
FIG. 46 shows the plasmid pSUN2-SBPP-AtγTMT-35ST-USPP-AtTATase5-nosT.

Fragment A (678 bp) in FIG. 46 comprises the promoter of the *Vicia faba* "unknown seed protein gene", fragment B (1389 bp) encodes the *Arabidopsis thaliana* tyrosine aminotransferase gene 5 and fragment C (272 bp) encodes the termination signal of the nopaline synthase gene. Fragment D (1788 bp) comprises the promoter of the *Vicia faba* SBP gene, fragment E (1047 bp) encodes the *Arabidopsis thaliana* γ-tocopherol methyltransferase gene, fragment F (291 bp) encodes the cauliflower mosaic virus 35S terminator.

Example 59

Generation of DNA constructs for expressing the *Arabidopsis thaliana* tyrosine aminotransferase 6 under the control of a seed-specific promoter and the *Arabidopsis thaliana* γ-tocopherol methyltransferase under the control of a seed-specific promoter To prepare chimeric DNA constructs for generating transgenic *Brassica napus* plants which express the *Arabidopsis thaliana* tyrosine aminotransferase 6 under the control of a seed-specific promoter and the *Arabidopsis thaliana* γ-tocopherol methyltransferase in a seed-specific manner, the vectors pSUN2-SBPP-AtγTMT-35sT and pSUN2-USPP-AtTATase6-nosT are combined with each other.

The DNA fragment encoding the expression cassette consisting of: USP promoter, *Arabidopsis thaliana* tyrosine aminotransferase 6 gene and nos terminator is isolated as SmaI/EcoRI fragment from the plasmid pSUN2-USPP-AtTATase6-nosT, the EcoRI end is filled in with Klenow enzyme, and the construct is cloned into the SrfI-digested vector pSUN2-SBPP-AtγTMT-35sT.

This plasmid (pSUN2-SBPP-AtγTMT-35sT/USPP-At-TATase6-nosT, FIG. 47) is used for generating transgenic *Brassica napus* plants.

Figure 47:
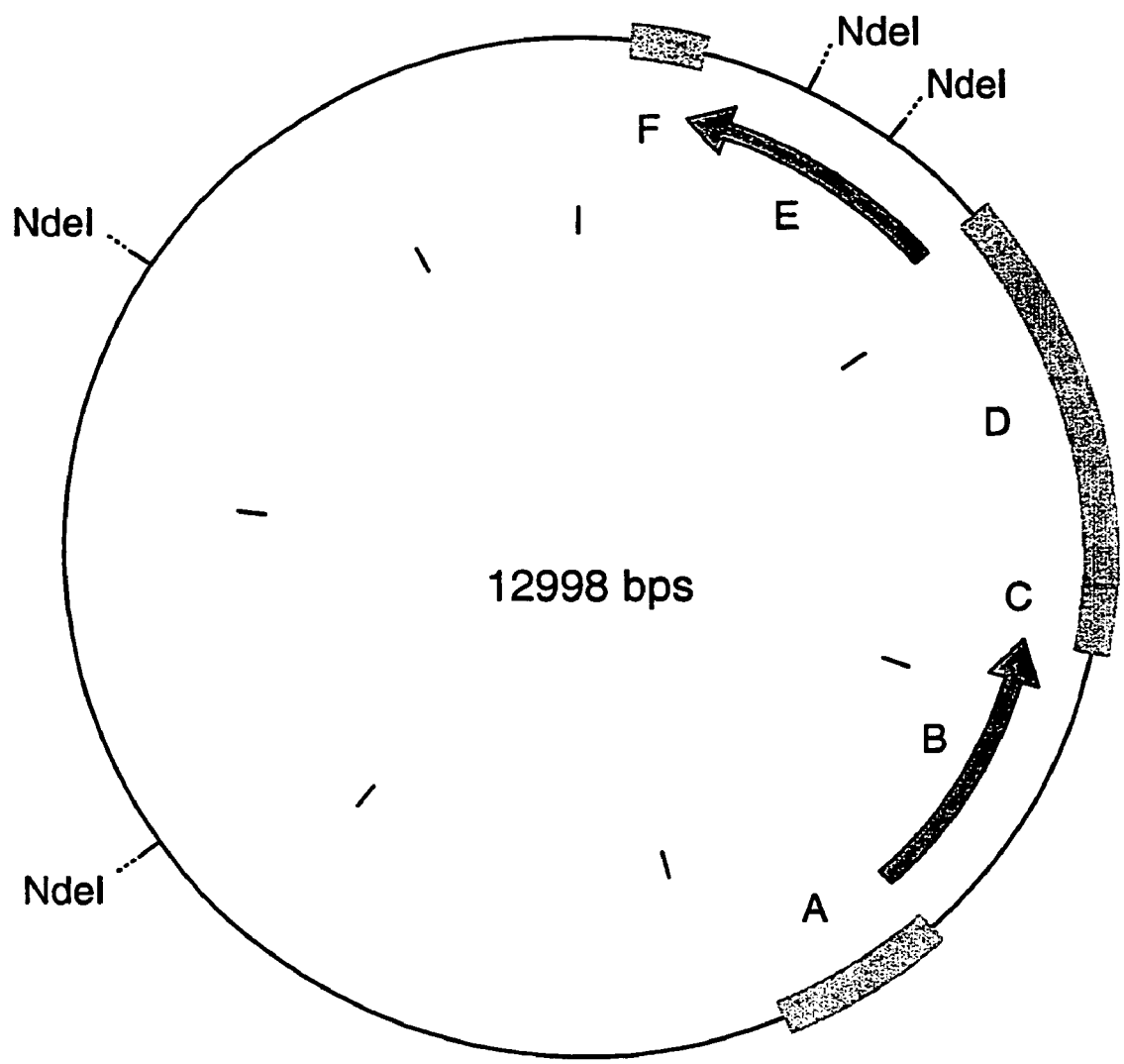
FIG. 47 shows the plasmid pSUN2-SBPP-AtγTMT-35ST-USPP-AtTATase6-nosT.

Fragment A (678 bp) in FIG. 47 comprises the promoter of the *Vicia faba* "unknown seed protein gene", fragment B (1243 bp) encodes the *Arabidopsis thaliana* tyrosine aminotransferase gene 6 and fragment C (272 bp) encodes the termination signal of the nopaline synthase gene. Fragment D (1788 bp) comprises the promoter of the *Vicia faba* SBP gene, fragment E (1047 bp) encodes the *Arabidopsis thaliana* γ-tocopherol methyltransferase gene, fragment F (291 bp) encodes the cauliflower mosaic virus 35S terminator.

Example 60

Generation of DNA constructs for expressing the *Nicotiana tabacum* geranylgeranyl-pyrophosphate oxidoreductase under the control of a seed-specific promoter and for the seed-specific suppression of the expression of the *Brassica napus* homogentisate dioxygenase gene To prepare chimeric DNA constructs for generating transgenic *Brassica napus* plants which express the *Nicotiana tabacum* geranylgeranyl-pyrophosphate oxidoreductase under the control of a seed-specific promoter and suppress the expression of the endogenous *Brassica napus* homogentisate dioxygenase gene in a seed-specific manner, the vectors pCR4topoblunt-LeB4-NtGGPPOR-nosT (see hereinbelow) and pSUN2-Pvic-*BnHGD-STLS1-α*BnHGD-ocsT are combined with each other.

The expression cassette consisting of LeB4 promoter, *Nicotiana tabacum* geranylgeranyl-pyrophosphate oxidoreductase gene and nos termination sequence is amplified by means of PCR using a sense-specific primer (LeB4-SrfI 5': SEQ. ID. No. 54) and an antisense-specific primer (nosT-SrfI 3' SEQ. ID. No. 53), and cloned into the vector pCR4topoblunt (Invitrogen).

The resulting plasmid is pCR4topoblunt-LeB4-NtGGP-POR-nosT

The PCR conditions were as follows:

The PCR was carried out with a 50 µl reaction mix consisting of:

1 µl of a puc19-LeB4-NtGGPPOR-nosT plasmid DNA
0.2 mM DATP, dTTP, dGTP, dCTP
1.5 mM Mg(OAc)$_2$
5 µg of bovine serum albumin
40 pmol of LeB4-SrfI 5' primer
40 pmol of nosT-SrfI 3' primer
5 µl of 10× Pfu1 DNA polymerase buffer (Stratagene)
5 U of Pfu1 DNA polymerase (Stratagene)

The PCR was carried out under the following cycle conditions:
Step 1: 5 minutes at 94° C. (denaturing)
Step 2: 3 seconds at 94° C.
Step 3: 1 minute at 55° C. (annealing)
Step 4: 10 minutes at 68° C. (elongation) 30 cycles of steps 2-4
Step 5: 10 minutes at 72° C. (post-elongation)

The DNA fragment encoding the expression cassette composed of: LeB4 promoter, *Nicotiana tabacum* geranylgeranyl-pyrophosphate oxidoreductase gene and nos terminator is isolated as SrfI fragment from the plasmid pCR4topoblunt-LeB4-NtGGPPOR-nosT and cloned into the EcoRV-digested vector pSUN2-Pvic-*BnHGD-STLS1-α*BnHGD-ocsT.

This plasmid (pSUN2-Pvic-*BnHGD-STLS1-α*Bn-HGD-ocsT/LeB4-NtGGPPOR-nosT, FIG. 48) is used for generating transgenic *Brassica napus* plants.

Figure 48:
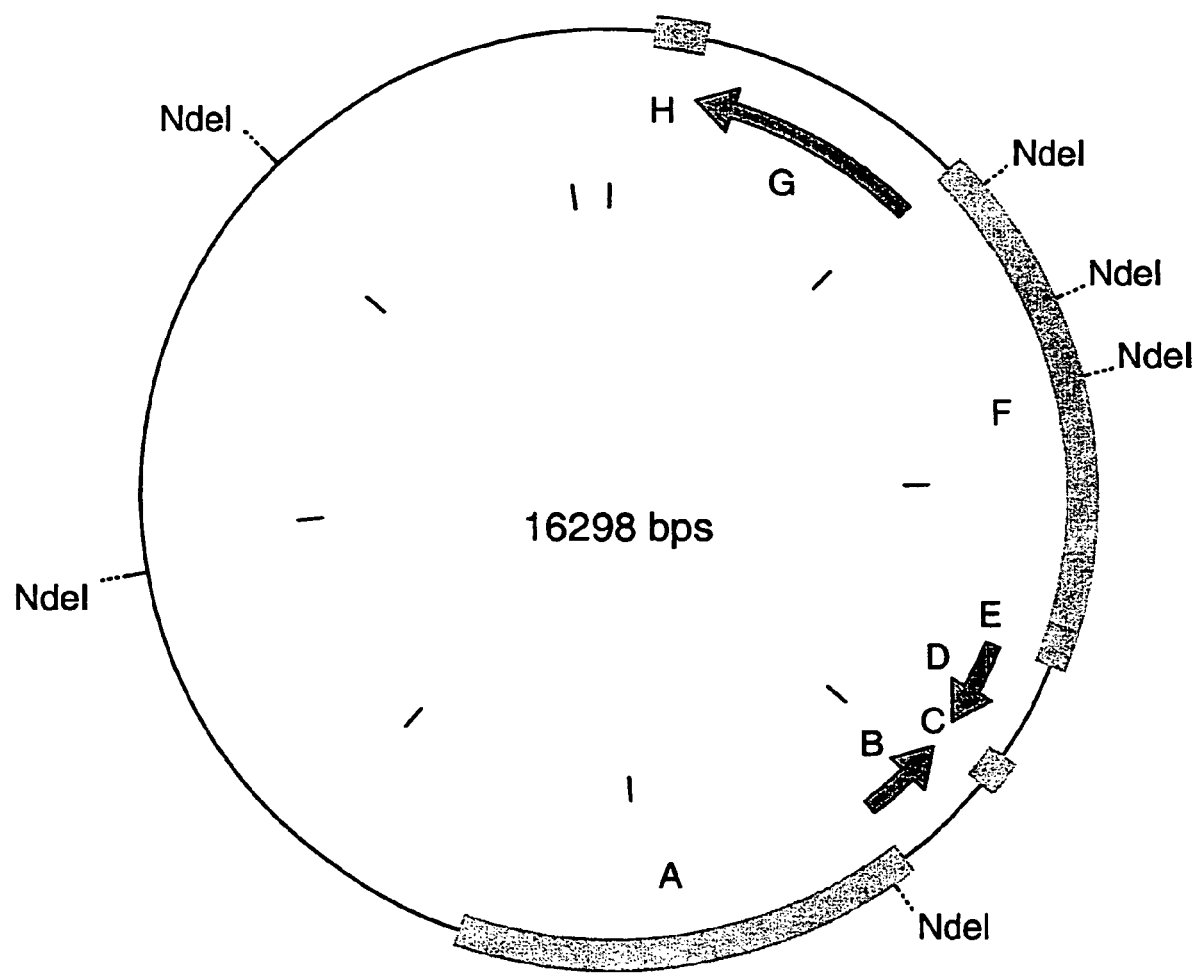
FIG. 48 shows the plasmid pSUN2-Pvic-*BnHGD-STLS1-α*BnHGD-ocsT-LeB4-NtGGPPOR-nosT.

Fragment A (2559 bp) in FIG. 48 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal 2 of the octopine gene. Fragment F (2764 bp) comprises the promoter of the *Vicia faba* legumin B4 gene, fragment G (1509 bp) encodes the *Nicotiana tabacum* geranylgeranyl-pyrophosphate oxidoreductase gene. Fragment H (272 bp) encodes the termination signal of the nopaline synthase gene.

Example 61

Generation of DNA constructs for expressing the *Arabidopsis thaliana* hydroxyphenylpyruvate dioxygenase under the control of a seed-specific promoter and for the seed-specific suppression of the expression of the *Brassica napus* homogentisate dioxygenase gene.

To prepare chimeric DNA constructs for generating transgenic *Brassica napus* plants which express the *Arabidopsis thaliana* hydroxyphenylpyruvate dioxygenase under the control of a seed-specific promoter and which suppress the expression of the endogenous *Brassica napus* homogentisate dioxygenase gene in a seed-specific fashion, the vectors pCR4topoblunt-USPP-AtHPPD-ocsT (see below) and pSUN2-Pvic-*BnHGD-STLS1-α*BnHGD-ocsT are combined with each other.

The expression cassette composed of: USP promoter, *Arabidopsis thaliana* hydroxyphenylpyruvate dioxygenase and ocs termination sequence 1 is amplified by means of PCR using a sense-specific primer (USPP-SrfI-5': SEQ. ID. No. 52) and an antisense-specific primer (ocsT-SrfI-3': SEQ. ID. No. 55) and cloned into the vector pCR4topoblunt (Invitrogen). The resulting plasmid is pCR4topoblunt-USPP-AtHPPD-ocsT.

The PCR conditions were as follows:

The PCR was carried out with a 50 µl reaction mix consisting of:

1 µl of a pSUN2-USPP-AtHPPD-ocsT plasmid DNA
0.2 mM dATP, dTTP, dGTP, dCTP
1.5 mM Mg(OAc)$_2$
5 µg of bovine serum albumin
40 pmol of USPP-SrfI 5' primer
40 pmol of ocsT-SrfI 3' primer
5 µl of 10×Pfu1 DNA polymerase buffer (Stratagene)
5 U of Pfu1 DNA polymerase (Stratagene)

The PCR was carried out under the following cycle conditions:
Step 1: 5 minutes at 94° C. (denaturing)
Step 2: 3 seconds at 94° C.
Step 3: 1 minute at 55° C. (annealing)
Step 4: 10 minutes at 68° C. (elongation) 30 cycles of steps 2-4
Step 5: 10 minutes at 72° C. (post-elongation)

The DNA fragment consisting of USP promoter, *Arabiaopsis thaliana* hydroxyphenylpyruvate dioxygenase and ocs termination sequence is isolated as SrfI fragment from the plasmid pCR4TOPOblunt/USPP-AtHPPD-ocsT and cloned into the EcoRV-digested vector pSUN2-Pvic-*Bn-HGD-STLS1-α*BnHGD-ocsT.

This plasmid (pSUN2-Pvic-*BnHGD-STLS1-α*Bn-HGD-ocsT/USPP-AtHPPD-ocsT, FIG. 49) is used for generating transgenic *Brassica napus* plants.

Figure 49:
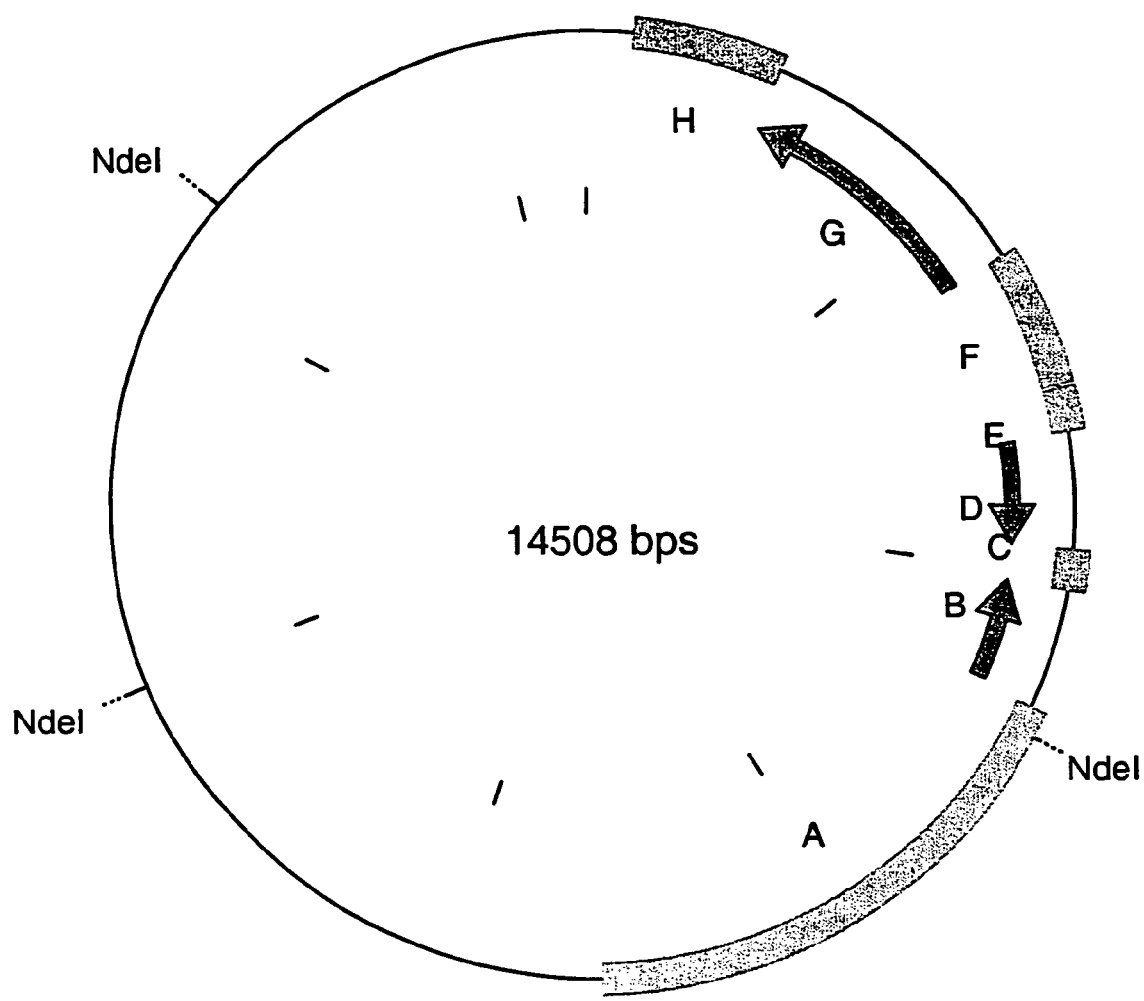
FIG. 49 shows the plasmid pSUN2-Pvic-*BnHGD-STLS1-α*BnHGD-ocsT-USPP-AtHPPD-ocsT.

Fragment A (2559 bp) in FIG. 49 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal 2 of the octopine gene. Fragment F (678 bp) comprises the promoter of the *Vicia faba* "unknown seed protein gene", fragment G (1338 bp) encodes the *Arabidopsis thaliana* hydroxyphenylpyruvate dioxygenase gene. Fragment H (713 bp) encodes the octopine synthase termination signal 1.

Example 62

Generation of DNA constructs for expressing the *Arabidopsis thaliana* homogentisate phytyltransferase under the control of a seed-specific promoter and for the seed-specific suppression of the expression of the *Brassica napus* homogentisate dioxygenase gene To prepare chimeric DNA constructs for generating transgenic *Brassica napus* plants which express the *Arabidopsis thaliana* homogentisate phytyltransferase under the control of a seed-specific promoter and which suppress the expression of the endogenous *Brassica napus* homogentisate dioxygenase gene in a seed-specific fashion, the vectors pCR4topoblunt-USPP-AtHPT-ocsT (see below) and pSUN2-Pvic-*BnHGD-STLS1-α*BnHGD-ocsT are combined with each other.

The expression cassette composed of: USP promoter, *Arabidopsis thaliana* homogentisate phytyltransferase and ocs termination sequence is amplified by means of PCR using a sense-specific primer (USPP-SrfI-5' SEQ. ID. No. 52) and an antisense-specific primer (ocsT-SrfI-3' SEQ. ID. No. 55) and cloned into the vector pCR4topoblunt (Invitrogen).

The resulting plasmid is pCR4topoblunt-USPP-AtHPT-ocsT.

The PCR conditions were as follows:
The PCR was carried out with a 50 µl reaction mix consisting of:
1 µl of a pSUN2-USPP-AtHPT-ocsT plasmid DNA
0.2 mM DATP, dTTP, dGTP, dCTP
1.5 mM Mg(OAc)$_2$
5 µg of bovine serum albumin
40 pmol of USPP-SrfI 5' primer
40 pmol of ocsT-SrfI 3' primer
5 µl of 10× Pfu1 DNA polymerase buffer (Stratagene)
5 U of Pfu1 DNA polymerase (Stratagene)
The PCR was carried out under the following cycle conditions:
Step 1: 5 minutes at 94° C. (denaturing)
Step 2: 3 seconds at 94° C.
Step 3: 1 minute at 55° C. (annealing)
Step 4: 10 minutes at 68° C. (elongation) 30 cycles of steps 2-4
Step 5: 10 minutes at 72° C. (post-elongation)

The DNA fragment consisting of USP promoter, *Arabidopsis thaliana* homogentisate phytyltransferase and ocs termination sequence 1 is isolated as SrfI fragment from the plasmid pCR4TOPOblunt/USPP-AtHPT-ocsT and cloned into the EcoRV-digested vector pSUN2-Pvic-*BnHGD-STLS1-α*BnHGD-ocsT.

This plasmid (pSUN2-Pvic-*BnHGD-STLS1-α*Bn-HGD-ocsT/USPP-AtHPT-ocsT, FIG. 50) is used for generating transgenic *Brassica napus* plants.

Figure 50:
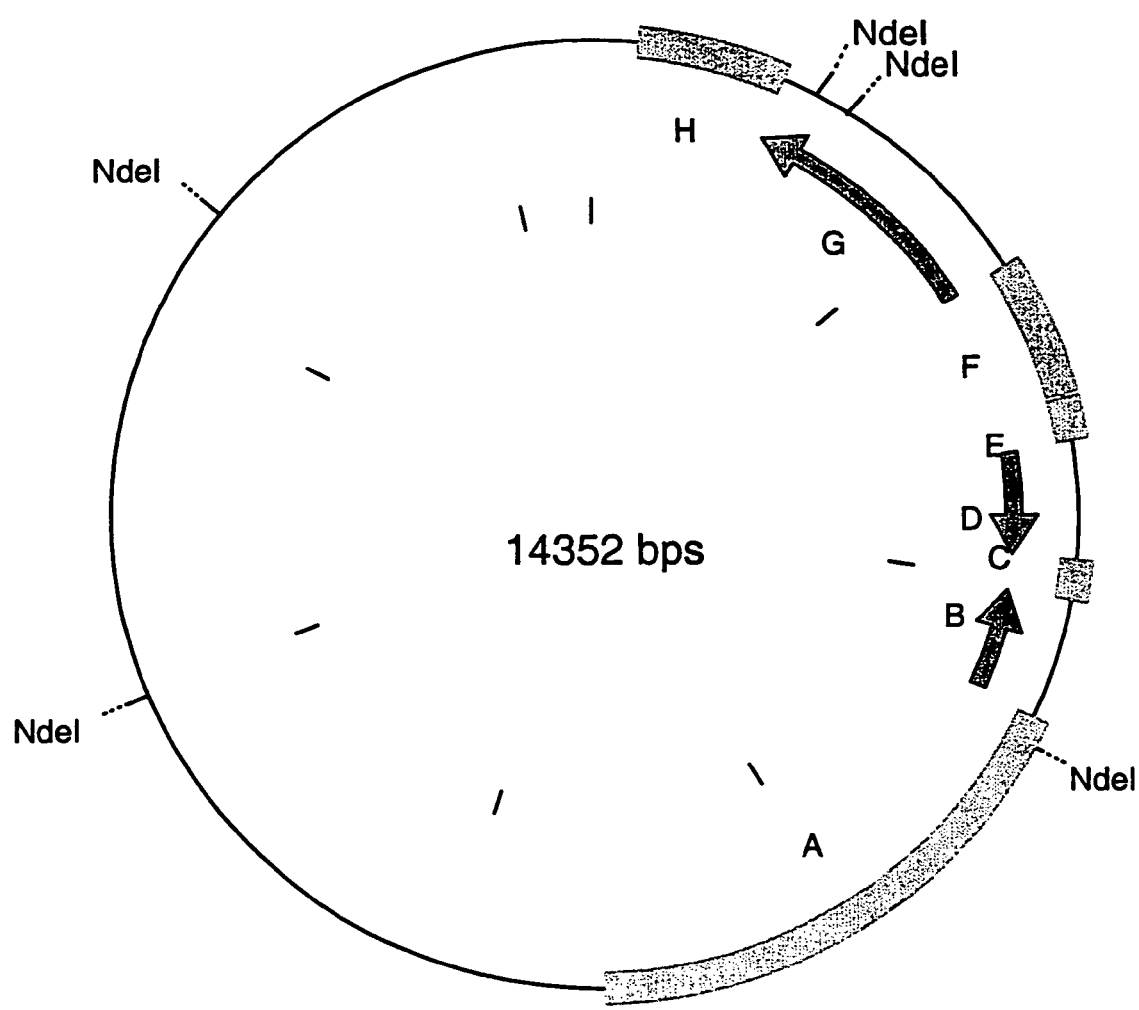
FIG. 50 shows the plasmid pSUN2-Pvic-*BnHGD-STLS1-α*BnHGD-ocsT-USPP-AtHPPD-ocsT.

Fragment A (2559 bp) in FIG. 50 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal 2 of the octopine gene. Fragment F (678 bp) comprises the promoter of the *Vicia faba* "unknown seed protein gene", fragment G (1182 bp) encodes the *Arabidopsis thaliana* homogentisate phytyltransferase gene. Fragment H (713 bp) encodes the octopine synthase gene termination signal 1.

Example 63

Generation of DNA constructs for expressing the *Synechocystis* spec PCC6803 2-methyl-6-phytylhydroquinone methyltransferase under the control of a seed-specific promoter and for the seed-specific suppression of the expression of the *Brassica napus* homogentisate dioxygenase gene To prepare chimeric DNA constructs for generating transgenic *Brassica napus* plants which express the *Synechocystis* spec PCC6803 2-methyl-6-phytylhydroquinone methyltransferase under the control of a seed-specific promoter and which suppress the expression of the endogenous *Brassica napus* homogentisate dioxygenase gene in a seed-specific fashion, the vectors pCR4topoblunt-LeB4-IPP-SynMt1-nosT (see hereinbelow) and pSUN2-Pvic-*BnHGD-STLS1-α*BnHGD-ocsT are combined with each other.

The expression cassette composed of: LeB4 promoter, the sequence encoding the transit peptide of the *A. thaliana* plastid-specific isopentenyl-pyrophosphate isomerase 2 (IPP-2), the *Synechocystis* spec PCC6803 2-methyl-6-phytylhydroquinone methyltranserase and nos termination sequence is amplified by means of PCR using a sense-specific primer (LeB4-SrfI-5': SEQ. ID. No. 54) and an antisense-specific primer (nosT-SrfI-3': SEQ. ID. No. 53) and cloned into the vector pCR4topoblunt (Invitrogen). The resulting plasmid is pCR4topoblunt-LeB4-IPP-SynMt1-nosT.

The PCR conditions were as follows:
The PCR was carried out with a 50 µl reaction mix consisting of:
1 µl of a pSUN2-LeB4-IPP-SynMT1-nosT plasmid DNA
0.2 mM dATP, dTTP, dGTP, dCTP
1.5 mM Mg(OAc)$_2$
5 µg of bovine serum albumin
40 pmol of LeB4-SrfI 5' primer
40 pmol of nosT-SrfI 3' primer
5 µl of 10× Pfu1 DNA polymerase buffer (Stratagene)
5 U of Pfu1 DNA polymerase (Stratagene)
The PCR was carried out under the following cycle conditions:
Step 1: 5 minutes at 94° C. (denaturing)
Step 2: 3 seconds at 94° C.
Step 3: 1 minute at 55° C. (annealing)
Step 4: 10 minutes at 68° C. (elongation) 30 cycles of steps 2-4
Step 5: 10 minutes at 72° C. (post-elongation)

The DNA fragment consisting of LeB4 promoter, the sequence encoding the transit peptide of the *A. thaliana* plastid-specific isopentenyl-pyrophosphate isomerase 2 (IPP-2), the *Synechocystis* spec PCC6803 2-methyl-6-phytylhydroquinone methyltransferase and the nos termination sequence is isolated as SrfI fragment from the plasmid pCR4topoblunt/LeB4-IPP-SynMT1-nosT and cloned into the EcoRV-digested vector pSUN2-Pvic-*nHGD-STLS1-α*nHGD-ocsT.

Figure 51:
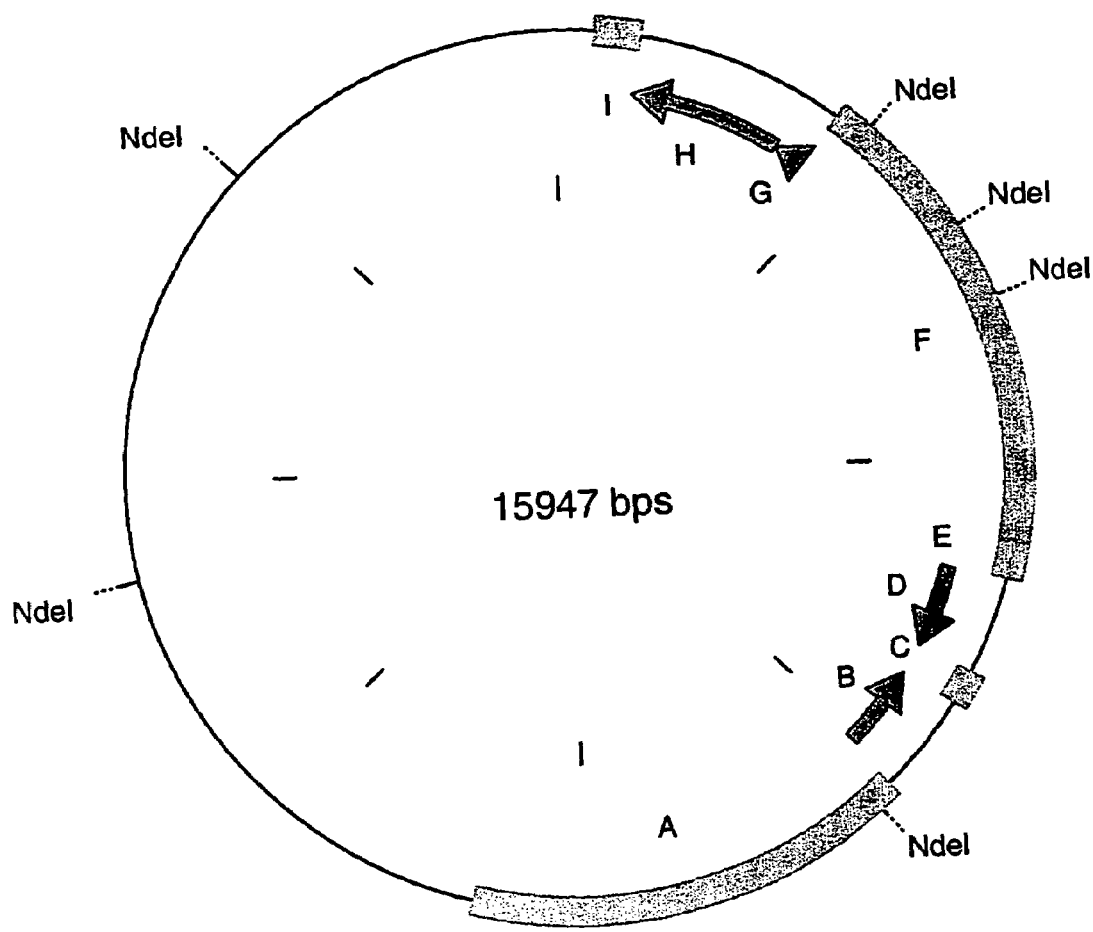
FIG. 51 shows the plasmid pSUN2-Pvic-*BnHGD-STLS1-α*BnHGD-ocsT-LeB4-IPP-SynMT1-nosT.

This plasmid (pSUN2-Pvic-*nHGD-STLS1-α*nHGD-ocsT/USPP-LeB4-IPP-SynMT1-nosT, FIG. 51) is used for generating transgenic *Brassica napus* plants.

Fragment A (2559 bp) in FIG. 51 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal 2 of the octopine gene. Fragment F (2764 bp) comprises the promoter of the *Vicia faba* legumin B4 gene, fragment G (235 bp) encodes the transit peptide of the *A. thaliana* isopentenyl-pyrophosphate isomerase 2. Fragment H (957 bp) encodes the *Synechocystis* sp. PCC6803 2-methyl-6-phytylhydroquinone methyltransferase gene. Fragment I (272 bp) encodes the termination signal of the nopaline synthase gene.

Example 64

Generation of DNA constructs for expressing the *Synechocystis* spec PCC6803 2,3-dimethyl-5-phytylplastoquinol cyclase under the control of a seed-specific promoter and for the seed-specific suppression of the expression of the *Brassica napus* homogentisate dioxygenase gene To prepare chimeric DNA constructs for generating transgenic *Brassica napus* plants which express the *Synechocystis* spec PCC6803 2,3-dimethyl-5-phytylplastoquinol cyclase under the control of a seed-specific promoter and which suppress the expression of the endogenous *Brassica napus* homogentisate dioxygenase gene in a seed-specific fashion, the vectors pCR4topoblunt-LeB4-IPP-SynCyc-nosT (see below) and pSUN27Pvic-*BnHGD-STLS1-α*BnHGD-ocsT are combined with each other.

The expression cassette composed of: LeB4 promoter, the sequence encoding the transit peptide of the *Arabidopsis thaliana* plastid-specific isopentenyl-pyrophosphate isomerase 2 (IPP-2), the *Synechocystis* spec PCC6803 2,3-dimethyl-5-phytylplastoquinol cyclase and nos termination sequence is amplified by means of PCR using a sense-specific primer (LeB4-EcoR5-5': SEQ. ID. No. 56) and an antisense-specific primer (nosT-EcoR5-3': SEQ. ID. No. 57) and cloned into the vector pCR4topoblunt (Invitrogen). The resulting plasmid is pCR4topoblunt-LeB4-IPP-SynMt1-nosT.

The PCR conditions were as follows:
The PCR was carried out with a 50 µl reaction mix comprising:

1 µl of a pSUN2-Leb4-IPP-SynCyc-nosT plasmid DNA
0.2 mM DATP, dTTP, dGTP, dCTP
1.5 mM Mg(OAc)₂
5 µg of bovine serum albumin
40 pmol of LeB4-EcoR5 5' primer
40 pmol of nosT-EcoR5 3' primer
5 µl of 10× Pfu1 DNA polymerase buffer (Stratagene)
5 U of Pfu1 DNA polymerase (Stratagene)

The PCR was carried out under the following cycle conditions:
Step 1: 5 minutes at 94° C. (denaturing)
Step 2: 3 seconds at 94° C.
Step 3: 1 minute at 55° C. (annealing)
Step 4: 10 minutes at 68° C. (elongation) 30 cycles of steps 2-4
Step 5: 10 minutes at 72° C. (post-elongation)

The DNA fragment consisting of LeB4 promoter, the sequence encoding the transit peptide of the *Arabidopsis thaliana* plastid-specific isopentenyl-pyrophosphate isomerase 2 (IPP-2), the *Synechocystis* spec PCC6808 2,3-dimethyl-5-phytylplastoquinol cyclase and the nos termination sequence is isolated as EcoR5 fragment from the plasmid pCR4TOPOblunt/LeB-IPP-SynCyc-nosT and cloned into the EcoR5-digested vector SUN2-Pvic-*BnHGD-STLS1-α*BnHGD-ocsT.

Figure 52:
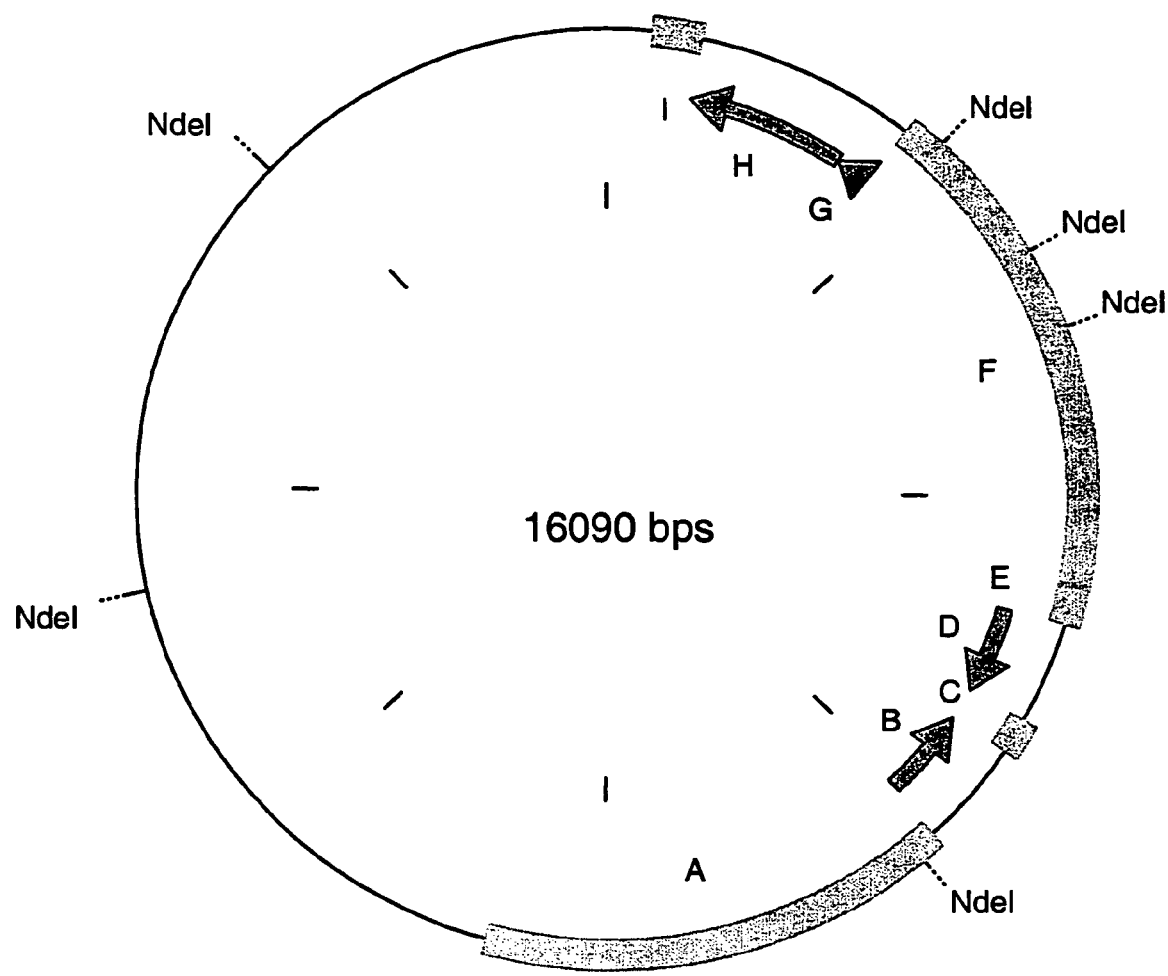
FIG. 52 shows the plasmid pSUN2-Pvic-*BnHGD-STLS1-α*BnHGD-ocsT-LeB4-IPP-SynCyc1-nosT.

This plasmid (pSUN2-Pvic-*BnHGD-STLS1-α*BnHGD-ocsT/LeB-IPP-SynCyc-nosT, FIG. 52) is used for generating transgenic *Brassica napus* plants:

Fragment A (2559 bp) in FIG. 52 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal of the octopine gene. Fragment F (2764 bp) comprises the promoter of the *Vicia faba* legumin B4 gene, fragment G (235 bp) encodes the transit peptide of the *A. thaliana* isopentenyl-pyrophosphate isomerase 2. Fragment H (1100 bp) encodes the *Synechocystis* sp. PCC6808 2,3-dimethyl-5-phytylplastoquinol cyclase gene. Fragment I (272 bp) encodes the termination signal of the nopaline synthase gene.

Example 65

Generation of DNA constructs for expressing the *Arabidopsis thaliana* γ-tocopherol methyltransferase under the control of a seed-specific promoter and for the seed-specific suppression of the expression of the *Brassica napus* homogentisate dioxygenase gene.

To prepare chimeric DNA constructs for generating transgenic *Brassica napus* plants which express the *Arabidopsis thaliana* γ-tocopherol methyltransferase under the control of a seed-specific promoter and which suppress the expression of the endogenous *Brassica napus* homogentisate dioxygenase gene in a seed-specific fashion, the vectors pCR4topoblunt-SBPP-γTMT-35sT (see below) and pSUN2-Pvic-*BnHGD-STLS1-α*BnHGD-ocsT are combined with each other.

The expression cassette consisting of: LeB4 promoter, the sequence encoding the transit peptide of the *A. thaliana* plastid-specific isopentenyl-pyrophosphate isomerase-2 (IPP-2), the *Arabidopsis thaliana* γ-tocopherol methyltransferase and the nos termination sequence is amplified by means of PCR using a sense-specific primer (SBPP-SRFI-5': SEQ. ID. No. 58) and an antisense-specific primer (nosT-SRFI-3' SEQ. ID. No. 53) and cloned into the vector pCR4topoblunt (Invitrogen). The resulting plasmid is pCR4topoblunt-SBPP-γTMT-35sT.

The PCR conditions were as follows:
The PCR was carried out with a 50 µl reaction mix comprising:

1 µl of a pSUN2-SBPP-γTMT-35sT plasmid DNA
0.2 mM DATP, dTTP, dGTP, dCTP
1.5 mM Mg(OAc)₂
5 µg of bovine serum albumin
40 pmol of SBPP-SRFI 5' primer
40 pmol of 35sT-SRFI 3' primer 5 μl of 10× Pful DNA polymerase buffer (Stratagene)
5 U of Pful DNA polymerase (Stratagene)
The PCR was carried out under the following cycle conditions:
Step 1: 5 minutes at 94° C. (denaturing)
Step 2: 3 seconds at 94° C.
Step 3: 1 minute at 55° C. (annealing)
Step 4: 10 minutes at 68° C. (elongation) 30 cycles of steps 2-4
Step 5: 10 minutes at 72° C. (post-elongation)

The DNA fragment consisting of LeB4 promoter, the sequence encoding the transit peptide of the *A. thaliana* plastid-specific isopentenyl-pyrophosphate isomerase 2 (IPP-2), the *Arabidopsis thaliana* γ-tocopherol methyltransferase and the nos termination sequence is isolated as SrfI fragment from the plasmid pCR4TOPOblunt/SBPP-γTMT-35sT and cloned into the EcoRV-digested vector pSUN2-Pvic-*BnHGD-STLS1-α*BnHGD-ocsT.

Figure 53:
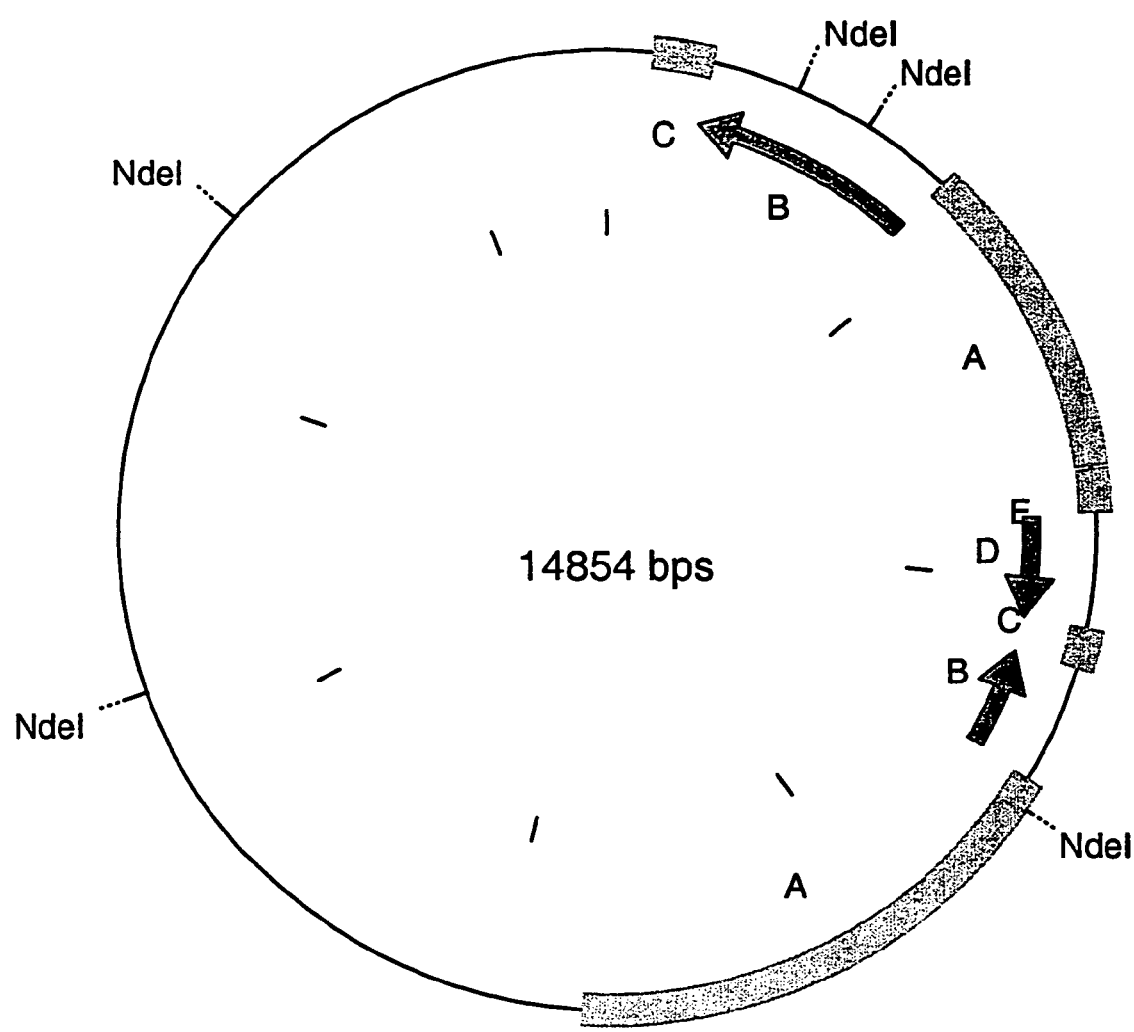
FIG. 53 shows the plasmid pSUN2-Pvic-*BnHGD-STLS1-α*BnHGD-ocsT-USPP-AtγTMT-35ST.

This plasmid (pSUN2-Pvic-*BnHGD-STLS1-α*BnHGD-ocsT/SBPP-γTMT-35sT, FIG. 53) is used for generating transgenic *Brassica napus* plants:

Fragment A (2559 bp) in FIG. 53 comprises the promoter of the *Vicia faba* vicilin gene, fragment B (580 bp) encodes a fragment of the *Brassica napus* homogentisate dioxygenase gene. Fragment C (190 bp) encodes the intron 2 (IV2) of the *Solanum tuberosum* ST-LS1 gene. Fragment D is identical with fragment B, but has the opposite orientation in the vector relative to B. Fragment E (208 bp) encodes the termination signal 2 of the octopine gene. Fragment F (1788 bp) comprises the promoter of the *Vicia faba* SBP gene, fragment G (1047 bp) encodes the *Arabidopsis thaliana* γ-tocopherol methyltransferase gene, fragment H (291 bp) encodes the cauliflower mosaic virus 35S terminator.

Example 66

Generation of DNA constructs for expressing the *Arabidopsis thaliana* hydroxyphenylpyruvate dioxygenase under the control of a seed-specific promoter and the *Nicotiana tabacum* geranylgeranyl-pyrophosphate oxidoreductase under the control of a seed-specific promoter To prepare chimeric DNA constructs for generating transgenic *Brassica napus* plants which express the *Arabidopsis thaliana* hydroxyphenylpyruvate dioxygenase under the control of a seed-specific promoter and which express the *Nicotiana tabacum* geranylgeranyl-pyrophosphate oxidoreductase in a seed-specific manner, the vectors pSUN2-NtGGPPOR-nosT and CR4topoblunt-USPP-AtHPPD-ocsT are combined with each other.

The DNA fragment consisting of USP promoter, *Arabidopsis thaliana* hydroxyphenylpyruvate dioxygenase gene and ocs termination sequence is isolated as SrfI fragment from the plasmid pCR4TOPOblunt/USPP-AtHPPD-ocsT and cloned into the SmaI-digested vector pSUN2-LeB4-NtGGPPOR-nosT.

This plasmid (pSUN2LeB4-NtGGPPORnosT/USPP-AtHPPD-ocsT, FIG. 54) is used for generating transgenic *Brassica napus* plants.

Figure 54:
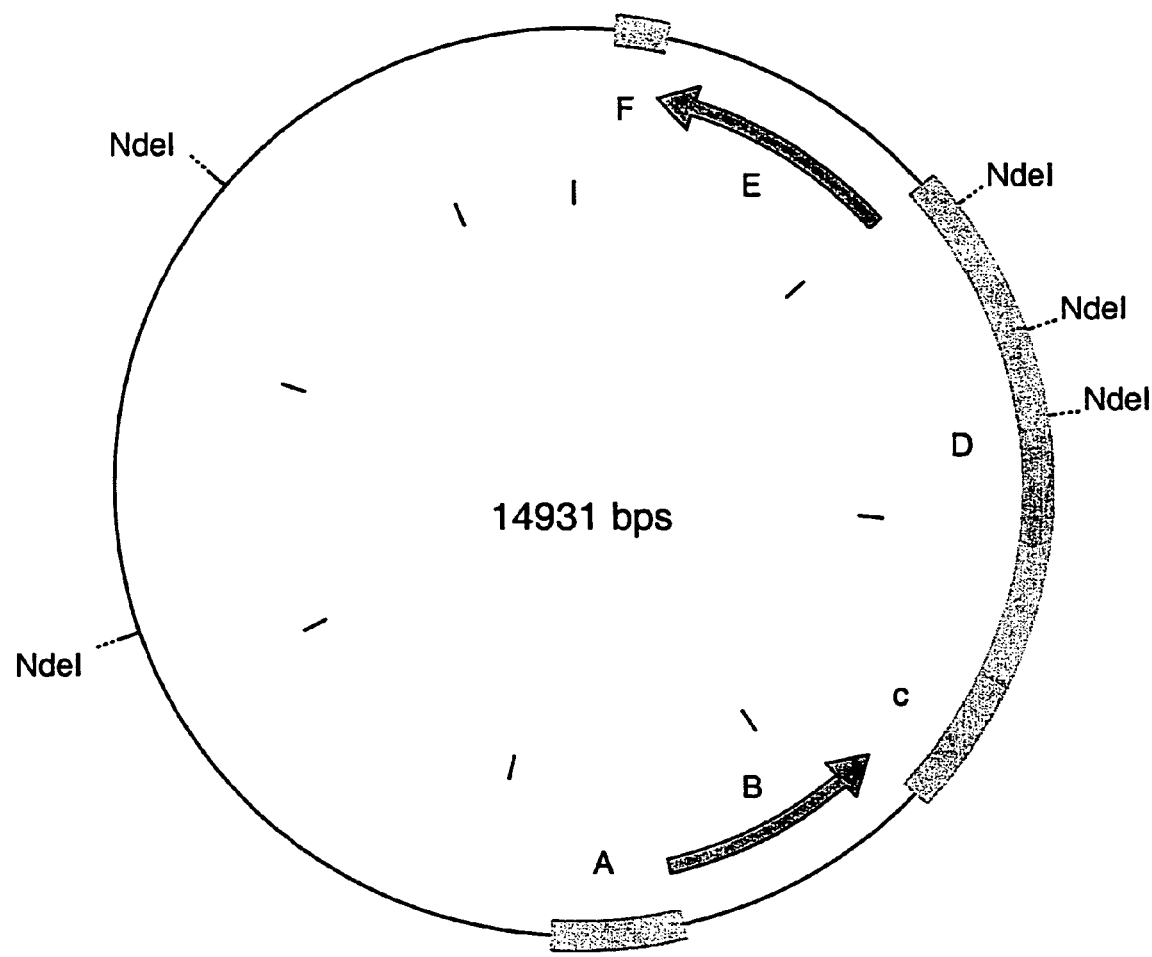
FIG. 54 shows the plasmid pSUN2-LeB4-NtGGPPOR-nosT-USPP-AtHPPD-ocsT.

Fragment A (678 bp) in FIG. 54 comprises the promoter of the *Vicia faba* "unknown seed protein gene", fragment B (1338 bp) encodes the *Arabidopsis thaliana* hydroxyphenylpyruvate dioxygenase gene. Fragment C (713 bp) encodes the termination signal 1 of the octopine synthase gene. Fragment D (2764 bp) comprises the promoter of the *Vicia faba* legumin B4 gene, fragment E (1509 bp) encodes the *Nicotiana tabacum* geranylgeranyl-pyrophosphate oxidoreductase gene. Fragment F (272 bp) encodes the termination signal of the nopaline synthase gene.

Example 67

Generation of DNA constructs for expressing the *Arabidopsis thaliana* homogentisate phytyltransferase under the control of a seed-specific promoter and the *Nicotiana tabacum* geranylgeranyl-pyrophosphate oxidoreductase under the control of a seed-specific promoter To prepare chimeric DNA constructs for generating transgenic *Brassica napus* plants which express the *Arabidopsis thaliana* homogentisate phytyltransferase under the control of a seed-specific promoter and which express the *Nicotiana tabacum* geranylgeranyl-pyrophosphate oxidoreductase in a seed-specific manner, the vectors pSUN2-LeB4-NtGGP-POR-nosT and pCR4topoblunt-USPP-AtHPT-ocsT are combined with each other.

The DNA fragment consisting of USP promoter, *Arabidopsis thaliana* homogentisate phytyltransferase and ocs termination sequence is isolated as SrfI fragment from the plasmid pCR4TOPOblunt/USPP-AtHPT-ocsT and cloned into the SmaI-digested vector pSUN2-LeB-NtGGPPOR-nosT.

Figure 55:
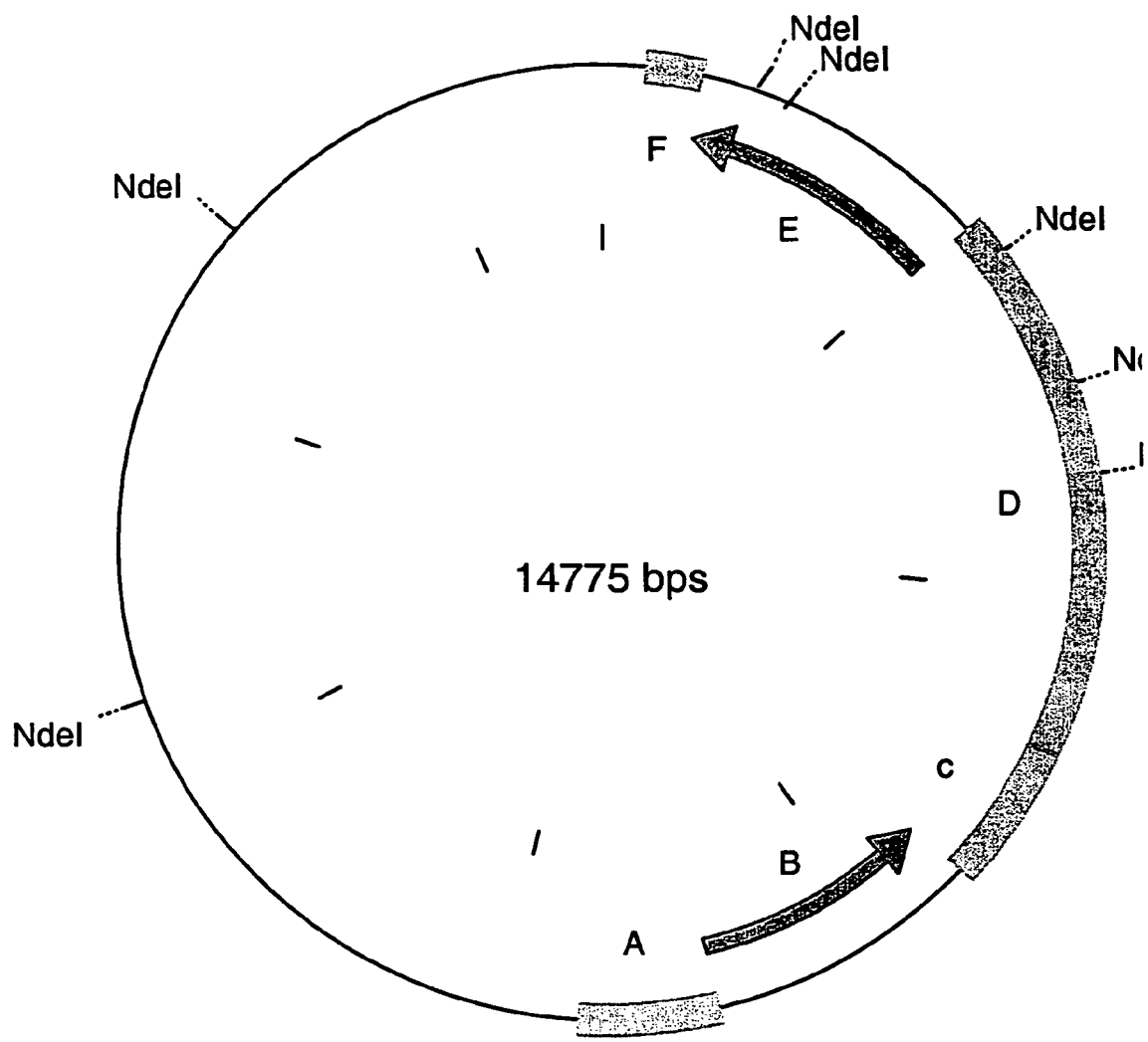
FIG. 55 shows the plasmid pSUN2-LeB4-NtGGPPOR-nosT-USPP-AtHPT-ocsT.

This plasmid (pSUN2-LeB4-NtGGPPOR-nosT/USPP-AtHPT-ocsT, FIG. 55) is used for generating transgenic *Brassica napus* plants:

Fragment A (678 bp) in FIG. 55 comprises the promoter of the *Vicia faba* "unknown seed protein gene", fragment B (1182 bp) encodes the *Arabidopsis thaliana* homogentisic acid phytyltransferase gene. Fragment C (713 bp) encodes the termination signal 1 of the octopine synthase gene. Fragment D (2764 bp) comprises the promoter of the *Vicia faba* legumin B4 gene, fragment E (1509 bp) encodes the *Nicotiana tabacum* geranylgeranyl-pyrophosphate oxidoreductase gene. Fragment F (272 bp) encodes the termination signal of the nopaline synthase gene.

Example 68

Generation of DNA constructs for expressing the *Arabidopsis thaliana* hydroxyphenylpyruvate dioxygenase under the control of a seed-specific promoter, the *Synechocystis* spec PCC6803 2-methyl-6-phytylhydroquinone methyltransferase under the control of a seed-specific promoter and the *Arabidopsis thaliana* γ-tocopherol methyltransferase under the control of a seed-specific promoter To prepare chimeric DNA constructs for generating transgenic *Brassica napus* plants which express the *Arabidopsis thaliana* hydroxyphenylpyruvate dioxygenase under the control of a seed-specific promoter, the *Synechocystis* spec PCC6803 2-methyl-6-phytylhydroquinone methyltransferase under the control of a seed-specific promoter and the *Arabidopsis thaliana* γ-tocopherol methyltransferase under the control of a seed-specific promoter, the vectors pSUN2-SBPP-AtγTMT35ST and pCR4topoblunt-LeB4-IPP-SynMT1-nosT and pCR4topoblunt-USPP-AtHPPDocsT are combined with each other.

The DNA fragment consisting of USP promoter, *Arabidopsis thaliana* hydroxyphenylpyruvate dioxygenase gene and ocs termination sequence 1 is isolated as SrfI fragment from the plasmid pCR4TOPOblunt/USPP-AtHPPD-ocsT and cloned into the SrfI-digested vector pSUN2-SBPP-AtγTMT 35ST, which is likewise previously digested with the restriction enzyme SrfI. The DNA fragment composed of LeB4 promoter, *Synechocystis* spec PCC6803 2-methyl-6-phytylhydroquinone methyltransferase and nos termination sequence is isolated as SrfI fragment from the plasmid pCR4TOPOblunt/LeB-SynMT1-nosT into the above-obtained plasmid pSUN2-SBPP-AtγTMT-35sT/USPP-AtHPPD-ocsT and cloned into the XhoI-digested vector pSUN2-SBPP-AtγTMT35sT/USPP-AtHPPD-ocsT after the XhoI ends had been filled in.

Figure 56:
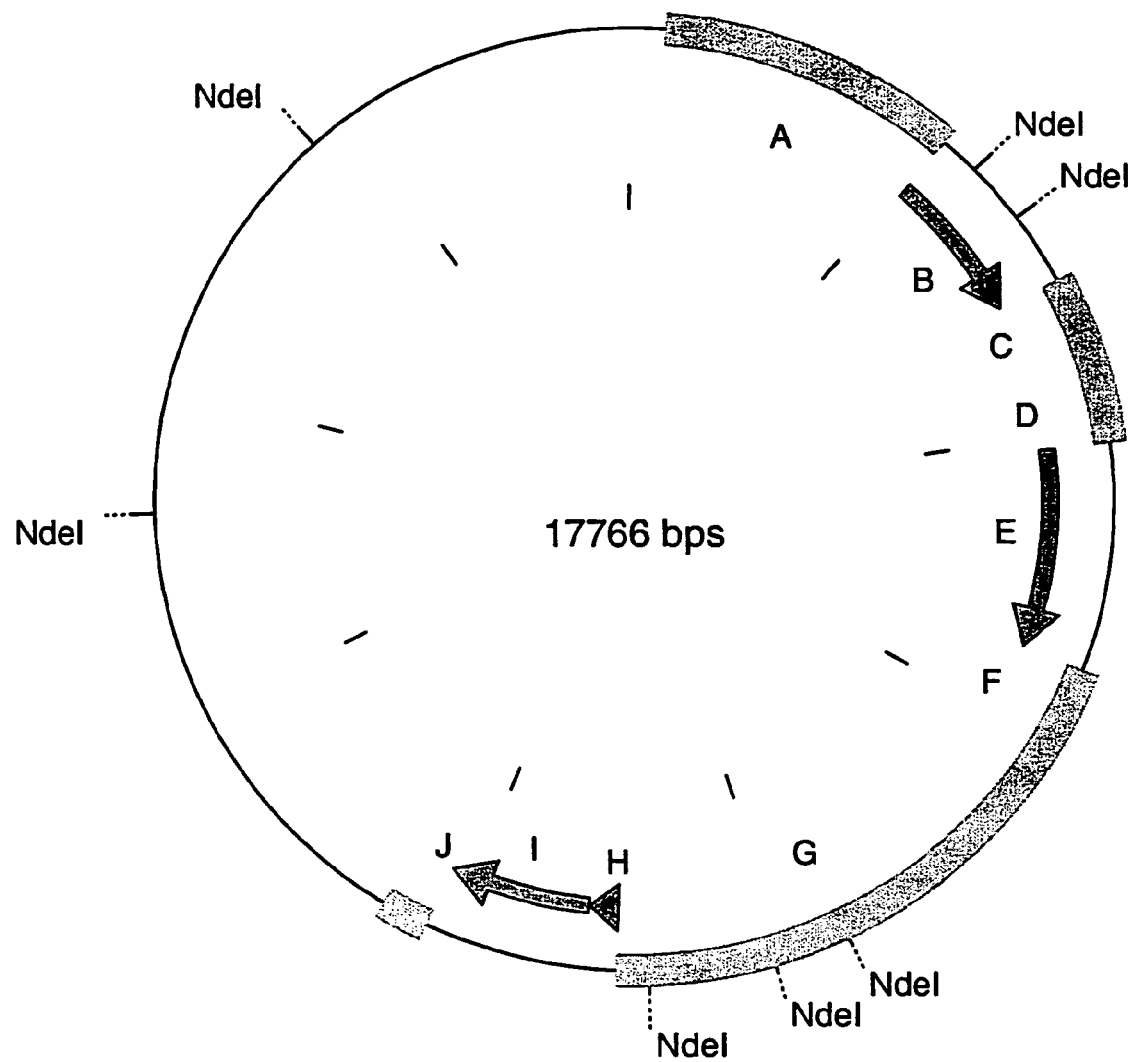
FIG. 56 shows the plasmid pSUN2-SBPP-AtγTMT-35ST-USPP-AtHPPD-ocsT-LeB4-SynMT1-nosT.

This plasmid pSUN2-SBPP-AtγTMT35sT/USPP-AtHPPD-ocsT/LeB-SynMT1-nosT, FIG. 56) is used for generating transgenic *Brassica napus* plants:

Fragment A (1788 bp) in FIG. 56 comprises the promoter of the *Vicia faba* SBP gene, fragment B (1047 bp) encodes the *Arabidopsis thaliana* γ-tocopherol methyltransferase gene, fragment C (291 bp) encodes the cauliflower mosaic virus 35S terminator. Fragment D (678 bp) comprises the promoter of the *Vicia faba* "unknown seed protein gene", fragment E (1338 bp) encodes the *Arabidopsis thaliana* hydroxyphenylpyruvate dioxygenase gene. Fragment F (713 bp) encodes the termination signal 1 of the octopine synthase gene. Fragment G (2764 bp) comprises the promoter of the *Vicia faba* legumin B4 gene, fragment H (235 bp) encodes the transit peptide of the *A. thaliana* isopentenyl-pyrophosphate isomerase 2. Fragment I (957 bp) encodes the *Synechocystis* sp. PCC6803 2-methyl-6-phytylhydroquinone methyltransferase gene. Fragment J (272 bp) encodes the termination signal of the nopaline synthase gene.

Example 69

Generation of DNA constructs for expressing the *Arabidopsis thaliana* hydroxyphenylpyruvate dioxygenase under the control of a seed-specific promoter, the *Synechocystis* spec PCC6803 2-methyl-6-phytylhydroquinone methyltransferase under the control of a seed-specific promoter To prepare chimeric DNA constructs for generating transgenic *Brassica napus* plants which express the *Arabidopsis thaliana* hydroxyphenylpyruvate dioxygenase under the control of a seed-specific promoter and the *Synechocystis* spec PCC6803 2-methyl-6-phytylhydroquinone methyltransferase under the control of a seed-specific promoter, the vector pSUN2-USPP-AtHPPDocsT and the vector pCR4topoblunt-LeB4-IPP-SynMT1-nosT are combined with each other.

The DNA fragment consisting of LeB4 promoter, *Synechocystis* spec PCC6803 2-methyl-6-phytylhydroquinone methyltransferase and nos termination sequence is isolated as SrfI fragment from the plasmid pCR4TOPOblunt/LeB-SynMT1-nosT and cloned into the XhoI-digested vector pSUN2-USPP-AtHPPD-ocsT kloniert whose XhoI ends are filled in.

Figure 57:
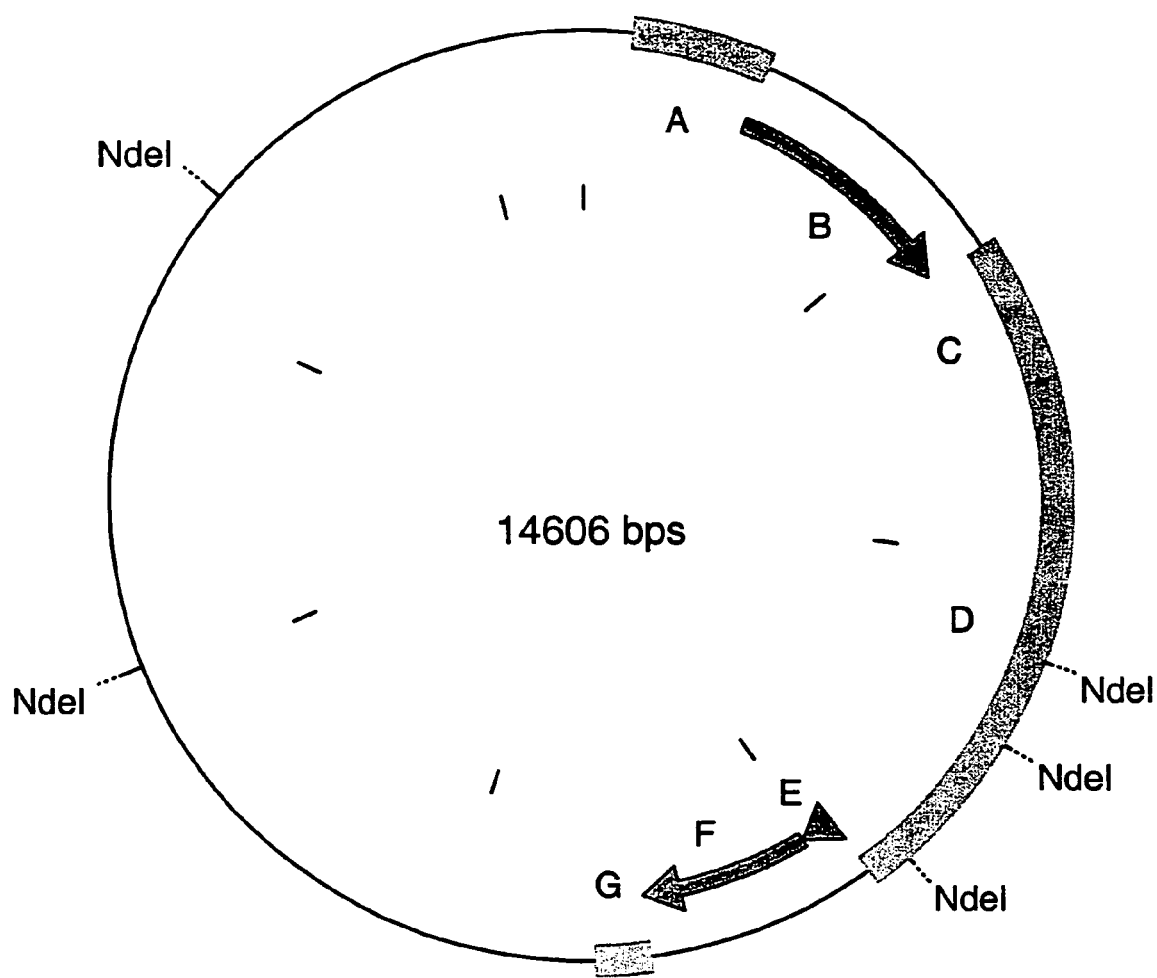
FIG. 57 shows the plasmid pSUN2-USPP-AtHPPD-ocsT-LeB4-SynMT1-nosT.

This plasmid pSUN2-USPP-AtHPPD-ocsT/LeB-SynMT1-nosT, FIG. 57) is used for generating transgenic *Brassica napus* plants:

Fragment A (678 bp) in FIG. 57 comprises the promoter of the *Vicia faba* "unknown seed protein gene", fragment B (1338 bp) encodes the *Arabidopsis thaliana* hydroxyphenylpyruvate dioxygenase gene and fragment C (713 bp) encodes the termination signal 1 of the octopine synthase gene. Fragment D (2764 bp) comprises the promoter of the *Vicia faba* legumin B4 gene, fragment E (235 bp) encodes the transit peptide of the *A. thaliana* isopentenyl-pyrophosphate isomerase 2. Fragment F (957 bp) encodes the *Synechocystis* sp. PCC6803 2-methyl-6-phytylhydroquinone methyltransferase gene. Fragment G (272 bp) encodes the termination signal of the nopaline synthase gene.

Example 70

Generation of DNA constructs for expressing the *Arabidopsis thaliana* hydroxyphenylpyruvate dioxygenase under the control of a seed-specific promoter and the *Nicotiana tabacum* geranylgeranyl-pyrophosphate oxidoreductase under the control of a seed-specific promoter and the *Arabidopsis thaliana* homogentisate phytyltransferase under the control of a seed-specific promoter.

To prepare chimeric DNA constructs for generating transgenic *Brassica napus* plants which express the *Arabidopsis thaliana* hydroxyphenylpyruvate dioxygenase under the control of a seed-specific promoter and the *Nicotiana tabacum* geranylgeranyl-pyrophosphate oxidoreductase under the control of a seed-specific promoter and the *Arabidopsis thaliana* homogentisate phytyltransferase under the control of a seed-specific promoter, the vectors pSUN2-LeB4-NtGGPPOR-nosT/USPP-AtHPT-ocsT and pCR4topoblunt-USPP-AtHPPD-ocsT are combined with each other.

The DNA fragment consisting of USP promoter, *Arabidopsis thaliana* hydroxyphenylpyruvate dioxygenase and ocs termination sequence 1 is isolated as SrfI fragment from the plasmid pCR4TOPOblunt/USPP-AtHPPD-ocsT and cloned into the XhoI-digested vector pSUN2-LeB4-NtGGPPOR-nosT/USPP-AtHPT-ocsT after the XhoI ends have previously been made blunt-ended with Klenow polymerase.

This plasmid (pSUN2LeB4-NtGGPPORnosT/USPP-AtHPPD-ocsT/USPP-AtHPT-ocsT, FIG. 58) is used for generating transgenic *Brassica napus* plants.

Figure 58:
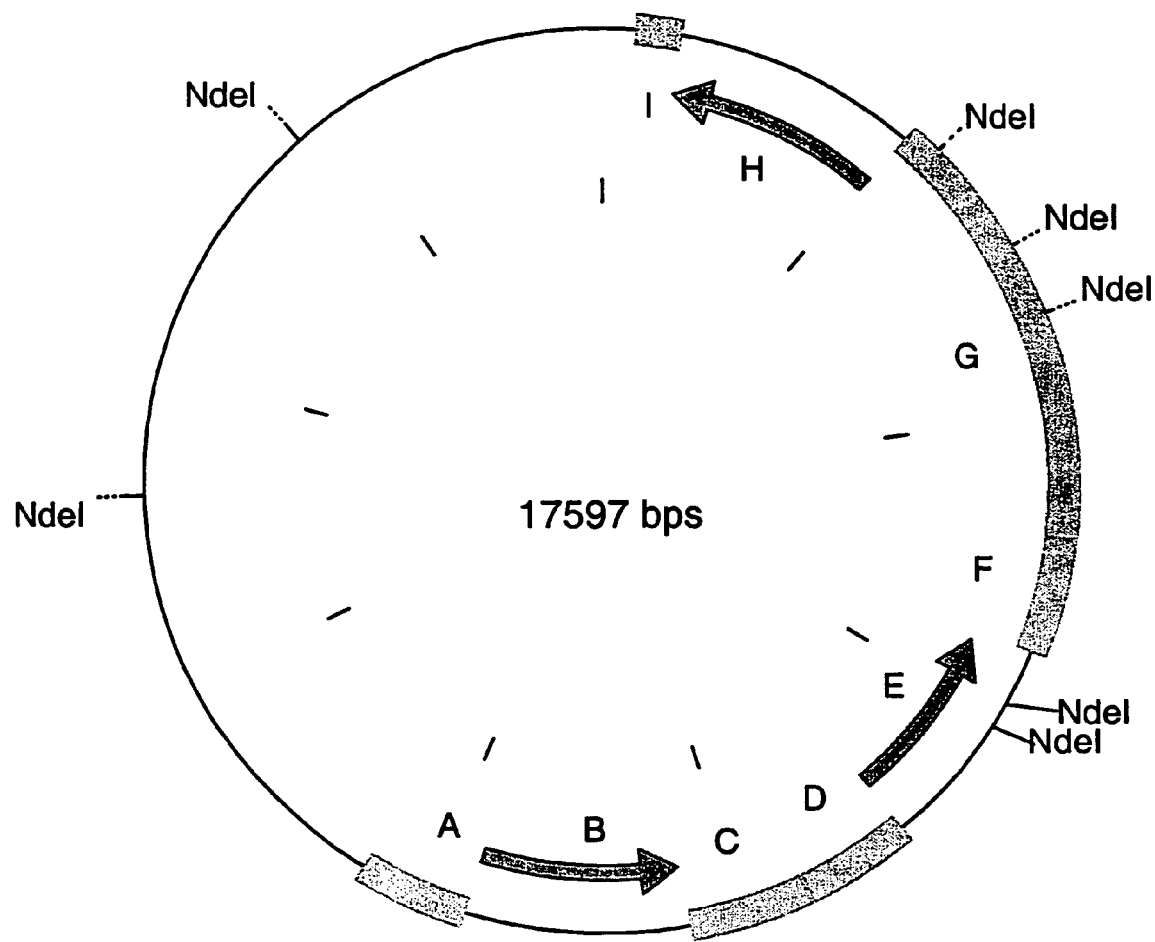
FIG. 58 shows the plasmid pSUN2-LeB4-NtGGPPOR-nosT-USPP-AtHPPD-ocsT-USPP-AtHPT-ocsT.

Fragment A (678 bp) in FIG. 58 comprises the promoter of the *Vicia faba* "unknown seed protein gene", fragment B (1338 bp) encodes the *Arabidopsis thaliana* hydroxyphenylpyruvate dioxygenase gene. Fragment C (713 bp) encodes the termination signal 1 of the octopine synthase gene. Fragment D (678 bp) comprises the promoter of the *Vicia faba* "unknown seed protein gene", fragment E (1182 bp) encodes the *Arabidopsis thaliana* homogentisate phytyltransferase gene. Fragment F (713 bp) encodes the termination signal 1 of the octopine synthase gene. Fragment G (2764 bp) comprises the promoter of the *Vicia faba* legumin B4 gene, fragment H (1509 bp) encodes the *Nicotiana tabacum* geranylgeranyl-pyrophosphate oxidoreductase gene. Fragment I (272 bp) encodes the termination signal of the nopaline synthase gene.

Example 71

Generation of DNA constructs for expressing the *Synechocystis* spec PCC6803 2,3-dimethyl-5-phytylplastoquinol cyclase under the control of a seed-specific promoter, the *Synechocystis* spec PCC6803 2-methyl-6-phytylhydroquinone methyltransferase under the control of a seed-specific promoter, and the *Arabidopsis thaliana* γ-tocopherol methyltransferase under the control of a seed-specific promoter.

To prepare chimeric DNA constructs for generating transgenic *Brassica napus* plants which express the *Synechocystis* spec PCC6803 2,3-dimethyl-5-phytylplastoquinol cyclase under the control of a seed-specific promoter, the *Synechocystis* spec PCC6803 2-methyl-6-phytylhydroquinone methyltransferase under the control of a seed-specific promoter, and the *Arabidopsis thaliana* γ-tocopherol methyltransferase under the control of a seed-specific promoter, the constructs pSUN2-SBPP-AtγTMT35ST/USPP- AtHPPD-ocsT/LeB-SynMT1-nosT and pCR4topoblunt/LeB-IPP-SynCyc-nosT are used.

The DNA fragment consisting of LeB4 promoter, Synechocystis spec PCC6803 2,3-dimethyl-5-phytylplastoquinol cyclase and nos termination sequence is isolated as EcoR5 fragment from the plasmid pCR4topoblunt/LeB-IPP-SynCyc-nosT and cloned into the SrfI-digested vector pSUN2-SBPP-AtγTMT-35ST/USPP-AtHPPD-ocsT/LeB-SynMT1-nosT which is previously digested with the restriction enzyme SrfI. Thus, the expression cassette composed of USP promoter, Arabidopsis thaliana hydroxyphenylpyruvate dihydrogenase gene and ocs termination sequence is exchanged for the expression cassette composed of LeB4 promoter, the Synechocystis spec PCC6803 2,3-dimethyl-5-phytylplastochinol cyclase gene and the nos termination sequence.

Figure 59:
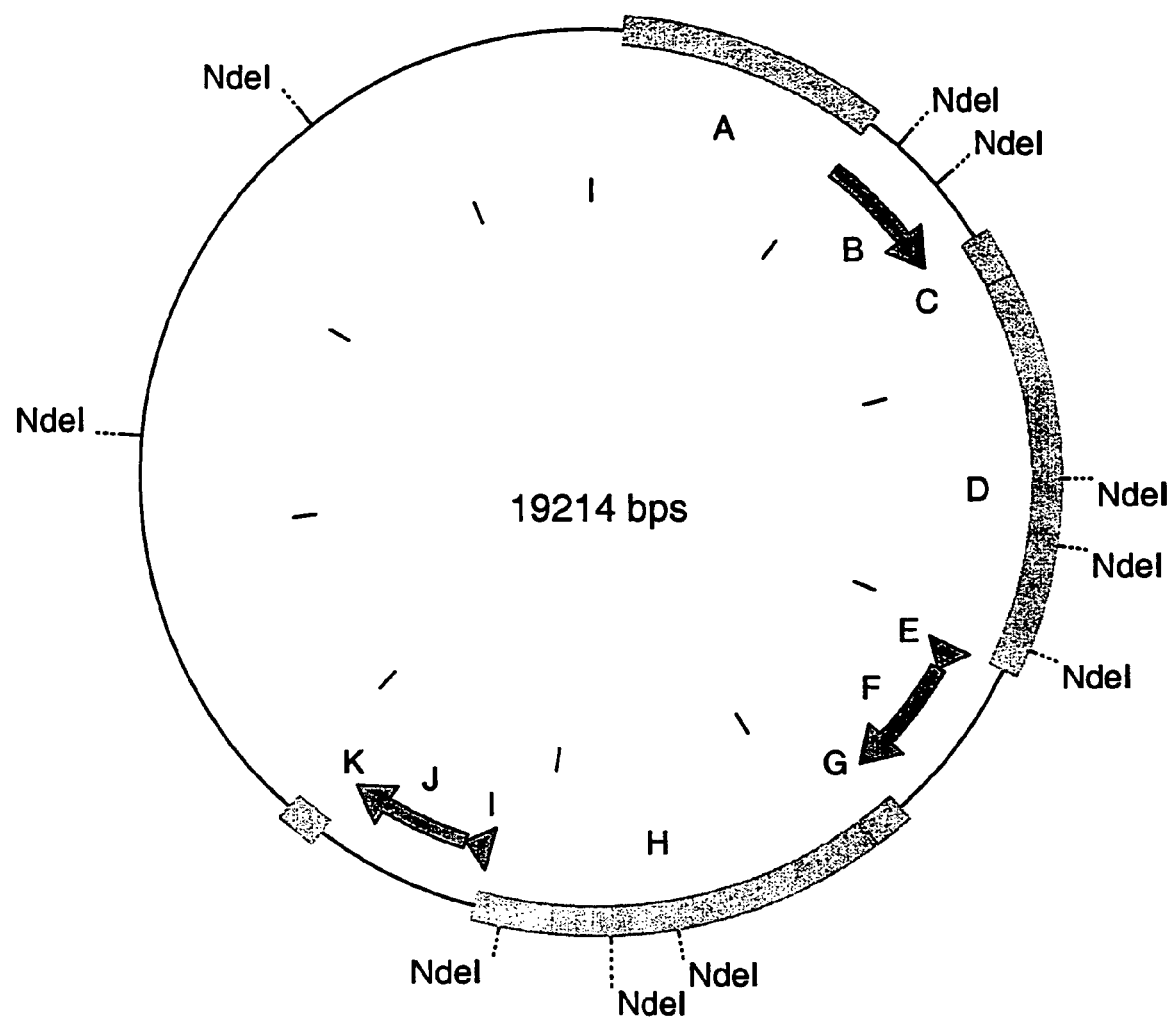
FIG. 59 shows the plasmid pSUN2-SBPP-AtγTMT-35ST-LeB4-IPP-SynCyc-nosT-LeB4-IPP-SynMT1-nosT.

This plasmid pSUN2-SBPP-AtγTMT35sT/LeB-IPP-SynCyc-nosT/LeB-IPP-SynMT1-nosT, FIG. 59) is used for generating transgenic Brassica napus plants.

Fragment A (1788 bp) in FIG. 59 comprises the promoter of the Vicia faba SBP gene, fragment B (1047 bp) encodes the Arabidopsis thaliana γ-tocopherol methyltransferase gene, fragment C (291 bp) encodes the cauliflower mosaic virus 35S terminator. Fragment D (2764 bp) comprises the promoter of the Vicia faba legumin B4 gene, fragment E (235 bp) encodes the transit peptide of the A. thaliana isopentenyl-pyrophosphate isomerase 2. Fragment F (1100 bp) encodes the Synechocystis sp. PCC6803 2,3-dimethyl-5-phytylplastoquinol cyclase gene. Fragment G (272 bp) encodes the termination signal of the nopaline synthase gene. Fragment H (2764 bp) comprises the promoter of the Vicia faba legumin B4 gene, fragment I (235 bp) encodes the transit peptide of the A. thaliana isopentenyl-pyrophosphate isomerase 2. Fragment J (957 bp) encodes the Synechocystis sp. PCC6803 2-methyl-6-phytylhydroquinone methyltransferase gene. Fragment K (272 bp) encodes the termination signal of the nopaline synthase gene.

Example 72

Generation of DNA constructs for expressing the Rattus norvegicus tyrosine aminotransferase under the control of a seed-specific promoter.

To prepare chimeric DNA constructs for generating transgenic A. thaliana, Nicotiana tabacum and B. napus plants which express the Rattus norvegicus tyrosine aminotransferase (Seq. ID. No. 1) under the control of a seed-specific promoter, a derivative of the vector pGPTVkan (D. Becker, E. Kemper, J. Schell, R. Masterson. Plant Molecular Biology 20: 1195-1197, 1992) was used.

This vector was modified in such a way that it contains the seed-specific promoter of the legumin B4 gene (Kafatos et al., Nuc. Acid. Res., 14(6):2707-2720, 1986), the sequence encoding the transit peptide of the A. thaliana plastid-specific isopentenyl-pyrophosphate isomerase 2 (IPP-2) (Badur, unpublished) and the termination signal of the A. tumefaciens nopaline synthase (Depikker et al., J. Mol. Appl. Genet. 1, 561-73, 1982).

The DNA fragment encoding the Rattus norvegicus tyrosine aminotransferase gene was cloned as EcoR5 fragment into the vector pPTVKan-LeP-IPPTP11 after the latter had been digested with the restriction enzyme SalI, and the ends of the linearized plasmid had been made blunt-ended with Klenow enzyme. This generated a translational fusion with the IPP-2 transit peptide and thus ensures the import of tyrosine aminotransferase into the plastids. This plasmid pPTVkan-IPPTP11-TATaseRNnos (also termed pPTVkan-LeB4-IPP-RnTATase-nosT, FIG. 61) was used for generating transgenic Brassica napus and A. thaliana plants.

Figure 61:
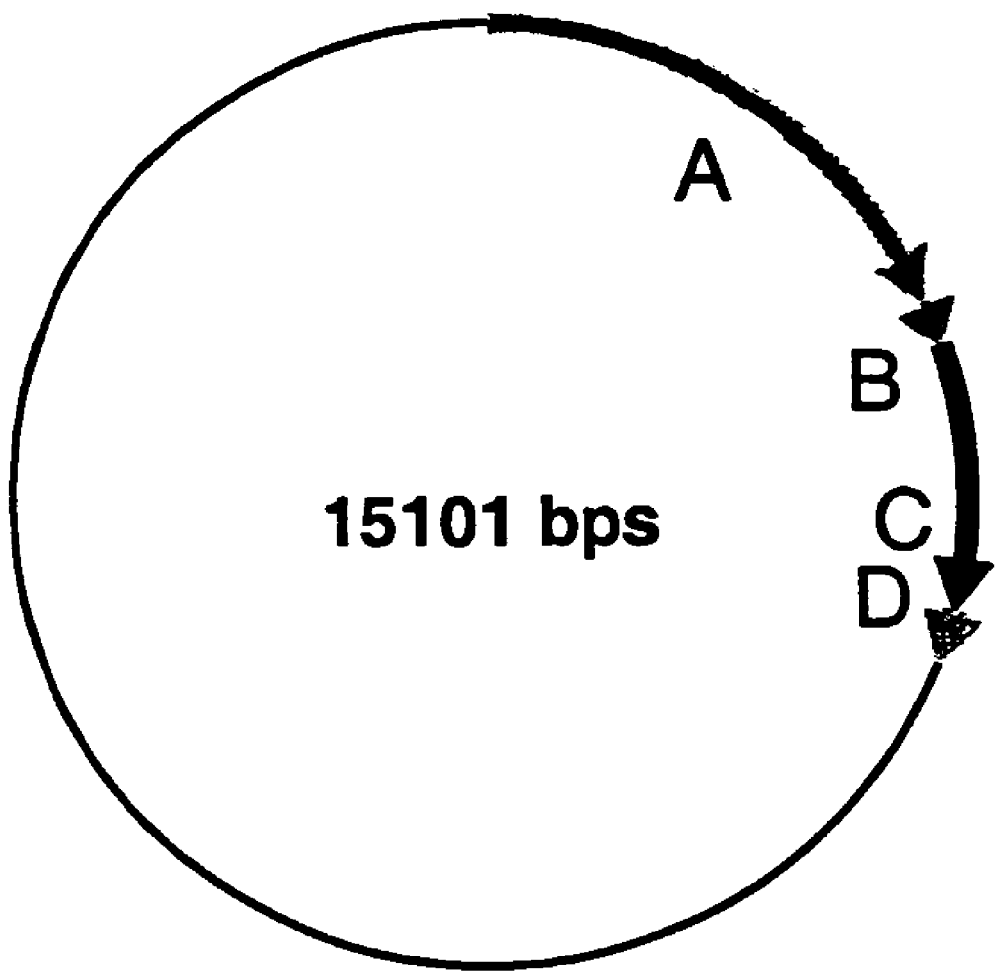
FIG. 61 shows the plasmid pPTVkan-IPPTP11-TATaseRN-nosT (also termed pPTVkan-LeB4-IPP-RnTA-Tase-nosT).
Figure 62:
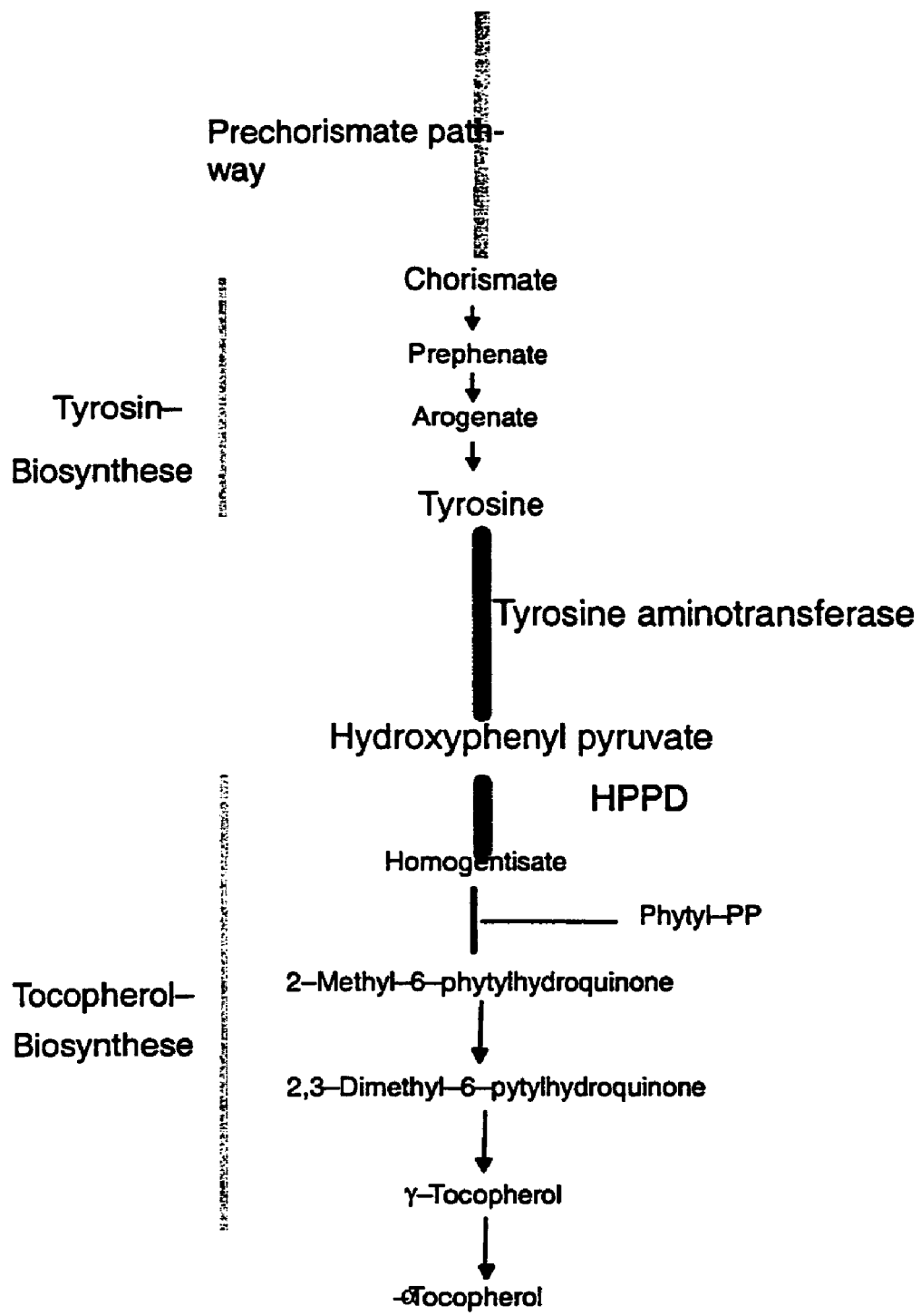
FIG. 62 shows a biosynthesis scheme of α-tocopherol in higher plants.

Fragment A (2764 bp) in FIG. 61 comprises the promoter of the Vicia faba legumin B4 gene, fragment B (207 bp) encodes the transit peptide of the A. thaliana isopentenyl-pyrophosphate isomerase 2. Fragment C (1377 bp) encodes the Rattus norvegicus tyrosine aminotransferase gene. Fragment D (272 bp) encodes the termination signal of the nopaline synthase gene.

Example 73

Generation of expression cassettes comprising the Rattus norvegicus tyrosine aminotransferase gene Transgenic Nicotiana tabacum and Arabidopsis thaliana plants which express the Rattus norvegicus tyrosine aminotransferase (Seq. ID. No. 1) under the control of the constitutive CaMV (cauliflower mosaic virus) 35S promoter were generated (Franck et al., Cell 21: 285-294, 1980).

The basis of the plasmid generated for the constitutive expression of the Rattus norvegicus tyrosine aminotransferase 1 was pBinAR-IPP-Tp-10 (Ralf Badur, PhD thesis, University of Göttingen, 1998). This vector is a derivative of pBinAR (Höfgen and Willmitzer, Plant Sci. 66: 221-230, 1990) and comprises the CaMV (cauliflower mosaic virus) 35S promoter (Franck et al., 1980), the termination signal of the octopine synthase gene (Gielen et al., EMBO J. 3: 835-846, 1984) and the sequence encoding the transit peptide of the A. thaliana plastid-specific isopentenyl-pyrophosphate isomerase 2 (IPP-2) (Badur, unpublished). Cloning the Rattus norvegicus tyrosine aminotransferase into this vector, taking into consideration the correct reading frame, gives rise to a translational fusion of tyrosine aminotransferase with the plastid transit peptide. Thus, the transgene is transported into the plastids.

To generate this plasmid, the tyrosine aminotransferase gene was isolated from the plasmid pGEM-T/tyrosine aminotransferase using the flanking EcoRV restriction cleavage sites. This fragment was ligated into an SmaI-cut pBinAR-IPP-Tp-10, using standard methods (see FIG. 60). This plasmid pBinAR-IPP-Tp-10/tyrosine aminotransferase (alternatively also termed pBinAr-35SP-IPP-RnTATase-ocsT) was used for generating transgenic Nicotiana tabacum and A. thaliana plants.

Figure 60:
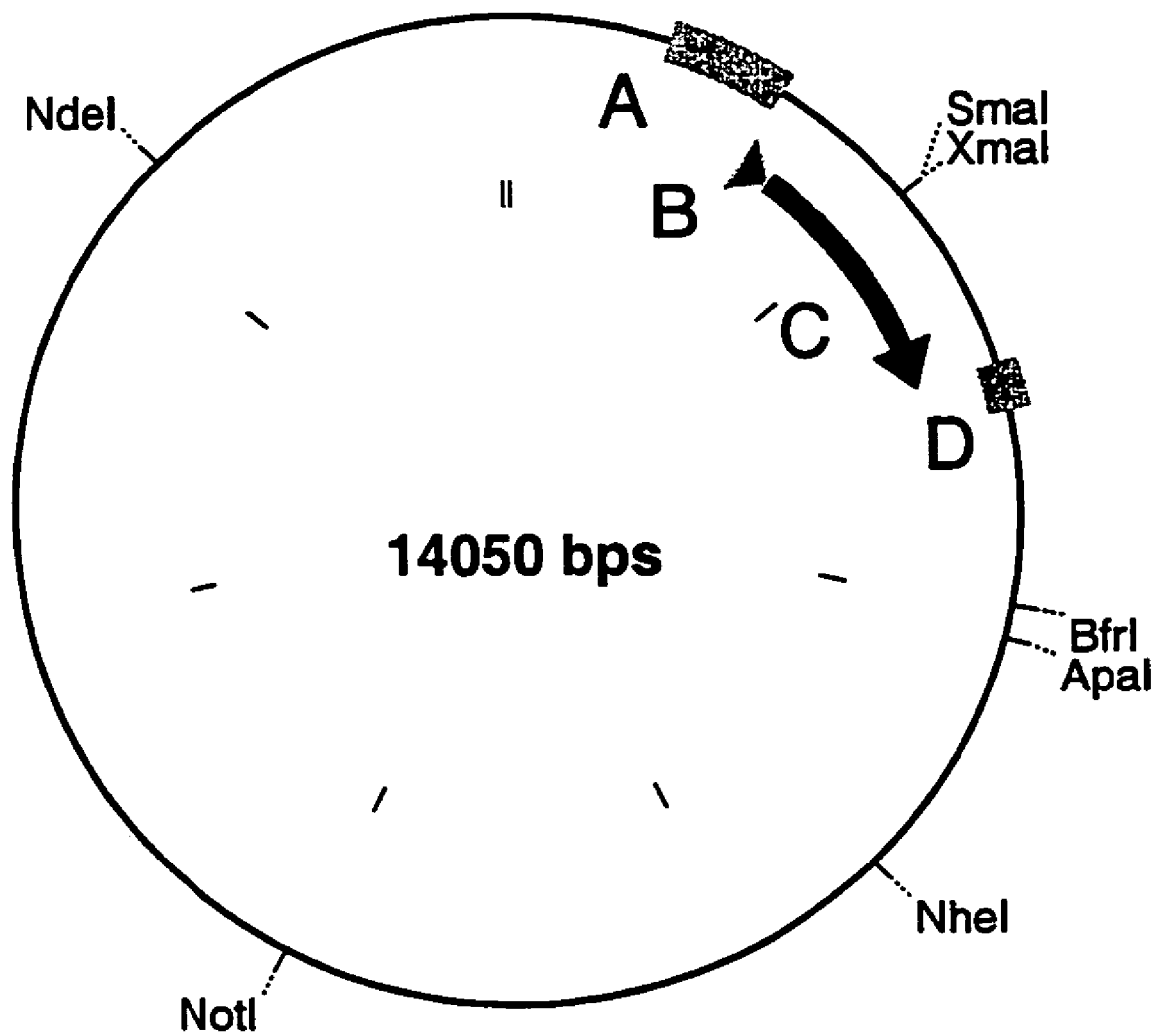
FIG. 60 shows the plasmid pBinAR-IPP-Tp-10/tyrosine aminotransferase (also termed pBinAR-35SP-IPP-RnTA-Tase-ocsT).

Fragment A (529 bp) in FIG. 60 comprises the cauliflower mosaic virus 35S promoter (nucleotides 6909 to 7437 of the cauliflower mosaic virus), fragment B (207 bp) encodes the transit peptide of the isopentenyl-pyrophosphate isomerase 2, fragment C (1377 bp) encodes the Rattus norvegicus tyrosine aminotransferase gene 1, fragment D (208 bp) encodes the termination signal of the octopine synthase gene.

Example 74

Generation of transgenic Arabidopsis thaliana plants

Wild-type Arabidopsis thaliana plants (Columbia) are transformed with Agrobacterium tumefaciens strain (GV3101 [pMP90]) based on a modified vacuum infiltration method (Steve Clough and Andrew Bent. Floral dip: a simplified method for Agrobacterium mediated transformation of A. thaliana. Plant J 16(6):735-43, 1998; Bechtold, N. Ellis, J. and Pelltier, G., in: Planta Agrobacterium-mediated gene transfer by infiltration of adult Arabidopsis thaliana plants. CRAcad Sci Paris, 1993, 1144(2):204-212). The Agrobacterium tumefaciens cells used are previously transformed with the above-described DNA constructs.

Seeds of the primary transformants are selected on the basis of their resistance to antibiotics. Seedlings which are resistant to antibiotics were transplanted into soil and used for biochemical analysis for fully-developed plants.

Example 75

Generation of transgenic *Nicotiana tabacum* plants

Ten ml of YEB medium supplemented with antibiotic (5 g/l beef extract, 1 g/l yeast extract, 5 g/l peptone, 5 g/l sucrose and 2 mM $MgSO_4$) are inoculated with a colony of *Agrobacterium tumefaciens*, and the culture was grown overnight at 28° C. The cells were pelleted for 20 minutes at 4° C., 3500 rpm, using a bench-top centrifuge and then resuspended under sterile conditions in fresh YEB medium without antibiotics. The cell suspension is used for the transformation.

The sterile-grown wild-type plants are obtained by vegetative propagation. To this end, only the tip of the plant is cut off and transferred to fresh 2 MS medium in a sterile preserving jar. As regards the rest of the plant, the hairs on the upper side of the leaves and the central veins of the leaves are removed. Using a razor blade, the leaves are cut into sections of approximate size 1 cm². The agrobacterial culture is transferred into a small Petri dish (diameter 2 cm). The leaf sections are briefly drawn through this solution and placed with the underside of the leaf on 2 MS medium in Petri dishes (diameter 9 cm) in such a way that they touch the medium. After two days in the dark at 25° C., the explants are transferred to plates with callus induction medium and warmed to 28° C. in the controlled-environment cabinet. The medium needs to be changed every 7 to 10 days. As soon as calli form, the explants are transferred into sterile preserving jars onto shoot induction medium supplemented with Claforan (0.6% BiTec agar (w/v), 2.0 mg/l zeatin ribose, 0.02 mg/l naphthylacetic acid, 0.02 mg/l gibberellic acid, 0.25 g/ml claforan, 1.6% glucose (w/v) and 50 mg/l Kanamycin). Organogenesis starts after approximately one month and it is possible to cut off the shoots which had formed. The shoots are grown on 2 MS medium supplemented with Claforan and selection marker. As soon as a substantial root ball has developed, it is possible to put up the plants in seed compost.

Example 76

Generation of transgenic *Brassica napus* plants

Transgenic oilseed rape plants were generated approximately as described by Bade, J. B. and Damm, B. (in Gene Transfer to Plants, Potrykus, I. and Spangenberg, G., eds, Springer Lab Manual, Springer Verlag, 1995, 30-38), which also specifies the composition of the media and buffers used.

The transformations are effected with the *Agrobacterium tumefaciens* strain GV3101 [pMP90]. The DNA construct which confers specific expression in the seed is used for the transformation (FIG. 61). Additionally used constructs are those which confer specific expression in seeds and which are described in FIGS. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59. Seeds of *Brassica napus* var. Westar are surface-sterilized with 70% ethanol (v/v), washed in water for 10 minutes at 55° C., incubated in 1% strength hypochlorite solution (25% v/v Teepol, 0.1% v/v Tween 20) for 20 minutes and washed six times with sterile water for in each case 20 minutes. The seeds are dried for three days on filter paper, and 10-15 seeds are germinated in a glass flask containing 15 ml of germination medium. The roots and apices are excised from several seedlings (approximate size 10 cm), and the hypocotyls which remain are cut into segments approx. 6 mm in length. The approximately 600 explants thus obtained are washed for 30 minutes with 50 ml of basal medium and transferred into a 300 ml flask. After addition of 100 ml of callus induction medium, the cultures are incubated for 24 hours at 100 rpm.

An overnight culture of the agrobacterial strain is set up at 29° C. in Luria broth medium supplemented with kanamycin (20 mg/l), and 2 ml of this are incubated for 4 hours in 50 ml of Luria broth medium without kanamycin for 4 hours at 29° C. to an $OD_{600}$ of 0.4-0.5. After the culture has been pelleted for 25 minutes at 2000 rpm, the cell pellet is resuspended in 25 ml of basal medium. The bacterial concentration in the solution is brought to an $OD_{600}$ of 0.3 by addition of further basal medium.

The callus induction medium is removed from the oilseed rape explants using sterile pipettes, 50 ml of agrobacterial solution are added, and the mixture is mixed carefully and incubated for 20 minutes. The agrobacterial suspension is removed, the oilseed rape explants are washed for 1 minute with 50 ml of callus induction medium, and 100 ml of callus induction medium are subsequently added. The material is cocultured for 24 hours on an orbital shaker at 100 rpm. Coculturing is stopped by removing the callus induction medium, and the explants are washed twice for in each case 1 minute with 25 ml and twice for 60 minutes with in each case 100 ml of wash medium at 100 rpm. The wash medium together with the explants is transferred to 15 cm Petri dishes, and the medium is removed using sterile pipettes.

For the regeneration, batches of 20-30 explants are transferred into 90 mm Petri dishes containing 25 ml of shoot induction medium supplemented with kanamycin. The Petri dishes are sealed with 2 layers of Leukopor and incubated at 25° C. and 2000 Lux at 8-hour-darkness photoperiods. Every 12 days, the developing calli are transferred to fresh Petri dishes containing shoot induction medium. All further steps for regenerating intact plants were carried out as described by Bade, J. B and Damm, B. (in: Gene Transfer to Plants, Potrykus, I. and Spangenberg, G., eds, Springer Lab Manual, Springer Verlag, 1995, 30-38).

Example 77 a) Characterization of the Transgenic *Arabidopsis thaliana* and *Nicotiana tabacum* Plants The tocopherol and tocotrienol contents in the leaves and seeds of the plants transformed with the above-described constructs (*Arabidopsis thaliana* and *Nicotiana tabacum*) are analyzed. To this end, the transgenic plants are grown in the greenhouse, and plants which express the gene encoding the *Rattus norvegicus* tyrosine aminotransferase 1 are analyzed at Northern level. The tocopherol content and the tocotrienol content in the leaves and seeds of these plants are determined.

To this end, the leaf material of plants is frozen in liquid nitrogen immediately after sampling. The subsequent disruption of the cells is effected by means of a stirring apparatus by three incubations in an Eppendorf shaker at 30° C., 1000 rpm, in 100% methanol, for 15 minutes, the supernatants obtained in each case being combined.

Further incubation steps revealed no further release of tocopherols or tocotrienols.

To avoid oxidation, the extracts obtained were analyzed directly after the extraction with the aid of an HPLC system (Waters Alliance 2690). Tocopherols and tocotrienols were separated using a reverse-phase column (ProntoSil 200-3-C30$^{(R)}$, Bischoff) using a mobile phase of 100% methanol, and identified with the aid of standards (Merck). The detection system used was the fluorescence of the substances (excitation 295 nm, emission 320 nm), which was detected with the aid of a Jasco FP 920 fluorescence detector.

In all cases, the tocopherol and/or tocotrienol concentration in transgenic plants was increased in comparison with untransformed plants.

b) Characterization of the Transgenic *Brassica napus* Plants

To illustrate that the vitamin E content in plants is increased by expressing the *Rattus norvegicus* tyrosine aminotransferase gene, the *Arabidopsis thaliana* tyrosine aminotransferase gene 1, the *Arabidopsis thaliana* tyrosine aminotransferase gene 3, the *Arabidopsis thaliana* tyrosine aminotransferase gene 5 or the *Arabidopsis thaliana* tyrosine aminotransferase gene 6, alone or in combination with at least one further gene selected from the group consisting of the *Arabidopsis thaliana* hydroxyphenylpyruvate dioxygenase gene, the *Arabidopsis thaliana* homogentisate phytyltransferase gene, the *Nicotiana tabacum* geranylgeranyl-pyrophosphate oxidoreductase gene, the *Synechocystis* sp. PCC6803 2-methyl-6-phytylhydroquinone methyltransferase gene, the *Synechocystis* sp. PCC6803 2,3-dimethyl-5-phytylplastoquinol cyclase gene, the *Arabidopsis thaliana* γ-tocopherol methyltransferase gene and the suppression of the expression of the homogentisate dioxygenase gene, the tocopherol and tocotrienol contents in the seeds of the plants (*Brassica napus*) transformed with the above-described constructs are analyzed.

To this end, the transgenic plants are grown in the greenhouse and analyzed at the Northern level. The tocopherol content and the tocotrienol content in the seeds of these plants are determined analogously to Example 77 a).

Example 78

Generation of transgenic *Arabidopsis thaliana* plants which overexpress tyrosine aminotransferase Wild-type *Arabidopsis thaliana* plants (Columbia) were transformed with *Agrobacterium tumefaciens* strain (GV3101 [pMP90]) based on a modified vacuum infiltration method (Steve Clough and Andrew Bent. Floral dip: a simplified method for *Agrobacterium* mediated transformation of *A. thaliana*. Plant J 16(6):735-43, 1998; Bechtold, N. Ellis, J. and Pelltier, G., in: Planta *Agrobacterium*-mediated gene transfer by infiltration of adult *Arabidopsis thaliana* plants. CRAcad Sci Paris, 1993, 1144(2):204-212).

The *Agrobacterium tumefaciens* cells used had previously been transformed with the plasmids pBinAR-35SP-IPP-RnTATase-ocsT (Example 73, FIG. 60) and pPTVkan-LeB4-IPP-RnTATase-nosT (Example 72, FIG. 61) following the method described by R. HÖFGEN and L. WILLMITZER (Plant Sci. 1990, 66, 221-230 and Nucleic Acids Res. 1988, Oct. 25, 16(20), 9877).

Seeds of the primary transformants were selected on the basis of their resistance to antibiotics. Seedlings which are resistant to antibiotics were transplanted into soil and used for biochemical analysis as fully-developed plants.

Example 79

Generation of transgenic *Brassica napus* plants which overexpress tyrosine aminotransferase Transgenic oilseed rape plants were generated approximately as described by Bade, J. B. and Damm, B. (in Gene Transfer to Plants, Potrykus, I. and Spangenberg, G., eds, Springer Lab Manual, Springer Verlag, 1995, 30-38), which also specifies the composition of the media and buffers used.

The transformations are effected with the *Agrobacterium tumefaciens* strain GV3101 [pMP90]. The *Agrobacterium tumefaciens* cells used had previously been transformed with the plasmid pPTVkan-LeB4-IPP-RnTATase-nosT (Example 72, FIG. 61) in accordance with the method described by R. HÖFGEN and L. WILLMITZER (Plant Sci. 1990, 66, 221-230 and Nucleic Acids Res. 1988, Oct. 25, 16(20), 9877).

Seeds of *Brassica napus* var. Westar are surface-sterilized with 70% ethanol (v/v), washed in water for 10 minutes at 55° C., incubated in 1% strength hypochlorite solution (25% v/v Teepol, 0.1% v/v Tween 20) for 20 minutes and washed six times with sterile water for in each case 20 minutes. The seeds were dried for three days on filter paper, and 10-15 seeds are germinated in a glass flask containing 15 ml of germination medium. The roots and apices are excised from several seedlings (approximate size 10 cm), and the hypocotyls which remain are cut into segments approx. 6 mm in length. The approximately 600 explants thus obtained were washed for 30 minutes with 50 ml of basal medium and transferred into a 300 ml flask. After addition of 100 ml of callus induction medium, the cultures were incubated for 24 hours at 100 rpm.

An overnight culture of the agrobacterial strain is set up at 29° C. in Luria broth medium supplemented with kanamycin (20 mg/l), and 2 ml of this are incubated in 50 ml of Luria broth medium without kanamycin for 4 hours at 29° C. to an $OD_{600}$ of 0.4-0.5. After the culture has been pelleted for 25 minutes at 2000 rpm, the cell pellet was resuspended in 25 ml of basal medium. The bacterial concentration in the solution was brought to an $OD_{600}$ of 0.3 by addition of further basal medium.

The callus induction medium was removed from the oilseed rape explants using sterile pipettes, 50 ml of agrobacterial solution were added, and the mixture was mixed carefully and incubated for 20 minutes. The agrobacterial suspension was removed, the oilseed rape explants were washed for 1 minutes to 50 ml of callus induction medium, and 100 ml of callus induction medium were subsequently added. The material was cocultured for 24 hours on an orbital shaker at 100 rpm. Coculturing was stopped by removing the callus induction medium, and the explants were washed twice for in each case 1 minute with 25 ml and twice for 60 minutes with in each case 100 ml of wash medium at 100 rpm. The wash medium together with the explants was transferred to 15 cm Petri dishes, and the medium was removed using sterile pipettes.

For the regeneration, batches of 20-30 explants were transferred into 90 mm Petri dishes containing 25 ml of shoot induction medium supplemented with kanamycin. The Petri dishes were sealed with 2 layers of Leukopor and incubated at 25° C. and 2000 Lux at 8-hour-darkness photoperiods. Every 12 days, the developing calli were transferred to fresh Petri dishes containing shoot induction medium. All further steps for regenerating intact plants were carried out as described by Bade, J. B and Damm, B. (in: Gene Transfer to Plants, Potrykus, I. and Spangenberg, G., eds, Springer Lab Manual, Springer Verlag, 1995, 30-38).

Example 80

Generation of transgenic *Nicotiana tabacum* plants which overexpress tyrosine aminotransferase Ten ml of YEB medium supplemented with antibiotic (5 g/l beef extract, 1 g/l yeast extract, 5 g/l peptone, 5 g/l sucrose and 2 mM MgSO$_4$) were inoculated with a colony of *Agrobacterium tumefaciens*, and the culture was grown overnight at 28° C. The cells were pelleted for 20 minutes at 4° C., 3500 rpm, using a bench-top centrifuge and then resuspended under sterile conditions in fresh YEB medium without antibiotics. The cell suspension was used for the transformation.

The *Agrobacterium tumefaciens* cells used had previously been transformed with the plasmid pBinAR-35SP-IPP-Rn-TATase-ocsT (Example 73, FIG. 60) in accordance with the method described by R. HÖFGEN and L. WILLMITZER (Plant Sci. 1990, 66, 221-230 and Nucleic Acids Res. 1988, Oct. 25, 16(20), 9877).

The sterile-grown wild-type plants were obtained by vegetative propagation. To this end, only the tip of the plant was cut off and transferred to fresh 2 MS medium in a sterile preserving jar. As regards the rest of the plant, the hairs on the upper side of the leaves and the central veins of the leaves were removed. Using a razor blade, the leaves were cut into sections of approximate size 1 cm$^2$. The agrobacterial culture was transferred into a small Petri dish (diameter 2 cm). The leaf sections were briefly drawn through this solution and placed with the underside of the leaf on 2 MS medium in Petri dishes (diameter 9 cm) in such a way that they touched the medium.

After two days in the dark at 25° C., the explants were transferred to plates with callus induction medium and warmed to 28° C. in a controlled-environment cabinet. The medium needed changing every 7-10 days. As soon as calli formed, the explants were transferred into sterile preserving jars containing shoot induction medium supplemented with Claforan (0.6% BiTec-Agar (w/v), 2.0 mg/l zeatin ribose, 0.02 mg/l naphthylacetic acid, 0.02 mg/l gibberelic acid, 0.25 g/ml Claforan, 1.6% glucose (w/v) and 50 mg/l kanamycin). After approximately one month, organogenesis took place, and the shoots formed could be cut off.

The shoots were grown on 2 MS medium supplemented with Claforan and selection marker. As soon as a substantial root ball developed, the plants could be potted up in seed compost.

Example 81

Characterization of the transgenic plants of examples 78, 79 and 80

The tocopherol and tocotrienol contents in the leaves and seeds of the plants transformed with the above-described constructs, of Examples 78, 79 and 80 (*Arabidopsis thaliana, Brassica napus* and *Nicotiana tabacum*) are analyzed. To this end, the transgenic plants were grown in the greenhouse, and the plants which express the gene encoding the *Rattus norvegicus* tyrosine aminotransferase are analyzed at Northern level. The tocopherol content and the tocotrienol content in the leaves and seeds of these plants were determined.

To this end, the leaf material of plants is frozen in liquid nitrogen immediately after sampling. The subsequent disruption of the cells is effected by means of a stirring apparatus by three incubations in an Eppendorf shaker at 30° C., 1000 rpm in 100% methanol, for 15 minutes, the supernatants obtained in each case being combined.

Further incubation steps revealed no further release of tocopherols or tocotrienols.

To avoid oxidation, the extracts obtained were analyzed directly after the extraction with the aid of an HPLC system (Waters Allience 2690). Tocopherols and tocotrienols were separated using a reverse-phase column (ProntoSil 200-3-C30$^{(R)}$, Bischoff) using a mobile phase of 100% methanol, and identified with the aid of standards (Merck). The detection system used was the fluorescence of the substances (excitation 295 nm, emission 320 nm), which was detected with the aid of a Jasco FP 920 fluorescence detector.

Table 1 shows the result of the overexpression of the *Rattus norvegicus* tyrosine aminotransferase in 16 lines (lines 1 to 24) of the transgenic *Nicotiana tabacum* plants, generated in accordance with Example 80, in comparison with the wild type (WT, 4 replications). The second column shows the vitamin E content (total content=sum of all 8 isomers) in young leaf material in [µg/g FW]. The third column shows the tocotrienol content of the line in question of the total vitamin E content in [% by weight].

TABLE 1

| Line of the transgenic *Nicotiana tabacum* plants of Example 80 | Total vitamin E content in [µg/g FW] | Tocotrienol content in [% by weight] based on the total content |
|---|---|---|
| 1 | 9.13 | 48.5 |
| 2 | 2.95 | 4.6 |
| 3 | 5.94 | 49.5 |
| 4 | 7.24 | 5.8 |
| 6 | 5.97 | 7.6 |
| 7 | 8.02 | 6.4 |
| 9 | 16.26 | 53.1 |
| 10 | 8.95 | 41.3 |
| 11 | 13.28 | 51.6 |
| 16 | 8.96 | 42.9 |
| 17 | 3.99 | 3.2 |
| 18 | 10.58 | 51.7 |
| 19 | 7.57 | 41.3 |
| 24 | 14.76 | 56.7 |
| WT n = 4 | 5.4 +/− 0.5 | 4.75 +/− 2.4 |

Figure 63:
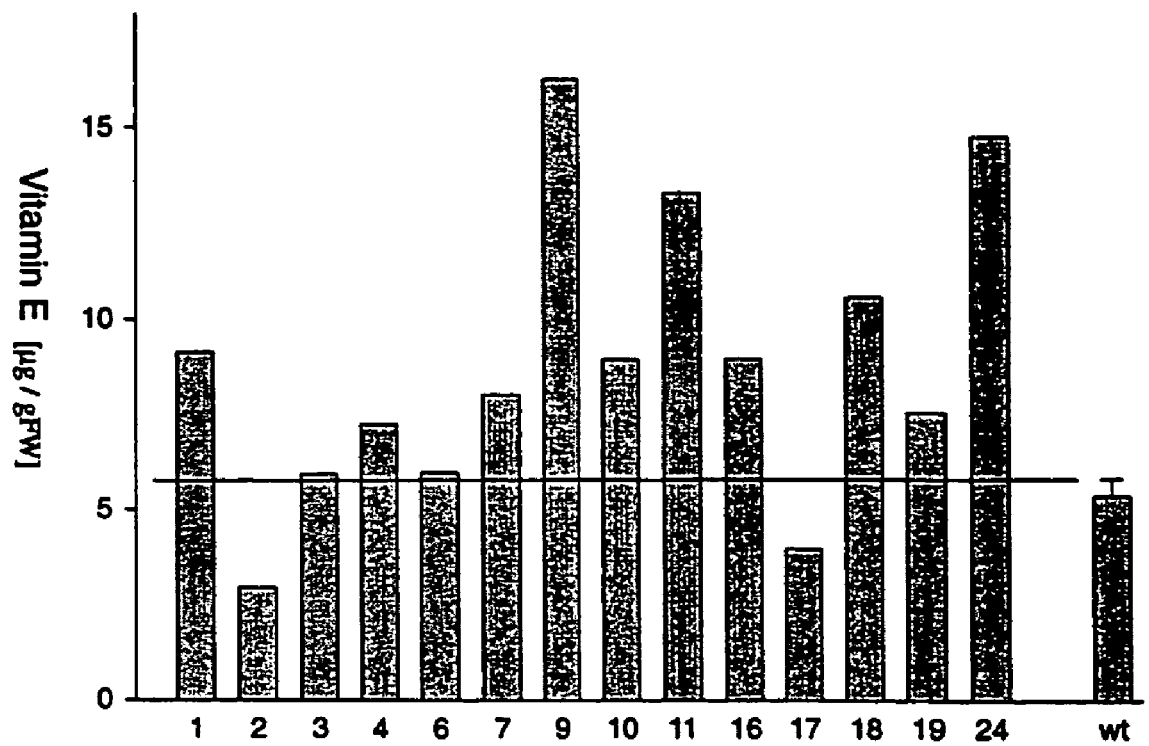
FIG. 63 shows a graphic representation of the result of the overexpression of the *Rattus norvegicus* tyrosine aminotransferase in *Nicotiana tabacum* (see Example 80) in comparison with the wild type. The data shown are the vitamin E contents (sum of all 8 isomers) in young leaf material. The description of the axes indicates the individual transgenic lines. The data shown for the wild-type plants (wt) corresponds to the mean +/−SD of 4 replications.

FIG. 63 is a graphic representation of the result of the overexpression of the *Rattus norvegicus* tyrosine aminotransferase in *Nicotiana tabacum* (Example 80) in comparison with the wild type. The data shown are the vitamin E contents (sum of all 8 isomers) in young leaf material. The description of the axes indicates the individual transgenic lines. The data shown for the wild-type plants (wt) corresponds to the mean +/− SD of 4 replications.

We claim:

1. A process for increasing the production of vitamin E in a vitamin E producing plant, wherein said process comprises expressing a recombinant nucleic acid that encodes a tyrosine aminotransferase which increases tyrosine aminotransferase activity as compared to the wild-type plant, wherein said nucleic acid comprises a sequence selected from the group consisting of:
   (a) a polynucleotide sequence encoding a protein comprising the amino acid sequence as set forth in SEQ ID NO: 8, 10, or 12, and
   (b) the polynucleotide sequence as set forth in SEQ ID NO: 5;
and growing said recombinant plant, thereby increasing the production of vitamin E in said plant.

2. The process as claimed in claim 1, wherein the nucleic acid comprises the sequence as set forth in SEQ ID NO: 5.

3. The process of claim 1, wherein the plant is further transformed with a nucleic acid that expresses at least one enzyme activity selected from the group consisting of hydroxyphenylpyruvate dioxygenase activity, homogentisate phytyltransferase activity, geranylgeranyl-pyrophosphate oxidoreductase activity, 2-methyl-6-phytylhydroquinone methyltransferase activity, tocopherol cyclase activity and γ-tocopherol methyltransferase activity, and wherein said enzyme activity is increased as compared to the wild type enzyme activity of said plant.

4. The process of claim 1, wherein the plant comprises a reduction of at least one enzyme activity selected from the group consisting of homogentisate dioxygenase activity, maleylacetoacetate isomerase activity and fumarylacetoacetate hydrolase activity as compared to the wild-type activity.

5. The process as claimed in claim 4, wherein the reduced activity is homogentisate dioxygenase activity.

6. The process as claimed in claim 5, further comprising introducing an RNA into said plant wherein said RNA contains a region with duplex structure and said region contains a nucleic acid sequence that is identical to or hybridizes with at least a part of the homogentisate dioxygenase gene thereby cleaving the mRNA for said gene.

7. The process as claimed in claim 1, further comprising harvesting said plant and isolating vitamin E.

8. A process for increasing the vitamin E content of a plant in a vitamin E producing plant, comprising introducing a nucleic acid construct encoding a tyrosine aminotransferase operably linked to one or more regulatory signals that allow for transcription and translation of said nucleic acid by said plant and growing the plant, wherein said nucleic acid comprises a sequence selected from the group consisting of:
   (a) a polynucleotide sequence encoding a protein comprising the amino acid sequence as set forth in SEQ ID NO: 8, 10, or 12, and
   (b) the polynucleotide sequence as set forth in SEQ ID NO: 5;
thereby increasing the production of vitamin E in said plant.

9. A process for increasing the vitamin E content of a vitamin E producing plant comprising introducing a combination of nucleic acid constructs into said plant, wherein the combination comprises a first nucleic acid construct encoding a tyrosine aminotransferase operably linked to one or more regulatory signals that allow for transcription and translation of said first nucleic acid and one or more nucleic acid constructs selected from the group consisting of:
- A. a nucleic acid construct encoding a hydroxyphenylpyruvate dioxygenase operably linked with one or more regulatory signals that allow for transcription and translation in said plant,
- B. a nucleic acid construct encoding a homogentisate phytyltransferase operably linked with one or more regulatory signals that allow for transcription and translation in said plant,
- C. a nucleic acid construct encoding a geranylgeranyl-pyrophosphate oxidoreductase operably linked with one or more regulatory signals that allow for transcription and translation in said plant,
- D. a nucleic acid construct encoding a 2-methyl-6-phytylhydroquinone methyltransferase operably linked with one or more regulatory signals that allow for transcription and translation in said plant,
- E. a nucleic acid construct encoding a tocopherol cyclase operably linked With one or more regulatory signals that allow for transcription and translation in said plant, and
- F. a nucleic acid construct encoding a γ-tocopherol methyltransferase operably linked with one or more regulatory signals that allow for transcription and translation in said plant, and growing the plant wherein the first nucleic acid comprises a sequence selected from the group consisting of:

(a) a polynucleotide sequence encoding a protein comprising the amino acid sequence as set forth in SEQ ID NO: 8, 10, or 12, and (b) the polynucleotide sequence as set forth in SEQ ID NO: 5;

thereby increasing the production of vitamin E in said plant.

10. The process as claimed in claim 8 wherein the nucleic acid construct is introduced into the genome of said plant.

11. The process as claimed in claim 9 wherein the combination of nucleic acid constructs is introduced into the genome of said plant.

12. The process as claimed in claim 1, wherein the nucleic acid comprises the polynucleotide sequence as set forth in SEQ ID NO: 7, 9, or 11.

13. The process as claimed in claim 8, wherein the nucleic acid comprises the polynucleotide sequence as set forth in SEQ ID NO: 7, 9, or 11.

14. The process as claimed in claim 9, wherein the nucleic acid comprises the polynucleotide sequence as set forth in SEQ ID NO: 7, 9, or 11.

15. The process as claimed in claim 1, wherein the nucleic acid encodes a protein comprising the amino acid sequence as set forth in SEQ ID NO: 8, 10, or 12 and possesses enzymatic activity of a tyrosine aminotransferase.

* * * * *

SEQUENCE LISTING

<160> NUMBER OF SEQ ID NOS: 58

<210> SEQ ID NO 1

<211> LENGTH: 1377
<212> TYPE: DNA
<213> ORGANISM: Rattus norvegicus
<220> FEATURE:
<221> NAME/KEY: CDS
<222> LOCATION: (1)..(1371)

<400> SEQUENCE: 1

| | | | | | | | | | | | | | | | | |
|---|---|---|---|---|---|---|---|---|---|---|---|---|---|---|---|---|
| gat | atc | atg | gac | tcc | tac | gtg | att | cag | acg | gat | gtc | gac | gac | agc | ttg | 48 |
| Asp | Ile | Met | Asp | Ser | Tyr | Val | Ile | Gln | Thr | Asp | Val | Asp | Asp | Ser | Leu | |
| 1 | | | | 5 | | | | | 10 | | | | | 15 | | |
| tcc | tca | gtt | ctg | gat | gtg | cat | gtc | aat | att | ggt | ggg | aga | aac | tcg | gta | 96 |
| Ser | Ser | Val | Leu | Asp | Val | His | Val | Asn | Ile | Gly | Gly | Arg | Asn | Ser | Val | |
| | | | 20 | | | | | 25 | | | | | 30 | | | |
| caa | gga | aga | aag | aaa | ggc | agg | aag | gcc | aga | tgg | gac | gtg | aga | ccc | tct | 144 |
| Gln | Gly | Arg | Lys | Lys | Gly | Arg | Lys | Ala | Arg | Trp | Asp | Val | Arg | Pro | Ser | |
| | 35 | | | | | 40 | | | | | 45 | | | | | |
| gac | atg | tcc | aat | aag | acc | ttc | aat | ccc | atc | cga | gcc | atc | gtg | gac | aac | 192 |
| Asp | Met | Ser | Asn | Lys | Thr | Phe | Asn | Pro | Ile | Arg | Ala | Ile | Val | Asp | Asn | |
| 50 | | | | | 55 | | | | | 60 | | | | | | |
| atg | aag | gtg | cag | ccc | aat | ccg | aac | aag | acc | gtg | att | tct | ctg | tca | att | 240 |
| Met | Lys | Val | Gln | Pro | Asn | Pro | Asn | Lys | Thr | Val | Ile | Ser | Leu | Ser | Ile | |
| 65 | | | | 70 | | | | | 75 | | | | | 80 | | |
| ggg | gac | cct | act | gtg | ttt | ggg | aac | ctg | cct | aca | gac | cct | gaa | gtt | acc | 288 |
| Gly | Asp | Pro | Thr | Val | Phe | Gly | Asn | Leu | Pro | Thr | Asp | Pro | Glu | Val | Thr | |
| | | | 85 | | | | | 90 | | | | | 95 | | | |
| caa | gcc | atg | aaa | gat | gcc | ctg | gac | tcg | ggg | aag | tac | aat | ggc | tat | gcc | 336 |
| Gln | Ala | Met | Lys | Asp | Ala | Leu | Asp | Ser | Gly | Lys | Tyr | Asn | Gly | Tyr | Ala | |
| | | 100 | | | | | 105 | | | | | 110 | | | | |
| ccg | tcc | atc | ggc | tac | cta | tcc | agt | cgg | gag | gag | gtc | gct | tct | tac | tac | 384 |
| Pro | Ser | Ile | Gly | Tyr | Leu | Ser | Ser | Arg | Glu | Glu | Val | Ala | Ser | Tyr | Tyr | |
| | 115 | | | | | 120 | | | | | 125 | | | | | |
| cac | tgt | cat | gag | gct | cct | ctg | gaa | gct | aag | gat | gtc | att | ctg | aca | agc | 432 |
| His | Cys | His | Glu | Ala | Pro | Leu | Glu | Ala | Lys | Asp | Val | Ile | Leu | Thr | Ser | |
| 130 | | | | | 135 | | | | | 140 | | | | | | |
| ggc | tgc | agt | cag | gcc | att | gag | cta | tgt | cta | gct | gtg | ttg | gcc | aat | cct | 480 |
| Gly | Cys | Ser | Gln | Ala | Ile | Glu | Leu | Cys | Leu | Ala | Val | Leu | Ala | Asn | Pro | |
| 145 | | | | | 150 | | | | | 155 | | | | | 160 | |
| gga | caa | aac | atc | ctc | att | cca | agg | ccc | ggg | ttt | tcc | ctc | tat | agg | act | 528 |
| Gly | Gln | Asn | Ile | Leu | Ile | Pro | Arg | Pro | Gly | Phe | Ser | Leu | Tyr | Arg | Thr | |
| | | | 165 | | | | | 170 | | | | | 175 | | | |
| ttg | gct | gag | tct | atg | gga | att | gag | gtc | aag | ctc | tac | aat | ctc | ctg | cct | 576 |
| Leu | Ala | Glu | Ser | Met | Gly | Ile | Glu | Val | Lys | Leu | Tyr | Asn | Leu | Leu | Pro | |
| | | 180 | | | | | 185 | | | | | 190 | | | | |
| gag | aag | tct | tgg | gaa | att | gac | cta | aaa | caa | ctg | gaa | tct | ctg | atc | gat | 624 |
| Glu | Lys | Ser | Trp | Glu | Ile | Asp | Leu | Lys | Gln | Leu | Glu | Ser | Leu | Ile | Asp | |
| | 195 | | | | | 200 | | | | | 205 | | | | | |
| gaa | aaa | aca | gcg | tgt | ctt | gtt | gtc | aac | aac | cca | tcc | aat | ccc | tgt | ggc | 672 |
| Glu | Lys | Thr | Ala | Cys | Leu | Val | Val | Asn | Asn | Pro | Ser | Asn | Pro | Cys | Gly | |
| 210 | | | | | 215 | | | | | 220 | | | | | | |
| tcc | gtg | ttc | agt | aag | cga | cac | ctt | cag | aag | att | ttg | gca | gtg | gct | gaa | 720 |
| Ser | Val | Phe | Ser | Lys | Arg | His | Leu | Gln | Lys | Ile | Leu | Ala | Val | Ala | Glu | |
| 225 | | | | | 230 | | | | | 235 | | | | | 240 | |
| agg | cag | tgt | gtc | ccc | atc | tta | gct | gac | gag | atc | tat | ggt | gac | atg | gtg | 768 |
| Arg | Gln | Cys | Val | Pro | Ile | Leu | Ala | Asp | Glu | Ile | Tyr | Gly | Asp | Met | Val | |
| | | | 245 | | | | | 250 | | | | | 255 | | | |
| ttt | tca | gat | tgc | aaa | tac | gaa | cca | ctg | gcc | aac | ctc | agc | acc | aat | gtt | 816 |
| Phe | Ser | Asp | Cys | Lys | Tyr | Glu | Pro | Leu | Ala | Asn | Leu | Ser | Thr | Asn | Val | |
| | | 260 | | | | | 265 | | | | | 270 | | | | |
| ccc | atc | ctg | tcc | tgt | ggt | ggg | ctg | gcc | aag | cgc | tgg | ctg | gtt | cct | ggc | 864 |
| Pro | Ile | Leu | Ser | Cys | Gly | Gly | Leu | Ala | Lys | Arg | Trp | Leu | Val | Pro | Gly | |

-continued

```
                    275                 280                 285
tgg agg ttg ggc tgg atc ctc att cat gat cga aga gac att ttt ggc      912
Trp Arg Leu Gly Trp Ile Leu Ile His Asp Arg Arg Asp Ile Phe Gly
    290                 295                 300 aat gag att cga gac ggg ctg gtg aaa ctg agt cag cgg atc ctg gga      960
Asn Glu Ile Arg Asp Gly Leu Val Lys Leu Ser Gln Arg Ile Leu Gly
305                 310                 315                 320 cca tgc acc ata gtc cag ggt gct ctg aag agc atc ctt cag cga acc     1008
Pro Cys Thr Ile Val Gln Gly Ala Leu Lys Ser Ile Leu Gln Arg Thr
                325                 330                 335 cct cag gag ttc tat cac gac acg tta agc ttc ctc aag tcc aat gcg     1056
Pro Gln Glu Phe Tyr His Asp Thr Leu Ser Phe Leu Lys Ser Asn Ala
            340                 345                 350 gac ctc tgc tat ggg gca ctg gct gcc atc cct gga ctc cag ccg gtc     1104
Asp Leu Cys Tyr Gly Ala Leu Ala Ala Ile Pro Gly Leu Gln Pro Val
        355                 360                 365 cgc cct tct gga gcc atg tac ctt atg gtg gga att gag atg gag cat     1152
Arg Pro Ser Gly Ala Met Tyr Leu Met Val Gly Ile Glu Met Glu His
    370                 375                 380 ttc ccg gaa ttc gag aac gac gtg gag ttc aca gag cgg ttg att gcg     1200
Phe Pro Glu Phe Glu Asn Asp Val Glu Phe Thr Glu Arg Leu Ile Ala
385                 390                 395                 400 gag cag gct gtc cac tgt ctc cca gca acg tgc ttc gag tac cca aat     1248
Glu Gln Ala Val His Cys Leu Pro Ala Thr Cys Phe Glu Tyr Pro Asn
                405                 410                 415 ttc ttc cga gtg gtc atc aca gtc ccc gag gtg atg atg ctg gag gct     1296
Phe Phe Arg Val Val Ile Thr Val Pro Glu Val Met Met Leu Glu Ala
            420                 425                 430 tgt agc cgg atc cag gag ttc tgt gaa cag cac tac cac tgt gct gaa     1344
Cys Ser Arg Ile Gln Glu Phe Cys Glu Gln His Tyr His Cys Ala Glu
        435                 440                 445 ggc agc cag gag gag tgt gac aaa taa gatatc                          1377
Gly Ser Gln Glu Glu Cys Asp Lys
    450                 455

<210> SEQ ID NO 2
<211> LENGTH: 456
<212> TYPE: PRT
<213> ORGANISM: Rattus norvegicus

<400> SEQUENCE: 2

Asp Ile Met Asp Ser Tyr Val Ile Gln Thr Asp Val Asp Ser Leu
1               5                   10                  15

Ser Ser Val Leu Asp Val His Val Asn Ile Gly Gly Arg Asn Ser Val
            20                  25                  30

Gln Gly Arg Lys Lys Gly Arg Lys Ala Arg Trp Asp Val Arg Pro Ser
        35                  40                  45

Asp Met Ser Asn Lys Thr Phe Asn Pro Ile Arg Ala Ile Val Asp Asn
    50                  55                  60

Met Lys Val Gln Pro Asn Pro Asn Lys Thr Val Ile Ser Leu Ser Ile
65                  70                  75                  80

Gly Asp Pro Thr Val Phe Gly Asn Leu Pro Thr Asp Pro Glu Val Thr
                85                  90                  95

Gln Ala Met Lys Asp Ala Leu Asp Ser Gly Lys Tyr Asn Gly Tyr Ala
            100                 105                 110

Pro Ser Ile Gly Tyr Leu Ser Ser Arg Glu Glu Val Ala Ser Tyr Tyr
        115                 120                 125

His Cys His Glu Ala Pro Leu Glu Ala Lys Asp Val Ile Leu Thr Ser
```

```
            130                 135                 140
Gly Cys Ser Gln Ala Ile Glu Leu Cys Leu Ala Val Leu Ala Asn Pro
145                 150                 155                 160

Gly Gln Asn Ile Leu Ile Pro Arg Pro Gly Phe Ser Leu Tyr Arg Thr
                165                 170                 175

Leu Ala Glu Ser Met Gly Ile Glu Val Lys Leu Tyr Asn Leu Leu Pro
            180                 185                 190

Glu Lys Ser Trp Glu Ile Asp Leu Lys Gln Leu Glu Ser Leu Ile Asp
        195                 200                 205

Glu Lys Thr Ala Cys Leu Val Val Asn Pro Ser Asn Pro Cys Gly
210                 215                 220

Ser Val Phe Ser Lys Arg His Leu Gln Lys Ile Leu Ala Val Ala Glu
225                 230                 235                 240

Arg Gln Cys Val Pro Ile Leu Ala Asp Glu Ile Tyr Gly Asp Met Val
                245                 250                 255

Phe Ser Asp Cys Lys Tyr Glu Pro Leu Ala Asn Leu Ser Thr Asn Val
            260                 265                 270

Pro Ile Leu Ser Cys Gly Gly Leu Ala Lys Arg Trp Leu Val Pro Gly
        275                 280                 285

Trp Arg Leu Gly Trp Ile Leu Ile His Asp Arg Arg Asp Ile Phe Gly
290                 295                 300

Asn Glu Ile Arg Asp Gly Leu Val Lys Leu Ser Gln Arg Ile Leu Gly
305                 310                 315                 320

Pro Cys Thr Ile Val Gln Gly Ala Leu Lys Ser Ile Leu Gln Arg Thr
                325                 330                 335

Pro Gln Glu Phe Tyr His Asp Thr Leu Ser Phe Leu Lys Ser Asn Ala
            340                 345                 350

Asp Leu Cys Tyr Gly Ala Leu Ala Ala Ile Pro Gly Leu Gln Pro Val
        355                 360                 365

Arg Pro Ser Gly Ala Met Tyr Leu Met Val Gly Ile Glu Met Glu His
    370                 375                 380

Phe Pro Glu Phe Glu Asn Asp Val Glu Phe Thr Glu Arg Leu Ile Ala
385                 390                 395                 400

Glu Gln Ala Val His Cys Leu Pro Ala Thr Cys Phe Glu Tyr Pro Asn
                405                 410                 415

Phe Phe Arg Val Val Ile Thr Val Pro Glu Val Met Met Leu Glu Ala
            420                 425                 430

Cys Ser Arg Ile Gln Glu Phe Cys Glu Gln His Tyr His Cys Ala Glu
        435                 440                 445

Gly Ser Gln Glu Glu Cys Asp Lys
    450                 455

<210> SEQ ID NO 3
<211> LENGTH: 1365
<212> TYPE: DNA
<213> ORGANISM: Rattus norvegicus
<220> FEATURE:
<221> NAME/KEY: CDS
<222> LOCATION: (1)..(1365)

<400> SEQUENCE: 3 atg gac tcc tac gtg att cag acg gat gtc gac gac agc ttg tcc tca      48
Met Asp Ser Tyr Val Ile Gln Thr Asp Val Asp Asp Ser Leu Ser Ser
1               5                   10                  15 gtt ctg gat gtg cgt gtc aat gtt ggt ggg aga aac tcg gta caa gga      96
Val Leu Asp Val Arg Val Asn Val Gly Gly Arg Asn Ser Val Gln Gly
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| aga | aag | aaa | ggc | agg | aag | gcc | aga | tgg | gac | gtg | aga | ccc | tct | gac | atg | 144 |
| Arg | Lys | Lys | Gly | Arg | Lys | Ala | Arg | Trp | Asp | Val | Arg | Pro | Ser | Asp | Met |  |
|  |  | 35 |  |  |  |  | 40 |  |  |  |  | 45 |  |  |  |  |
| tcc | aat | aag | acc | ttc | aat | ccc | atc | cga | gcc | atc | gtg | gac | aac | atg | aag | 192 |
| Ser | Asn | Lys | Thr | Phe | Asn | Pro | Ile | Arg | Ala | Ile | Val | Asp | Asn | Met | Lys |  |
|  | 50 |  |  |  |  | 55 |  |  |  |  | 60 |  |  |  |  |  |
| gtg | cag | ccc | aat | ccg | aac | aag | acc | gtg | att | tct | ctg | tca | att | ggg | gac | 240 |
| Val | Gln | Pro | Asn | Pro | Asn | Lys | Thr | Val | Ile | Ser | Leu | Ser | Ile | Gly | Asp |  |
| 65 |  |  |  |  | 70 |  |  |  |  | 75 |  |  |  |  | 80 |  |
| cct | act | gtg | ttt | ggg | aac | ctg | cct | aca | gac | cct | gaa | gtt | acc | caa | gcc | 288 |
| Pro | Thr | Val | Phe | Gly | Asn | Leu | Pro | Thr | Asp | Pro | Glu | Val | Thr | Gln | Ala |  |
|  |  |  |  | 85 |  |  |  |  | 90 |  |  |  |  | 95 |  |  |
| atg | aaa | gat | gcc | ctg | gac | tcg | ggg | aag | tac | aat | ggc | tat | gcc | ccg | tcc | 336 |
| Met | Lys | Asp | Ala | Leu | Asp | Ser | Gly | Lys | Tyr | Asn | Gly | Tyr | Ala | Pro | Ser |  |
|  |  |  | 100 |  |  |  |  | 105 |  |  |  |  | 110 |  |  |  |
| atc | ggc | tac | cta | tcc | agt | cgg | gag | gag | gtc | gct | tct | tac | tac | cac | tgt | 384 |
| Ile | Gly | Tyr | Leu | Ser | Ser | Arg | Glu | Glu | Val | Ala | Ser | Tyr | Tyr | His | Cys |  |
|  |  | 115 |  |  |  |  | 120 |  |  |  |  | 125 |  |  |  |  |
| cat | gag | gct | cct | ctg | gaa | gct | aag | gat | gtc | att | ctg | aca | agc | ggc | tgc | 432 |
| His | Glu | Ala | Pro | Leu | Glu | Ala | Lys | Asp | Val | Ile | Leu | Thr | Ser | Gly | Cys |  |
|  | 130 |  |  |  |  | 135 |  |  |  |  | 140 |  |  |  |  |  |
| agt | cag | gcc | att | gag | cta | tgt | cta | gct | gtg | ttg | gcc | aat | cct | gga | caa | 480 |
| Ser | Gln | Ala | Ile | Glu | Leu | Cys | Leu | Ala | Val | Leu | Ala | Asn | Pro | Gly | Gln |  |
| 145 |  |  |  |  | 150 |  |  |  |  | 155 |  |  |  |  | 160 |  |
| aac | atc | ctc | att | cca | agg | ccc | ggg | ttt | tcc | ctc | tat | agg | act | ttg | gct | 528 |
| Asn | Ile | Leu | Ile | Pro | Arg | Pro | Gly | Phe | Ser | Leu | Tyr | Arg | Thr | Leu | Ala |  |
|  |  |  |  | 165 |  |  |  |  | 170 |  |  |  |  | 175 |  |  |
| gag | tct | atg | gga | att | gag | gtc | aag | ctc | tac | aat | ctc | ctg | ccc | gag | aag | 576 |
| Glu | Ser | Met | Gly | Ile | Glu | Val | Lys | Leu | Tyr | Asn | Leu | Leu | Pro | Glu | Lys |  |
|  |  |  | 180 |  |  |  |  | 185 |  |  |  |  | 190 |  |  |  |
| tct | tgg | gaa | att | gac | cta | aaa | caa | ctg | gaa | tct | ctg | atc | gat | gaa | aaa | 624 |
| Ser | Trp | Glu | Ile | Asp | Leu | Lys | Gln | Leu | Glu | Ser | Leu | Ile | Asp | Glu | Lys |  |
|  |  | 195 |  |  |  |  | 200 |  |  |  |  | 205 |  |  |  |  |
| aca | gcg | tgt | ctt | gtt | gtc | aac | aac | cca | tcc | aat | ccc | tgt | ggc | tcc | gtg | 672 |
| Thr | Ala | Cys | Leu | Val | Val | Asn | Asn | Pro | Ser | Asn | Pro | Cys | Gly | Ser | Val |  |
|  | 210 |  |  |  |  | 215 |  |  |  |  | 220 |  |  |  |  |  |
| ttc | agt | aag | cgg | cac | ctt | cag | aag | att | ttg | gca | gtg | gct | gaa | agg | cag | 720 |
| Phe | Ser | Lys | Arg | His | Leu | Gln | Lys | Ile | Leu | Ala | Val | Ala | Glu | Arg | Gln |  |
| 225 |  |  |  |  | 230 |  |  |  |  | 235 |  |  |  |  | 240 |  |
| tgt | gtc | ccc | atc | tta | gct | gac | gag | atc | tat | ggt | gac | atg | gtg | ttt | tca | 768 |
| Cys | Val | Pro | Ile | Leu | Ala | Asp | Glu | Ile | Tyr | Gly | Asp | Met | Val | Phe | Ser |  |
|  |  |  |  | 245 |  |  |  |  | 250 |  |  |  |  | 255 |  |  |
| gac | tgc | aaa | tac | gaa | cca | ctg | gcc | aac | ctc | agc | acc | aat | gtt | ccc | atc | 816 |
| Asp | Cys | Lys | Tyr | Glu | Pro | Leu | Ala | Asn | Leu | Ser | Thr | Asn | Val | Pro | Ile |  |
|  |  |  | 260 |  |  |  |  | 265 |  |  |  |  | 270 |  |  |  |
| ctg | tcc | tgt | ggt | ggg | ctg | gcc | aag | cgc | tgg | ctg | gtt | cct | ggc | tgg | agg | 864 |
| Leu | Ser | Cys | Gly | Gly | Leu | Ala | Lys | Arg | Trp | Leu | Val | Pro | Gly | Trp | Arg |  |
|  |  | 275 |  |  |  |  | 280 |  |  |  |  | 285 |  |  |  |  |
| ttg | ggc | tgg | atc | ctc | att | cat | gat | cga | aga | gac | att | ttt | ggc | aat | gag | 912 |
| Leu | Gly | Trp | Ile | Leu | Ile | His | Asp | Arg | Arg | Asp | Ile | Phe | Gly | Asn | Glu |  |
|  | 290 |  |  |  |  | 295 |  |  |  |  | 300 |  |  |  |  |  |
| att | cga | gac | ggg | ctg | gtg | aaa | ctg | agt | cag | cgg | atc | ctg | gga | cca | tgc | 960 |
| Ile | Arg | Asp | Gly | Leu | Val | Lys | Leu | Ser | Gln | Arg | Ile | Leu | Gly | Pro | Cys |  |
| 305 |  |  |  |  | 310 |  |  |  |  | 315 |  |  |  |  | 320 |  |
| acc | ata | gtc | cag | ggt | gct | ctg | aag | agc | atc | ctt | cag | cga | acc | cct | cag | 1008 |
| Thr | Ile | Val | Gln | Gly | Ala | Leu | Lys | Ser | Ile | Leu | Gln | Arg | Thr | Pro | Gln |  |
|  |  |  |  | 325 |  |  |  |  | 330 |  |  |  |  | 335 |  |  |
| gag | ttc | tat | cac | gac | acg | tta | agc | ttc | ctc | aag | tcc | aat | gcg | gac | ctc | 1056 |

```
Glu Phe Tyr His Asp Thr Leu Ser Phe Leu Lys Ser Asn Ala Asp Leu
                340                 345                 350 tgc tat ggg gca ctg gct gcc atc cct gga ctc cag ccg gtc cgc cct    1104
Cys Tyr Gly Ala Leu Ala Ala Ile Pro Gly Leu Gln Pro Val Arg Pro
            355                 360                 365 tct gga gcc atg tac ctt atg gtg gga att gag atg gag cat ctc ccg    1152
Ser Gly Ala Met Tyr Leu Met Val Gly Ile Glu Met Glu His Leu Pro
    370                 375                 380 gaa ttc gag aac gac gtg gag ttc aca gag cgg ttg att gcg gag cag    1200
Glu Phe Glu Asn Asp Val Glu Phe Thr Glu Arg Leu Ile Ala Glu Gln
385                 390                 395                 400 gct gtc cac tgt ctc cca gca acg tgc ttc gag tac cca aat ttc ttc    1248
Ala Val His Cys Leu Pro Ala Thr Cys Phe Glu Tyr Pro Asn Phe Phe
                405                 410                 415 cga gtg gtc atc aca gtc ccc gag gtg atg atg ctg gag gct tgt agc    1296
Arg Val Val Ile Thr Val Pro Glu Val Met Met Leu Glu Ala Cys Ser
            420                 425                 430 cgg atc cag gag ttc tgt gaa cag cac tac cac tgt gct gaa ggc agc    1344
Arg Ile Gln Glu Phe Cys Glu Gln His Tyr His Cys Ala Glu Gly Ser
    435                 440                 445 cag gag gag tgt gac aaa taa                                        1365
Gln Glu Glu Cys Asp Lys
        450                 455

<210> SEQ ID NO 4
<211> LENGTH: 454
<212> TYPE: PRT
<213> ORGANISM: Rattus norvegicus

<400> SEQUENCE: 4

Met Asp Ser Tyr Val Ile Gln Thr Asp Val Asp Ser Leu Ser Ser
1               5                   10                  15

Val Leu Asp Val Arg Val Asn Val Gly Gly Arg Asn Ser Val Gln Gly
            20                  25                  30

Arg Lys Lys Gly Arg Lys Ala Arg Trp Asp Val Arg Pro Ser Asp Met
        35                  40                  45

Ser Asn Lys Thr Phe Asn Pro Ile Arg Ala Ile Val Asp Asn Met Lys
    50                  55                  60

Val Gln Pro Asn Pro Asn Lys Thr Val Ile Ser Leu Ser Ile Gly Asp
65                  70                  75                  80

Pro Thr Val Phe Gly Asn Leu Pro Thr Asp Pro Glu Val Thr Gln Ala
                85                  90                  95

Met Lys Asp Ala Leu Asp Ser Gly Lys Tyr Asn Gly Tyr Ala Pro Ser
            100                 105                 110

Ile Gly Tyr Leu Ser Ser Arg Glu Glu Val Ala Ser Tyr Tyr His Cys
        115                 120                 125

His Glu Ala Pro Leu Glu Ala Lys Asp Val Ile Leu Thr Ser Gly Cys
    130                 135                 140

Ser Gln Ala Ile Glu Leu Cys Leu Ala Val Leu Ala Asn Pro Gly Gln
145                 150                 155                 160

Asn Ile Leu Ile Pro Arg Pro Gly Phe Ser Leu Tyr Arg Thr Leu Ala
                165                 170                 175

Glu Ser Met Gly Ile Glu Val Lys Leu Tyr Asn Leu Leu Pro Glu Lys
            180                 185                 190

Ser Trp Glu Ile Asp Leu Lys Gln Leu Glu Ser Leu Ile Asp Glu Lys
        195                 200                 205

Thr Ala Cys Leu Val Val Asn Asn Pro Ser Asn Pro Cys Gly Ser Val
```

```
                210                 215                 220
Phe Ser Lys Arg His Leu Gln Lys Ile Leu Ala Val Ala Glu Arg Gln
225                 230                 235                 240

Cys Val Pro Ile Leu Ala Asp Glu Ile Tyr Gly Asp Met Val Phe Ser
                245                 250                 255

Asp Cys Lys Tyr Glu Pro Leu Ala Asn Leu Ser Thr Asn Val Pro Ile
            260                 265                 270

Leu Ser Cys Gly Gly Leu Ala Lys Arg Trp Leu Val Pro Gly Trp Arg
        275                 280                 285

Leu Gly Trp Ile Leu Ile His Asp Arg Arg Asp Ile Phe Gly Asn Glu
    290                 295                 300

Ile Arg Asp Gly Leu Val Lys Leu Ser Gln Arg Ile Leu Gly Pro Cys
305                 310                 315                 320

Thr Ile Val Gln Gly Ala Leu Lys Ser Ile Leu Gln Arg Thr Pro Gln
                325                 330                 335

Glu Phe Tyr His Asp Thr Leu Ser Phe Leu Lys Ser Asn Ala Asp Leu
            340                 345                 350

Cys Tyr Gly Ala Leu Ala Ala Ile Pro Gly Leu Gln Pro Val Arg Pro
        355                 360                 365

Ser Gly Ala Met Tyr Leu Met Val Gly Ile Glu Met Glu His Leu Pro
    370                 375                 380

Glu Phe Glu Asn Asp Val Glu Phe Thr Glu Arg Leu Ile Ala Glu Gln
385                 390                 395                 400

Ala Val His Cys Leu Pro Ala Thr Cys Phe Glu Tyr Pro Asn Phe Phe
                405                 410                 415

Arg Val Val Ile Thr Val Pro Glu Val Met Met Leu Glu Ala Cys Ser
            420                 425                 430

Arg Ile Gln Glu Phe Cys Glu Gln His Tyr His Cys Ala Glu Gly Ser
        435                 440                 445

Gln Glu Glu Cys Asp Lys
    450

<210> SEQ ID NO 5
<211> LENGTH: 1269
<212> TYPE: DNA
<213> ORGANISM: Arabidopsis thaliana
<220> FEATURE:
<221> NAME/KEY: CDS
<222> LOCATION: (1)..(1269)

<400> SEQUENCE: 5 atg gca acc ctt aag tgc att gat tgg caa ttc agc gga agc gag gcg    48
Met Ala Thr Leu Lys Cys Ile Asp Trp Gln Phe Ser Gly Ser Glu Ala
1               5                   10                  15 gcc aaa gat gct gct gcg gcc tcc tta ggc tca tat acc tct gca ctc    96
Ala Lys Asp Ala Ala Ala Ala Ser Leu Gly Ser Tyr Thr Ser Ala Leu
            20                  25                  30 tat gcc ctg tgc gat cct cat ggc aaa ccc att ttg ccc cca cga aat   144
Tyr Ala Leu Cys Asp Pro His Gly Lys Pro Ile Leu Pro Pro Arg Asn
        35                  40                  45 gag atc ctg gag acc agc aat aca gcc gaa aaa gca gtt gtt aaa gct   192
Glu Ile Leu Glu Thr Ser Asn Thr Ala Glu Lys Ala Val Val Lys Ala
    50                  55                  60 gtt ctt tat ggc tcg gga aac gcc tat gct cct agc tta ggc ctc gcg   240
Val Leu Tyr Gly Ser Gly Asn Ala Tyr Ala Pro Ser Leu Gly Leu Ala
65                  70                  75                  80 gcc gcc aaa agt gcc gta gca gag tat cta aac caa ggt ctt cca aag   288
```

```
                Ala Ala Lys Ser Ala Val Ala Glu Tyr Leu Asn Gln Gly Leu Pro Lys
                         85                  90                  95 aag ctt acc gca gat gac gtg ttt atg act ctg gga tgc aaa caa gct     336
Lys Leu Thr Ala Asp Asp Val Phe Met Thr Leu Gly Cys Lys Gln Ala
            100                 105                 110 att gag ctc gcg gta gac att ctc gct aaa ccg aaa gcc aac gtt ttg     384
Ile Glu Leu Ala Val Asp Ile Leu Ala Lys Pro Lys Ala Asn Val Leu
            115                 120                 125 ctt ccg agt ccc ggc ttc cca tgg gac cta gtc cgc tcc atc tac aag     432
Leu Pro Ser Pro Gly Phe Pro Trp Asp Leu Val Arg Ser Ile Tyr Lys
    130                 135                 140 aac ctt gag gtc cgc cac tat aat ttc ctt cca gaa aag aac ttt gaa     480
Asn Leu Glu Val Arg His Tyr Asn Phe Leu Pro Glu Lys Asn Phe Glu
145                 150                 155                 160 atc gac ttt gat agc gtc cga gcg ctc gtg gac gag aac aca ttt gcc     528
Ile Asp Phe Asp Ser Val Arg Ala Leu Val Asp Glu Asn Thr Phe Ala
                165                 170                 175 ata ttt ata atc aac ccc cac aac ccc aat ggt aac acc tac tcc gag     576
Ile Phe Ile Ile Asn Pro His Asn Pro Asn Gly Asn Thr Tyr Ser Glu
            180                 185                 190 gct cat ctc aaa cag ctg gct gaa ctg gct aag gaa ctc aag att atg     624
Ala His Leu Lys Gln Leu Ala Glu Leu Ala Lys Glu Leu Lys Ile Met
            195                 200                 205 gtg gtt tct gac gag gtt ttt aga tgg aca ctc ttt ggt agt aac cct     672
Val Val Ser Asp Glu Val Phe Arg Trp Thr Leu Phe Gly Ser Asn Pro
    210                 215                 220 ttt gtt cct atg gga aaa ttc tcg tcg atc gta cca gtg gtt aca ctc     720
Phe Val Pro Met Gly Lys Phe Ser Ser Ile Val Pro Val Val Thr Leu
225                 230                 235                 240 gga tcc ata tca aag gga tgg aaa gtc cca gga tgg cga act ggt tgg     768
Gly Ser Ile Ser Lys Gly Trp Lys Val Pro Gly Trp Arg Thr Gly Trp
                245                 250                 255 ctc acg cta cat gat cta gac ggt gtc ttc aga aac acc aag gtc tta     816
Leu Thr Leu His Asp Leu Asp Gly Val Phe Arg Asn Thr Lys Val Leu
            260                 265                 270 caa gct gct caa gat ttt ctc cag ata aac aat aac cct ccg aca gtt     864
Gln Ala Ala Gln Asp Phe Leu Gln Ile Asn Asn Asn Pro Pro Thr Val
            275                 280                 285 atc cag gcg gct att cct gac atc ttg gag aaa act cct caa gag ttt     912
Ile Gln Ala Ala Ile Pro Asp Ile Leu Glu Lys Thr Pro Gln Glu Phe
    290                 295                 300 ttt gat aag agg cag agt ttt ctg aaa gat aaa gta gaa ttt ggt tat     960
Phe Asp Lys Arg Gln Ser Phe Leu Lys Asp Lys Val Glu Phe Gly Tyr
305                 310                 315                 320 tct aag ctc aag tac att cct agc ctc act tgc tac atg aaa ccc gaa    1008
Ser Lys Leu Lys Tyr Ile Pro Ser Leu Thr Cys Tyr Met Lys Pro Glu
                325                 330                 335 gcc tgc acc ttc tta tgg acc gag ctt gat tta tcg agc ttt gtg gac    1056
Ala Cys Thr Phe Leu Trp Thr Glu Leu Asp Leu Ser Ser Phe Val Asp
            340                 345                 350 atc gaa gac gat caa gac ttt tgc aat aag ctt gct aaa gaa gaa aac    1104
Ile Glu Asp Asp Gln Asp Phe Cys Asn Lys Leu Ala Lys Glu Glu Asn
            355                 360                 365 ctc gtc gtt tta cca ggg att gca ttc agt cag aag aac tgg ttg agg    1152
Leu Val Val Leu Pro Gly Ile Ala Phe Ser Gln Lys Asn Trp Leu Arg
    370                 375                 380 cat tct atc gat atg gag act ccg gta ttg gag gat gca ttg gaa aga    1200
His Ser Ile Asp Met Glu Thr Pro Val Leu Glu Asp Ala Leu Glu Arg
385                 390                 395                 400
```

```
ttg aag agc ttc tgc gat cgc cat tcc aac aaa aaa gct ccc ctc aaa    1248
Leu Lys Ser Phe Cys Asp Arg His Ser Asn Lys Lys Ala Pro Leu Lys
            405                 410                 415 gac gtc aat ggt gtt aag taa                                        1269
Asp Val Asn Gly Val Lys
            420
```

<210> SEQ ID NO 6
<211> LENGTH: 422
<212> TYPE: PRT
<213> ORGANISM: Arabidopsis thaliana

<400> SEQUENCE: 6

```
Met Ala Thr Leu Lys Cys Ile Asp Trp Gln Phe Ser Gly Ser Glu Ala
1               5                   10                  15

Ala Lys Asp Ala Ala Ala Ser Leu Gly Ser Tyr Thr Ser Ala Leu
            20                  25                  30

Tyr Ala Leu Cys Asp Pro His Gly Lys Pro Ile Leu Pro Pro Arg Asn
            35                  40                  45

Glu Ile Leu Glu Thr Ser Asn Thr Ala Glu Lys Ala Val Val Lys Ala
50                  55                  60

Val Leu Tyr Gly Ser Gly Asn Ala Tyr Ala Pro Ser Leu Gly Leu Ala
65                  70                  75                  80

Ala Ala Lys Ser Ala Val Ala Glu Tyr Leu Asn Gln Gly Leu Pro Lys
            85                  90                  95

Lys Leu Thr Ala Asp Asp Val Phe Met Thr Leu Gly Cys Lys Gln Ala
            100                 105                 110

Ile Glu Leu Ala Val Asp Ile Leu Ala Lys Pro Lys Ala Asn Val Leu
            115                 120                 125

Leu Pro Ser Pro Gly Phe Pro Trp Asp Leu Val Arg Ser Ile Tyr Lys
            130                 135                 140

Asn Leu Glu Val Arg His Tyr Asn Phe Leu Pro Glu Lys Asn Phe Glu
145                 150                 155                 160

Ile Asp Phe Asp Ser Val Arg Ala Leu Val Asp Glu Asn Thr Phe Ala
                165                 170                 175

Ile Phe Ile Ile Asn Pro His Asn Pro Asn Gly Asn Thr Tyr Ser Glu
            180                 185                 190

Ala His Leu Lys Gln Leu Ala Glu Leu Ala Lys Glu Leu Lys Ile Met
            195                 200                 205

Val Val Ser Asp Glu Val Phe Arg Trp Thr Leu Phe Gly Ser Asn Pro
210                 215                 220

Phe Val Pro Met Gly Lys Phe Ser Ser Ile Val Pro Val Val Thr Leu
225                 230                 235                 240

Gly Ser Ile Ser Lys Gly Trp Lys Val Pro Gly Trp Arg Thr Gly Trp
            245                 250                 255

Leu Thr Leu His Asp Leu Asp Gly Val Phe Arg Asn Thr Lys Val Leu
            260                 265                 270

Gln Ala Ala Gln Asp Phe Leu Gln Ile Asn Asn Asn Pro Pro Thr Val
            275                 280                 285

Ile Gln Ala Ala Ile Pro Asp Ile Leu Glu Lys Thr Pro Gln Glu Phe
            290                 295                 300

Phe Asp Lys Arg Gln Ser Phe Leu Lys Asp Lys Val Glu Phe Gly Tyr
305                 310                 315                 320

Ser Lys Leu Lys Tyr Ile Pro Ser Leu Thr Cys Tyr Met Lys Pro Glu
                325                 330                 335
```

```
Ala Cys Thr Phe Leu Trp Thr Glu Leu Asp Leu Ser Ser Phe Val Asp
            340                 345                 350

Ile Glu Asp Asp Gln Asp Phe Cys Asn Lys Leu Ala Lys Glu Glu Asn
            355                 360                 365

Leu Val Val Leu Pro Gly Ile Ala Phe Ser Gln Lys Asn Trp Leu Arg
        370                 375                 380

His Ser Ile Asp Met Glu Thr Pro Val Leu Glu Asp Ala Leu Glu Arg
385                 390                 395                 400

Leu Lys Ser Phe Cys Asp Arg His Ser Asn Lys Lys Ala Pro Leu Lys
                405                 410                 415

Asp Val Asn Gly Val Lys
            420

<210> SEQ ID NO 7
<211> LENGTH: 1334
<212> TYPE: DNA
<213> ORGANISM: Arabidopsis thaliana
<220> FEATURE:
<221> NAME/KEY: CDS
<222> LOCATION: (1)..(1332)

<400> SEQUENCE: 7
```

| | | | | | | | | | | | | | | | | |
|---|---|---|---|---|---|---|---|---|---|---|---|---|---|---|---|---|
| atg | gcg | agc | aac | gga | gtt | acc | aac | tgt | aac | gca | aac | gcc | aat | gtt | tgg | 48 |
| Met | Ala | Ser | Asn | Gly | Val | Thr | Asn | Cys | Asn | Ala | Asn | Ala | Asn | Val | Trp | |
| 1 | | | | 5 | | | | | 10 | | | | | 15 | | |
| cgg | ttc | aaa | gga | aac | ggt | gca | acg | agt | gat | gcg | acg | gcg | gtg | acg | ttg | 96 |
| Arg | Phe | Lys | Gly | Asn | Gly | Ala | Thr | Ser | Asp | Ala | Thr | Ala | Val | Thr | Leu | |
| | | | 20 | | | | | 25 | | | | | 30 | | | |
| aga | aag | ctt | gct | ttt | ggg | atg | ttt | aaa | aac | tgc | acc | atg | aac | agt | gga | 144 |
| Arg | Lys | Leu | Ala | Phe | Gly | Met | Phe | Lys | Asn | Cys | Thr | Met | Asn | Ser | Gly | |
| | | 35 | | | | | 40 | | | | | 45 | | | | |
| aag | acc | att | ttg | ttc | cca | act | ccc | ggc | gag | ccc | tcc | gcc | cat | tcc | aac | 192 |
| Lys | Thr | Ile | Leu | Phe | Pro | Thr | Pro | Gly | Glu | Pro | Ser | Ala | His | Ser | Asn | |
| | 50 | | | | | 55 | | | | | 60 | | | | | |
| ttc | agg | act | tgc | ccg | gaa | gcc | gag | gaa | gcc | gtt | gcc | gac | gct | gca | cgc | 240 |
| Phe | Arg | Thr | Cys | Pro | Glu | Ala | Glu | Glu | Ala | Val | Ala | Asp | Ala | Ala | Arg | |
| 65 | | | | | 70 | | | | | 75 | | | | | 80 | |
| tcc | ggc | atg | gct | aac | tct | tac | gca | ccc | agc | cct | gga | gtt | ttc | aag | gct | 288 |
| Ser | Gly | Met | Ala | Asn | Ser | Tyr | Ala | Pro | Ser | Pro | Gly | Val | Phe | Lys | Ala | |
| | | | | 85 | | | | | 90 | | | | | 95 | | |
| aga | agg | gcg | gtg | gct | gaa | tat | tta | aac | gga | gaa | ctt | ccg | acg | aag | ctg | 336 |
| Arg | Arg | Ala | Val | Ala | Glu | Tyr | Leu | Asn | Gly | Glu | Leu | Pro | Thr | Lys | Leu | |
| | | | 100 | | | | | 105 | | | | | 110 | | | |
| aag | gcc | gag | gat | gtg | tat | atc | acc | gga | gga | tgt | aac | caa | gcc | ata | gag | 384 |
| Lys | Ala | Glu | Asp | Val | Tyr | Ile | Thr | Gly | Gly | Cys | Asn | Gln | Ala | Ile | Glu | |
| | | 115 | | | | | 120 | | | | | 125 | | | | |
| atc | gtg | ata | gat | tct | ctt | gcc | gga | aat | cca | tcc | acc | aac | att | cta | ctt | 432 |
| Ile | Val | Ile | Asp | Ser | Leu | Ala | Gly | Asn | Pro | Ser | Thr | Asn | Ile | Leu | Leu | |
| | 130 | | | | | 135 | | | | | 140 | | | | | |
| cca | agg | ccg | ggg | tat | cct | cac | tac | gat | gct | cgt | gct | gtc | tat | agc | ggc | 480 |
| Pro | Arg | Pro | Gly | Tyr | Pro | His | Tyr | Asp | Ala | Arg | Ala | Val | Tyr | Ser | Gly | |
| 145 | | | | | 150 | | | | | 155 | | | | | 160 | |
| ctc | gag | att | cgc | gaa | tac | gat | ctt | ctc | ccc | gag | agt | gat | tgg | gaa | atc | 528 |
| Leu | Glu | Ile | Arg | Glu | Tyr | Asp | Leu | Leu | Pro | Glu | Ser | Asp | Trp | Glu | Ile | |
| | | | | 165 | | | | | 170 | | | | | 175 | | |
| aat | ctc | gat | ggc | ctc | gag | gcg | gct | gcg | gat | gag | aat | acc | gtc | gca | atg | 576 |
| Asn | Leu | Asp | Gly | Leu | Glu | Ala | Ala | Ala | Asp | Glu | Asn | Thr | Val | Ala | Met | |
| | | | 180 | | | | | 185 | | | | | 190 | | | |
| gta | atc | atc | aac | ccc | aac | aat | cca | tgt | gga | aac | gtc | tac | acc | tac | gac | 624 |
| Val | Ile | Ile | Asn | Pro | Asn | Asn | Pro | Cys | Gly | Asn | Val | Tyr | Thr | Tyr | Asp | |

```
                195                 200                 205
cat ctc aac aag gtc gcg gag atg gct aga aaa ctc ggt ata atg ata        672
His Leu Asn Lys Val Ala Glu Met Ala Arg Lys Leu Gly Ile Met Ile
        210                 215                 220 ata tcc gac gaa gta tat gat cat gtt gta tat gga gac aag cct ttt        720
Ile Ser Asp Glu Val Tyr Asp His Val Val Tyr Gly Asp Lys Pro Phe
225                 230                 235                 240 att ccc atg ggg aag ttt gca tca ata gct ccg gtg atc acg ctc gga        768
Ile Pro Met Gly Lys Phe Ala Ser Ile Ala Pro Val Ile Thr Leu Gly
                245                 250                 255 tcc ata tcc aaa gga tgg gtc aac cca ggc tgg aga gtt ggc tgg atc        816
Ser Ile Ser Lys Gly Trp Val Asn Pro Gly Trp Arg Val Gly Trp Ile
            260                 265                 270 gcc atg aac gat cct aat ggt atc ttt gta tct aca ggg gta gtt caa        864
Ala Met Asn Asp Pro Asn Gly Ile Phe Val Ser Thr Gly Val Val Gln
        275                 280                 285 gca ata gag gat ttt ctt gat tta act cca cag cct tca ttt att ctc        912
Ala Ile Glu Asp Phe Leu Asp Leu Thr Pro Gln Pro Ser Phe Ile Leu
    290                 295                 300 cag gaa gca ctt cct gat ata ttg gag aaa aca cct aaa gag ttc ttc        960
Gln Glu Ala Leu Pro Asp Ile Leu Glu Lys Thr Pro Lys Glu Phe Phe
305                 310                 315                 320 gag aag aag atc aaa gcc atg aga cgc aac gtc gag ctt tca tgt gag       1008
Glu Lys Lys Ile Lys Ala Met Arg Arg Asn Val Glu Leu Ser Cys Glu
                325                 330                 335 agg ctc aag gat att cct tgt ctc ttt tgt ccc aag aaa ccc gaa tct       1056
Arg Leu Lys Asp Ile Pro Cys Leu Phe Cys Pro Lys Lys Pro Glu Ser
            340                 345                 350 tgt tct tat tta tgg ttg aag ctt gac aca tca atg ttg aat aat atc       1104
Cys Ser Tyr Leu Trp Leu Lys Leu Asp Thr Ser Met Leu Asn Asn Ile
        355                 360                 365 aaa aat gat ttt gat ttc tgc acg aag cta gtt agt gag gag agt ctt       1152
Lys Asn Asp Phe Asp Phe Cys Thr Lys Leu Val Ser Glu Glu Ser Leu
    370                 375                 380 atc ctt ata cca gga gtg gct cta ggg gca gag aat tgg gtg agg ata       1200
Ile Leu Ile Pro Gly Val Ala Leu Gly Ala Glu Asn Trp Val Arg Ile
385                 390                 395                 400 tcg ata gga acc gac gaa tca gtg gta caa gaa ata ttt gac aga cta       1248
Ser Ile Gly Thr Asp Glu Ser Val Val Gln Glu Ile Phe Asp Arg Leu
                405                 410                 415 aaa ggt ttc tat gat cgt cat gcc atc tcc aag gaa gct atc aaa ctc       1296
Lys Gly Phe Tyr Asp Arg His Ala Ile Ser Lys Glu Ala Ile Lys Leu
            420                 425                 430 agt ggc cat gcc att aac cag atc gtc gtc tct gtc aa                    1334
Ser Gly His Ala Ile Asn Gln Ile Val Val Ser Val
        435                 440

<210> SEQ ID NO 8
<211> LENGTH: 444
<212> TYPE: PRT
<213> ORGANISM: Arabidopsis thaliana

<400> SEQUENCE: 8

Met Ala Ser Asn Gly Val Thr Asn Cys Asn Ala Asn Ala Asn Val Trp
1               5                   10                  15

Arg Phe Lys Gly Asn Gly Ala Thr Ser Asp Ala Thr Ala Val Thr Leu
            20                  25                  30

Arg Lys Leu Ala Phe Gly Met Phe Lys Asn Cys Thr Met Asn Ser Gly
        35                  40                  45
```

```
Lys Thr Ile Leu Phe Pro Thr Pro Gly Glu Pro Ser Ala His Ser Asn
 50                  55                  60

Phe Arg Thr Cys Pro Glu Ala Glu Ala Val Ala Asp Ala Ala Arg
 65                  70                  75                  80

Ser Gly Met Ala Asn Ser Tyr Ala Pro Ser Pro Gly Val Phe Lys Ala
                 85                  90                  95

Arg Arg Ala Val Ala Glu Tyr Leu Asn Gly Glu Leu Pro Thr Lys Leu
            100                 105                 110

Lys Ala Glu Asp Val Tyr Ile Thr Gly Gly Cys Asn Gln Ala Ile Glu
            115                 120                 125

Ile Val Ile Asp Ser Leu Ala Gly Asn Pro Ser Thr Asn Ile Leu Leu
        130                 135                 140

Pro Arg Pro Gly Tyr Pro His Tyr Asp Ala Arg Ala Val Tyr Ser Gly
145                 150                 155                 160

Leu Glu Ile Arg Glu Tyr Asp Leu Leu Pro Glu Ser Asp Trp Glu Ile
                165                 170                 175

Asn Leu Asp Gly Leu Glu Ala Ala Asp Glu Asn Thr Val Ala Met
            180                 185                 190

Val Ile Ile Asn Pro Asn Asn Pro Cys Gly Asn Val Tyr Thr Tyr Asp
        195                 200                 205

His Leu Asn Lys Val Ala Glu Met Ala Arg Lys Leu Gly Ile Met Ile
    210                 215                 220

Ile Ser Asp Glu Val Tyr Asp His Val Val Tyr Gly Asp Lys Pro Phe
225                 230                 235                 240

Ile Pro Met Gly Lys Phe Ala Ser Ile Ala Pro Val Ile Thr Leu Gly
                245                 250                 255

Ser Ile Ser Lys Gly Trp Val Asn Pro Gly Trp Arg Val Gly Trp Ile
            260                 265                 270

Ala Met Asn Asp Pro Asn Gly Ile Phe Val Ser Thr Gly Val Val Gln
        275                 280                 285

Ala Ile Glu Asp Phe Leu Asp Leu Thr Pro Gln Pro Ser Phe Ile Leu
    290                 295                 300

Gln Glu Ala Leu Pro Asp Ile Leu Glu Lys Thr Pro Lys Glu Phe Phe
305                 310                 315                 320

Glu Lys Lys Ile Lys Ala Met Arg Arg Asn Val Glu Leu Ser Cys Glu
                325                 330                 335

Arg Leu Lys Asp Ile Pro Cys Leu Phe Cys Pro Lys Lys Pro Glu Ser
            340                 345                 350

Cys Ser Tyr Leu Trp Leu Lys Leu Asp Thr Ser Met Leu Asn Asn Ile
        355                 360                 365

Lys Asn Asp Phe Asp Phe Cys Thr Lys Leu Val Ser Glu Glu Ser Leu
    370                 375                 380

Ile Leu Ile Pro Gly Val Ala Leu Gly Ala Glu Asn Trp Val Arg Ile
385                 390                 395                 400

Ser Ile Gly Thr Asp Glu Ser Val Val Gln Glu Ile Phe Asp Arg Leu
                405                 410                 415

Lys Gly Phe Tyr Asp Arg His Ala Ile Ser Lys Glu Ala Ile Lys Leu
            420                 425                 430

Ser Gly His Ala Ile Asn Gln Ile Val Val Ser Val
        435                 440

<210> SEQ ID NO 9
<211> LENGTH: 1389
<212> TYPE: DNA
```

<213> ORGANISM: Arabidopsis thaliana
<220> FEATURE:
<221> NAME/KEY: CDS
<222> LOCATION: (1)..(1389)

<400> SEQUENCE: 9

| | | | | | | | | | | | | | | | | |
|---|---|---|---|---|---|---|---|---|---|---|---|---|---|---|---|---|
| atg | agc | gaa | gaa | caa | caa | cac | gcc | aat | cta | gcg | gtt | ccc | gcg | ttt | aaa | 48 |
| Met | Ser | Glu | Glu | Gln | Gln | His | Ala | Asn | Leu | Ala | Val | Pro | Ala | Phe | Lys | |
| 1 | | | | 5 | | | | | 10 | | | | | 15 | | |

| act | gag | aaa | gat | ccc | gta | acg | caa | acg | caa | aat | ggt | caa | agt | agc | gtt | 96 |
|---|---|---|---|---|---|---|---|---|---|---|---|---|---|---|---|---|
| Thr | Glu | Lys | Asp | Pro | Val | Thr | Gln | Thr | Gln | Asn | Gly | Gln | Ser | Ser | Val | |
| | | | 20 | | | | | 25 | | | | | 30 | | | |

| tgg | cgt | ttc | ggt | gga | agt | gat | aag | gca | gcg | aaa | gca | tcc | acc | gta | acg | 144 |
|---|---|---|---|---|---|---|---|---|---|---|---|---|---|---|---|---|
| Trp | Arg | Phe | Gly | Gly | Ser | Asp | Lys | Ala | Ala | Lys | Ala | Ser | Thr | Val | Thr | |
| | | 35 | | | | | 40 | | | | | 45 | | | | |

| ctt | aga | ggt | gtc | atc | tac | atg | ctc | ttc | gac | aac | tgc | agc | aaa | gac | gtc | 192 |
|---|---|---|---|---|---|---|---|---|---|---|---|---|---|---|---|---|
| Leu | Arg | Gly | Val | Ile | Tyr | Met | Leu | Phe | Asp | Asn | Cys | Ser | Lys | Asp | Val | |
| | 50 | | | | | 55 | | | | | 60 | | | | | |

| aat | aag | acc | att | tta | ccc | ctc | ggc | cac | ggt | gac | cct | tcc | gtc | tac | cct | 240 |
|---|---|---|---|---|---|---|---|---|---|---|---|---|---|---|---|---|
| Asn | Lys | Thr | Ile | Leu | Pro | Leu | Gly | His | Gly | Asp | Pro | Ser | Val | Tyr | Pro | |
| 65 | | | | 70 | | | | | 75 | | | | | 80 | | |

| tgc | ttc | cgt | acc | tgt | atc | gaa | gct | gaa | gac | gcc | gtc | gtc | gac | gtc | ctt | 288 |
|---|---|---|---|---|---|---|---|---|---|---|---|---|---|---|---|---|
| Cys | Phe | Arg | Thr | Cys | Ile | Glu | Ala | Glu | Asp | Ala | Val | Val | Asp | Val | Leu | |
| | | | 85 | | | | | 90 | | | | | 95 | | | |

| cgc | tcc | ggc | aaa | ggc | aat | tct | tac | ggt | ccc | gga | gct | ggg | att | ctc | ccc | 336 |
|---|---|---|---|---|---|---|---|---|---|---|---|---|---|---|---|---|
| Arg | Ser | Gly | Lys | Gly | Asn | Ser | Tyr | Gly | Pro | Gly | Ala | Gly | Ile | Leu | Pro | |
| | | 100 | | | | | 105 | | | | | 110 | | | | |

| gca | aga | cga | gcc | gtt | gct | gat | tat | atg | aac | cga | gat | ctt | ccg | cac | aag | 384 |
|---|---|---|---|---|---|---|---|---|---|---|---|---|---|---|---|---|
| Ala | Arg | Arg | Ala | Val | Ala | Asp | Tyr | Met | Asn | Arg | Asp | Leu | Pro | His | Lys | |
| | 115 | | | | | 120 | | | | | 125 | | | | | |

| tta | acg | ccc | gaa | gat | att | ttt | ctg | acc | gct | gga | tgc | aac | caa | ggg | ata | 432 |
|---|---|---|---|---|---|---|---|---|---|---|---|---|---|---|---|---|
| Leu | Thr | Pro | Glu | Asp | Ile | Phe | Leu | Thr | Ala | Gly | Cys | Asn | Gln | Gly | Ile | |
| 130 | | | | 135 | | | | | 140 | | | | | | | |

| gag | atc | gtg | ttc | gaa | tcg | ttg | gct | cga | cca | aac | gca | aac | atc | ttg | ctc | 480 |
|---|---|---|---|---|---|---|---|---|---|---|---|---|---|---|---|---|
| Glu | Ile | Val | Phe | Glu | Ser | Leu | Ala | Arg | Pro | Asn | Ala | Asn | Ile | Leu | Leu | |
| 145 | | | | 150 | | | | | 155 | | | | | 160 | | |

| cca | cgt | cct | ggc | ttc | cct | cat | tac | gac | gct | cgt | gct | gct | tac | agt | ggt | 528 |
|---|---|---|---|---|---|---|---|---|---|---|---|---|---|---|---|---|
| Pro | Arg | Pro | Gly | Phe | Pro | His | Tyr | Asp | Ala | Arg | Ala | Ala | Tyr | Ser | Gly | |
| | | | 165 | | | | | 170 | | | | | 175 | | | |

| ctc | gag | gtt | cgc | aag | ttt | gat | ctt | ctt | ccc | gag | aaa | gaa | tgg | gag | att | 576 |
|---|---|---|---|---|---|---|---|---|---|---|---|---|---|---|---|---|
| Leu | Glu | Val | Arg | Lys | Phe | Asp | Leu | Leu | Pro | Glu | Lys | Glu | Trp | Glu | Ile | |
| | | 180 | | | | | 185 | | | | | 190 | | | | |

| gat | ctt | gaa | ggt | atc | gaa | gcc | att | gca | gac | gag | aaa | act | gtg | gct | atg | 624 |
|---|---|---|---|---|---|---|---|---|---|---|---|---|---|---|---|---|
| Asp | Leu | Glu | Gly | Ile | Glu | Ala | Ile | Ala | Asp | Glu | Lys | Thr | Val | Ala | Met | |
| | 195 | | | | | 200 | | | | | 205 | | | | | |

| gtt | gta | att | aac | ccc | aac | aat | ccc | tgt | gga | aat | gtc | tac | tct | cac | gac | 672 |
|---|---|---|---|---|---|---|---|---|---|---|---|---|---|---|---|---|
| Val | Val | Ile | Asn | Pro | Asn | Asn | Pro | Cys | Gly | Asn | Val | Tyr | Ser | His | Asp | |
| 210 | | | | 215 | | | | | 220 | | | | | | | |

| cat | ctc | aaa | aag | gtt | gca | gag | acg | gct | agg | aag | ctc | ggg | ata | atg | gtg | 720 |
|---|---|---|---|---|---|---|---|---|---|---|---|---|---|---|---|---|
| His | Leu | Lys | Lys | Val | Ala | Glu | Thr | Ala | Arg | Lys | Leu | Gly | Ile | Met | Val | |
| 225 | | | | 230 | | | | | 235 | | | | | 240 | | |

| atc | tca | gac | gaa | gta | tat | gac | cga | act | ata | ttc | gga | gac | aat | cca | ttt | 768 |
|---|---|---|---|---|---|---|---|---|---|---|---|---|---|---|---|---|
| Ile | Ser | Asp | Glu | Val | Tyr | Asp | Arg | Thr | Ile | Phe | Gly | Asp | Asn | Pro | Phe | |
| | | | 245 | | | | | 250 | | | | | 255 | | | |

| gtt | cca | atg | ggg | aag | ttt | gct | tcg | ata | gtc | cct | gta | ttg | aca | cta | gca | 816 |
|---|---|---|---|---|---|---|---|---|---|---|---|---|---|---|---|---|
| Val | Pro | Met | Gly | Lys | Phe | Ala | Ser | Ile | Val | Pro | Val | Leu | Thr | Leu | Ala | |
| | | 260 | | | | | 265 | | | | | 270 | | | | |

| ggc | ata | tct | aag | gga | tgg | gtt | gtt | cct | gga | tgg | aaa | att | ggc | tgg | att | 864 |
|---|---|---|---|---|---|---|---|---|---|---|---|---|---|---|---|---|
| Gly | Ile | Ser | Lys | Gly | Trp | Val | Val | Pro | Gly | Trp | Lys | Ile | Gly | Trp | Ile | |
| | 275 | | | | | 280 | | | | | 285 | | | | | |

|  |  |
|---|---:|
| gcc ttg aat gat ccc gag ggc gtt ttc gag acc acc aag gtg tta caa<br>Ala Leu Asn Asp Pro Glu Gly Val Phe Glu Thr Thr Lys Val Leu Gln<br>290                              295                          300 | 912 |
| tcc atc aaa cag aat ctt gac gta act cct gac cct gcc aca ata att<br>Ser Ile Lys Gln Asn Leu Asp Val Thr Pro Asp Pro Ala Thr Ile Ile<br>305                       310                          315                   320 | 960 |
| cag gct gca ctt cca gcg atc ctg gag aaa gcg gac aaa aac ttc ttt<br>Gln Ala Ala Leu Pro Ala Ile Leu Glu Lys Ala Asp Lys Asn Phe Phe<br>                       325                          330                        335 | 1008 |
| gca aag aag aac aag ata ctc aaa cat aat gtt gat ttg gtg tgt gat<br>Ala Lys Lys Asn Lys Ile Leu Lys His Asn Val Asp Leu Val Cys Asp<br>                   340                         345                       350 | 1056 |
| agg ctc aag gac atc ccc tgt gtc gtc tgt ccc aag aaa cct gag tct<br>Arg Leu Lys Asp Ile Pro Cys Val Val Cys Pro Lys Lys Pro Glu Ser<br>                355                          360                       365 | 1104 |
| tgc act tac tta ttg aca aag ttg gag ctg tca ctg atg gat aat atc<br>Cys Thr Tyr Leu Leu Thr Lys Leu Glu Leu Ser Leu Met Asp Asn Ile<br>370                              375                          380 | 1152 |
| aag gac gat ata gat ttt tgc gta aaa ctg gcc aga gag gag aat ctc<br>Lys Asp Asp Ile Asp Phe Cys Val Lys Leu Ala Arg Glu Glu Asn Leu<br>385                              390                        395                       400 | 1200 |
| gtg ttt cta cca ggg gat gct ctg ggt ttg aag aac tgg acg agg ata<br>Val Phe Leu Pro Gly Asp Ala Leu Gly Leu Lys Asn Trp Thr Arg Ile<br>                             405                          410                       415 | 1248 |
| acc atc gga gtc gaa gct cat atg ctt gag gat gca ctt gag aga ctg<br>Thr Ile Gly Val Glu Ala His Met Leu Glu Asp Ala Leu Glu Arg Leu<br>                     420                         425                       430 | 1296 |
| aag ggt ttc tgt aca cgt cat gcc aag aag aca gag aca gaa act gag<br>Lys Gly Phe Cys Thr Arg His Ala Lys Lys Thr Glu Thr Glu Thr Glu<br>                             435                          440                       445 | 1344 |
| tca ctt caa gct ttg aaa ctg agt gat aat aat ctc gaa atg taa<br>Ser Leu Gln Ala Leu Lys Leu Ser Asp Asn Asn Leu Glu Met<br>450                              455                          460 | 1389 |

<210> SEQ ID NO 10
<211> LENGTH: 462
<212> TYPE: PRT
<213> ORGANISM: Arabidopsis thaliana

<400> SEQUENCE: 10

Met Ser Glu Glu Gln Gln His Ala Asn Leu Ala Val Pro Ala Phe Lys
1               5                   10                  15

Thr Glu Lys Asp Pro Val Thr Gln Thr Gln Asn Gly Gln Ser Ser Val
            20                  25                  30

Trp Arg Phe Gly Gly Ser Asp Lys Ala Ala Lys Ala Ser Thr Val Thr
        35                  40                  45

Leu Arg Gly Val Ile Tyr Met Leu Phe Asp Asn Cys Ser Lys Asp Val
    50                  55                  60

Asn Lys Thr Ile Leu Pro Leu Gly His Gly Asp Pro Ser Val Tyr Pro
65                  70                  75                  80

Cys Phe Arg Thr Cys Ile Glu Ala Glu Asp Ala Val Val Asp Val Leu
                85                  90                  95

Arg Ser Gly Lys Gly Asn Ser Tyr Gly Pro Gly Ala Gly Ile Leu Pro
            100                 105                 110

Ala Arg Arg Ala Val Ala Asp Tyr Met Asn Arg Asp Leu Pro His Lys
        115                 120                 125

Leu Thr Pro Glu Asp Ile Phe Leu Thr Ala Gly Cys Asn Gln Gly Ile
    130                 135                 140

-continued

```
Glu Ile Val Phe Glu Ser Leu Ala Arg Pro Asn Ala Asn Ile Leu Leu
145                 150                 155                 160

Pro Arg Pro Gly Phe Pro His Tyr Asp Ala Arg Ala Ala Tyr Ser Gly
                165                 170                 175

Leu Glu Val Arg Lys Phe Asp Leu Leu Pro Glu Lys Glu Trp Glu Ile
            180                 185                 190

Asp Leu Glu Gly Ile Glu Ala Ile Ala Asp Glu Lys Thr Val Ala Met
        195                 200                 205

Val Val Ile Asn Pro Asn Asn Pro Cys Gly Asn Val Tyr Ser His Asp
    210                 215                 220

His Leu Lys Lys Val Ala Glu Thr Ala Arg Lys Leu Gly Ile Met Val
225                 230                 235                 240

Ile Ser Asp Glu Val Tyr Asp Arg Thr Ile Phe Gly Asp Asn Pro Phe
                245                 250                 255

Val Pro Met Gly Lys Phe Ala Ser Ile Val Pro Val Leu Thr Leu Ala
            260                 265                 270

Gly Ile Ser Lys Gly Trp Val Pro Gly Trp Lys Ile Gly Trp Ile
        275                 280                 285

Ala Leu Asn Asp Pro Glu Gly Val Phe Glu Thr Thr Lys Val Leu Gln
    290                 295                 300

Ser Ile Lys Gln Asn Leu Asp Val Thr Pro Asp Pro Ala Thr Ile Ile
305                 310                 315                 320

Gln Ala Ala Leu Pro Ala Ile Leu Glu Lys Ala Asp Lys Asn Phe Phe
                325                 330                 335

Ala Lys Lys Asn Lys Ile Leu Lys His Asn Val Asp Leu Val Cys Asp
            340                 345                 350

Arg Leu Lys Asp Ile Pro Cys Val Val Cys Pro Lys Lys Pro Glu Ser
        355                 360                 365

Cys Thr Tyr Leu Leu Thr Lys Leu Glu Leu Ser Leu Met Asp Asn Ile
370                 375                 380

Lys Asp Asp Ile Asp Phe Cys Val Lys Leu Ala Arg Glu Glu Asn Leu
385                 390                 395                 400

Val Phe Leu Pro Gly Asp Ala Leu Gly Leu Lys Asn Trp Thr Arg Ile
                405                 410                 415

Thr Ile Gly Val Glu Ala His Met Leu Glu Asp Ala Leu Glu Arg Leu
            420                 425                 430

Lys Gly Phe Cys Thr Arg His Ala Lys Lys Thr Glu Thr Glu Thr Glu
        435                 440                 445

Ser Leu Gln Ala Leu Lys Leu Ser Asp Asn Asn Leu Glu Met
    450                 455                 460

<210> SEQ ID NO 11
<211> LENGTH: 1243
<212> TYPE: DNA
<213> ORGANISM: Arabidopsis thaliana
<220> FEATURE:
<221> NAME/KEY: CDS
<222> LOCATION: (1)..(1242)

<400> SEQUENCE: 11 atg gag aat gga gca acg acg acg agc aca att acc atc aaa ggg att      48
Met Glu Asn Gly Ala Thr Thr Thr Ser Thr Ile Thr Ile Lys Gly Ile
1               5                   10                  15 ctg agt ttg cta atg gaa agc atc aca aca gag gaa gat gaa gga gga      96
Leu Ser Leu Leu Met Glu Ser Ile Thr Thr Glu Glu Asp Glu Gly Gly
            20                  25                  30
```

```
aag aga gta ata tct ctg gga atg gga gac cca aca ctc tac tcg tgt      144
Lys Arg Val Ile Ser Leu Gly Met Gly Asp Pro Thr Leu Tyr Ser Cys
         35                  40                  45 ttt cgt aca aca caa gtc tct ctt caa gct gtt tct gat tct ctc ctc      192
Phe Arg Thr Thr Gln Val Ser Leu Gln Ala Val Ser Asp Ser Leu Leu
 50                  55                  60 tcc aac aag ttc cat ggt tac tct cct acc gtc ggt ctt ccc caa gct      240
Ser Asn Lys Phe His Gly Tyr Ser Pro Thr Val Gly Leu Pro Gln Ala
 65                  70                  75                  80 cga agg gca ata gca gag tat cta tcg cgt gat ctt cca tac aaa ctt      288
Arg Arg Ala Ile Ala Glu Tyr Leu Ser Arg Asp Leu Pro Tyr Lys Leu
                 85                  90                  95 tca cag gat gat gtg ttt atc aca tcg ggt tgc acg caa gcg atc gat      336
Ser Gln Asp Asp Val Phe Ile Thr Ser Gly Cys Thr Gln Ala Ile Asp
            100                 105                 110 gta gca ttg tcg atg tta gct cgt ccc agg gct aat ata ctt ctt cca      384
Val Ala Leu Ser Met Leu Ala Arg Pro Arg Ala Asn Ile Leu Leu Pro
        115                 120                 125 agg cct ggt ttc cca atc tat gaa ctc tgt gct aag ttt aga cac ctt      432
Arg Pro Gly Phe Pro Ile Tyr Glu Leu Cys Ala Lys Phe Arg His Leu
130                 135                 140 gaa gtt cgc tac gtc gat ctt ctt ccg gaa aat gga tgg gag atc gat      480
Glu Val Arg Tyr Val Asp Leu Leu Pro Glu Asn Gly Trp Glu Ile Asp
145                 150                 155                 160 ctt gat gct gtc gag gct ctt gca gac gaa aac acg gtt gct ttg gtt      528
Leu Asp Ala Val Glu Ala Leu Ala Asp Glu Asn Thr Val Ala Leu Val
                165                 170                 175 gtt ata aac cct ggt aat cct tgc ggg aat gtc tat agc tac cag cat      576
Val Ile Asn Pro Gly Asn Pro Cys Gly Asn Val Tyr Ser Tyr Gln His
            180                 185                 190 ttg atg aag att gcg gaa tcg gcg aaa aaa cta ggg ttt ctt gtg att      624
Leu Met Lys Ile Ala Glu Ser Ala Lys Lys Leu Gly Phe Leu Val Ile
        195                 200                 205 gct gat gag gtt tac ggt cat ctt gct ttt ggt agc aaa ccg ttt gtg      672
Ala Asp Glu Val Tyr Gly His Leu Ala Phe Gly Ser Lys Pro Phe Val
210                 215                 220 cca atg ggt gtg ttt gga tct att gtt cct gtg ctt act ctt ggc tct      720
Pro Met Gly Val Phe Gly Ser Ile Val Pro Val Leu Thr Leu Gly Ser
225                 230                 235                 240 tta tca aag aga tgg ata gtt cca ggt tgg cga ctc ggg tgg ttt gtc      768
Leu Ser Lys Arg Trp Ile Val Pro Gly Trp Arg Leu Gly Trp Phe Val
                245                 250                 255 acc act gat cct tct ggt tcc ttt aag gac cct aag atc att gag agg      816
Thr Thr Asp Pro Ser Gly Ser Phe Lys Asp Pro Lys Ile Ile Glu Arg
            260                 265                 270 ttt aag aaa tac ttt gat att ctt ggt gga cca gct aca ttt att cag      864
Phe Lys Lys Tyr Phe Asp Ile Leu Gly Gly Pro Ala Thr Phe Ile Gln
        275                 280                 285 gct gca gtt ccc act att ttg gaa cag acg gat gag tct ttc ttc aag      912
Ala Ala Val Pro Thr Ile Leu Glu Gln Thr Asp Glu Ser Phe Phe Lys
290                 295                 300 aaa acc ttg aac tcg ttg aag aac tct tcg gat att tgt tgt gac tgg      960
Lys Thr Leu Asn Ser Leu Lys Asn Ser Ser Asp Ile Cys Cys Asp Trp
305                 310                 315                 320 atc aag gag att cct tgc att gat tcc tcg cat cga cca gaa gga tcc     1008
Ile Lys Glu Ile Pro Cys Ile Asp Ser Ser His Arg Pro Glu Gly Ser
                325                 330                 335 atg gca atg atg gtc aag ctg aat ctc tca tta ctt gaa gat gta agt     1056
Met Ala Met Met Val Lys Leu Asn Leu Ser Leu Leu Glu Asp Val Ser
            340                 345                 350
```

```
gac gat atc gac ttc tgt ttc aag tta gct agg gaa gaa tca gtc atc      1104
Asp Asp Ile Asp Phe Cys Phe Lys Leu Ala Arg Glu Glu Ser Val Ile
        355                 360                 365 ctt ctt cct ggt acc gcg gtg ggg ctg aag aac tgg ctg agg ata acg      1152
Leu Leu Pro Gly Thr Ala Val Gly Leu Lys Asn Trp Leu Arg Ile Thr
370                 375                 380 ttt gca gca gat gca act tcg att gaa gaa gct ttt aaa agg atc aaa      1200
Phe Ala Ala Asp Ala Thr Ser Ile Glu Glu Ala Phe Lys Arg Ile Lys
385                 390                 395                 400 tgt ttc tat ctt aga cat gcc aag act caa tat cca acc ata t            1243
Cys Phe Tyr Leu Arg His Ala Lys Thr Gln Tyr Pro Thr Ile
            405                 410
```

<210> SEQ ID NO 12
<211> LENGTH: 414
<212> TYPE: PRT
<213> ORGANISM: Arabidopsis thaliana

<400> SEQUENCE: 12

```
Met Glu Asn Gly Ala Thr Thr Thr Ser Thr Ile Thr Lys Gly Ile
1               5                   10                  15

Leu Ser Leu Leu Met Glu Ser Ile Thr Thr Glu Glu Asp Glu Gly Gly
                20                  25                  30

Lys Arg Val Ile Ser Leu Gly Met Gly Asp Pro Thr Leu Tyr Ser Cys
            35                  40                  45

Phe Arg Thr Thr Gln Val Ser Leu Gln Ala Val Ser Asp Ser Leu Leu
        50                  55                  60

Ser Asn Lys Phe His Gly Tyr Ser Pro Thr Val Gly Leu Pro Gln Ala
65                  70                  75                  80

Arg Arg Ala Ile Ala Glu Tyr Leu Ser Arg Asp Leu Pro Tyr Lys Leu
                85                  90                  95

Ser Gln Asp Asp Val Phe Ile Thr Ser Gly Cys Thr Gln Ala Ile Asp
            100                 105                 110

Val Ala Leu Ser Met Leu Ala Arg Pro Arg Ala Asn Ile Leu Leu Pro
        115                 120                 125

Arg Pro Gly Phe Pro Ile Tyr Glu Leu Cys Ala Lys Phe Arg His Leu
130                 135                 140

Glu Val Arg Tyr Val Asp Leu Leu Pro Glu Asn Gly Trp Glu Ile Asp
145                 150                 155                 160

Leu Asp Ala Val Glu Ala Leu Ala Asp Glu Asn Thr Val Ala Leu Val
                165                 170                 175

Val Ile Asn Pro Gly Asn Pro Cys Gly Asn Val Tyr Ser Tyr Gln His
            180                 185                 190

Leu Met Lys Ile Ala Glu Ser Ala Lys Lys Leu Gly Phe Leu Val Ile
        195                 200                 205

Ala Asp Glu Val Tyr Gly His Leu Ala Phe Gly Ser Lys Pro Phe Val
210                 215                 220

Pro Met Gly Val Phe Gly Ser Ile Val Pro Val Leu Thr Leu Gly Ser
225                 230                 235                 240

Leu Ser Lys Arg Trp Ile Val Pro Gly Trp Arg Leu Gly Trp Phe Val
                245                 250                 255

Thr Thr Asp Pro Ser Gly Ser Phe Lys Asp Pro Lys Ile Ile Glu Arg
            260                 265                 270

Phe Lys Lys Tyr Phe Asp Ile Leu Gly Gly Pro Ala Thr Phe Ile Gln
        275                 280                 285
```

```
Ala Ala Val Pro Thr Ile Leu Glu Gln Thr Asp Glu Ser Phe Phe Lys
        290                 295                 300

Lys Thr Leu Asn Ser Leu Lys Asn Ser Ser Asp Ile Cys Cys Asp Trp
305                 310                 315                 320

Ile Lys Glu Ile Pro Cys Ile Asp Ser Ser His Arg Pro Glu Gly Ser
                325                 330                 335

Met Ala Met Val Lys Leu Asn Leu Ser Leu Leu Glu Asp Val Ser
            340                 345                 350

Asp Asp Ile Asp Phe Cys Phe Lys Leu Ala Arg Glu Glu Ser Val Ile
                355                 360                 365

Leu Leu Pro Gly Thr Ala Val Gly Leu Lys Asn Trp Leu Arg Ile Thr
370                 375                 380

Phe Ala Ala Asp Ala Thr Ser Ile Glu Glu Ala Phe Lys Arg Ile Lys
385                 390                 395                 400

Cys Phe Tyr Leu Arg His Ala Lys Thr Gln Tyr Pro Thr Ile
                405                 410
```

<210> SEQ ID NO 13
<211> LENGTH: 1338
<212> TYPE: DNA
<213> ORGANISM: Arabidopsis thaliana
<220> FEATURE:
<221> NAME/KEY: CDS
<222> LOCATION: (1)..(1338)

<400> SEQUENCE: 13

```
atg ggc cac caa aac gcc gcc gtt tca gag aat caa aac cat gat gac      48
Met Gly His Gln Asn Ala Ala Val Ser Glu Asn Gln Asn His Asp Asp
1               5                   10                  15 ggc gct gcg tcg tcg ccg gga ttc aag ctc gtc gga ttt tcc aag ttc      96
Gly Ala Ala Ser Ser Pro Gly Phe Lys Leu Val Gly Phe Ser Lys Phe
                20                  25                  30 gta aga aag aat cca aag tct gat aaa ttc aag gtt aag cgc ttc cat    144
Val Arg Lys Asn Pro Lys Ser Asp Lys Phe Lys Val Lys Arg Phe His
            35                  40                  45 cac atc gag ttc tgg tgc ggc gac gca acc aac gtc gct cgt cgc ttc    192
His Ile Glu Phe Trp Cys Gly Asp Ala Thr Asn Val Ala Arg Arg Phe
        50                  55                  60 tcc tgg ggt ctg ggg atg aga ttc tcc gcc aaa tcc gat ctt tcc acc    240
Ser Trp Gly Leu Gly Met Arg Phe Ser Ala Lys Ser Asp Leu Ser Thr
65                  70                  75                  80 gga aac atg gtt cac gcc tct tac cta ctc acc tcc ggt gac ctc cga    288
Gly Asn Met Val His Ala Ser Tyr Leu Leu Thr Ser Gly Asp Leu Arg
                85                  90                  95 ttc ctt ttc act gct cct tac tct ccg tct ctc tcc gcc gga gag att    336
Phe Leu Phe Thr Ala Pro Tyr Ser Pro Ser Leu Ser Ala Gly Glu Ile
                100                 105                 110 aaa ccg aca acc aca gct tct atc cca agt ttc gat cac ggc tct tgt    384
Lys Pro Thr Thr Thr Ala Ser Ile Pro Ser Phe Asp His Gly Ser Cys
            115                 120                 125 cgt tcc ttc ttc tct tca cat ggt ctc ggt gtt aga gcc gtt gcg att    432
Arg Ser Phe Phe Ser Ser His Gly Leu Gly Val Arg Ala Val Ala Ile
        130                 135                 140 gaa gta gaa gac gca gag tca gct ttc tcc atc agt gta gct aat ggc    480
Glu Val Glu Asp Ala Glu Ser Ala Phe Ser Ile Ser Val Ala Asn Gly
145                 150                 155                 160 gct att cct tcg tcg cct cct atc gtc ctc aat gaa gca gtt acg atc    528
Ala Ile Pro Ser Ser Pro Pro Ile Val Leu Asn Glu Ala Val Thr Ile
                165                 170                 175
```

```
gct gag gtt aaa cta tac ggc gat gtt gtt ctc cga tat gtt agt tac      576
Ala Glu Val Lys Leu Tyr Gly Asp Val Val Leu Arg Tyr Val Ser Tyr
        180                 185                 190 aaa gca gaa gat acc gaa aaa tcc gaa ttc ttg cca ggg ttc gag cgt      624
Lys Ala Glu Asp Thr Glu Lys Ser Glu Phe Leu Pro Gly Phe Glu Arg
        195                 200                 205 gta gag gat gcg tcg tcg ttc cca ttg gat tat ggt atc cgg cgg ctt      672
Val Glu Asp Ala Ser Ser Phe Pro Leu Asp Tyr Gly Ile Arg Arg Leu
210                 215                 220 gac cac gcc gtg gga aac gtt cct gag ctt ggt ccg gct tta act tat      720
Asp His Ala Val Gly Asn Val Pro Glu Leu Gly Pro Ala Leu Thr Tyr
225                 230                 235                 240 gta gcg ggg ttc act ggt ttt cac caa ttc gca gag ttc aca gca gac      768
Val Ala Gly Phe Thr Gly Phe His Gln Phe Ala Glu Phe Thr Ala Asp
                245                 250                 255 gac gtt gga acc gcc gag agc ggt tta aat tca gcg gtc ctg gct agc      816
Asp Val Gly Thr Ala Glu Ser Gly Leu Asn Ser Ala Val Leu Ala Ser
                260                 265                 270 aat gat gaa atg gtt ctt cta ccg att aac gag cca gtg cac gga aca      864
Asn Asp Glu Met Val Leu Leu Pro Ile Asn Glu Pro Val His Gly Thr
            275                 280                 285 aag agg aag agt cag att cag acg tat ttg gaa cat aac gaa ggc gca      912
Lys Arg Lys Ser Gln Ile Gln Thr Tyr Leu Glu His Asn Glu Gly Ala
        290                 295                 300 ggg cta caa cat ctg gct ctg atg agt gaa gac ata ttc agg acc ctg      960
Gly Leu Gln His Leu Ala Leu Met Ser Glu Asp Ile Phe Arg Thr Leu
305                 310                 315                 320 aga gag atg agg aag agg agc agt att gga gga ttc gac ttc atg cct     1008
Arg Glu Met Arg Lys Arg Ser Ser Ile Gly Gly Phe Asp Phe Met Pro
                325                 330                 335 tct cct ccg cct act tac tac cag aat ctc aag aaa cgg gtc ggc gac     1056
Ser Pro Pro Pro Thr Tyr Tyr Gln Asn Leu Lys Lys Arg Val Gly Asp
                340                 345                 350 gtg ctc agc gat gat cag atc aag gag tgt gag gaa tta ggg att ctt     1104
Val Leu Ser Asp Asp Gln Ile Lys Glu Cys Glu Glu Leu Gly Ile Leu
            355                 360                 365 gta gac aga gat gat caa ggg acg ttg ctt caa atc ttc aca aaa cca     1152
Val Asp Arg Asp Asp Gln Gly Thr Leu Leu Gln Ile Phe Thr Lys Pro
        370                 375                 380 cta ggt gac agg ccg acg ata ttt ata gag ata atc cag aga gta gga     1200
Leu Gly Asp Arg Pro Thr Ile Phe Ile Glu Ile Ile Gln Arg Val Gly
385                 390                 395                 400 tgc atg atg aaa gat gag gaa ggg aag gct tac cag agt gga gga tgt     1248
Cys Met Met Lys Asp Glu Glu Gly Lys Ala Tyr Gln Ser Gly Gly Cys
                405                 410                 415 ggt ggt ttt ggc aaa ggc aat ttc tct gag ctc ttc aag tcc att gaa     1296
Gly Gly Phe Gly Lys Gly Asn Phe Ser Glu Leu Phe Lys Ser Ile Glu
                420                 425                 430 gaa tac gaa aag act ctt gaa gcc aaa cag tta gtg gga tga              1338
Glu Tyr Glu Lys Thr Leu Glu Ala Lys Gln Leu Val Gly
            435                 440                 445

<210> SEQ ID NO 14
<211> LENGTH: 445
<212> TYPE: PRT
<213> ORGANISM: Arabidopsis thaliana

<400> SEQUENCE: 14

Met Gly His Gln Asn Ala Ala Val Ser Glu Asn Gln Asn His Asp Asp
1               5                   10                  15
```

-continued

```
Gly Ala Ala Ser Ser Pro Gly Phe Lys Leu Val Gly Phe Ser Lys Phe
             20                  25                  30

Val Arg Lys Asn Pro Lys Ser Asp Lys Phe Lys Val Lys Arg Phe His
         35                  40                  45

His Ile Glu Phe Trp Cys Gly Asp Ala Thr Asn Val Ala Arg Arg Phe
 50                  55                  60

Ser Trp Gly Leu Gly Met Arg Phe Ser Ala Lys Ser Asp Leu Ser Thr
 65                  70                  75                  80

Gly Asn Met Val His Ala Ser Tyr Leu Leu Thr Ser Gly Asp Leu Arg
                 85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
            115                 120                 125

Arg Ser Phe Phe Ser Ser His Gly Leu Gly Val Arg Ala Val Ala Ile
130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
            165                 170                 175

Ala Glu Val Lys Leu Tyr Gly Asp Val Val Leu Arg Tyr Val Ser Tyr
            180                 185                 190

Lys Ala Glu Asp Thr Glu Lys Ser Glu Phe Leu Pro Gly Phe Glu Arg
            195                 200                 205

Val Glu Asp Ala Ser Ser Phe Pro Leu Asp Tyr Gly Ile Arg Arg Leu
            210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
            245                 250                 255

Asp Val Gly Thr Ala Glu Ser Gly Leu Asn Ser Ala Val Leu Ala Ser
            260                 265                 270

Asn Asp Glu Met Val Leu Leu Pro Ile Asn Glu Pro Val His Gly Thr
            275                 280                 285

Lys Arg Lys Ser Gln Ile Gln Thr Tyr Leu Glu His Asn Glu Gly Ala
            290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
            325                 330                 335

Ser Pro Pro Pro Thr Tyr Tyr Gln Asn Leu Lys Lys Arg Val Gly Asp
            340                 345                 350

Val Leu Ser Asp Asp Gln Ile Lys Glu Cys Glu Glu Leu Gly Ile Leu
            355                 360                 365

Val Asp Arg Asp Asp Gln Gly Thr Leu Leu Gln Ile Phe Thr Lys Pro
            370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
            405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
```

-continued

```
                435                 440                 445

<210> SEQ ID NO 15
<211> LENGTH: 1182
<212> TYPE: DNA
<213> ORGANISM: Arabidopsis thaliana
<220> FEATURE:
<221> NAME/KEY: CDS
<222> LOCATION: (1)..(1182)

<400> SEQUENCE: 15 atg gag tct ctg ctc tct agt tct tct ctt gtt tcc gct gct ggt ggg     48
Met Glu Ser Leu Leu Ser Ser Ser Ser Leu Val Ser Ala Ala Gly Gly
1               5                   10                  15 ttt tgt tgg aag aag cag aat cta aag ctc cac tct tta tca gaa atc     96
Phe Cys Trp Lys Lys Gln Asn Leu Lys Leu His Ser Leu Ser Glu Ile
            20                  25                  30 cga gtt ctg cgt tgt gat tcg agt aaa gtt gtc gca aaa ccg aag ttt    144
Arg Val Leu Arg Cys Asp Ser Ser Lys Val Val Ala Lys Pro Lys Phe
        35                  40                  45 agg aac aat ctt gtt agg cct gat ggt caa gga tct tca ttg ttg ttg    192
Arg Asn Asn Leu Val Arg Pro Asp Gly Gln Gly Ser Ser Leu Leu Leu
    50                  55                  60 tat cca aaa cat aag tcg aga ttt cgg gtt aat gcc act gcg ggt cag    240
Tyr Pro Lys His Lys Ser Arg Phe Arg Val Asn Ala Thr Ala Gly Gln
65                  70                  75                  80 ccc gag gct ttc gac tcg aat agc aaa cag aag tct ttt aga gac tcg    288
Pro Glu Ala Phe Asp Ser Asn Ser Lys Gln Lys Ser Phe Arg Asp Ser
                85                  90                  95 tta gat gcg ttt tac agg ttt tct agg cct cat aca gtt att ggc aca    336
Leu Asp Ala Phe Tyr Arg Phe Ser Arg Pro His Thr Val Ile Gly Thr
            100                 105                 110 gtg ctt agc att tta tct gta tct ttc tta gca gta gag aag gtt tct    384
Val Leu Ser Ile Leu Ser Val Ser Phe Leu Ala Val Glu Lys Val Ser
        115                 120                 125 gat ata tct cct tta ctt ttc act ggc atc ttg gag gct gtt gtt gca    432
Asp Ile Ser Pro Leu Leu Phe Thr Gly Ile Leu Glu Ala Val Val Ala
    130                 135                 140 gct ctc atg atg aac att tac ata gtt ggg cta aat cag ttg tct gat    480
Ala Leu Met Met Asn Ile Tyr Ile Val Gly Leu Asn Gln Leu Ser Asp
145                 150                 155                 160 gtt gaa ata gat aag gtt aac aag ccc tat ctt cca ttg gca tca gga    528
Val Glu Ile Asp Lys Val Asn Lys Pro Tyr Leu Pro Leu Ala Ser Gly
                165                 170                 175 gaa tat tct gtt aac acc ggc att gca ata gta gct tcc ttc tcc atc    576
Glu Tyr Ser Val Asn Thr Gly Ile Ala Ile Val Ala Ser Phe Ser Ile
            180                 185                 190 atg agt ttc tgg ctt ggg tgg att gtt ggt tca tgg cca ttg ttc tgg    624
Met Ser Phe Trp Leu Gly Trp Ile Val Gly Ser Trp Pro Leu Phe Trp
        195                 200                 205 gct ctt ttt gtg agt ttc atg ctc ggt act gca tac tct atc aat ttg    672
Ala Leu Phe Val Ser Phe Met Leu Gly Thr Ala Tyr Ser Ile Asn Leu
    210                 215                 220 cca ctt tta cgg tgg aaa aga ttt gca ttg gtt gca gca atg tgt atc    720
Pro Leu Leu Arg Trp Lys Arg Phe Ala Leu Val Ala Ala Met Cys Ile
225                 230                 235                 240 ctc gct gtc cga gct att att gtt caa atc gcc ttt tat cta cat att    768
Leu Ala Val Arg Ala Ile Ile Val Gln Ile Ala Phe Tyr Leu His Ile
                245                 250                 255 cag aca cat gtg ttt gga aga cca atc ttg ttc act agg cct ctt att    816
Gln Thr His Val Phe Gly Arg Pro Ile Leu Phe Thr Arg Pro Leu Ile
            260                 265                 270
```

```
                        260                 265                 270
ttc gcc act gcg ttt atg agc ttt ttc tct gtc gtt att gca ttg ttt      864
Phe Ala Thr Ala Phe Met Ser Phe Phe Ser Val Val Ile Ala Leu Phe
            275                 280                 285 aag gat ata cct gat atc gaa ggg gat aag ata ttc gga atc cga tca      912
Lys Asp Ile Pro Asp Ile Glu Gly Asp Lys Ile Phe Gly Ile Arg Ser
        290                 295                 300 ttc tct gta act ctg ggt cag aaa cgg gtg ttt tgg aca tgt gtt aca      960
Phe Ser Val Thr Leu Gly Gln Lys Arg Val Phe Trp Thr Cys Val Thr
305                 310                 315                 320 cta ctt caa atg gct tac gct gtt gca att cta gtt gga gcc aca tct     1008
Leu Leu Gln Met Ala Tyr Ala Val Ala Ile Leu Val Gly Ala Thr Ser
                325                 330                 335 cca ttc ata tgg agc aaa gtc atc tcg gtt gtg ggt cat gtt ata ctc     1056
Pro Phe Ile Trp Ser Lys Val Ile Ser Val Val Gly His Val Ile Leu
            340                 345                 350 gca aca act ttg tgg gct cga gct aag tcc gtt gat ctg agt agc aaa     1104
Ala Thr Thr Leu Trp Ala Arg Ala Lys Ser Val Asp Leu Ser Ser Lys
        355                 360                 365 acc gaa ata act tca tgt tat atg ttc ata tgg aag ctc ttt tat gca     1152
Thr Glu Ile Thr Ser Cys Tyr Met Phe Ile Trp Lys Leu Phe Tyr Ala
    370                 375                 380 gag tac ttg ctg tta cct ttt ttg aag tga                             1182
Glu Tyr Leu Leu Leu Pro Phe Leu Lys
385                 390

<210> SEQ ID NO 16
<211> LENGTH: 393
<212> TYPE: PRT
<213> ORGANISM: Arabidopsis thaliana

<400> SEQUENCE: 16

Met Glu Ser Leu Leu Ser Ser Ser Leu Val Ser Ala Ala Gly Gly
1               5                   10                  15

Phe Cys Trp Lys Lys Gln Asn Leu Lys Leu His Ser Leu Ser Glu Ile
                20                  25                  30

Arg Val Leu Arg Cys Asp Ser Ser Lys Val Val Ala Lys Pro Lys Phe
            35                  40                  45

Arg Asn Asn Leu Val Arg Pro Asp Gly Gln Gly Ser Ser Leu Leu Leu
    50                  55                  60
Tyr Pro Lys His Lys Ser Arg Phe Arg Val Asn Ala Thr Ala Gly Gln
65                  70                  75                  80

Pro Glu Ala Phe Asp Ser Asn Ser Lys Gln Lys Ser Phe Arg Asp Ser
                85                  90                  95

Leu Asp Ala Phe Tyr Arg Phe Ser Arg Pro His Thr Val Ile Gly Thr
            100                 105                 110

Val Leu Ser Ile Leu Ser Val Ser Phe Leu Ala Val Glu Lys Val Ser
        115                 120                 125

Asp Ile Ser Pro Leu Leu Phe Thr Gly Ile Leu Glu Ala Val Val Ala
    130                 135                 140

Ala Leu Met Met Asn Ile Tyr Ile Val Gly Leu Asn Gln Leu Ser Asp
145                 150                 155                 160

Val Glu Ile Asp Lys Val Asn Lys Pro Tyr Leu Pro Leu Ala Ser Gly
                165                 170                 175

Glu Tyr Ser Val Asn Thr Gly Ile Ala Ile Val Ala Ser Phe Ser Ile
            180                 185                 190

Met Ser Phe Trp Leu Gly Trp Ile Val Gly Ser Trp Pro Leu Phe Trp
        195                 200                 205
```

```
Ala Leu Phe Val Ser Phe Met Leu Gly Thr Ala Tyr Ser Ile Asn Leu
    210                 215                 220

Pro Leu Arg Trp Lys Arg Phe Ala Leu Val Ala Ala Met Cys Ile
225                 230                 235                 240

Leu Ala Val Arg Ala Ile Ile Val Gln Ile Ala Phe Tyr Leu His Ile
                245                 250                 255

Gln Thr His Val Phe Gly Arg Pro Ile Leu Phe Thr Arg Pro Leu Ile
            260                 265                 270

Phe Ala Thr Ala Phe Met Ser Phe Ser Val Val Ile Ala Leu Phe
        275                 280                 285

Lys Asp Ile Pro Asp Ile Glu Gly Asp Lys Ile Phe Gly Ile Arg Ser
290                 295                 300

Phe Ser Val Thr Leu Gly Gln Lys Arg Val Phe Trp Thr Cys Val Thr
305                 310                 315                 320

Leu Leu Gln Met Ala Tyr Ala Val Ala Ile Leu Val Gly Ala Thr Ser
                325                 330                 335

Pro Phe Ile Trp Ser Lys Val Ile Ser Val Val Gly His Val Ile Leu
            340                 345                 350

Ala Thr Thr Leu Trp Ala Arg Ala Lys Ser Val Asp Leu Ser Ser Lys
        355                 360                 365

Thr Glu Ile Thr Ser Cys Tyr Met Phe Ile Trp Lys Leu Phe Tyr Ala
370                 375                 380

Glu Tyr Leu Leu Leu Pro Phe Leu Lys
385                 390

<210> SEQ ID NO 17
<211> LENGTH: 1509
<212> TYPE: DNA
<213> ORGANISM: Nicotiana tabacum
<220> FEATURE:
<221> NAME/KEY: CDS
<222> LOCATION: (1)..(1395)

<400> SEQUENCE: 17 atg gct tcc att gct ctc aaa act ttc acc ggc ctc cgt caa tcc tcg    48
Met Ala Ser Ile Ala Leu Lys Thr Phe Thr Gly Leu Arg Gln Ser Ser
1               5                   10                  15 ccg gaa aac aat tcc att act ctt tct aaa tcc ctc ccc ttc acc caa    96
Pro Glu Asn Asn Ser Ile Thr Leu Ser Lys Ser Leu Pro Phe Thr Gln
            20                  25                  30 acc cac cgt agg ctc cga atc aat gct tcc aaa tcc agc cca aga gtc   144
Thr His Arg Arg Leu Arg Ile Asn Ala Ser Lys Ser Ser Pro Arg Val
        35                  40                  45 aac ggc cgc aat ctt cgt gtt gcg gtg gtg ggc ggt ggt cct gct ggt   192
Asn Gly Arg Asn Leu Arg Val Ala Val Val Gly Gly Gly Pro Ala Gly
    50                  55                  60 ggc gcc gcc gct gaa aca ctc gcc aag gga gga att gaa acc ttc tta   240
Gly Ala Ala Ala Glu Thr Leu Ala Lys Gly Gly Ile Glu Thr Phe Leu
65                  70                  75                  80 atc gaa cgc aaa atg gac aac tgc aaa ccc tgc ggt ggg gcc atc cca   288
Ile Glu Arg Lys Met Asp Asn Cys Lys Pro Cys Gly Gly Ala Ile Pro
                85                  90                  95 ctt tgc atg gtg gga gaa ttt gac ctc cct ttg gat atc att gac cgg   336
Leu Cys Met Val Gly Glu Phe Asp Leu Pro Leu Asp Ile Ile Asp Arg
            100                 105                 110 aaa gtt aca aag atg aag atg att tcc cca tcc aac gtt gct gtt gat   384
Lys Val Thr Lys Met Lys Met Ile Ser Pro Ser Asn Val Ala Val Asp
        115                 120                 125
```

| | | |
|---|---|---|
| att ggt cag act tta aag cct cac gag tac atc ggt atg gtg cgc cgc<br>Ile Gly Gln Thr Leu Lys Pro His Glu Tyr Ile Gly Met Val Arg Arg<br>130                    135                    140 | 432 |
| gaa gta ctc gat gct tac ctc cgt gac cgc gct gct gaa gcc gga gcc<br>Glu Val Leu Asp Ala Tyr Leu Arg Asp Arg Ala Ala Glu Ala Gly Ala<br>145                    150                    155                    160 | 480 |
| tct gtt ctc aac ggc ttg ttc ctc aaa atg gac atg ccc aaa gct ccc<br>Ser Val Leu Asn Gly Leu Phe Leu Lys Met Asp Met Pro Lys Ala Pro<br>                    165                    170                    175 | 528 |
| aac gca cct tac gtc ctt cac tac aca gct tac gac tcc aaa act aat<br>Asn Ala Pro Tyr Val Leu His Tyr Thr Ala Tyr Asp Ser Lys Thr Asn<br>                        180                    185                    190 | 576 |
| ggc gcg ggg gag aag cgt acc ctg gaa gtt gac gcc gtt atc ggc gct<br>Gly Ala Gly Glu Lys Arg Thr Leu Glu Val Asp Ala Val Ile Gly Ala<br>                  195                    200                    205 | 624 |
| gac ggt gca aat tcc cgt gtc gca aaa tcc ata aac gcc ggt gac tac<br>Asp Gly Ala Asn Ser Arg Val Ala Lys Ser Ile Asn Ala Gly Asp Tyr<br>210                    215                    220 | 672 |
| gag tac gct att gca ttc caa gaa agg att aaa att tcc gat gat aaa<br>Glu Tyr Ala Ile Ala Phe Gln Glu Arg Ile Lys Ile Ser Asp Asp Lys<br>225                    230                    235                    240 | 720 |
| atg aag tat tac gag aat tta gct gaa atg tac gtg ggt gat gac gtg<br>Met Lys Tyr Tyr Glu Asn Leu Ala Glu Met Tyr Val Gly Asp Asp Val<br>                        245                    250                    255 | 768 |
| tcc cct gat ttt tac ggg tgg gtt ttc ccc aaa tgt gac cac gtt gcc<br>Ser Pro Asp Phe Tyr Gly Trp Val Phe Pro Lys Cys Asp His Val Ala<br>                  260                    265                    270 | 816 |
| gtt ggc act ggc aca gtc acc cac aaa gct gac atc aaa aaa ttc cag<br>Val Gly Thr Gly Thr Val Thr His Lys Ala Asp Ile Lys Lys Phe Gln<br>                  275                    280                    285 | 864 |
| cta gct aca aga ttg aga gct gat tcc aaa atc acc ggc gga aaa att<br>Leu Ala Thr Arg Leu Arg Ala Asp Ser Lys Ile Thr Gly Gly Lys Ile<br>290                    295                    300 | 912 |
| atc cgg gtc gag gcc cac ccg att cca gaa cac cca aga ccc aga aga<br>Ile Arg Val Glu Ala His Pro Ile Pro Glu His Pro Arg Pro Arg Arg<br>305                    310                    315                    320 | 960 |
| tta caa gac aga gtt gca ttg gtt ggt gat gcg gca ggg tac gtg acc<br>Leu Gln Asp Arg Val Ala Leu Val Gly Asp Ala Ala Gly Tyr Val Thr<br>                  325                    330                    335 | 1008 |
| aaa tgt tcg ggc gaa ggg att tac ttc gcg gca aag agt gga cgt atg<br>Lys Cys Ser Gly Glu Gly Ile Tyr Phe Ala Ala Lys Ser Gly Arg Met<br>                  340                    345                    350 | 1056 |
| tgt gct gaa gca att gtt gaa ggg tca gaa atg gga aaa aga atg gtg<br>Cys Ala Glu Ala Ile Val Glu Gly Ser Glu Met Gly Lys Arg Met Val<br>                      355                    360                    365 | 1104 |
| gac gag agt gat ttg agg aag tat ttg gag aaa tgg gac aag act tat<br>Asp Glu Ser Asp Leu Arg Lys Tyr Leu Glu Lys Trp Asp Lys Thr Tyr<br>370                    375                    380 | 1152 |
| tgg cca acg tac aag gtg ctt gat ata ttg cag aag gta ttt tac agg<br>Trp Pro Thr Tyr Lys Val Leu Asp Ile Leu Gln Lys Val Phe Tyr Arg<br>385                    390                    395                    400 | 1200 |
| tcg aat ccg gcg agg gaa gca ttt gtt gaa atg tgc gca gat gag tat<br>Ser Asn Pro Ala Arg Glu Ala Phe Val Glu Met Cys Ala Asp Glu Tyr<br>                        405                    410                    415 | 1248 |
| gtg cag aag atg aca ttt gac agc tat ttg tac aag aaa gta gca cca<br>Val Gln Lys Met Thr Phe Asp Ser Tyr Leu Tyr Lys Lys Val Ala Pro<br>                      420                    425                    430 | 1296 |
| gga aac cca att gaa gac ttg aag ctt gct gtg aat acc att gga agt<br>Gly Asn Pro Ile Glu Asp Leu Lys Leu Ala Val Asn Thr Ile Gly Ser | 1344 |

```
                435             440             445
ttg gta aga gct aat gca cta aga agg gaa atg gac aag ctc agt gta        1392
Leu Val Arg Ala Asn Ala Leu Arg Arg Glu Met Asp Lys Leu Ser Val
        450             455             460 taa gaagattaac agcattaata ttttcttgta attgaaggat ttatttctca             1445
aattactctg taaacacctt tcatcctgcc tttaatcgga tttatgtaac ttcataattt      1505
gagc                                                                   1509
```

<210> SEQ ID NO 18
<211> LENGTH: 464
<212> TYPE: PRT
<213> ORGANISM: Nicotiana tabacum

<400> SEQUENCE: 18

```
Met Ala Ser Ile Ala Leu Lys Thr Phe Thr Gly Leu Arg Gln Ser Ser
1               5                   10                  15

Pro Glu Asn Asn Ser Ile Thr Leu Ser Lys Ser Leu Pro Phe Thr Gln
            20                  25                  30

Thr His Arg Arg Leu Arg Ile Asn Ala Ser Lys Ser Ser Pro Arg Val
        35                  40                  45

Asn Gly Arg Asn Leu Arg Val Ala Val Val Gly Gly Pro Ala Gly
    50                  55                  60

Gly Ala Ala Ala Glu Thr Leu Ala Lys Gly Gly Ile Glu Thr Phe Leu
65                  70                  75                  80

Ile Glu Arg Lys Met Asp Asn Cys Lys Pro Cys Gly Gly Ala Ile Pro
                85                  90                  95

Leu Cys Met Val Gly Glu Phe Asp Leu Pro Leu Asp Ile Ile Asp Arg
            100                 105                 110

Lys Val Thr Lys Met Lys Met Ile Ser Pro Ser Asn Val Ala Val Asp
        115                 120                 125

Ile Gly Gln Thr Leu Lys Pro His Glu Tyr Ile Gly Met Val Arg Arg
    130                 135                 140

Glu Val Leu Asp Ala Tyr Leu Arg Asp Arg Ala Ala Glu Ala Gly Ala
145                 150                 155                 160

Ser Val Leu Asn Gly Leu Phe Leu Lys Met Asp Met Pro Lys Ala Pro
                165                 170                 175

Asn Ala Pro Tyr Val Leu His Tyr Thr Ala Tyr Asp Ser Lys Thr Asn
            180                 185                 190

Gly Ala Gly Glu Lys Arg Thr Leu Glu Val Asp Ala Val Ile Gly Ala
        195                 200                 205

Asp Gly Ala Asn Ser Arg Val Ala Lys Ser Ile Asn Ala Gly Asp Tyr
    210                 215                 220

Glu Tyr Ala Ile Ala Phe Gln Glu Arg Ile Lys Ile Ser Asp Asp Lys
225                 230                 235                 240

Met Lys Tyr Tyr Glu Asn Leu Ala Glu Met Tyr Val Gly Asp Asp Val
                245                 250                 255

Ser Pro Asp Phe Tyr Gly Trp Val Phe Pro Lys Cys Asp His Val Ala
            260                 265                 270

Val Gly Thr Gly Thr Val Thr His Lys Ala Asp Ile Lys Lys Phe Gln
        275                 280                 285

Leu Ala Thr Arg Leu Arg Ala Asp Ser Lys Ile Thr Gly Gly Lys Ile
    290                 295                 300

Ile Arg Val Glu Ala His Pro Ile Pro Glu His Pro Arg Pro Arg Arg
305                 310                 315                 320
```

```
Leu Gln Asp Arg Val Ala Leu Val Gly Asp Ala Ala Gly Tyr Val Thr
            325                 330                 335

Lys Cys Ser Gly Glu Gly Ile Tyr Phe Ala Ala Lys Ser Gly Arg Met
            340                 345                 350

Cys Ala Glu Ala Ile Val Glu Gly Ser Glu Met Gly Lys Arg Met Val
            355                 360                 365

Asp Glu Ser Asp Leu Arg Lys Tyr Leu Glu Lys Trp Asp Lys Thr Tyr
            370                 375                 380

Trp Pro Thr Tyr Lys Val Leu Asp Ile Leu Gln Lys Val Phe Tyr Arg
385                 390                 395                 400

Ser Asn Pro Ala Arg Glu Ala Phe Val Glu Met Cys Ala Asp Glu Tyr
                405                 410                 415

Val Gln Lys Met Thr Phe Asp Ser Tyr Leu Tyr Lys Lys Val Ala Pro
                420                 425                 430

Gly Asn Pro Ile Glu Asp Leu Lys Leu Ala Val Asn Thr Ile Gly Ser
                435                 440                 445

Leu Val Arg Ala Asn Ala Leu Arg Arg Glu Met Asp Lys Leu Ser Val
        450                 455                 460

<210> SEQ ID NO 19
<211> LENGTH: 957
<212> TYPE: DNA
<213> ORGANISM: Synechocystis PCC6803
<220> FEATURE:
<221> NAME/KEY: CDS
<222> LOCATION: (1)..(957)

<400> SEQUENCE: 19 atg ccc gag tat ttg ctt ctg ccc gct ggc cta att tcc ctc tcc ctg      48
Met Pro Glu Tyr Leu Leu Leu Pro Ala Gly Leu Ile Ser Leu Ser Leu
1               5                   10                  15 gcg atc gcc gct gga ctg tat ctc cta act gcc cgg ggc tat cag tca      96
Ala Ile Ala Ala Gly Leu Tyr Leu Leu Thr Ala Arg Gly Tyr Gln Ser
                20                  25                  30 tcg gat tcc gtg gcc aac gcc tac gac caa tgg aca gag gac ggc att     144
Ser Asp Ser Val Ala Asn Ala Tyr Asp Gln Trp Thr Glu Asp Gly Ile
            35                  40                  45 ttg gaa tat tac tgg ggc gac cat atc cac ctc ggc cat tat ggc gat     192
Leu Glu Tyr Tyr Trp Gly Asp His Ile His Leu Gly His Tyr Gly Asp
        50                  55                  60 ccg cca gtg gcc aag gat ttc atc caa tcg aaa att gat ttt gtc cat     240
Pro Pro Val Ala Lys Asp Phe Ile Gln Ser Lys Ile Asp Phe Val His
65                  70                  75                  80 gcc atg gcc cag tgg ggc gga tta gat aca ctt ccc ccc ggc aca acg     288
Ala Met Ala Gln Trp Gly Gly Leu Asp Thr Leu Pro Pro Gly Thr Thr
                85                  90                  95 gta ttg gat gtg ggt tgc ggc att ggc ggt agc agt cgc att ctc gcc     336
Val Leu Asp Val Gly Cys Gly Ile Gly Gly Ser Ser Arg Ile Leu Ala
                100                 105                 110 aaa gat tat ggt ttt aac gtt acc ggc atc acc att agt ccc caa cag     384
Lys Asp Tyr Gly Phe Asn Val Thr Gly Ile Thr Ile Ser Pro Gln Gln
            115                 120                 125 gtg aaa cgg gcg acg gaa tta act cct ccc gat gtg acg gcc aag ttt     432
Val Lys Arg Ala Thr Glu Leu Thr Pro Pro Asp Val Thr Ala Lys Phe
        130                 135                 140 gcg gtg gac gat gct atg gct ttg tct ttt cct gac ggt agt ttc gac     480
Ala Val Asp Asp Ala Met Ala Leu Ser Phe Pro Asp Gly Ser Phe Asp
145                 150                 155                 160
```

```
gta gtt tgg tcg gtg gaa gca ggg ccc cac atg cct gac aaa gct gtg      528
Val Val Trp Ser Val Glu Ala Gly Pro His Met Pro Asp Lys Ala Val
            165                 170                 175 ttt gcc aag gaa tta ctg cgg gtc gtg aaa cca ggg ggc att ctg gtg      576
Phe Ala Lys Glu Leu Leu Arg Val Val Lys Pro Gly Gly Ile Leu Val
        180                 185                 190 gtg gcg gat tgg aat caa cgg gac gat cgc caa gtg ccc ctc aac ttc      624
Val Ala Asp Trp Asn Gln Arg Asp Asp Arg Gln Val Pro Leu Asn Phe
    195                 200                 205 tgg gaa aaa cca gtg atg cga caa ctg ttg gat caa tgg tcc cac cct      672
Trp Glu Lys Pro Val Met Arg Gln Leu Leu Asp Gln Trp Ser His Pro
210                 215                 220 gcc ttt gcc agc att gaa ggt ttt gcg gaa aat ttg gaa gcc acg ggt      720
Ala Phe Ala Ser Ile Glu Gly Phe Ala Glu Asn Leu Glu Ala Thr Gly
225                 230                 235                 240 ttg gtg gag ggc cag gtg act act gct gat tgg act gta ccg acc ctc      768
Leu Val Glu Gly Gln Val Thr Thr Ala Asp Trp Thr Val Pro Thr Leu
            245                 250                 255 ccc gct tgg ttg gat acc att tgg cag ggc att atc cgg ccc cag ggc      816
Pro Ala Trp Leu Asp Thr Ile Trp Gln Gly Ile Ile Arg Pro Gln Gly
        260                 265                 270 tgg tta caa tac ggc att cgt ggg ttt atc aaa tcc gtg cgg gaa gta      864
Trp Leu Gln Tyr Gly Ile Arg Gly Phe Ile Lys Ser Val Arg Glu Val
    275                 280                 285 ccg act att tta ttg atg cgc ctt gcc ttt ggg gta gga ctt tgt cgc      912
Pro Thr Ile Leu Leu Met Arg Leu Ala Phe Gly Val Gly Leu Cys Arg
290                 295                 300 ttc ggt atg ttc aaa gca gtg cga aaa aac gcc act caa gct taa          957
Phe Gly Met Phe Lys Ala Val Arg Lys Asn Ala Thr Gln Ala
305                 310                 315

<210> SEQ ID NO 20
<211> LENGTH: 318
<212> TYPE: PRT
<213> ORGANISM: Synechocystis PCC6803

<400> SEQUENCE: 20

Met Pro Glu Tyr Leu Leu Leu Pro Ala Gly Leu Ile Ser Leu Ser Leu
1               5                   10                  15

Ala Ile Ala Ala Gly Leu Tyr Leu Leu Thr Ala Arg Gly Tyr Gln Ser
            20                  25                  30

Ser Asp Ser Val Ala Asn Ala Tyr Asp Gln Trp Thr Glu Asp Gly Ile
        35                  40                  45

Leu Glu Tyr Tyr Trp Gly Asp His Ile His Leu Gly His Tyr Gly Asp
    50                  55                  60

Pro Pro Val Ala Lys Asp Phe Ile Gln Ser Lys Ile Asp Phe Val His
65                  70                  75                  80

Ala Met Ala Gln Trp Gly Gly Leu Asp Thr Leu Pro Pro Gly Thr Thr
                85                  90                  95

Val Leu Asp Val Gly Cys Gly Ile Gly Gly Ser Ser Arg Ile Leu Ala
            100                 105                 110

Lys Asp Tyr Gly Phe Asn Val Thr Gly Ile Thr Ile Ser Pro Gln Gln
        115                 120                 125

Val Lys Arg Ala Thr Glu Leu Thr Pro Pro Asp Val Thr Ala Lys Phe
    130                 135                 140

Ala Val Asp Asp Ala Met Ala Leu Ser Phe Pro Asp Gly Ser Phe Asp
145                 150                 155                 160

Val Val Trp Ser Val Glu Ala Gly Pro His Met Pro Asp Lys Ala Val
```

```
                165                 170                 175
Phe Ala Lys Glu Leu Leu Arg Val Val Lys Pro Gly Gly Ile Leu Val
                180                 185                 190

Val Ala Asp Trp Asn Gln Arg Asp Asp Arg Gln Val Pro Leu Asn Phe
            195                 200                 205

Trp Glu Lys Pro Val Met Arg Gln Leu Leu Asp Gln Trp Ser His Pro
        210                 215                 220

Ala Phe Ala Ser Ile Glu Gly Phe Ala Glu Asn Leu Glu Ala Thr Gly
225                 230                 235                 240

Leu Val Glu Gly Gln Val Thr Thr Ala Asp Trp Thr Val Pro Thr Leu
                245                 250                 255

Pro Ala Trp Leu Asp Thr Ile Trp Gln Gly Ile Ile Arg Pro Gln Gly
            260                 265                 270

Trp Leu Gln Tyr Gly Ile Arg Gly Phe Ile Lys Ser Val Arg Glu Val
        275                 280                 285

Pro Thr Ile Leu Leu Met Arg Leu Ala Phe Gly Val Gly Leu Cys Arg
        290                 295                 300

Phe Gly Met Phe Lys Ala Val Arg Lys Asn Ala Thr Gln Ala
305                 310                 315

<210> SEQ ID NO 21
<211> LENGTH: 1100
<212> TYPE: DNA
<213> ORGANISM: Synechocystis PCC6803
<220> FEATURE:
<221> NAME/KEY: CDS
<222> LOCATION: (1)..(1092)

<400> SEQUENCE: 21 atg aaa ttt ccg ccc cac agt ggt tac cat tgg caa ggt caa tca cct     48
Met Lys Phe Pro Pro His Ser Gly Tyr His Trp Gln Gly Gln Ser Pro
1               5                   10                  15 ttc ttt gaa ggt tgg tac gtg cgc ctg ctt ttg ccc caa tcc ggg gaa     96
Phe Phe Glu Gly Trp Tyr Val Arg Leu Leu Leu Pro Gln Ser Gly Glu
                20                  25                  30 agt ttt gct ttt atg tac tcc atc gaa aat cct gct agc gat cat cat    144
Ser Phe Ala Phe Met Tyr Ser Ile Glu Asn Pro Ala Ser Asp His His
            35                  40                  45 tac ggc ggt ggt gct gtg caa att tta ggg ccg gct acg aaa aaa caa    192
Tyr Gly Gly Gly Ala Val Gln Ile Leu Gly Pro Ala Thr Lys Lys Gln
        50                  55                  60 gaa aat cag gaa gac caa ctt gtt tgg cgg aca ttt ccc tcg gta aaa    240
Glu Asn Gln Glu Asp Gln Leu Val Trp Arg Thr Phe Pro Ser Val Lys
65                  70                  75                  80 aaa ttt tgg gcc agt cct cgc cag ttt gcc cta ggg cat tgg gga aaa    288
Lys Phe Trp Ala Ser Pro Arg Gln Phe Ala Leu Gly His Trp Gly Lys
                85                  90                  95 tgt agg gat aac agg cag gcg aaa ccc cta ctc tcc gaa gaa ttt ttt    336
Cys Arg Asp Asn Arg Gln Ala Lys Pro Leu Leu Ser Glu Glu Phe Phe
                100                 105                 110 gcc acg gtc aag gaa ggt tat caa atc cat caa aat cag cac caa gga    384
Ala Thr Val Lys Glu Gly Tyr Gln Ile His Gln Asn Gln His Gln Gly
            115                 120                 125 caa atc att cat ggc gat cgc cat tgt cgt tgg cag ttc acc gta gaa    432
Gln Ile Ile His Gly Asp Arg His Cys Arg Trp Gln Phe Thr Val Glu
        130                 135                 140 ccg gaa gta act tgg ggg agt cct aac cga ttt cct cgg gct aca gcg    480
Pro Glu Val Thr Trp Gly Ser Pro Asn Arg Phe Pro Arg Ala Thr Ala
145                 150                 155                 160
```

| | | |
|---|---|---|
| ggt tgg ctt tcc ttt tta ccc ttg ttt gat ccc ggt tgg caa att ctt<br>Gly Trp Leu Ser Phe Leu Pro Leu Phe Asp Pro Gly Trp Gln Ile Leu<br>165 170 175 | | 528 |
| tta gcc caa ggt aga gcg cac ggc tgg ctg aaa tgg cag agg gaa cag<br>Leu Ala Gln Gly Arg Ala His Gly Trp Leu Lys Trp Gln Arg Glu Gln<br>180 185 190 | | 576 |
| tat gaa ttt gac cac gcc cta gtt tat gcc gaa aaa aat tgg ggt cac<br>Tyr Glu Phe Asp His Ala Leu Val Tyr Ala Glu Lys Asn Trp Gly His<br>195 200 205 | | 624 |
| tcc ttt ccc tcc cgc tgg ttt tgg ctc caa gca aat tat ttt cct gac<br>Ser Phe Pro Ser Arg Trp Phe Trp Leu Gln Ala Asn Tyr Phe Pro Asp<br>210 215 220 | | 672 |
| cat cca gga ctg agc gtc act gcc gct ggg gaa cgg att gtt ctt<br>His Pro Gly Leu Ser Val Thr Ala Ala Gly Glu Arg Ile Val Leu<br>225 230 235 240 | | 720 |
| ggt cgc ccc gaa gag gta gct tta att ggc tta cat cac caa ggt aat<br>Gly Arg Pro Glu Glu Val Ala Leu Ile Gly Leu His His Gln Gly Asn<br>245 250 255 | | 768 |
| ttt tac gaa ttt ggc ccg ggc cat ggc aca gtc act tgg caa gta gct<br>Phe Tyr Glu Phe Gly Pro Gly His Gly Thr Val Thr Trp Gln Val Ala<br>260 265 270 | | 816 |
| ccc tgg ggc cgt tgg caa tta aaa gcc agc aat gat agg tat tgg gtc<br>Pro Trp Gly Arg Trp Gln Leu Lys Ala Ser Asn Asp Arg Tyr Trp Val<br>275 280 285 | | 864 |
| aag ttg tcc gga aaa aca gat aaa aaa ggc agt tta gtc cac act ccc<br>Lys Leu Ser Gly Lys Thr Asp Lys Lys Gly Ser Leu Val His Thr Pro<br>290 295 300 | | 912 |
| acc gcc cag ggc tta caa ctc aac tgc cga gat acc act agg ggc tat<br>Thr Ala Gln Gly Leu Gln Leu Asn Cys Arg Asp Thr Thr Arg Gly Tyr<br>305 310 315 320 | | 960 |
| ttg tat ttg caa ttg gga tct gtg ggt cac ggc ctg ata gtg caa ggg<br>Leu Tyr Leu Gln Leu Gly Ser Val Gly His Gly Leu Ile Val Gln Gly<br>325 330 335 | | 1008 |
| gaa acg gac acc gcg ggg cta gaa gtt gga ggt gat tgg ggt tta aca<br>Glu Thr Asp Thr Ala Gly Leu Glu Val Gly Gly Asp Trp Gly Leu Thr<br>340 345 350 | | 1056 |
| gag gaa aat ttg agc aaa aaa aca gtg cca ttc tga gggaataa<br>Glu Glu Asn Leu Ser Lys Lys Thr Val Pro Phe<br>355 360 | | 1100 |

<210> SEQ ID NO 22
<211> LENGTH: 363
<212> TYPE: PRT
<213> ORGANISM: Synechocystis PCC6803

<400> SEQUENCE: 22

Met Lys Phe Pro Pro His Ser Gly Tyr His Trp Gln Gly Gln Ser Pro
1               5                   10                  15

Phe Phe Glu Gly Trp Tyr Val Arg Leu Leu Pro Gln Ser Gly Glu
            20                  25                  30

Ser Phe Ala Phe Met Tyr Ser Ile Glu Asn Pro Ala Ser Asp His His
        35                  40                  45

Tyr Gly Gly Gly Ala Val Gln Ile Leu Gly Pro Ala Thr Lys Lys Gln
    50                  55                  60

Glu Asn Gln Glu Asp Gln Leu Val Trp Arg Thr Phe Pro Ser Val Lys
65                  70                  75                  80

Lys Phe Trp Ala Ser Pro Arg Gln Phe Ala Leu Gly His Trp Gly Lys
                85                  90                  95

```
Cys Arg Asp Asn Arg Gln Ala Lys Pro Leu Leu Ser Glu Glu Phe Phe
            100                 105                 110
Ala Thr Val Lys Glu Gly Tyr Gln Ile His Gln Asn Gln His Gln Gly
        115                 120                 125
Gln Ile Ile His Gly Asp Arg His Cys Arg Trp Gln Phe Thr Val Glu
    130                 135                 140
Pro Glu Val Thr Trp Gly Ser Pro Asn Arg Phe Pro Arg Ala Thr Ala
145                 150                 155                 160
Gly Trp Leu Ser Phe Leu Pro Leu Phe Asp Pro Gly Trp Gln Ile Leu
                165                 170                 175
Leu Ala Gln Gly Arg Ala His Gly Trp Leu Lys Trp Gln Arg Glu Gln
            180                 185                 190
Tyr Glu Phe Asp His Ala Leu Val Tyr Ala Glu Lys Asn Trp Gly His
        195                 200                 205
Ser Phe Pro Ser Arg Trp Phe Trp Leu Gln Ala Asn Tyr Phe Pro Asp
    210                 215                 220
His Pro Gly Leu Ser Val Thr Ala Ala Gly Gly Glu Arg Ile Val Leu
225                 230                 235                 240
Gly Arg Pro Glu Glu Val Ala Leu Ile Gly Leu His His Gln Gly Asn
                245                 250                 255
Phe Tyr Glu Phe Gly Pro Gly His Gly Thr Val Thr Trp Gln Val Ala
            260                 265                 270
Pro Trp Gly Arg Trp Gln Leu Lys Ala Ser Asn Asp Arg Tyr Trp Val
        275                 280                 285
Lys Leu Ser Gly Lys Thr Asp Lys Lys Gly Ser Leu Val His Thr Pro
    290                 295                 300
Thr Ala Gln Gly Leu Gln Leu Asn Cys Arg Asp Thr Thr Arg Gly Tyr
305                 310                 315                 320
Leu Tyr Leu Gln Leu Gly Ser Val Gly His Gly Leu Ile Val Gln Gly
                325                 330                 335
Glu Thr Asp Thr Ala Gly Leu Glu Val Gly Gly Asp Trp Gly Leu Thr
            340                 345                 350
Glu Glu Asn Leu Ser Lys Lys Thr Val Pro Phe
        355                 360

<210> SEQ ID NO 23
<211> LENGTH: 1047
<212> TYPE: DNA
<213> ORGANISM: Arabidopsis thaliana
<220> FEATURE:
<221> NAME/KEY: CDS
<222> LOCATION: (1)..(1047)

<400> SEQUENCE: 23 atg aaa gca act cta gca gca ccc tct tct ctc aca agc ctc cct tat    48
Met Lys Ala Thr Leu Ala Ala Pro Ser Ser Leu Thr Ser Leu Pro Tyr
1               5                   10                  15 cga acc aac tct tct ttc ggc tca aag tca tcg ctt ctc ttt cgg tct    96
Arg Thr Asn Ser Ser Phe Gly Ser Lys Ser Ser Leu Leu Phe Arg Ser
            20                  25                  30 cca tcc tcc tcc tcc tca gtc tct atg acg aca acg cgt gga aac gtg    144
Pro Ser Ser Ser Ser Ser Val Ser Met Thr Thr Thr Arg Gly Asn Val
        35                  40                  45 gct gtg gcg gct gct gct aca tcc act gag gcg cta aga aaa gga ata    192
Ala Val Ala Ala Ala Ala Thr Ser Thr Glu Ala Leu Arg Lys Gly Ile
    50                  55                  60 gcg gag ttc tac aat gaa act tcg ggt ttg tgg gaa gag att tgg gga    240
```

```
                                                              -continued

Ala Glu Phe Tyr Asn Glu Thr Ser Gly Leu Trp Glu Glu Ile Trp Gly
 65              70                  75                  80 gat cat atg cat cat ggc ttt tgt gac cct gat tct tct gtt caa ctt      288
Asp His Met His His Gly Phe Cys Asp Pro Asp Ser Ser Val Gln Leu
                 85                  90                  95 tct gat tct ggt cac aag gaa gct cag atc cgt atg att gaa gag tct      336
Ser Asp Ser Gly His Lys Glu Ala Gln Ile Arg Met Ile Glu Glu Ser
            100                 105                 110 ctc cgt ttt gcc ggt gtt act gat gaa gag gag gag aaa aag ata aag      384
Leu Arg Phe Ala Gly Val Thr Asp Glu Glu Glu Glu Lys Lys Ile Lys
        115                 120                 125 aaa gta gtg gat gtt ggg tgt ggg att gga gga agc tca aga tat ctt      432
Lys Val Val Asp Val Gly Cys Gly Ile Gly Gly Ser Ser Arg Tyr Leu
    130                 135                 140 gcc tct aaa ttt gga gct gaa tgc att ggc att act ctc agc cct gtt      480
Ala Ser Lys Phe Gly Ala Glu Cys Ile Gly Ile Thr Leu Ser Pro Val
145                 150                 155                 160 cag gcc aag aga gcc aat gat ctc gcg gct gct caa tca ctc gct cat      528
Gln Ala Lys Arg Ala Asn Asp Leu Ala Ala Ala Gln Ser Leu Ala His
                165                 170                 175 aag gct tcc ttc caa gtt gcg gat gcg ttg gat cag cca ttc gaa gat      576
Lys Ala Ser Phe Gln Val Ala Asp Ala Leu Asp Gln Pro Phe Glu Asp
            180                 185                 190 gga aaa ttc gat ata gtg tgg tcg atg gag agt ggt gag cat atg cct      624
Gly Lys Phe Asp Ile Val Trp Ser Met Glu Ser Gly Glu His Met Pro
        195                 200                 205 gac aag gcc aag ttt gta aaa gag ttg gta cgt gtg gcg gct cca gga      672
Asp Lys Ala Lys Phe Val Lys Glu Leu Val Arg Val Ala Ala Pro Gly
    210                 215                 220 ggt agg ata ata ata gtg aca tgg tgc cat aga aat cta tct gcg ggg      720
Gly Arg Ile Ile Ile Val Thr Trp Cys His Arg Asn Leu Ser Ala Gly
225                 230                 235                 240 gag gaa gct ttg cag ccg tgg gag caa aac atc ttg gac aaa atc cgt      768
Glu Glu Ala Leu Gln Pro Trp Glu Gln Asn Ile Leu Asp Lys Ile Arg
                245                 250                 255 aag acg ttc tat ctc ccg gct tgg tgc tcc acc gat gat tat gtc aac      816
Lys Thr Phe Tyr Leu Pro Ala Trp Cys Ser Thr Asp Asp Tyr Val Asn
            260                 265                 270 ttg ctt caa tcc cat tct ctc cag gat att aag tgt gcg gat tgg tca      864
Leu Leu Gln Ser His Ser Leu Gln Asp Ile Lys Cys Ala Asp Trp Ser
        275                 280                 285 gag aac gta gct cct ttc tgg cct gcg gtt ata cgg act gca tta aca      912
Glu Asn Val Ala Pro Phe Trp Pro Ala Val Ile Arg Thr Ala Leu Thr
    290                 295                 300 tgg aag ggc ctt gtg tct ctg ctt cgt agt ggt atg aaa agt att aaa      960
Trp Lys Gly Leu Val Ser Leu Leu Arg Ser Gly Met Lys Ser Ile Lys
305                 310                 315                 320 gga gca ttg aca atg cca ttg atg att gaa ggt tac aag aaa ggt gtc     1008
Gly Ala Leu Thr Met Pro Leu Met Ile Glu Gly Tyr Lys Lys Gly Val
                325                 330                 335 att aag ttt ggt atc atc act tgc cag aag cca ctc taa                 1047
Ile Lys Phe Gly Ile Ile Thr Cys Gln Lys Pro Leu
            340                 345

<210> SEQ ID NO 24
<211> LENGTH: 348
<212> TYPE: PRT
<213> ORGANISM: Arabidopsis thaliana

<400> SEQUENCE: 24
```

```
Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
            20                  25                  30

Pro Ser Ser Ser Ser Val Ser Met Thr Thr Thr Arg Gly Asn Val
        35                  40                  45

Ala Val Ala Ala Ala Ala Thr Ser Thr Glu Ala Leu Arg Lys Gly Ile
50                          55                  60

Ala Glu Phe Tyr Asn Glu Thr Ser Gly Leu Trp Glu Ile Trp Gly
65              70                      75                  80

Asp His Met His His Gly Phe Cys Asp Pro Asp Ser Ser Val Gln Leu
                85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
            115                 120                 125

Lys Val Val Asp Val Gly Cys Gly Ile Gly Gly Ser Ser Arg Tyr Leu
130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Ala Gln Ser Leu Ala His
            165                 170                 175

Lys Ala Ser Phe Gln Val Ala Asp Ala Leu Asp Gln Pro Phe Glu Asp
            180                 185                 190

Gly Lys Phe Asp Ile Val Trp Ser Met Glu Ser Gly Glu His Met Pro
        195                 200                 205

Asp Lys Ala Lys Phe Val Lys Glu Leu Val Arg Val Ala Ala Pro Gly
210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Arg
            245                 250                 255

Lys Thr Phe Tyr Leu Pro Ala Trp Cys Ser Thr Asp Asp Tyr Val Asn
            260                 265                 270

Leu Leu Gln Ser His Ser Leu Gln Asp Ile Lys Cys Ala Asp Trp Ser
            275                 280                 285

Glu Asn Val Ala Pro Phe Trp Pro Ala Val Ile Arg Thr Ala Leu Thr
            290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
            325                 330                 335

Ile Lys Phe Gly Ile Ile Thr Cys Gln Lys Pro Leu
            340                 345

<210> SEQ ID NO 25
<211> LENGTH: 580
<212> TYPE: DNA
<213> ORGANISM: Brassica napus
<220> FEATURE:
<221> NAME/KEY: misc_structure
<222> LOCATION: (1)..(580)

<400> SEQUENCE: 25
gtcgacgagc tcatggggcg aagggtcttg ctgcaccaag agattttctt gcaccaacgg    60
```

-continued

```
catggtttga ggaagggcta cggcctgact acactattgt tcagaagttt ggcggtgaac      120
tctttactgc taaacaagat ttctctccgt tcaatgtggt tgcctggcat ggcaattacg      180
tgccttataa gtatgacctg cacaagttct gtccatacaa cactgtcctt gtagaccatg      240
gagatccatc tgtaaataca gttctgacag caccaacgga taaacctggt gtggccttgc      300
ttgattttgt catattccct cctcgttggt tggttgctga gcatacctt cgacctcctt       360 actaccatcg taactgcatg agtgaattta tgggcctaat ctatggtgct tacgaggcca      420
aagctgatgg atttctacct ggtggcgcaa gtcttcacag ttgtatgaca cctcatggtc      480
cagatacaac cacatacgag gcgacgattg ctcgtgtaaa tgcaatggct ccttataagc      540
tcacaggcac catggccttc atgtttgagg taccagtact                            580
```

<210> SEQ ID NO 26
<211> LENGTH: 30
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(30)

<400> SEQUENCE: 26

```
gatatcatgg actcctacgt gattcagacg                                        30
```

<210> SEQ ID NO 27
<211> LENGTH: 29
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(29)

<400> SEQUENCE: 27

```
gatatcttat ttgtcacact cctcctggc                                         29
```

<210> SEQ ID NO 28
<211> LENGTH: 24
<212> TYPE: DNA
<213> ORGANISM: Artificial Sequence
<220> FEATURE:
<223> OTHER INFORMATION: Description of artificial sequence:Primer
<220> FEATURE:
<221> NAME/KEY: primer_bind
<222> LOCATION: (1)..(24)

<400> SEQUENCE: 28

```
gtcgacatgg caaccctta gtgc                                               24
```

<210> SEQ ID NO 29
<211> LENGTH: 25
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(25)

<400> SEQUENCE: 29

```
gtcgacttac ttaacaccat tgacg                                             25
```

```
<210> SEQ ID NO 30
<211> LENGTH: 24
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(24)

<400> SEQUENCE: 30
gtcgacatgg cgagcaacgg agtt                                            24

<210> SEQ ID NO 31
<211> LENGTH: 25
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(25)

<400> SEQUENCE: 31
gtcgactcag ttgacagaga cgacg                                           25

<210> SEQ ID NO 32
<211> LENGTH: 30
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(30)

<400> SEQUENCE: 32
ggatccgatc catgagcgaa gaacaaccac                                      30

<210> SEQ ID NO 33
<211> LENGTH: 27
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(27)

<400> SEQUENCE: 33
ggatccttac atttcgagat tattatc                                         27

<210> SEQ ID NO 34
<211> LENGTH: 27
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(27)

<400> SEQUENCE: 34
agatctatgg agaatggagc aacgacg                                         27

<210> SEQ ID NO 35
<211> LENGTH: 31
<212> TYPE: DNA
<213> ORGANISM: Artificial Sequence
```

```
<220> FEATURE:
<223> OTHER INFORMATION: Description of artificial sequence: Primer
<220> FEATURE:
<221> NAME/KEY: primer_bind
<222> LOCATION: (1)..(31)

<400> SEQUENCE: 35
agatctatat ggttggatat tgagtcttgg c                               31

<210> SEQ ID NO 36
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(26)

<400> SEQUENCE: 36
gcccgggcat ggcttccatt gctctc                                     26

<210> SEQ ID NO 37
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(26)

<400> SEQUENCE: 37
gcccgggcgc tcaaattatg aagtta                                     26

<210> SEQ ID NO 38
<211> LENGTH: 24
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(24)

<400> SEQUENCE: 38
ggatccatgg gccaccaaaa cgcc                                       24

<210> SEQ ID NO 39
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(26)

<400> SEQUENCE: 39
gtcgactcat cccactaact gtttgg                                     26

<210> SEQ ID NO 40
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
```

```
<222> LOCATION: (1)..(26)

<400> SEQUENCE: 40
ggatccatgg agtctctgct ctctag                                              26

<210> SEQ ID NO 41
<211> LENGTH: 32
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(32)

<400> SEQUENCE: 41
ccatggatcc tcacttcaaa aaaggtaaca gc                                       32

<210> SEQ ID NO 42
<211> LENGTH: 31
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(31)

<400> SEQUENCE: 42
gatatcacca tggccgctgg actgtatctc c                                        31

<210> SEQ ID NO 43
<211> LENGTH: 30
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(30)

<400> SEQUENCE: 43
gtcgacctta agaatttaag cttgagtggc                                          30

<210> SEQ ID NO 44
<211> LENGTH: 27
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(27)

<400> SEQUENCE: 44
gatatcatgg aaatttccgc cccacag                                             27

<210> SEQ ID NO 45
<211> LENGTH: 28
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(28)

<400> SEQUENCE: 45
```

```
gatatccagt gttattccct cagaatgg                                              28
```

```
<210> SEQ ID NO 46
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(26)

<400> SEQUENCE: 46
ggatccatga aagcaactct agcagc                                                26
```

```
<210> SEQ ID NO 47
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(26)

<400> SEQUENCE: 47
gtcgacttag agtggcttct ggcaag                                                26
```

```
<210> SEQ ID NO 48
<211> LENGTH: 24
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(24)

<400> SEQUENCE: 48
gtcgacgagc tcatgggggc gaag                                                  24
```

```
<210> SEQ ID NO 49
<211> LENGTH: 21
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(21)

<400> SEQUENCE: 49
agtactggta cctcaaacat g                                                     21
```

```
<210> SEQ ID NO 50
<211> LENGTH: 23
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(23)

<400> SEQUENCE: 50
tctagactag aatccaactt ctg                                                   23
```

```
<210> SEQ ID NO 51
```

-continued

```
<211> LENGTH: 24
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(24)

<400> SEQUENCE: 51
tctagagctc gatcgagcgg ccgc                                              24

<210> SEQ ID NO 52
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(26)

<400> SEQUENCE: 52
gcccgggcca aatttacaat tgccac                                            26

<210> SEQ ID NO 53
<211> LENGTH: 23
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(23)

<400> SEQUENCE: 53
gcccgggcta attcccgatc tag                                               23

<210> SEQ ID NO 54
<211> LENGTH: 26
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(26)

<400> SEQUENCE: 54
gcccgggcat ctgtcgtctc aaactc                                            26

<210> SEQ ID NO 55
<211> LENGTH: 28
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(28)

<400> SEQUENCE: 55
gcccgggctg ttgtcgcaaa attcgccc                                          28

<210> SEQ ID NO 56
<211> LENGTH: 26
<212> TYPE: DNA
<213> ORGANISM: Artificial Sequence
<220> FEATURE:
```

-continued

```
<223> OTHER INFORMATION: Description of artificial sequence: Primer
<220> FEATURE:
<221> NAME/KEY: primer_bind
<222> LOCATION: (1)..(26)

<400> SEQUENCE: 56
gcccgggcat ctgtcgtctc aaactc                                          26

<210> SEQ ID NO 57
<211> LENGTH: 23
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(23)

<400> SEQUENCE: 57
gcccgggcta attcccgatc tag                                             23

<210> SEQ ID NO 58
<211> LENGTH: 25
<212> TYPE: DNA
<213> ORGANISM: Artificial Sequence
<220> FEATURE:
<223> OTHER INFORMATION: Description of artificial sequence: Primer
<220> FEATURE:
<221> NAME/KEY: primer_bind
<222> LOCATION: (1)..(25)

<400> SEQUENCE: 58
gcccgggcct agaatccaac ttctg                                           25
```